US009272008B2

(12) United States Patent
Lauer et al.

(10) Patent No.: US 9,272,008 B2
(45) Date of Patent: Mar. 1, 2016

(54) ONCOLYTIC MEASLES VIRUS

(76) Inventors: Ulrich M. Lauer, Tuebingen (DE); Michael Bitzer, Rottenburg (DE); Johanna Lampe, Helsinki (FI); Martina Zimmermann, Tuebingen (DE); Susanne Berchtold, Tuebingen (DE); Sebastian Lange, Tuebingen (DE); Wolfgang J. Neubert, Greifenberg (DE); Sascha Bossow, Heidelberg (DE)

( * ) Notice: Subject to any disclaimer, the term of this patent is extended or adjusted under 35 U.S.C. 154(b) by 0 days.

(21) Appl. No.: 13/818,053

(22) PCT Filed: Aug. 19, 2011

(86) PCT No.: PCT/EP2011/004200

§ 371 (c)(1), (2), (4) Date: May 6, 2013

(87) PCT Pub. No.: WO2012/022495

PCT Pub. Date: Feb. 23, 2012

(65) Prior Publication Data

US 2013/0217757 A1 Aug. 22, 2013

(30) Foreign Application Priority Data

Aug. 20, 2010 (EP) .................................... 10008726

(51) Int. Cl.

| | |
|---|---|
| ***C12N 7/00*** | (2006.01) |
| ***A61K 39/165*** | (2006.01) |
| ***A61K 39/00*** | (2006.01) |
| ***A61K 35/768*** | (2015.01) |
| ***C12N 9/10*** | (2006.01) |
| ***C12N 9/78*** | (2006.01) |
| ***A61K 31/7088*** | (2006.01) |

(52) U.S. Cl.

CPC ........... *A61K 35/768* (2013.01); *A61K 31/7088* (2013.01); *C12N 7/00* (2013.01); *C12N 9/1077* (2013.01); *C12N 9/78* (2013.01); *C07K 2319/00* (2013.01); *C12N 2760/18421* (2013.01); *C12N 2760/18432* (2013.01); *C12N 2760/18443* (2013.01); *C12N 2760/18471* (2013.01); *C12N 2830/60* (2013.01); *C12Y 305/04001* (2013.01)

(58) Field of Classification Search

None

See application file for complete search history.

(56) References Cited

U.S. PATENT DOCUMENTS 5,654,136 A 8/1997 Sasaki et al.

FOREIGN PATENT DOCUMENTS

| | | | |
|---|---|---|---|
| EP | 1 375 512 | B1 | 7/2009 |
| WO | WO 97/06270 | A1 | 2/1997 |
| WO | WO 98/13501 | A2 | 4/1998 |
| WO | WO 99/49017 | A2 | 9/1999 |
| WO | WO 2004000876 | A1 | 12/2003 |

OTHER PUBLICATIONS

Msaouel et al., Curr Opin Mol Ther. 2009; 11: 43-53.*

Erbs et al. Cancer Res. 2000; 60:3813-22.*

Tillieux et al., Vaccine, 2009; 27(16)2265-2273.*

Blechacz, et al: "Engineered Measles Virus as a Novel Oncolytic Viral Therapy System for Heptacellular Carcinoma," Hepatology, 2006, pp. 1465-1477.

Cathomen, et al., "Measles Viruses with Altered Envelope Protein Cytoplasmic Tails Gain Cell Fusion Competence," J. Virol., Feb. 1998, vol. 72, No. 2, pp. 1224-1234.

Cattaneo, et al: "Reprogrammed viruses as cancer therapeutics: targeted, armed and shielded" Nature Reviews. Microbiology, Jul. 1, 2008, vol. 6, No. 7, pp. 529-540.

Duprex, et al., "Observation of Measles Virus Cell-to-Cell Spread in Astrocytoma Cells by Using a Green Fluorescent Protein-Expressing Recombinant Virus," J. Virol., Nov. 1999, vol. 73, No. 11, pp. 9568-9575.

Erbs, et al: "In Vivo Cancer Gene Therapy by Adenovirus-mediated Transfer of a Bifunctional Yeast Cytosine Deaminase/Uracil Phosphoribosyltransferase Fusion Gene," Cancer Research, 2000, vol. 60, pp. 3813-3822.

Galanis, et al: "Phase I Trial of Interperitoneal Administration of an Oncolytic Measels Virus Strain Engineered to Express Carcinoembryonic Antigen for Recurrent Ovarian Cancer," Cancer Research, 2010, vol. 70, pp. 875-882.

Gassen, et al., "Establishment of a Rescue System for Canine Distemper Virus," J. Virol., Nov. 2000, vol. 74, No. 22, pp. 10737-10744.

Inoue, et al: "An Improved Method for Recovering Rabies Virus from Cloned cDNA" J. Virol, 2003, vol. 107, pp. 229-236.

Kievit, et al.: "Yeast Cytosine Deaminase Improves Radiosensitization and Bystander Effect by 5-Fluorocytosine of Human Colorectal Cancer Xenografts" Cancer Research, 2000, vol. 60, pp. 6649-6655.

Laassri,et al: "Microarray Assay for Evaluation of the Genetic Stability of Modified Vaccinia Virus Ankara B5R Gene," J. Medical Virology, 2007, vol. 79, pp. 791-802.

Martin, et al.: "RNA Polymerase II-Controlled Expression of Antigenomic RNA Enhances the Rescue Efficacies of Two Different Members of the Monogavirales Independently of the Site of Genome Replication", J. Virol., Jun. 20, 2006, vol. 80, pp. 5708-5715.

(Continued)

*Primary Examiner* — Doug Schultz

(74) *Attorney, Agent, or Firm* — Arnold & Porter LLP; Todd A. Lorenz

(57) ABSTRACT

The present invention pertains to a pharmaceutical composition comprising a recombinant measles virus encoding a suicide gene for use in the treatment of malignant cells with primary or secondary resistances against an oncolytic measles virus without suicide gene activity. Further, the present invention pertains to a recombinant measles virus based on measles vaccine strain Schwarz encoding a suicide gene, which comprises a fusion of a cytosine deaminase, particularly yeast cytosine deaminase, and a uracil phosphoribosyltransferase, particularly yeast uracil phosphoribosyltransferase, to a method and a kit for preparing the recombinant measles virus as claimed herein.

42 Claims, 79 Drawing Sheets

(56) References Cited

OTHER PUBLICATIONS

Maisner, et al., "Recombinant measles virus requiring an exogenous protease for activation of infectivity," J. Gen. Virol., 2000, vol. 81, pp. 441-449.
Moeller, et al., "Recombinant Measles Viruses Expressing Altered Hemagglutinin (H) Genes: Functional Separation of Mutations Determining H Antibody Escape from Neurovirulence," J. Virol, Aug. 2001, vol. 75, No. 16, pp. 7612-7620.
Msaouel, et al: "Clinical Testing of Engineered Oncolytic Measles Vius Strains in the Treatmet of Cancer: An Overview," Curr. Opin. Mol. Ther., 2009, vol. 11 No. 1, pp. 43-53.
Nakayama, et al, "Leucine at position 278 of the AIK-C measles virus vaccine strain fusion protein is responsible for reduced syncytium formation," J. Gen. Virol., 2001, vol. 82, pp. 2143-2150.
NCBI Blast:bg-AF266286.1 Measles virus strain Edmonston (AIK-C vaccine), complete genome(15894bp), (http://blast.ncbi.nlm.nih.gov/Blast.cgi).
Neumann, et al., "A decade after the generation of a negative-sense RNA virus from cloned cDNA—what have we learned?," J. Gen. Virol., 2002, vol. 83, pp. 2635-2662.
Parks, et al., "Enhanced Measles Virus cDNA Rescue and Gene Expression after Heat Shock," J. Virol., May 1999, Vo. 73, No. 5, pp. 3560-3566.
Parks, et al: "Comparison of Predicted Amindo Acid Sequences of Measles Virus Strains in the Edmonston Vaccine Lineage," J. Virol., 2001, vol. 75, No. 2, pp. 910-920.
Parks, et al: "Analysis of the Noncoding Regions of Measles Virus Strains in the Edmonston Vaccine Lineage," J. Virol., 2001, vol. 75, No. 2, pp. 921-933.
Peng, et al: "Non-invasive in vivo Monitoring of Trackable Viruses Expressing Soluble Marker Peptides," Nature Medicine, 2002, vol. 8, No. 5, pp. 527-531.
Radecke, et al.: "Rescue of measles viruses from cloned DNA," EMBO Journal, vol. 14, Nov. 19, 2007, vol. 14, No. 23, pp. 5773-5784.
Romer-Oberdörfer, et al., "Generation of recombinant lentogenic Newcastle disease virus from cDNA," J. Gen. Virol., 1999, vol. 80, pp. 2987-2995.
Singh, et al., "A Recombinant Measles Virus Expressing Hepatitis B Virus Surface Antigen Induces Humoral Immune Response in Genetically Modified Mice," J. Virol., Jun. 1999, vol. 73, No. 6, pp. 4823-4828.
Singh, et al., "A recombinant measles virus expressing biologically active human interleukin-12," J. Gen. Virol., 1999, vol. 80, pp. 101-106.
Springfield, et al.: "Recombinant Measles viruses encoding suicide genes for oncolytic therapy," Molecular Therapy, May 2004, vol. 9, No. Supplement 1, 593, p. S224.
Stritzker, et al: "Prodrug converting enzyme gene delivery by L. monocytogenes," BMC Cancer, 2008, vol. 8, No. 94, pp. 1-10.
Takeda, et al., "Recovery of Pathogenic Measles Virus from Cloned cDNA," J. Virol., Jul. 2000, vol. 74, No. 14, pp. 6643-6647.
Takeuchi, et al, "Recombinant Wild-Type and Edmonston Strain Measles Viruses Bearing Heterologous H Proteins: Role of H Protein in Cell Fusion and Host Cell Specificity," J. Virol., May 2002, vol. 76, No. 10, pp. 4891-4900.
Tillieux, et al.: "Comparative analysis of the complete nucleotide sequences of measles, mumps, and rubella strain genomes contained in Priorix-TetraT," and ProQuadTM live attenuated combined vaccines, Vaccine, Apr. 2009, vol. 27, pp. 2265-2273.
Tiraby, et al: "Concomitant Expression of *E. coli* Cytosine Deaminase and Uracil Phosphoribosyltransferase Improves the Cytotoxicity of 5-fluorocytosine," FEMS Microbiologyy Letters, 1998, vol. 167, pp. 41-49.
Ungerechts, et al: "Next General Measles Virus Vetor for Oncolytic Therapy: Targeted, Armed and Stealth," Molecular Therapy, May 2006, vol. 13, supplement1, p. S373.
Ungerechts, et al: "An Immunocompetent Murine Model for Oncolysis with an Armed and Targeted Measles Virus," Molecular Therapy, Nov. 2007, vol. 15, No. 11, pp. 1991-1997.
Ungerechts, et al: "Lymphoma chemoviortherapy: CD20-targeted and convertase-armed measles virus can synergize with fludarabine," Cancer Research, Nov. 15, 2007, vol. 67, No. 22, pp. 10939-10947.
Wybranietz, et al: "Enhanced Suicide Gene Effect by Adenviral Transduction of a VP22-cytosine Deaminase (CD) Fusion Gene," Gene Therapy, Nov. 1, 2001, vol. 8, No. 21, pp. 1654-1664.
Bossow, et al., "Engineered Measles Viruses for Oncolytic Therapy of Pancreatic Cancer," Molecular Therapy, May 2010, vol. 18, Supplement 1, p. S321.
Fielding, Adele K., "Measles as a potential oncolytic virus," Rev. Med. Virol. 2005; vol. 15: pp. 135-142.

* cited by examiner

FIG. 1A http://www.ncbi.nlm.nih.gov/nuccore/AF266291.1

```
   1 accaaacaaa gttgggtaag gatagttcaa tcaatgatca tcttctagtg cacttaggat
  61 tcaagatcct attatcaggg acaagagcag gattagggat atccgagatg gccacacttt
 121 taaggagctt agcattgttc aaaagaaaca aggacaaacc acccattaca tcaggatccg
 181 gtggagccat cagaggaatc aaacacatta ttatagtacc aatccctgga gattcctcaa
 241 ttaccactcg atccagactt ctggaccggt tggtgaggtt aattggaaac ccggatgtga
 301 gcgggcccaa actaacaggg gcactaatag gtatattatc cttatttgtg gagtctccag
 361 gtcaattgat tcagaggatc accgatgacc ctgacgttag cataaggctg ttagaggttg
 421 tccagagtga ccagtcacaa tctggcctta ccttcgcatc aagaggtacc aacatggagg
 481 atgaggcgga ccaatacttt tcacatgatg atccaattag tagtgatcaa tccaggttcg
 541 gatggttcgg gaacaaggaa atctcagata ttgaagtgca agaccctgag ggattcaaca
 601 tgattctggg taccatccta gcccaaattt gggtcttgct cgcaaaggcg gttacggccc
 661 cagacacggc agctgattcg gagctaagaa ggtggataaa gtacacccaa caaagaaggg
 721 tagttggtga atttagattg gagagaaaat ggttggatgt ggtgaggaac aggattgccg
 781 aggacctctc cttacgccga ttcatggtcg ctctaatcct ggatatcaag agaacacccg
 841 gaaacaaacc caggattgct gaaatgatat gtgacattga tacatatatc gtagaggcag
 901 gattagccag ttttatcctg actattaagt ttgggataga aactatgtat cctgctcttg
 961 gactgcatga atttgctggt gagttatcca cacttgagtc cttgatgaac ctttaccagc
1021 aaatggggga aactgcaccc tacatggtaa tcctggagaa ctcaattcag aacaagttca
1081 gtgcaggatc ataccctctg ctctggagct atgccatggg agtaggagtg gaacttgaaa
1141 actccatggg aggtttgaac tttggccgat cttactttga tccagcatat tttagattag
1201 ggcaagagat ggtaaggagg tcagctggaa aggtcagttc cacattggca tctgaactcg
1261 gtatcactgc cgaggatgca aggcttgttt cagagattgc aatgcatact actgaggaca
1321 agatcagtag agcggttgga cccagacaag cccaagtatc atttctacac ggtgatcaaa
1381 gtgagaatga gctaccgaga ttgggggcca aggaagatag gagggtcaaa cagagtcgag
1441 gagaagccag ggagagctac agagaaaccg ggcccagcag agcaagtgat gcgagagctg
1501 cccatcttcc aaccggcaca cccctagaca ttgacactgc aacggagtcc agccaagatc
1561 cgcaggacag tcgaaggtca gctgacgccc tgcttaggct gcaagccatg gcaggaatct
1621 cggaagaaca aggctcagac acggacaccc ctatagtgta caatgacaga aatcttctag
1681 actaggtgcg agaggccgag ggccagaaca acatccgcct accatccatc attgttataa
1741 aaaacttagg aaccaggtcc acacagccgc cagcccatca accatccact cccacgattg
1801 gagccaatgg cagaagagca ggcacgccat gtcaaaaacg gactggaatg catccgggct
1861 ctcaaggccg agcccatcgg ctcactggcc atcgaggaag ctatggcagc atggtcagaa
1921 atatcagaca acccaggaca ggagcgagcc acctgcaggg aagagaaggc aggcagttcg
1981 ggtctcagca aaccatgcct ctcagcaatt ggatcaactg aaggcggtgc acctcgcatc
2041 cgcggtcagg gacctggaga gagcgatgac gacgctgaaa ctttgggaat cccccaaga
2101 aatctccagg catcaagcac tgggttacag tgttattacg tttatgatca cagcggtgaa
2161 gcggttaagg gaatccaaga tgctgactct atcatggttc aatcaggcct tgatggtgat
2221 agcaccctct caggaggaga caatgaatct gaaaacagcg atgtggatat tggcgaacct
2281 gataccgagg gatatgctat cactgaccgg ggatctgctc ccatctctat ggggttcagg
2341 gcttctgatg ttgaaactgc agaaggaggg gagatccacg agctcctgag actccaatcc
2401 agaggcaaca actttccgaa gcttgggaaa actctcaatg ttcctccgcc cccggacccc
2461 ggtagggcca gcacttccgg gacacccatt aaaaagggca cagacgcgag attagcctca
2521 tttggaacgg agatcgcgtc tttattgaca ggtggtgcaa cccaatgtgc tcgaaagtca
2581 ccctcggaac catcagggcc aggtgcacct gcggggaatg tccccgagtg tgtgagcaat
2641 gccgcactga tacaggagtg gacacccgaa tctggtacca caatctcccc gagatcccag
2701 aataatgaag aagggggaga ctattatgat gatgagctgt tctctgatgt ccaagatatt
2761 aaaacagcct tggccaaaat acacgaggat aatcagaaga taatctccaa gctagaatca
2821 ctgctgttat tgaagggaga agttgagtca attaagaagc agatcaacag gcaaaatatc
2881 agcatatcca ccctggaagg acacctctca agcatcatga tcgccattcc tggacttggg
2941 aaggatccca acgaccccac tgcagatgtc gaaatcaatc ccgacttgaa acccatcata
3001 ggcagagatt caggccgagc actggccgaa gttctcaaga aacccgttgc cagccgacaa
3061 ctccaaggaa tgacaaatgg acggaccagt tccagaggac agctgctgaa ggaatttcag
3121 ctaaagccga tcgggaaaaa gatgagctca gccgtcgggt ttgttcctga caccggccct
3181 gcatcacgca gtgtaatccg ctccattata aaatccagcc ggctagagga ggatcggaag
3241 cgttacctga tgactctcct tgatgatatc aaaggagcca atgatcttgc caagttccac
3301 cagatgctga tgaagataat aatgaagtag ctacagctca acttacctgc caaccccatg
```

FIG. 1B

```
3361 ccagtcgacc caactagtac aacctaaatc cattataaaa aacttaggag caaagtgatt
3421 gcctcccaag gtccacaatg acagagacct acgacttcga caagtcggca tgggacatca
3481 aagggtcgat cgctccgata caacccacca cctacagtga tggcaggctg gtgccccagg
3541 tcagagtcat agatcctggt ctaggcgaca ggaaggatga atgctttatg tacatgtttc
3601 tgctgggggt tgttgaggac agcgattccc tagggcctcc aatcgggcga gcatttgggt
3661 tcctgccctt aggtgttggc agatccacag caaagcccga aaaactcctc aaagaggcca
3721 ctgagcttga catagttgtt agacgtacag cagggctcaa tgaaaaactg gtgttctaca
3781 acaacacccc actaactctc ctcacacctt ggagaaaggt cctaacaaca gggagtgtct
3841 tcaacgcaaa ccaagtgtgc aatgcggtta atctgatacc gctcgatacc ccgcagaggt
3901 tccgtgttgt ttatatgagc atcacccgtc tttcggataa cgggtattac accgttccta
3961 gaagaatgct ggaattcaga tcggtcaatg cagtggcctt caacctgctg gtgaccctta
4021 ggattgacaa ggcgataggc cctgggaaga tcatcgacaa tacagagcaa cttcctgagg
4081 caacatttat ggtccacatc gggaacttca ggagaaagaa gagtgaagtc tactctgccg
4141 attattgcaa aatgaaaatc gaaaagatgg gcctggtttt tgcacttggt gggatagggg
4201 gcaccagtct tcacattaga agcacaggca aaatgagcaa gactctccat gcacaactcg
4261 ggttcaagaa gaccttatgt tacccgctga tggatatcaa tgaagacctt aatcgattac
4321 tctggaggag cagatgcaag atagtaagaa tccaggcagt tttgcagcca tcagttcctc
4381 aagaattccg catttacgac gacgtgatca taaatgatga ccaaggacta ttcaaagttc
4441 tgtagaccgt agtgcccagc aatgcccgaa aacgaccccc ctcacaatga cagccagaag
4501 gcccggacaa aaaagccccc tccgaaagac tccacggacc aagcgagagg ccagccagca
4561 gccgacggca agcgcgaaca ccaggcggcc ccagcacaga acagccctga cacaaggcca
4621 ccaccagcca ccccaatctg catcctcctc gtgggacccc cgaggaccaa cccccaaggc
4681 tgcccccgat ccaaaccacc aaccgcatcc ccaccacccc cgggaaagaa acccccagca
4741 attggaaggc ccctcccccct cttcctcaac acaagaactc cacaaccgaa ccgcacaagc
4801 gaccgaggtg acccaaccgc aggcatccga ctccctagac agatcctctc tccccggcaa
4861 actaaacaaa acttagggcc aaggaacata cacacccaac agaacccaga ccccggccca
4921 cggcgccgcg cccccaaccc ccgacaacca gagggagccc ccaaccaatc ccgccggctc
4981 ccccggtgcc cacaggcagg gacaccaacc cccgaacaga cccagcaccc aaccatcgac
5041 aatccaagac gggggggccc ccccaaaaaa aggcccccag ggccgacag ccagcaccgc
5101 gaggaagccc acccacccca cacacgacca cggcaaccaa accagaaccc agaccaccct
5161 gggccaccag ctcccagact cggccatcac cccgcagaaa ggaaaggcca caacccgcgc
5221 accccagccc cgatccggcg gggagccacc caacccgaac cagcacccaa gagcgatccc
5281 cgaaggaccc ccgaaccgca aaggacatca gtatcccaca gcctctccaa gtcccccggt
5341 ctcctcctct tctcgaaggg accaaaagat caatccacca cacccgacga cactcaactc
5401 cccaccccta aaggagacac cgggaatccc agaatcaaga ctcatccaat gtccatcatg
5461 ggtctcaagg tgaacgtctc tgccatattc atggcagtac tgttaactct ccaaacaccc
5521 accggtcaaa tccattgggg caatctctct aagatagggg tggtaggaat aggaagtgca
5581 agctacaaag ttatgactcg ttccagccat caatcattag tcataaaatt aatgcccaat
5641 ataactctcc tcaataactg cacgagggta gagattgcag aatacaggag actactgaga
5701 acagttttgg aaccaattag agatgcactt aatgcaatga cccagaatat aagaccggtt
5761 cagagtgtag cttcaagtag gagacacaag agatttgcgg gagtagtcct ggcaggtgcg
5821 gccctaggcg ttgccacagc tgctcagata acagccggca ttgcacttca ccagtccatg
5881 ctgaactctc aagccatcga caatctgaga gcgagcctgg aaactactaa tcaggcaatt
5941 gagacaatca gacaagcagg gcaggagatg atattggctg ttcagggtgt ccaagactac
6001 atcaataatg agctgatacc gtctatgaac caactatctt gtgatttaat cggccagaag
6061 ctcgggctca aattgctcag atactataca gaaatcctgt cattatttgg ccccagttta
6121 cgggacccca tatctgcgga gatatctatc caggctttga gctatgcgct tggaggagac
6181 atcaataagg tgttagaaaa gctcggatac agtggaggtg atttactggg catcttagag
6241 agcggaggaa taaaggcccg gataactcac gtcgacacag agtcctactt cattgtcctc
6301 agtatagcct atccgacgct gtccgagatt aaggggggtga ttgtccaccg gctagagggg
6361 gtctcgtaca acataggctc tcaagagtgg tataccactg tgcccaagta tgttgcaacc
6421 caagggtacc ttatctcgaa ttttgatgag tcatcgtgta ctttcatgcc agaggggact
6481 gtgtgcagcc aaaatgcctt gtacccgatg agtcctctgc tccaagaatg cctccggggg
6541 tacaccaagt cctgtgctcg tacactcgta tccgggtctt ttgggaaccg gttcatttta
6601 tcacaaggga acctaatagc caattgtgca tcaatccttt gcaagtgtta cacaacagga
6661 acgatcatta atcaagaccc tgacaagatc ctaacataca ttgctgccga tcactgcccg
6721 gtagtcgagg tgaacggcgt gaccatccaa gtcgggagca ggaggtatcc agacgctgtg
6781 tacttgcaca gaattgacct cggtcctccc atatcattgg agaggttgga cgtagggaca
6841 aatctgggga atgcaattgc taagttggag gatgccaagg aattgttgga gtcatcggac
6901 cagatattga ggagtatgaa aggtttatcg agcactagca tagtctacat cctgattgca
```

FIG. 1C

```
 6961 gtgtgtcttg gagggttgat agggatcccc gctttaatat gttgctgcag gggcgttgt
 7021 aacaaaaagg gagaacaagt tggtatgtca agaccaggcc taaagcctga tcttacggga
 7081 acatcaaaat cctatgtaag gtcgctctga tcctctacaa ctcttgaaac acaaatgtcc
 7141 cacaagtctc ctcttcgtca tcaagcaacc accgcaccca gcatcaagcc cacctgaaat
 7201 tatctccggc ttccctctgg ccgaacaata tcggtagtta atcaaaactt agggtgcaag
 7261 atcatccaca atgtcaccac aacgagaccg gataaatgcc ttctacaaag ataaccccca
 7321 tcccaaggga agtaggatag tcattaacag agaacatctt atgattgata gaccttatgt
 7381 tttgctggct gttctgtttg tcatgtttct gagcttgatc gggttgctag ccattgcagg
 7441 cattagactt catcgggcag ccatctacac cgcagagatc cataaaagcc tcagcaccaa
 7501 tctagatgta actaactcaa tcgagcatca ggtcaaggac gtgctgacac cactcttcaa
 7561 aatcatcggt gatgaagtgg gcctgaggac acctcagaga ttcactgacc tagtgaaatt
 7621 aatctctgac aagattaaat tccttaatcc ggatagggag tacgacttca gagatctcac
 7681 ttggtgtatc aacccgccag agagaatcaa attggattat gatcaatact gtgcagatgt
 7741 ggctgctgaa gagctcatga atgcattggt gaactcaact ctactggaga ccagaacaac
 7801 caatcagttc ctagctgtct caaagggaaa ctgctcaggg cccactacaa tcagaggtca
 7861 attctcaaac atgtcgctgt ccctgttaga cttgtattta ggtcgaggtt acaatgtgtc
 7921 atctatagtc actatgacat cccagggaat gtatggggga acttacctag tggaaaagcc
 7981 taatctgagc agcaaaaggt cagagttgtc acaactgagc atgtaccgag tgtttgaagt
 8041 aggtgttatc agaaatccgg gtttgggggc tccggtgttc catatgacaa actatcttga
 8101 gcaaccagtc agtaatgatc tcagcaactg tatggtggct ttgggggagc tcaaactcgc
 8161 agccctttgt cacggggaag attctatcac aattccctat cagggatcag ggaaaggtgt
 8221 cagcttccag ctcgtcaagc taggtgtctg gaaatcccca accgacatgc aatcctgggt
 8281 ccccttatca acggatgatc cagtgataga caggctttac ctctcatctc acagaggtgt
 8341 tatcgctgac aatcaagcaa aatgggctgt cccgacaaca cgaacagatg acaagttgcg
 8401 aatggagaca tgcttccaac aggcgtgtaa gggtaaaatc caagcactct gcgagaatcc
 8461 cgagtgggca ccattgaagg ataacaggat tccttcatac ggggtcttgt ctgttgatct
 8521 gagtctgaca gttgagctta aaatcaaaat tgcttcggga ttcgggccat tgatcacaca
 8581 cggttcaggg atggacctat acaaatccaa ccacaacaat gtgtattggc tgactatccc
 8641 gccaatgaag aacctagcct taggtgtaat caacacattg gagtggatac cgagattcaa
 8701 ggttagtccc tacctcttca ctgtcccaat taaggaagca ggcgaagact gccatgcccc
 8761 aacataccta cctgcggagg tggatggtga tgtcaaactc agttccaatc tggtgattct
 8821 acctggtcaa gatctccaat atgttttggc aacctacgat acttccaggg ttgaacatgc
 8881 tgtggtttat tacgtttaca gcccaagccg ctcattttct tacttttatc cttttaggtt
 8941 gcctataaag gggtccccca tcgaattaca agtggaatgc ttcacatggg accaaaaact
 9001 ctggtgccgt cacttctgtg tgcttgcgga ctcagaatct ggtggacata tcactcactc
 9061 tgggatggtg ggcatgggag tcagctgcac agtcacccgg gaagatggaa ccaatcgcag
 9121 atagggctgc tagtgaacca atcacatgat gtcacccaga catcaggcat acccactagt
 9181 gtgaaataga catcagaatt aagaaaaacg tagggtccaa gtggttcccc gttatggact
 9241 cgctatctgt caaccagatc ttataccctg aagttcacct agatagcccg atagttacca
 9301 ataagatagt agccatcctg gagtatgctc gagtccctca cgcttacagc ctggaggacc
 9361 ctacactgtg tcagaacatc aagcaccgcc taaaaaacgg attttccaac caaatgatta
 9421 taaacaatgt ggaagttggg aatgtcatca agtccaagct taggagttat ccggcccact
 9481 ctcatattcc atatccaaat tgtaatcagg atttatttaa catagaagac aaagagtcaa
 9541 cgaggaagat ccgtgaactc ctcaaaaagg ggaattcgct gtactccaaa gtcagtgata
 9601 aggtttttcca atgcttaagg gacactaact cacggcttgg cctaggctcc gaattgaggg
 9661 aggacatcaa ggagaaagtt attaacttgg gagtttacat gcacagctcc cagtggtttg
 9721 agccctttct gttttggttt acagtcaaga ctgagatgag gtcagtgatt aaatcacaaa
 9781 cccatacttg ccataggagg agacacacac ctgtattctt cactggtagt tcagttgagt
 9841 tgctaatctc tcgtgacctt gttgctataa tcagtaaaga gtctcaacat gtatattacc
 9901 tgacatttga actggttttg atgtattgtg atgtcataga ggggaggtta atgacagaga
 9961 ccgctatgac tattgatgct aggtatacag agcttctagg aagagtcaga tacatgtgga
10021 aactgataga tggtttcttc cctgcactcg ggaatccaac ttatcaaatt gtagccatgc
10081 tggagcctct ttcacttgct tacctgcagc tgagggatat aacagtagaa ctcagaggtg
10141 ctttccttaa ccactgcttt actgaaatac atgatgttct tgaccaaaac gggttttctg
10201 atgaaggtac ttatcatgag ttaactgaag ctctagatta cattttcata actgatgaca
10261 tacatctgac aggggagatt ttctcatttt tcagaagttt cggccacccc agacttgaag
10321 cagtaacggc tgctgaaaat gttaggaaat acatgaatca gcctaaagtc attgtgtatg
10381 agactctgat gaaaggtcat gccatatttt gtggaatcat aatcaacggc tatcgtgaca
10441 ggcacggagg cagttggcca ccgctgaccc tcccctgca tgctgcagac acaatccgga
10501 atgctcaagc ttcaggtgaa gggttaacac atgagcagtg cgttgataac tggaaatctt
```

FIG. 1D

```
10561 ttgctggagt gaaatttggc tgctttatgc ctcttagcct ggatagtgat ctgacaatgt
10621 acctaaagga caaggcactt gctgctctcc aaagggaatg ggattcagtt tacccgaaag
10681 agttcctgcg ttacgaccct cccaagggaa ccgggtcacg gaggcttgta gatgttttcc
10741 ttaatgattc gagctttgac ccatatgatg tgataatgta tgttgtaagt ggagcttacc
10801 tccatgaccc tgagttcaac ctgtcttaca gcctgaaaga aaaggagatc aaggaaacag
10861 gtagactttt tgctaaaatg acttacaaaa tgagggcatg ccaagtgatt gctgaaaatc
10921 taatctcaaa cgggattggc aaatatttta aggacaatgg gatggccaag gatgagcacg
10981 atttgactaa ggcactccac actctagctg tctcaggagt ccccaaagat ctcaaagaaa
11041 gtcacagggg ggggccagtc ttaaaaacct actcccgaag cccagtccac acaagtacca
11101 ggaacgtgag agcagcaaaa gggtttatag ggttccctca agtaattcgg caggaccaag
11161 acactgatca tccggagaat atggaagctt acgagacagt cagtgcattt atcacgactg
11221 atctcaagaa gtactgcctt aattggagat atgagaccat cagcttgttt gcacagaggc
11281 taaatgagat ttacggattg ccctcatttt tccagtggct gcataagagg cttgagacct
11341 ctgtcctgta tgtaagtgac cctcattgcc cccccgacct tgacgcccat atcccgttat
11401 ataaagtccc caatgatcaa atcttcatta agtaccctat gggaggtata gaagggtatt
11461 gtcagaagct gtggaccatc agcaccattc cctatctata cctggctgct tatgagagcg
11521 gagtaaggat tgcttcgtta gtgcaagggg acaatcagac catagccgta acaaaaaggg
11581 tacccagcac atggccctac aaccttaaga aacgggaagc tgctagagta actagagatt
11641 actttgtaat tcttaggcaa aggctacatg atattggcca tcacctcaag gcaaatgaga
11701 caattgtttc atcacatttt tttgtctatt caaaaggaat atattatgat gggctacttg
11761 tgtcccaatc actcaagagc atcgcaagat gtgtattctg gtcagagact atagttgatg
11821 aaacaagggc agcatgcagt aatattgcta caacaatggc taaaagcatc gagagaggtt
11881 atgaccgtta ccttgcatat tccctgaacg tcctaaaagt gatacagcaa attctgatct
11941 ctcttggctt cacaatcaat tcaaccatga cccgggatgt agtcataccc ctcctcacaa
12001 acaacgacct cttaataagg atggcactgt tgcccgctcc tattgggggg atgaattatc
12061 tgaatatgag caggctgttt gtcagaaaca tcggtgatcc agtaacatca tcaattgctg
12121 atctcaagag aatgattctc gcctcactaa tgcctgaaga gaccctccat caagtaatga
12181 cacaacaacc ggggggactct tcattcctag actgggctag cgacccttac tcagcaaatc
12241 ttgtatgtgt ccagagcatc actagactcc tcaagaacat aactgcaagg tttgtcctga
12301 tccatagtcc aaacccaatg ttaaaaggat tattccatga tgacagtaaa gaagaggacg
12361 agggactggc ggcattcctc atggacaggc atattatagt acctagggca gctcatgaaa
12421 tcctggatca tagtgtcaca ggggcaagag agtctattgc aggcatgctg gataccacaa
12481 aaggcttgat tcgagccagc atgaggaagg gggggttaac ctctcgagtg ataaccagat
12541 tgtccaatta tgactatgaa caattcagag cagggatggt gctattgaca ggaagaaaga
12601 gaaatgtcct cattgacaaa gagtcatgtt cagtgcagct ggcgagagct ctaagaagcc
12661 atatgtgggc gaggctagct cgaggacggc ctatttacgg ccttgaggtc cctgatgtac
12721 tagaatctat gcgaggccac cttattcggc gtcatgagac atgtgtcatc tgcgagtgtg
12781 gatcagtcaa ctacggatgg tttttgtcc cctcgggttg ccaactggat gatattgaca
12841 aggaaacatc atccttgaga gtcccatata ttggttctac cactgatgag agaacagaca
12901 tgaagcttgc cttcgtaaga gccccaagtc gatccttgcg atctgctgtt agaatagcaa
12961 cagtgtactc atgggcttac ggtgatgatg atagctcttg gaacgaagcc tggttgttgg
13021 ctaggcaaag ggccaatgtg agcctggagg agctaagggt gatcactccc atctcaactt
13081 cgactaattt agcgcatagg ttgagggatc gtagcactca agtgaaatac tcaggtacat
13141 cccttgtccg agtggcgagg tataccacaa tctccaacga caatctctca tttgtcatat
13201 cagataagaa ggttgatact aactttatat accaacaagg aatgcttcta gggttgggtg
13261 ttttagaaac attgtttcga ctcgagaaag ataccggatc atctaacacg gtattacatc
13321 ttcacgtcga aacagattgt tgcgtgatcc cgatgataga tcatcccagg atacccagct
13381 cccgcaagct agagctgagg gcagagctat gtaccaaccc attgatatat gataatgcac
13441 ctttaattga cagagatgca acaaggctat acacccagag ccataggagg caccttgtgg
13501 aatttgttac atggtccaca ccccaactat atcacatttt agctaagtcc acagcactat
13561 ctatgattga cctggtaaca aaatttgaga aggaccatat gaatgaaatt tcagctctca
13621 taggggatga cgatatcaat agtttcataa ctgagtttct gctcatagag ccaagattat
13681 tcactatcta cttgggccag tgtgcggcca tcaattgggc atttgatgta cattatcata
13741 gaccatcagg gaaatatcag atgggtgagc tgttgtcatc gttcctttct agaatgagca
13801 aaggagtgtt taaggtgctt gtcaatgctc taagccaccc aaagatctac aagaaattct
13861 ggcattgtgg tattatagag cctatccatg gtccttcact tgatgctcaa aacttgcaca
13921 caactgtgtg caacatggtt tacacatgct atatgaccta cctcgacctg ttgttgaatg
13981 aagagttaga agagttcaca tttctcttgt gtgaaagcga cgaggatgta gtaccggaca
14041 gattcgacaa catccaggca aaacacttat gtgttctggc agatttgtac tgtcaaccag
14101 ggacctgccc accaattcga ggtctaagac cggtagagaa atgtgcagtt ctaaccgacc
```

FIG. 1E

```
14161 atatcaaggc agaggctatg ttatctccag caggatcttc gtggaacata aatccaatta
14221 ttgtagacca ttactcatgc tctctgactt atctccggcg aggatcgatc aaacagataa
14281 gattgagagt tgatccagga ttcattttcg acgccctcgc tgaggtaaat gtcagtcagc
14341 caaagatcgg cagcaacaac atctcaaata tgagcatcaa ggctttcaga cccccacacg
14401 atgatgttgc aaaattgctc aaagatatca acacaagcaa gcacaatctt cccatttcag
14461 ggggcaatct cgccaattat gaaatccatg ctttccgcag aatcgggttg aactcatctg
14521 cttgctacaa agctgttgag atatcaacat taattaggag atgccttgag ccaggggagg
14581 acggcttgtt cttgggtgag ggatcgggtt ctatgttgat cacttataaa gagatactta
14641 aactaaacaa gtgcttctat aatagtgggg tttccgccaa ttctagatct ggtcaaaggg
14701 aattagcacc ctatccctcc gaagttggcc ttgtcgaaca cagaatggga gtaggtaata
14761 ttgtcaaagt gctctttaac gggaggcccg aagtcacgtg ggtaggcagt gtagattgct
14821 tcaatttcat agttagtaat atccctacct ctagtgtggg gtttatccat tcagatatag
14881 agaccttgcc tgacaaagat actatagaga agctagagga attggcagcc atcttatcga
14941 tggctctgct cctgggcaaa ataggatcaa tactggtgat taagcttatg cctttcagcg
15001 gggattttgt tcagggattt ataagttatg tagggtctca ttatagagaa gtgaaccttg
15061 tataccctag atacagcaac ttcatctcta ctgaatctta tttggttatg acagatctca
15121 aggctaaccg gctaatgaat cctgaaaaga ttaagcagca gataattgaa tcatctgtga
15181 ggacttcacc tggacttata ggtcacatcc tatccattaa gcaactaagc tgcatacaag
15241 caattgtggg agacgcagtt agtagaggtg atatcaatcc tactctgaaa aaacttacac
15301 ctatagagca ggtgctgatc aattgcgggt tggcaattaa cggacctaag ctgtgcaaag
15361 aattgatcca ccatgatgtt gcctcagggc aagatggatt gcttaattct atactcatcc
15421 tctacaggga gttggcaaga ttcaaagaca accaaagaag tcaacaaggg atgttccacg
15481 cttaccccgt attggtaagt agcaggcaac gagaacttat atctaggatc acccgcaaat
15541 tctgggggca cattcttctt tactccggga acaaaaagtt gataaataag tttatccaga
15601 atctcaagtc cggctatctg atactagact tacaccagaa tatcttcgtt aagaatctat
15661 ccaagtcaga gaaacagatt attatgacgg ggggtttgaa acgtgagtgg gtttttaagg
15721 taacagtcaa ggagaccaaa gaatggtata agttagtcgg atacagtgcc ctgattaagg
15781 actaattggt tgaactccgg aaccctaatc ctgccctagg tggttaggca ttatttgcaa
15841 tatattaaag aaaactttga aaatacgaag tttctattcc cagctttgtc tggt
```

FIG. 2 atggtgacagggggaatggcaagcaagtgggatcagaagggtatggacattgcctatgagga
ggcggccttaggttacaaagagggtggtgttcctattggcggatgtcttatcaataacaaag
acggaagtgttctcggtcgtggtcacaacatgagatttcaaaagggatccgccacactacat
ggtgagatctccactttggaaaactgtgggagattagagggcaaagtgtacaaagataccac
tttgtatacgacgctgtctccatgcgacatgtgtacaggtgccatcatcatgtatggtattc
cacgctgtgttgtcggtgagaacgttaatttcaaaagtaagggcgagaaatatttacaaact
agaggtcacgaggttgttgttgttgacgatgagaggtgtaaaaagatcatgaaacaatttat
cgatgaaagacctcaggattggtttgaagatattggtgaggcttcggaaccatttaagaacg
tctacttgctacctcaaacaaaccaattgctgggtttgtacaccatcatcagaaataagaat
acaactagacctgatttcattttctactccgatagaatcatcagattgttggttgaagaagg
tttgaaccatctacctgtgcaaaagcaaattgtggaaactgacaccaacgaaaacttcgaag
gtgtctcattcatgggtaaaatctgtggtgtttccattgtcagagctggtgaatcgatggag
caaggattaagagactgttgtaggtctgtgcgtatcggtaaaattttaattcaaaggacga
ggagactgctttaccaaagttattctacgaaaaattaccagaggatatatctgaaaggtatg
tcttcctattagacccaatgctggccaccggtggtagtgctatcatggctacagaagtcttg
attaagagaggtgttaagccagagagaatttacttcttaaacctaatctgtagtaaggaagg
gattgaaaaataccatgccgccttcccagaggtcagaattgttactggtgccctcgacagag
gtctagatgaaaacaagtatctagttccagggttgggtgactttggtgacagatactactgt
gtttaa cytosine deaminase (CD)
gct - linker (alanin)
uracil phosphoribosyltransferase(UPRT)

FIG. 3A pc3MerV2 Id-Trka viral:
nt 1 - 55: MeV leader
nt 56 - 66: gene start for transgene (originally from N gene; Phase 2)
nt 67 - 103: 5'-UTR (originally from N gene)
nt 103 - 108: cloning site XhoI (c'tcgag)
nt 109 - 114: cloning site PauI (g'cgcgc)or AscI(gg'cgcgcc); unique
nt 115 - 126: 3'-UTR
nt 127 - 136: gene end for transgene (originally from N gene)
nt 140 - 150: gene start N (Phase 2)
nt 192 - 1769: N ORF (1578 nt = 525 aa +stop)
nt 1891 - 3414: P ORF (1524 nt = 507 aa +stop)
nt 2036 - 2043: 3'-cloning site SdaI (CCTGCA'GG), unique
nt 1913 - 2473: C ORF (non-structural; 561 nt = 186 aa +stop)
nt 2575 - 2582: A5G3 editing box; G insertion behind nt 2580
nt 1891 - 2789: V trans-frame ORF after mRNA editing (non-structural; 900 nt = 299 aa +stop)
nt 3522 - 4529: M ORF (1008 nt = 335 aa +stop)
nt 5533 - 7194: F ORF (1662 nt = 553 aa + stop)
nt 7355 - 9208: H ORF (1854 nt = 617 aa +stop)
nt 9318 - 15869: L ORF (6552 nt = 2183 aa +stop)
nt 15942 - 15978: MeV trailer (37 nt)

```
accaaacaaagttgggtaaggatagttcaatcaatgatcatcttctagtgcacttaggattc
aagatcctattatcagggacaagagcaggattagggatatctcgaggcgcgccatccatcat
tgttataaaaaacttaggattcaagatcctattatcagggacaagagcaggattagggatat
ccgagatggccacacttttaaggagcttagcattgttcaaaagaaacaaggacaaaccaccc
attacatcaggatccggtggagccatcagaggaatcaaacacattattatagtaccaatccc
tggagattcctcaattaccactcgatccagacttctggaccggttggtgaggttaattggaa
acccggatgtgagcgggcccaaactaacaggggcactaataggtatattatccttatttgtg
gagtctccaggtcaattgattcagaggatcaccgatgaccctgacgttagcataaggctgtt
agaggttgtccagagtgaccagtcacaatctggccttaccttcgcatcaagaggtaccaaca
tggaggatgaggcggaccaatacttttcacatgatgatccaattagtagtgatcaatccagg
ttcggatggttcgggaacaaggaaatctcagatattgaagtgcaagaccctgagggattcaa
catgattctgggtaccatcctagcccaaatttgggtcttgctcgcaaaggcggttacggccc
cagacacggcagctgattcggagctaagaaggtggataaagtacacccaacaaagaagggta
gttggtgaatttagattggagagaaaatggttggatgtggtgaggaacaggattgccgagga
cctctccttacgccgattcatggtcgctctaatcctggatatcaagagaacacccggaaaca
aacccaggattgctgaaatgatatgtgacattgatacatatatcgtagaggcaggattagcc
agttttatcctgactattaagtttgggatagaaactatgtatcctgctcttggactgcatga
atttgctggtgagttatccacacttgagtccttgatgaacctttaccagcaaatgggggaaa
ctgcaccctacatggtaatcctggagaactcaattcagaacaagttcagtgcaggatcatac
cctctgctctggagctatgccatgggagtaggagtggaacttgaaaactccatgggaggttt
```

FIG. 3B gaactttggccgatcttactttgatccagcatattttagattagggcaagagatggtaagga
ggtcagctggaaaggtcagttccacattggcatctgaactcggtatcactgccgaggatgca
aggcttgtttcagagattgcaatgcatactactgaggacaagatcagtagagcggttggacc
cagacaagcccaagtatcatttctacacggtgatcaaagtgagaatgagctaccgagattgg
ggggcaaggaagataggagggtcaaacagagtcgaggagaagccagggagagctacagagaa
accgggcccagcagagcaagtgatgcgagagctgcccatcttccaaccggcacacccctaga
cattgacactgcaacggagtccagccaagatccgcaggacagtcgaaggtcagctgacgccc
tgcttaggctgcaagccatggcaggaatctcggaagaacaaggctcagacacggacacccct
atagtgtacaatgacagaaatcttctagactaggtgcgagaggccgagggccagaacaacat
ccgcctaccatccatcattgttataaaaacttaggaaccaggtccacacagccgccagccc
atcaaccatccactcccacgattggagccaatggcagaagagcaggcacgccatgtcaaaaa
cggactggaatgcatccgggctctcaaggccgagcccatcggctcactggccatcgaggaag
ctatggcagcatggtcagaaatatcagacaacccaggacaggagcgagccacctgcaggcaa
gagaaggcaggcagttcgggtctcagcaaaccatgcctctcagcaattggatcaactgaagg
cggtgcacctcgcatccgcggtcagggacctggagagagcgatgacgacgctgaaactttgg
gaatcccccaagaaatctccaggcatcaagcactgggttacagtgttattacgtttatgat
cacagcggtgaagcggttaagggaatccaagatgctgactctatcatggttcaatcaggcct
tgatggtgatagcaccctctcaggaggagacaatgaatctgaaaacagcgatgtggatattg
gcgaacctgataccgagggatatgctatcactgaccggggatctgctcccatctctatgggg
ttcagggcttctgatgttgaaactgcagaaggaggggagatccacgagctcctgagactcca
atccagaggcaacaactttccgaagcttgggaaaactctcaatgttcctccgcccccggacc
ccggtagggccagcacttccgggacacccattaaaaagggcacagacgcgagattagcctca
tttggaacggagatcgcgtctttattgacaggtggtgcaacccaatgtgctcgaaagtcacc
ctcggaaccatcagggccaggtgcacctgcggggaatgtccccgagtgtgtgagcaatgccg
cactgatacaggagtggacacccgaatctggtaccacaatctccccgagatcccagaataat
gaagaagggggagactattatgatgatgagctgttctctgatgtccaagatattaaaacagc
cttggccaaaatacacgaggataatcagaagataatctccaagctagaatcactgctgttat
tgaagggagaagttgagtcaattaagaagcagatcaacaggcaaaatatcagcatatccacc
ctggaaggacacctctcaagcatcatgatcgccattcctggacttgggaaggatcccaacga
ccccactgcagatgtcgaaatcaatcccgacttgaaacccatcataggcagagattcaggcc
gagcactggccgaagttctcaagaaacccgttgccagccgacaactccaaggaatgacaaat
ggacggaccagttccagaggacagctgctgaaggaatttcagctaaagccgatcgggaaaaa
gatgagctcagccgtcgggtttgttcctgacaccggccctgcatcacgcagtgtaatccgct
ccattataaaatccagccggctagaggaggatcggaagcgttacctgatgactctccttgat
gatatcaaaggagccaatgatcttgccaagttccaccagatgctgatgaagataataatgaa
gtagctacagctcaacttacctgccaaccccatgccagtcgacccaactagtacaacctaaa
tccattataaaaacttaggagcaaagtgattgcctcccaaggtccacaatgacagagacct
acgacttcgacaagtcggcatgggacatcaaagggtcgatcgctccgatacaacccaccacc
tacagtgatggcaggctggtgccccaggtcagagtcatagatcctggtctaggcgacaggaa
ggatgaatgctttatgtacatgtttctgctggggttgttgaggacagcgattccctagggc
ctccaatcgggcgagcatttgggttcctgcccttaggtgttggcagatccacagcaaagccc
gaaaaactcctcaaagaggccactgagcttgacatagttgttagacgtacagcagggctcaa
tgaaaaactggtgttctacaacaacaccccactaactctcctcacaccttggagaaaggtcc
taacaacagggagtgtcttcaacgcaaaccaagtgtgcaatgcggttaatctgataccgctc
gataccccgcagaggttccgtgttgtttatatgagcatcacccgtctttcggataacgggta
ttacaccgttcctagaagaatgctggaattcagatcggtcaatgcagtggccttcaacctgc
tggtgacccttaggattgacaaggcgataggccctgggaagatcatcgacaatacagagcaa
cttcctgaggcaacatttatggtccacatcgggaacttcaggagaaagaagagtgaagtcta
ctctgccgattattgcaaaatgaaaatcgaaaagatgggcctggtttttgcacttggtgga
taggggcaccagtcttcacattagaagcacaggcaaaatgagcaagactctccatgcacaa

FIG. 3C ctcgggttcaagaagaccttatgttacccgctgatggatatcaatgaagaccttaatcgatt
actctggaggagcagatgcaagatagtaagaatccaggcagttttgcagccatcagttcctc
aagaattccgcatttacgacgacgtgatcataaatgatgaccaaggactattcaaagttctg
tagaccgtagtgcccagcaatgcccgaaaacgaccccctcacaatgacagccagaaggccc
ggacaaaaaagccccctccgaaagactccacggaccaagcgagaggccagccagcagccgac
ggcaagcgcgaacaccaggcggccccagcacagaacagccctgacacaaggccaccaccagc
caccccaatctgcatcctcctcgtgggacccccgaggaccaacccccaaggctgcccccgat
ccaaaccaccaaccgcatccccaccacccccgggaaagaaacccccagcaattggaaggccc
ctccccctcttcctcaacacaagaactccacaaccgaaccgcacaagcgaccgaggtgaccc
aaccgcaggcatccgactccctagacagatcctctctccccggcaaactaaacaaaacttag
ggccaaggaacatacacacccaacagaacccagaccccggcccacggcgccgcgcccccaac
ccccgacaaccagagggagcccccaaccaatcccgccggctcccccggtgcccacaggcagg
gacaccaacccccgaacagacccagcacccaaccatcgacaatccaagacgggggggccccc
ccaaaaaaaggcccccaggggccgacagccagcaccgcgaggaagcccacccaccccacaca
cgaccacggcaaccaaaccagaacccagaccaccctgggccaccagctcccagactcggcca
tcaccccgcagaaaggaaaggccacaacccgcgcaccccagccccgatccggcggggagcca
cccaacccgaaccagcacccaagagcgatccccgaaggacccccgaaccgcaaaggacatca
gtatcccacagcctctccaagtcccccggtctcctcctcttctcgaagggaccaaaagatca
atccaccacacccgacgacactcaactccccaccccctaaaggagacaccgggaatcccagaa
tcaagactcatccaatgtccatcatgggtctcaaggtgaacgtctctgccatattcatggca
gtactgttaactctccaaacacccaccggtcaaatccattggggcaatctctctaagatagg
ggtggtaggaataggaagtgcaagctacaaagttatgactcgttccagccatcaatcattag
tcataaaattaatgcccaatataactctcctcaataactgcacgagggtagagattgcagaa
tacaggagactactgagaacagttttggaaccaattagagatgcacttaatgcaatgaccca
gaatataagaccggttcagagtgtagcttcaagtaggagacacaagagatttgcgggagtag
tcctggcaggtgcggccctaggcgttgccacagctgctcagataacagccggcattgcactt
caccagtccatgctgaactctcaagccatcgacaatctgagagcgagcctggaaactactaa
tcaggcaattgagacaatcagacaagcagggcaggagatgatattggctgttcagggtgtcc
aagactacatcaataatgagctgataccgtctatgaaccaactatcttgtgatttaatcggc
cagaagctcgggctcaaattgctcagatactatacagaaatcctgtcattatttggccccag
tttacgggaccccatatctgcggagatatctatccaggctttgagctatgcgcttggaggag
acatcaataaggtgttagaaaagctcggatacagtggaggtgatttactgggcatcttagag
agcggaggaataaaggcccggataactcacgtcgacacagagtcctacttcattgtcctcag
tatagcctatccgacgctgtccgagattaaggggtgattgtccaccggctagaggggtct
cgtacaacataggctctcaagagtggtataccactgtgcccaagtatgttgcaacccaaggg
taccttatctcgaattttgatgagtcatcgtgtactttcatgccagaggggactgtgtgcag
ccaaaatgccttgtacccgatgagtcctctgctccaagaatgcctccggggggtacaccaagt
cctgtgctcgtacactcgtatccgggtcttttgggaaccggttcattttatcacaagggaac
ctaatagccaattgtgcatcaatcctttgcaagtgttacacaacaggaacgatcattaatca
agaccctgacaagatcctaacatacattgctgccgatcactgcccggtagtcgaggtgaacg
gcgtgaccatccaagtcgggagcaggaggtatccagacgctgtgtacttgcacagaattgac
ctcggtcctcccatatcattggagaggttggacgtagggacaaatctggggaatgcaattgc
taagttggaggatgccaaggaattgttggagtcatcggaccagatattgaggagtatgaaag
gtttatcgagcactagcatagtctacatcctgattgcagtgtgtcttggagggttgataggg
atccccgctttaatatgttgctgcagggggcgttgtaacaaaaagggagaacaagttggtat
gtcaagaccaggcctaaagcctgatcttacgggaacatcaaaatcctatgtaaggtcgctct
gatcctctacaactcttgaaacacaaatgtcccacaagtctcctcttcgtcatcaagcaacc
accgcacccagcatcaagcccacctgaaattatctccggcttccctctggccgaacaatatc
ggtagttaatcaaaacttagggtgcaagatcatccacaatgtcaccacaacgagaccggata
aatgccttctacaaagataacccccatcccaagggaagtaggatagtcattaacagagaaca

FIG. 3D

```
tcttatgattgatagaccttatgttttgctggctgttctgtttgtcatgtttctgagcttga
tcgggttgctagccattgcaggcattagacttcatcgggcagccatctacaccgcagagatc
cataaaagcctcagcaccaatctagatgtaactaactcaatcgagcatcaggtcaaggacgt
gctgacaccactcttcaaaatcatcggtgatgaagtgggcctgaggacacctcagagattca
ctgacctagtgaaattaatctctgacaagattaaattccttaatccggatagggagtacgac
ttcagagatctcacttggtgtatcaacccgccagagagaatcaaattggattatgatcaata
ctgtgcagatgtggctgctgaagagctcatgaatgcattggtgaactcaactctactggaga
ccagaacaaccaatcagttcctagctgtctcaaagggaaactgctcagggcccactacaatc
agaggtcaattctcaaacatgtcgctgtccctgttagacttgtatttaggtcgaggttacaa
tgtgtcatctatagtcactatgacatcccagggaatgtatggggaacttacctagtggaaa
agcctaatctgagcagcaaaaggtcagagttgtcacaactgagcatgtaccgagtgtttgaa
gtaggtgttatcagaaatccgggtttggggctccggtgttccatatgacaaactatcttga
gcaaccagtcagtaatgatctcagcaactgtatggtggctttgggggagctcaaactcgcag
ccctttgtcacggggaagattctatcacaattccctatcagggatcagggaaaggtgtcagc
ttccagctcgtcaagctaggtgtctggaaatccccaaccgacatgcaatcctgggtcccctt
atcaacggatgatccagtgatagacaggctttacctctcatctcacagaggtgttatcgctg
acaatcaagcaaaatgggctgtcccgacaacacgaacagatgacaagttgcgaatggagaca
tgcttccaacaggcgtgtaagggtaaaatccaagcactctgcgagaatcccgagtgggcacc
attgaaggataacaggattccttcatacggggtcttgtctgttgatctgagtctgacagttg
agcttaaaatcaaaattgcttcgggattcgggccattgatcacacacggttcagggatggac
ctatacaaatccaaccacaacaatgtgtattggctgactatcccgccaatgaagaacctagc
cttaggtgtaatcaacacattggagtggataccgagattcaaggttagtccctacctcttca
ctgtcccaattaaggaagcaggcgaagactgccatgccccaacatacctacctgcggaggtg
gatggtgatgtcaaactcagttccaatctggtgattctacctggtcaagatctccaatatgt
tttggcaacctacgatacttccagggttgaacatgctgtggtttattacgtttacagcccaa
gccgctcatttttcttacttttatcctttttaggttgcctataaaggggggtccccatcgaatta
caagtggaatgcttcacatgggaccaaaaactctggtgccgtcacttctgtgtgcttgcgga
ctcagaatctggtggacatatcactcactctgggatggtgggcatgggagtcagctgcacag
tcacccgggaagatggaaccaatcgcagatagggctgctagtgaaccaatcacatgatgtca
cccagacatcaggcatacccactagtgtgaaatagacatcagaattaagaaaaacgtagggt
ccaagtggttccccgttatggactcgctatctgtcaaccagatcttataccctgaagttcac
ctagatagcccgatagttaccaataagatagtagccatcctggagtatgctcgagtccctca
cgcttacagcctggaggaccctacactgtgtcagaacatcaagcaccgcctaaaaaacggat
tttccaaccaaatgattataaacaatgtggaagttgggaatgtcatcaagtccaagcttagg
agttatccggcccactctcatattccatatccaaattgtaatcaggatttatttaacataga
agacaaagagtcaacgaggaagatccgtgaactcctcaaaaaggggaattcgctgtactcca
aagtcagtgataaggttttccaatgcttaagggacactaactcacggcttggcctaggctcc
gaattgagggaggacatcaaggagaaagttattaacttgggagtttacatgcacagctccca
gtggtttgagccctttctgttttggtttacagtcaagactgagatgaggtcagtgattaaat
cacaaacccatacttgccataggaggagacacacacctgtattcttcactggtagttcagtt
gagttgctaatctctcgtgaccttgttgctataatcagtaaagagtctcaacatgtatatta
cctgacatttgaactggttttgatgtattgtgatgtcatagaggggaggttaatgacagaga
ccgctatgactattgatgctaggtatacagagcttctaggaagagtcagatacatgtggaaa
ctgatagatggtttcttccctgcactcgggaatccaacttatcaaattgtagccatgctgga
gcctctttcacttgcttacctgcagctgagggatataacagtagaactcagaggtgctttcc
ttaaccactgctttactgaaatacatgatgttcttgaccaaaacgggttttctgatgaaggt
acttatcatgagttaactgaagctctagattacattttcataactgatgacatacatctgac
aggggagatttttctcatttttcagaagtttcggccaccccagacttgaagcagtaacggctg
ctgaaaatgttaggaaatacatgaatcagcctaaagtcattgtgtatgagactctgatgaaa
ggtcatgccatattttgtggaatcataatcaacggctatcgtgacaggcacggaggcagttg
```

FIG. 3E gccaccgctgaccctcccccctgcatgctgcagacacaatccggaatgctcaagcttcaggtg
aagggttaacacatgagcagtgcgttgataactggaaatcttttgctggagtgaaatttggc
tgctttatgcctcttagcctggatagtgatctgacaatgtacctaaaggacaaggcacttgc
tgctctccaaagggaatgggattcagtttacccgaaagagttcctgcgttacgaccctccca
agggaaccgggtcacggaggcttgtagatgttttccttaatgattcgagctttgacccatat
gatgtgataatgtatgttgtaagtggagcttacctccatgaccctgagttcaacctgtctta
cagcctgaaagaaaaggagatcaaggaaacaggtagacttttgctaaaatgacttacaaaa
tgagggcatgccaagtgattgctgaaaatctaatctcaaacgggattggcaaatattttaag
gacaatgggatggccaaggatgagcacgatttgactaaggcactccacactctagctgtctc
aggagtccccaaagatctcaaagaaagtcacagggggggccagtcttaaaaacctactccc
gaagcccagtccacacaagtaccaggaacgtgagagcagcaaaagggtttatagggttccct
caagtaattcggcaggaccaagacactgatcatccggagaatatggaagcttacgagacagt
cagtgcatttatcacgactgatctcaagaagtactgccttaattggagatatgagaccatca
gcttgtttgcacagaggctaaatgagatttacggattgccctcatttttccagtggctgcat
aagaggcttgagacctctgtcctgtatgtaagtgaccctcattgcccccccgaccttgacgc
ccatatcccgttatataaagtccccaatgatcaaatcttcattaagtaccctatgggaggta
tagaagggtattgtcagaagctgtggaccatcagcaccattccctatctatacctggctgct
tatgagagcggagtaaggattgcttcgttagtgcaaggggacaatcagaccatagccgtaac
aaaaagggtacccagcacatggccctacaaccttaagaaacgggaagctgctagagtaacta
gagattactttgtaattcttaggcaaaggctacatgatattggccatcacctcaaggcaaat
gagacaattgtttcatcacatttttttgtctattcaaaaggaatatattatgatgggctact
tgtgtcccaatcactcaagagcatcgcaagatgtgtattctggtcagagactatagttgatg
aaacaagggcagcatgcagtaatattgctacaacaatggctaaaagcatcgagagaggttat
gaccgttaccttgcatattccctgaacgtcctaaaagtgatacagcaaattctgatctctct
tggcttcacaatcaattcaaccatgacccgggatgtagtcatacccctcctcacaaacaacg
acctcttaataaggatggcactgttgcccgctcctattgggggatgaattatctgaatatg
agcaggctgtttgtcagaaacatcggtgatccagtaacatcatcaattgctgatctcaagag
aatgattctcgcctcactaatgcctgaagagaccctccatcaagtaatgacacaacaaccgg
gggactcttcattcctagactgggctagcgacccttactcagcaaatcttgtatgtgtccag
agcatcactagactcctcaagaacataactgcaaggtttgtcctgatccatagtccaaaccc
aatgttaaaaggattattccatgatgacagtaaagaagaggacgagggactggcggcattcc
tcatggacaggcatattatagtacctagggcagctcatgaaatcctggatcatagtgtcaca
ggggcaagagagtctattgcaggcatgctggataccacaaaaggcttgattcgagccagcat
gaggaagggggggttaacctctcgagtgataaccagattgtccaattatgactatgaacaat
tcagagcagggatggtgctattgacaggaagaaagagaaatgtcctcattgacaaagagtca
tgttcagtgcagctggcgagagctctaagaagccatatgtgggcgaggctagctcgaggacg
gcctatttacggccttgaggtccctgatgtactagaatctatgcgaggccaccttattcggc
gtcatgagacatgtgtcatctgcgagtgtggatcagtcaactacggatggtttttttgtcccc
tcgggttgccaactggatgatattgacaaggaaacatcatccttgagagtcccatatattgg
ttctaccactgatgagagaacagacatgaagcttgccttcgtaagagccccaagtcgatcct
tgcgatctgctgttagaatagcaacagtgtactcatgggcttacggtgatgatgatagctct
tggaacgaagcctggttgttggctaggcaaagggccaatgtgagcctggaggagctaagggt
gatcactcccatctcaacttcgactaatttagcgcataggttgagggatcgtagcactcaag
tgaaatactcaggtacatcccttgtccgagtggcgaggtataccacaatctccaacgacaat
ctctcatttgtcatatcagataagaaggttgatactaactttatataccaacaaggaatgct
tctagggttgggtgttttagaaacattgtttcgactcgagaaagataccggatcatctaaca
cggtattacatcttcacgtcgaaacagattgttgcgtgatcccgatgatagatcatcccagg
atacccagctcccgcaagctagagctgagggcagagctatgtaccaacccattgatatatga
taatgcacctttaattgacagagatgcaacaaggctatacacccagagccataggaggcacc
ttgtggaatttgttacatggtccacaccccaactatatcacattttagctaagtccacagca

FIG. 3F ctatctatgattgacctggtaacaaaatttgagaaggaccatatgaatgaaatttcagctct
catagggggatgacgatatcaatagtttcataactgagtttctgctcatagagccaagattat
tcactatctacttggccagtgtgcggccatcaattgggcatttgatgtacattatcataga
ccatcagggaaatatcagatgggtgagctgttgtcatcgttcctttctagaatgagcaaagg
agtgtttaaggtgcttgtcaatgctctaagccacccaaagatctacaagaaattctggcatt
gtggtattatagagcctatccatggtccttcacttgatgctcaaaacttgcacacaactgtg
tgcaacatggtttacacatgctatatgacctacctcgacctgttgttgaatgaagagttaga
agagttcacatttctcttgtgtgaaagcgacgaggatgtagtaccggacagattcgacaaca
tccaggcaaaacacttatgtgttctggcagatttgtactgtcaaccagggacctgcccacca
attcgaggtctaagaccggtagagaaatgtgcagttctaaccgaccatatcaaggcagaggc
tatgttatctccagcaggatcttcgtggaacataaatccaattattgtagaccattactcat
gctctctgacttatctccggcgaggatcgatcaaacagataagattgagagttgatccagga
ttcattttcgacgccctcgctgaggtaaatgtcagtcagccaaagatcggcagcaacaacat
ctcaaatatgagcatcaaggctttcagacccccacacgatgatgttgcaaaattgctcaaag
atatcaacacaagcaagcacaatcttcccatttcaggggcaatctcgccaattatgaaatc
catgctttccgcagaatcgggttgaactcatctgcttgctacaaagctgttgagatatcaac
attaattaggagatgccttgagccaggggaggacggcttgttcttgggtgagggatcgggtt
ctatgttgatcacttataaagagatacttaaactaaacaagtgcttctataatagtggggtt
tccgccaattctagatctggtcaaagggaattagcaccctatccctccgaagttggccttgt
cgaacacagaatgggagtaggtaatattgtcaaagtgctctttaacgggaggcccgaagtca
cgtgggtaggcagtgtagattgcttcaatttcatagttagtaatatccctacctctagtgtg
gggtttatccattcagatatagagaccttgcctgacaaagatactatagagaagctagagga
attggcagccatcttatcgatggctctgctcctgggcaaaataggatcaatactggtgatta
agcttatgcctttcagcggggatttgttcagggatttataagttatgtagggtctcattat
agagaagtgaaccttgtataccctagatacagcaacttcatctctactgaatcttatttggt
tatgacagatctcaaggctaaccggctaatgaatcctgaaaagattaagcagcagataattg
aatcatctgtgaggacttcacctggacttataggtcacatcctatccattaagcaactaagc
tgcatacaagcaattgtgggagacgcagttagtagaggtgatatcaatcctactctgaaaaa
acttacacctatagagcaggtgctgatcaattgcgggttggcaattaacggacctaagctgt
gcaaagaattgatccaccatgatgttgcctcagggcaagatggattgcttaattctatactc
atcctctacagggagttggcaagattcaaagacaaccaaagaagtcaacaagggatgttcca
cgcttaccccgtattggtaagtagcaggcaacgagaacttatatctaggatcacccgcaaat
tctgggggcacattcttctttactccgggaacaaaaagttgataaataagtttatccagaat
ctcaagtccggctatctgatactagacttacaccagaatatcttcgttaagaatctatccaa
gtcagagaaacagattattatgacgggggtttgaaacgtgagtgggtttttaaggtaacag
tcaaggagaccaaagaatggtataagttagtcggatacagtgccctgattaaggactaattg
gttgaactccggaaccctaatcctgccctaggtggttaggcattatttgcaatatattaaag
aaaactttgaaaatacgaagtttctattcccagctttgtctggtggccggcatggtcccagc
ctcctcgctggcgccggctgggcaacattccgaggggaccgtcccctcggtaatggcgaatg
ggacgcggccggtcgatcgacgatccggctgctaacaaagcccgaaaggaagctgagttggc
tgctgccaccgctgagcaataactagcataaccccttggggcctctaaacgggtcttgaggg
gttttttgctgaaaggaggaactatatccggatcgagatcaattctgtgagcgtatggcaaa
cgaaggaaaaatagttatagtagccgcactcgatgggacatttcaacgtaaaccgtttaata
atattttgaatcttattccattatctgaaatggtggtaaaactaactgctgtgtgtatgaaa
tgctttaaggaggcttccttttctaaacgattgggtgaggaaaccgagatagaaataatagg
aggtaatgatatgtatcaatcggtgtgtagaaagtgttacatcgactcataatattatattt
tttatctaaaaaactaaaaataaacattgattaaattttaatataatacttaaaaatggatg
ttgtgtcgttagataaaccgtttatgtatttgaggaaattgataatgagttagattacgaa
ccagaaagtgcaaatgaggtcgcaaaaaaactgccgtatcaaggacagttaaaactattact
aggagaattatttttcttagtaagttacagcgacacggtatattagatggtgccaccgtag

FIG. 3G tgtatataggatctgctcccggtacacatatacgttatttgagagatcatttctataattta
ggagtgatcccgaaaggaagctgagttggctgctgccaccgctgagcaataactagcataac
cccttggggcctctaaacgggtcttgaggggttttttgctgaaaggaggaacgcgcctgatg
cggtattttctccttacgcatctgtgcggtatttcacaccgcatatatggtgcactctcagt
acaatctgctctgatgccgcatagttaagccagccccgacacccgccaacacccgctgacgc
gccctgacgggcttgtctgctcccggcatccgcttacagacaagctgtgaccgtctccggga
gctgcatgtgtcagaggttttcaccgtcatcaccgaaacgcgcgagacgaaagggcctcgtg
atacgcctatttttataggttaatgtcatgataataatggtttcttagacgtcaggtggcac
ttttcggggaaatgtgcgcggaacccctatttgtttatttttctaaatacattcaaatatgt
atccgctcatgagacaataaccctgataaatgcttcaataatattgaaaaaggaagagtatg
agtattcaacatttccgtgtcgcccttattcccttttttgcggcattttgccttcctgtttt
tgctcacccagaaacgctggtgaaagtaaaagatgctgaagatcagttgggtgcacgagtgg
gttacatcgaactggatctcaacagcggtaagatccttgagagttttcgccccgaagaacgt
tttccaatgatgagcacttttaaagttctgctatgtggcgcggtattatcccgtattgacgc
cgggcaagagcaactcggtcgccgcatacactattctcagaatgacttggttgagtactcac
cagtcacagaaaagcatcttacggatggcatgacagtaagagaattatgcagtgctgccata
accatgagtgataacactgcggccaacttacttctgacaacgatcggaggaccgaaggagct
aaccgcttttttgcacaacatgggggatcatgtaactcgccttgatcgttgggaaccggagc
tgaatgaagccataccaaacgacgagcgtgacaccacgatgcctgtagcaatggcaacaacg
ttgcgcaaactattaactggcgaactacttactctagcttcccggcaacaattaatagactg
gatggaggcggataaagttgcaggaccacttctgcgctcggcccttccggctggctggttta
ttgctgataaatctggagccggtgagcgtgggtctcgcggtatcattgcagcactggggcca
gatggtaagccctcccgtatcgtagttatctacacgacggggagtcaggcaactatggatga
acgaaatagacagatcgctgagataggtgcctcactgattaagcattggtaactgtcagacc
aagtttactcatatatactttagattgatttaaaacttcatttttaatttaaaaggatctag
gtgaagatcctttttgataatctcatgaccaaaatcccttaacgtgagttttcgttccactg
agcgtcagaccccgtagaaaagatcaaaggatcttcttgagatcctttttttctgcgcgtaa
tctgctgcttgcaaacaaaaaaaccaccgctaccagcggtggtttgtttgccggatcaagag
ctaccaactctttttccgaaggtaactggcttcagcagagcgcagataccaaatactgtcct
tctagtgtagccgtagttaggccaccacttcaagaactctgtagcaccgcctacatacctcg
ctctgctaatcctgttaccagtggctgctgccagtggcgataagtcgtgtcttaccgggttg
gactcaagacgatagttaccggataaggcgcagcggtcgggctgaacggggggttcgtgcac
acagcccagcttggagcgaacgacctacaccgaactgagatacctacagcgtgagcattgag
aaagcgccacgcttcccgaagggagaaaggcggacaggtatccggtaagcggcagggtcgga
acaggagagcgcacgagggagcttccagggggaaacgcctggtatctttatagtcctgtcgg
gtttcgccacctctgacttgagcgtcgatttttgtgatgctcgtcaggggggcggagcctat
ggaaaaacgccagcaacgcggcctttttacggttcctggccttttgctggccttttgctcac
atgttctttcctgcgttatcccctgattctgtggataaccgtattaccgcctttgagtgagc
tgataccgctcgccgcagccgaacgaccgagcgcagcgagtcagtgagcgaggaagcggaag
agcgcccaatacgcaaaccgcctctccccgcgcgttggccgattcattaatgcagctggcac
gacaggtttcccgactggaaagcgggcagtgagcgcaacgcaattaatgtgagttagctcac
tcattaggcaccccaggctttacactttatgcttccggctcgtatgttgtgtggaattgtga
gcggataacaatttcacacaggaaacagctatgaccatgattacgccaagcttacgcgtcct
ggcattatgcccagtacatgaccttatgggactttcctacttggcagtacatctacgtatta
gtcatcgctattaccatggtgatgcggttttggcagtacatcaatgggcgtggatagcggtt
tgactcacggggatttccaagtctccaccccattgacgtcaatgggagtttgttttggcacc
aaaatcaacgggactttccaaaatgtcgtaacaactccgccccattgacgcaaatgggcggt
aggcgtgtacggtgggaggtctatataagcagagctcgtttagtgaaccgtgg

FIG. 4A pc3MerV2 Id-SCD viral:
nt 1 - 55: MeV leader
nt 56 - 66: gene start of transgene (originally from N gene; Phase 2)
nt 67 - 103: 5'-UTR (originally from N gene)
nt 103 - 108: XhoI (c'tcgag); not singular in this context
nt 109 - 114: 5'-cloning site PauI+MluI (g'CGCGT)
nt 121 - 1242: SuperCD ORF (1122 nt = 373 aa +Stop)
nt 1243 - 1248: 3'-cloning site MluI+PauI (A'cgcgc)
nt 1249 - 1260: 3'-UTR
nt 1262 - 1270: gene end of transgene (originally from N gene)
nt 1274 - 1284: gene start N (Phase 2)
nt 1326 - 2903: N ORF (1578 nt = 525 aa +stop)
nt 3025 - 4548: P ORF (1524 nt = 507 aa +stop)
nt 3047 - 3607: C ORF (non-structural; 561 nt = 186 aa +stop)
nt 3709 - 3716: A5G3 editing box; G insertion behind nt 3714
nt 3025 - 3923: V trans-frame ORF after mRNA editing (non-structural; 900 nt = 299 aa +stop)
nt 4656 - 5663: M ORF (1008 nt = 335 aa +stop)
nt 6667 - 8328: F ORF (1662 nt = 553 aa + stop)
nt 8489 - 10342: H ORF (1854 nt = 617 aa +stop)
nt 10452 - 17003: L ORF (6552 nt = 2183 aa +stop)
nt 17076 - 17112: MeV trailer (37 nt)

```
accaaacaaagttgggtaaggatagttcaatcaatgatcatcttctagtgcacttaggattc
aagatcctattatcagggacaagagcaggattagggatatctcgaggcgcgtgccaccatgg
tgacagggggaatggcaagcaagtgggatcagaagggtatggacattgcctatgaggaggcg
gccttaggttacaaagagggtggtgttcctattggcggatgtcttatcaataacaaagacgg
aagtgttctcggtcgtggtcacaacatgagatttcaaaagggatccgccacactacatggtg
agatctccactttggaaaactgtgggagattagagggcaaagtgtacaaagataccactttg
tatacgacgctgtctccatgcgacatgtgtacaggtgccatcatcatgtatggtattccacg
ctgtgttgtcggtgagaacgttaatttcaaaagtaagggcgagaaatatttacaaactagag
gtcacgaggttgttgttgttgacgatgagaggtgtaaaaagatcatgaaacaatttatcgat
gaaagacctcaggattggtttgaagatattggtgaggcttcggaaccatttaagaacgtcta
cttgctacctcaaacaaaccaattgctgggtttgtacaccatcatcagaaataagaatacaa
ctagacctgatttcattttctactccgatagaatcatcagattgttggttgaagaaggtttg
aaccatctacctgtgcaaaagcaaattgtggaaactgacaccaacgaaaacttcgaaggtgt
ctcattcatgggtaaaatctgtggtgtttccattgtcagagctggtgaatcgatggagcaag
gattaagagactgttgtaggtctgtgcgtatcggtaaaattttaattcaaaggacgaggag
actgctttaccaaagttattctacgaaaaattaccagaggatatatctgaaaggtatgtctt
cctattagacccaatgctggccaccggtggtagtgctatcatggctacagaagtcttgatta
agagaggtgttaagccagagagaatttacttcttaaacctaatctgtagtaaggaagggatt
gaaaaataccatgccgccttcccagaggtcagaattgttactggtgccctcgacagaggtct
```

FIG. 4B agatgaaaacaagtatctagttccagggttgggtgactttggtgacagatactactgtgttt
aaacgcgccatccatcattgttataaaaaacttaggattcaagatcctattatcagggacaa
gagcaggattagggatatccgagatggccacacttttaaggagcttagcattgttcaaaaga
aacaaggacaaaccacccattacatcaggatccggtggagccatcagaggaatcaaacacat
tattatagtaccaatccctggagattcctcaattaccactcgatccagacttctggaccggt
tggtgaggttaattggaaacccggatgtgagcgggcccaaactaacaggggcactaataggt
atattatccttatttgtggagtctccaggtcaattgattcagaggatcaccgatgaccctga
cgttagcataaggctgttagaggttgtccagagtgaccagtcacaatctggccttaccttcg
catcaagaggtaccaacatggaggatgaggcggaccaatacttttcacatgatgatccaatt
agtagtgatcaatccaggttcggatggttcgggaacaaggaaatctcagatattgaagtgca
agaccctgagggattcaacatgattctgggtaccatcctagcccaaatttgggtcttgctcg
caaaggcggttacggccccagacacggcagctgattcggagctaagaaggtggataaagtac
acccaacaaagaagggtagttggtgaatttagattggagagaaaatggttggatgtggtgag
gaacaggattgccgaggacctctccttacgccgattcatggtcgctctaatcctggatatca
agagaacacccggaaacaaacccaggattgctgaaatgatatgtgacattgatacatatatc
gtagaggcaggattagccagttttatcctgactattaagtttgggatagaaactatgtatcc
tgctcttggactgcatgaatttgctggtgagttatccacacttgagtccttgatgaaccttt
accagcaaatggggggaaactgcaccctacatggtaatcctggagaactcaattcagaacaag
ttcagtgcaggatcatacccctctgctctggagctatgccatgggagtaggagtggaacttga
aaactccatgggaggtttgaactttggccgatcttactttgatccagcatattttagattag
ggcaagagatggtaaggaggtcagctggaaaggtcagttccacattggcatctgaactcggt
atcactgccgaggatgcaaggcttgtttcagagattgcaatgcatactactgaggacaagat
cagtagagcggttggacccagacaagcccaagtatcatttctacacggtgatcaaagtgaga
atgagctaccgagattgggggcaaggaagataggagggtcaaacagagtcgaggagaagcc
agggagagctacagagaaaccgggcccagcagagcaagtgatgcgagagctgcccatcttcc
aaccggcacacccctagacattgacactgcaacggagtccagccaagatccgcaggacagtc
gaaggtcagctgacgccctgcttaggctgcaagccatggcaggaatctcggaagaacaaggc
tcagacacggacacccctatagtgtacaatgacagaaatcttctagactaggtgcgagaggc
cgagggccagaacaacatccgcctaccatccatcattgttataaaaaacttaggaaccaggt
ccacacagccgccagcccatcaaccatccactcccacgattggagccaatggcagaagagca
ggcacgccatgtcaaaaacggactggaatgcatccgggctctcaaggccgagcccatcggct
cactggccatcgaggaagctatggcagcatggtcagaaatatcagacaacccaggacaggag
cgagccacctgcagggaagagaaggcaggcagttcgggtctcagcaaaccatgcctctcagc
aattggatcaactgaaggcggtgcacctcgcatccgcggtcagggacctggagagagcgatg
acgacgctgaaactttgggaatcccccaagaaatctccaggcatcaagcactgggttacag
tgttattacgtttatgatcacagcggtgaagcggttaagggaatccaagatgctgactctat
catggttcaatcaggccttgatggtgatagcaccctctcaggaggagacaatgaatctgaaa
acagcgatgtggatattggcgaacctgataccgagggatatgctatcactgaccggggatct
gctcccatctctatggggttcagggcttctgatgttgaaactgcagaaggaggggagatcca
cgagctcctgagactccaatccagaggcaacaactttccgaagcttgggaaaactctcaatg
ttcctccgcccccggaccccggtagggccagcacttccgggacacccattaaaaagggcaca
gacgcgagattagcctcatttggaacggagatcgcgtctttattgacaggtggtgcaaccca
atgtgctcgaaagtcaccctcggaaccatcagggccaggtgcacctgcggggaatgtccccg
agtgtgtgagcaatgccgcactgatacaggagtggacacccgaatctggtaccacaatctcc
ccgagatcccagaataatgaagaagggggagactattatgatgatgagctgttctctgatgt
ccaagatattaaaacagccttggccaaaatacacgaggataatcagaagataatctccaagc
tagaatcactgctgttattgaagggagaagttgagtcaattaagaagcagatcaacaggcaa
aatatcagcatatccaccctggaaggacacctctcaagcatcatgatcgccattcctggact
tgggaaggatcccaacgaccccactgcagatgtcgaaatcaatcccgacttgaaacccatca
taggcagagattcaggccgagcactggccgaagttctcaagaaacccgttgccagccgacaa

FIG. 4C ctccaaggaatgacaaatggacggaccagttccagaggacagctgctgaaggaatttcagct
aaagccgatcgggaaaaagatgagctcagccgtcgggtttgttcctgacaccggccctgcat
cacgcagtgtaatccgctccattataaaatccagccggctagaggaggatcggaagcgttac
ctgatgactctccttgatgatatcaaaggagccaatgatcttgccaagttccaccagatgct
gatgaagataataatgaagtagctacagctcaacttacctgccaaccccatgccagtcgacc
caactagtacaacctaaatccattataaaaaacttaggagcaaagtgattgcctcccaaggt
ccacaatgacagagacctacgacttcgacaagtcggcatgggacatcaaagggtcgatcgct
ccgatacaacccaccacctacagtgatggcaggctggtgccccaggtcagagtcatagatcc
tggtctaggcgacaggaaggatgaatgctttatgtacatgtttctgctggggggttgttgagg
acagcgattccctagggcctccaatcgggcgagcatttgggttcctgcccttaggtgttggc
agatccacagcaaagcccgaaaaactcctcaaagaggccactgagcttgacatagttgttag
acgtacagcagggctcaatgaaaaactggtgttctacaacaacaccccactaactctcctca
caccttggagaaaggtcctaacaacagggagtgtcttcaacgcaaaccaagtgtgcaatgcg
gttaatctgataccgctcgataccccgcagaggttccgtgttgtttatatgagcatcacccg
tctttcggataacgggtattacaccgttcctagaagaatgctggaattcagatcggtcaatg
cagtggccttcaacctgctggtgacccttaggattgacaaggcgataggccctgggaagatc
atcgacaatacagagcaacttcctgaggcaacatttatggtccacatcgggaacttcaggag
aaagaagagtgaagtctactctgccgattattgcaaaatgaaaatcgaaaagatgggcctgg
tttttgcacttggtgggataggggggcaccagtcttcacattagaagcacaggcaaaatgagc
aagactctccatgcacaactcgggttcaagaagaccttatgttacccgctgatggatatcaa
tgaagaccttaatcgattactctggaggagcagatgcaagatagtaagaatccaggcagttt
tgcagccatcagttcctcaagaattccgcatttacgacgacgtgatcataaatgatgaccaa
ggactattcaaagttctgtagaccgtagtgcccagcaatgcccgaaaacgaccccccctcaca
atgacagccagaaggcccggacaaaaaagcccccctccgaaagactccacggaccaagcgaga
ggccagccagcagccgacggcaagcgcgaacaccaggcggccccagcacagaacagccctga
cacaaggccaccaccagccaccccaatctgcatcctcctcgtgggacccccgaggaccaacc
cccaaggctgcccccgatccaaaccaccaaccgcatccccaccacccccgggaaagaaaccc
ccagcaattggaaggcccctccccctcttcctcaacacaagaactccacaaccgaaccgcac
aagcgaccgaggtgacccaaccgcaggcatccgactccctagacagatcctctctccccggc
aaactaaacaaaacttagggccaaggaacatacacacccaacagaacccagaccccggccca
cggcgccgcgcccccaacccccgacaaccagagggagcccccaaccaatcccgccggctccc
ccggtgcccacaggcagggacaccaacccccgaacagacccagcacccaaccatcgacaatc
caagacgggggggcccccccaaaaaaaggcccccaggggccgacagccagcaccgcgaggaa
gcccacccaccccacacacgaccacggcaaccaaaccagaacccagaccaccctgggccacc
agctcccagactcggccatcaccccgcagaaaggaaaggccacaacccgcgcaccccagccc
cgatccggcggggagccacccaacccgaaccagcacccaagagcgatccccgaaggaccccc
gaaccgcaaaggacatcagtatcccacagcctctccaagtcccccggtctcctcctcttctc
gaagggaccaaaagatcaatccaccacacccgacgacactcaactccccacccctaaaggag
acaccgggaatcccagaatcaagactcatccaatgtccatcatgggtctcaaggtgaacgtc
tctgccatattcatggcagtactgttaactctccaaacacccaccggtcaaatccattgggg
caatctctctaagataggggtggtaggaataggaagtgcaagctacaaagttatgactcgtt
ccagccatcaatcattagtcataaaattaatgcccaatataactctcctcaataactgcacg
agggtagagattgcagaatacaggagactactgagaacagttttggaaccaattagagatgc
acttaatgcaatgacccagaatataagaccggttcagagtgtagcttcaagtaggagacaca
agagatttgcgggagtagtcctggcaggtgcggccctaggcgttgccacagctgctcagata
acagccggcattgcacttcaccagtccatgctgaactctcaagccatcgacaatctgagagc
gagcctggaaactactaatcaggcaattgagacaatcagacaagcagggcaggagatgatat
tggctgttcagggtgtccaagactacatcaataatgagctgataccgtctatgaaccaacta
tcttgtgatttaatcggccagaagctcgggctcaaattgctcagatactatacagaaatcct
gtcattatttggccccagtttacgggaccccatatctgcggagatatctatccaggctttga

FIG. 4D gctatgcgcttggaggagacatcaataaggtgttagaaaagctcggatacagtggaggtgat
ttactgggcatcttagagagcggaggaataaaggcccggataactcacgtcgacacagagtc
ctacttcattgtcctcagtatagcctatccgacgctgtccgagattaagggggtgattgtcc
accggctagaggggtctcgtacaacataggctctcaagagtggtataccactgtgcccaag
tatgttgcaacccaagggtaccttatctcgaattttgatgagtcatcgtgtactttcatgcc
agaggggactgtgtgcagccaaaatgccttgtacccgatgagtcctctgctccaagaatgcc
tccgggggtacaccaagtcctgtgctcgtacactcgtatccgggtcttttgggaaccggttc
attttatcacaagggaacctaatagccaattgtgcatcaatcctttgcaagtgttacacaac
aggaacgatcattaatcaagaccctgacaagatcctaacatacattgctgccgatcactgcc
cggtagtcgaggtgaacggcgtgaccatccaagtcgggagcaggaggtatccagacgctgtg
tacttgcacagaattgacctcggtcctcccatatcattggagaggttggacgtagggacaaa
tctggggaatgcaattgctaagttggaggatgccaaggaattgttggagtcatcggaccaga
tattgaggagtatgaaaggtttatcgagcactagcatagtctacatcctgattgcagtgtgt
cttggagggttgatagggatccccgctttaatatgttgctgcagggggcgttgtaacaaaaa
gggagaacaagttggtatgtcaagaccaggcctaaagcctgatcttacgggaacatcaaaat
cctatgtaaggtcgctctgatcctctacaactcttgaaacacaaatgtcccacaagtctcct
cttcgtcatcaagcaaccaccgcacccagcatcaagcccacctgaaattatctccggcttcc
ctctggccgaacaatatcggtagttaatcaaaacttagggtgcaagatcatccacaatgtca
ccacaacgagaccggataaatgccttctacaaagataacccccatcccaagggaagtaggat
agtcattaacagagaacatcttatgattgatagaccttatgttttgctggctgttctgtttg
tcatgtttctgagcttgatcgggttgctagccattgcaggcattagacttcatcgggcagcc
atctacaccgcagagatccataaaagcctcagcaccaatctagatgtaactaactcaatcga
gcatcaggtcaaggacgtgctgacaccactcttcaaaatcatcggtgatgaagtgggcctga
ggacacctcagagattcactgacctagtgaaattaatctctgacaagattaaattccttaat
ccggatagggagtacgacttcagagatctcacttggtgtatcaacccgccagagagaatcaa
attggattatgatcaatactgtgcagatgtggctgctgaagagctcatgaatgcattggtga
actcaactctactggagaccagaacaaccaatcagttcctagctgtctcaaagggaaactgc
tcagggcccactacaatcagaggtcaattctcaaacatgtcgctgtccctgttagacttgta
tttaggtcgaggttacaatgtgtcatctatagtcactatgacatcccaggaatgtatgggg
gaacttacctagtggaaaagcctaatctgagcagcaaaaggtcagagttgtcacaactgagc
atgtaccgagtgtttgaagtaggtgttatcagaaatccgggtttgggggctccggtgttcca
tatgacaaactatcttgagcaaccagtcagtaatgatctcagcaactgtatggtggctttgg
gggagctcaaactcgcagccctttgtcacggggaagattctatcacaattccctatcaggga
tcagggaaaggtgtcagcttccagctcgtcaagctaggtgtctggaaatccccaaccgacat
gcaatcctgggtccccttatcaacggatgatccagtgatagacaggctttacctctcatctc
acagaggtgttatcgctgacaatcaagcaaaatgggctgtcccgacaacacgaacagatgac
aagttgcgaatggagacatgcttccaacaggcgtgtaagggtaaaatccaagcactctgcga
gaatcccgagtgggcaccattgaaggataacaggattccttcatacggggtcttgtctgttg
atctgagtctgacagttgagcttaaaatcaaaattgcttcgggattcggccattgatcaca
cacggttcagggatggacctatacaaatccaaccacaacaatgtgtattggctgactatccc
gccaatgaagaacctagccttaggtgtaatcaacacattggagtggataccgagattcaagg
ttagtccctacctcttcactgtcccaattaaggaagcaggcgaagactgccatgccccaaca
tacctacctgcggaggtggatggtgatgtcaaactcagttccaatctggtgattctacctgg
tcaagatctccaatatgttttggcaacctacgatacttccagggttgaacatgctgtggttt
attacgtttacagcccaagccgctcattttcttactttatccttttaggttgcctataaag
gggtccccatcgaattacaagtggaatgcttcacatgggaccaaaaactctggtgccgtca
cttctgtgtgcttgcggactcagaatctggtggacatatcactcactctgggatggtgggca
tgggagtcagctgcacagtcacccgggaagatggaaccaatcgcagatagggctgctagtga
accaatcacatgatgtcacccagacatcaggcatacccactagtgtgaaatagacatcagaa
ttaagaaaaacgtagggtccaagtggttccccgttatggactcgctatctgtcaaccagatc

FIG. 4E ttataccctgaagttcacctagatagcccgatagttaccaataagatagtagccatcctgga
gtatgctcgagtccctcacgcttacagcctggaggaccctacactgtgtcagaacatcaagc
accgcctaaaaaacggattttccaaccaaatgattataaacaatgtggaagttgggaatgtc
atcaagtccaagcttaggagttatccggcccactctcatattccatatccaaattgtaatca
ggatttatttaacatagaagacaaagagtcaacgaggaagatccgtgaactcctcaaaaagg
ggaattcgctgtactccaaagtcagtgataaggttttccaatgcttaagggacactaactca
cggcttggcctaggctccgaattgagggaggacatcaaggagaaagttattaacttgggagt
ttacatgcacagctcccagtggtttgagccctttctgttttggtttacagtcaagactgaga
tgaggtcagtgattaaatcacaaacccatacttgccataggaggagacacacacctgtattc
ttcactggtagttcagttgagttgctaatctctcgtgaccttgttgctataatcagtaaaga
gtctcaacatgtatattacctgacatttgaactggttttgatgtattgtgatgtcatagagg
ggaggttaatgacagagaccgctatgactattgatgctaggtatacagagcttctaggaaga
gtcagatacatgtggaaactgatagatggtttcttccctgcactcgggaatccaacttatca
aattgtagccatgctggagcctctttcacttgcttacctgcagctgagggatataacagtag
aactcagaggtgctttccttaaccactgctttactgaaatacatgatgttcttgaccaaaac
gggtttttctgatgaaggtacttatcatgagttaactgaagctctagattacattttcataac
tgatgacatacatctgacaggggagattttctcatttttcagaagtttcggccaccccagac
ttgaagcagtaacggctgctgaaaatgttaggaaatacatgaatcagcctaaagtcattgtg
tatgagactctgatgaaaggtcatgccatatttgtggaatcataatcaacggctatcgtga
caggcacggaggcagttggccaccgctgaccctcccctgcatgctgcagacacaatccgga
atgctcaagcttcaggtgaagggttaacacatgagcagtgcgttgataactggaaatctttt
gctggagtgaaatttggctgctttatgcctcttagcctggatagtgatctgacaatgtacct
aaaggacaaggcacttgctgctctccaaagggaatgggattcagtttacccgaaagagttcc
tgcgttacgaccctcccaagggaaccgggtcacggaggcttgtagatgttttccttaatgat
tcgagctttgacccatatgatgtgataatgtatgttgtaagtggagcttacctccatgaccc
tgagttcaacctgtcttacagcctgaaagaaaaggagatcaaggaaacaggtagactttttg
ctaaaatgacttacaaaatgagggcatgccaagtgattgctgaaaatctaatctcaaacggg
attggcaaatattttaaggacaatgggatggccaaggatgagcacgatttgactaaggcact
ccacactctagctgtctcaggagtccccaaagatctcaaagaaagtcacaggggggggccag
tcttaaaaacctactcccgaagcccagtccacacaagtaccaggaacgtgagagcagcaaaa
gggtttatagggttccctcaagtaattcggcaggaccaagacactgatcatccggagaatat
ggaagcttacgagacagtcagtgcatttatcacgactgatctcaagaagtactgccttaatt
ggagatatgagaccatcagcttgtttgcacagaggctaaatgagatttacggattgccctca
tttttccagtggctgcataagaggcttgagacctctgtcctgtatgtaagtgaccctcattg
cccccccgaccttgacgcccatatcccgttatataaagtccccaatgatcaaatcttcatta
agtaccctatgggaggtatagaagggtattgtcagaagctgtggaccatcagcaccattccc
tatctatacctggctgcttatgagagcggagtaaggattgcttcgttagtgcaaggggacaa
tcagaccatagccgtaacaaaaagggtacccagcacatggccctacaaccttaagaaacggg
aagctgctagagtaactagagattactttgtaattcttaggcaaaggctacatgatattggc
catcacctcaaggcaaatgagacaattgtttcatcacatttttttgtctattcaaaaggaat
atattatgatgggctacttgtgtcccaatcactcaagagcatcgcaagatgtgtattctggt
cagagactatagttgatgaaacaagggcagcatgcagtaatattgctacaacaatggctaaa
agcatcgagagaggttatgaccgttaccttgcatattccctgaacgtcctaaaagtgataca
gcaaattctgatctctcttggcttcacaatcaattcaaccatgacccgggatgtagtcatac
ccctcctcacaaacaacgacctcttaataaggatggcactgttgcccgctcctattgggggg
atgaattatctgaatatgagcaggctgtttgtcagaaacatcggtgatccagtaacatcatc
aattgctgatctcaagagaatgattctcgcctcactaatgcctgaagagaccctccatcaag
taatgacacaacaaccggggggactcttcattcctagactgggctagcgacccttactcagca
aatcttgtatgtgtccagagcatcactagactcctcaagaacataactgcaaggtttgtcct
gatccatagtccaaacccaatgttaaaaggattattccatgatgacagtaaagaagaggacg

FIG. 4F agggactggcggcattcctcatggacaggcatattatagtacctagggcagctcatgaaatc
ctggatcatagtgtcacaggggcaagagagtctattgcaggcatgctggataccacaaaagg
cttgattcgagccagcatgaggaaggggggttaacctctcgagtgataaccagattgtcca
attatgactatgaacaattcagagcagggatggtgctattgacaggaagaaagagaaatgtc
ctcattgacaaagagtcatgttcagtgcagctggcgagagctctaagaagccatatgtgggc
gaggctagctcgaggacggcctatttacggccttgaggtccctgatgtactagaatctatgc
gaggccaccttattcggcgtcatgagacatgtgtcatctgcgagtgtggatcagtcaactac
ggatggtttttgtcccctcgggttgccaactggatgatattgacaaggaaacatcatcctt
gagagtcccatatattggttctaccactgatgagagaacagacatgaagcttgccttcgtaa
gagccccaagtcgatccttgcgatctgctgttagaatagcaacagtgtactcatgggcttac
ggtgatgatgatagctcttggaacgaagcctggttgttggctaggcaaagggccaatgtgag
cctggaggagctaagggtgatcactcccatctcaacttcgactaatttagcgcataggttga
gggatcgtagcactcaagtgaaatactcaggtacatcccttgtccgagtggcgaggtatacc
acaatctccaacgacaatctctcatttgtcatatcagataagaaggttgatactaactttat
ataccaacaaggaatgcttctagggttgggtgttttagaaacattgtttcgactcgagaaag
ataccggatcatctaacacggtattacatcttcacgtcgaaacagattgttgcgtgatcccg
atgatagatcatcccaggatacccagctcccgcaagctagagctgagggcagagctatgtac
caacccattgatatatgataatgcacctttaattgacagagatgcaacaaggctatacaccc
agagccataggaggcaccttgtggaatttgttacatggtccacaccccaactatatcacatt
ttagctaagtccacagcactatctatgattgacctggtaacaaaatttgagaaggaccatat
gaatgaaatttcagctctcataggggatgacgatatcaatagtttcataactgagtttctgc
tcatagagccaagattattcactatctacttgggccagtgtgcggccatcaattgggcattt
gatgtacattatcatagaccatcagggaaatatcagatgggtgagctgttgtcatcgttcct
ttctagaatgagcaaaggagtgtttaaggtgcttgtcaatgctctaagccacccaaagatct
acaagaaattctggcattgtggtattatagagcctatccatggtccttcacttgatgctcaa
aacttgcacacaactgtgtgcaacatggtttacacatgctatatgacctacctcgacctgtt
gttgaatgaagagttagaagagttcacatttctcttgtgtgaaagcgacgaggatgtagtac
cggacagattcgacaacatccaggcaaaacacttatgtgttctggcagatttgtactgtcaa
ccagggacctgcccaccaattcgaggtctaagaccggtagagaaatgtgcagttctaaccga
ccatatcaaggcagaggctatgttatctccagcaggatcttcgtggaacataaatccaatta
ttgtagaccattactcatgctctctgacttatctccggcgaggatcgatcaaacagataaga
ttgagagttgatccaggattcattttcgacgccctcgctgaggtaaatgtcagtcagccaaa
gatcggcagcaacaacatctcaaatatgagcatcaaggctttcagacccccacacgatgatg
ttgcaaaattgctcaaagatatcaacacaagcaagcacaatcttcccatttcaggggcaat
ctcgccaattatgaaatccatgctttccgcagaatcgggttgaactcatctgcttgctacaa
agctgttgagatatcaacattaattaggagatgccttgagccaggggaggacggcttgttct
tgggtgagggatcgggttctatgttgatcacttataaagagatacttaaactaaacaagtgc
ttctataatagtggggtttccgccaattctagatctggtcaaagggaattagcaccctatcc
ctccgaagttggccttgtcgaacacagaatgggagtaggtaatattgtcaaagtgctcttta
acgggaggcccgaagtcacgtgggtaggcagtgtagattgcttcaatttcatagttagtaat
atccctacctctagtgtggggtttatccattcagatatagagaccttgcctgacaaagatac
tatagagaagctagaggaattggcagccatcttatcgatggctctgctcctgggcaaaatag
gatcaatactggtgattaagcttatgcctttcagcggggatttgttcaggatttataagt
tatgtagggtctcattatagagaagtgaaccttgtataccctagatacagcaacttcatctc
tactgaatcttatttggttatgacagatctcaaggctaaccggctaatgaatcctgaaaaga
ttaagcagcagataattgaatcatctgtgaggacttcacctggacttataggtcacatccta
tccattaagcaactaagctgcatacaagcaattgtgggagacgcagttagtagaggtgatat
caatcctactctgaaaaaacttacacctatagagcaggtgctgatcaattgcgggttggcaa
ttaacggacctaagctgtgcaaagaattgatccaccatgatgttgcctcagggcaagatgga
ttgcttaattctatactcatcctctacagggagttggcaagattcaaagacaaccaaagaag

FIG. 4G tcaacaagggatgttccacgcttaccccgtattggtaagtagcaggcaacgagaacttatat
ctaggatcacccgcaaattctgggggcacattcttctttactccgggaacaaaaagttgata
aataagtttatccagaatctcaagtccggctatctgatactagacttacaccagaatatctt
cgttaagaatctatccaagtcagagaaacagattattatgacgggggtttgaaacgtgagt
gggtttttaaggtaacagtcaaggagaccaaagaatggtataagttagtcggatacagtgcc
ctgattaaggactaattggttgaactccggaaccctaatcctgccctaggtggttaggcatt
atttgcaatatattaaagaaaactttgaaaatacgaagtttctattcccagctttgtctggt
ggccggcatggtcccagcctcctcgctggcgccggctgggcaacattccgaggggaccgtcc
cctcggtaatggcgaatgggacgcggccggtcgatcgacgatccggctgctaacaaagcccg
aaaggaagctgagttggctgctgccaccgctgagcaataactagcataaccccttggggcct
ctaaacgggtcttgaggggttttttgctgaaaggaggaactatatccggatcgagatcaatt
ctgtgagcgtatggcaaacgaaggaaaaatagttatagtagccgcactcgatgggacatttc
aacgtaaaccgtttaataatatttgaatcttattccattatctgaaatggtggtaaaacta
actgctgtgtgtatgaaatgctttaaggaggcttccttttctaaacgattgggtgaggaaac
cgagatagaaataataggaggtaatgatatgtatcaatcggtgtgtagaaagtgttacatcg
actcataatattatatttttatctaaaaaactaaaaataaacattgattaaattttaatat
aatacttaaaaatggatgttgtgtcgttagataaaccgtttatgtattttgaggaaattgat
aatgagttagattacgaaccagaaagtgcaaatgaggtcgcaaaaaaactgccgtatcaagg
acagttaaaactattactaggagaattatttttcttagtaagttacagcgacacggtatat
tagatggtgccaccgtagtgtatataggatctgctcccggtacacatatacgttatttgaga
gatcatttctataatttaggagtgatcccgaaaggaagctgagttggctgctgccaccgctg
agcaataactagcataaccccttggggcctctaaacgggtcttgaggggttttttgctgaaa
ggaggaacgcgcctgatgcggtattttctccttacgcatctgtgcggtatttcacaccgcat
atatggtgcactctcagtacaatctgctctgatgccgcatagttaagccagccccgacaccc
gccaacacccgctgacgcgccctgacgggcttgtctgctcccggcatccgcttacagacaag
ctgtgaccgtctccgggagctgcatgtgtcagaggttttcaccgtcatcaccgaaacgcgcg
agacgaaagggcctcgtgatacgcctatttttataggttaatgtcatgataataatggtttc
ttagacgtcaggtggcacttttcggggaaatgtgcgcggaacccctatttgtttatttttct
aaatacattcaaatatgtatccgctcatgagacaataaccctgataaatgcttcaataatat
tgaaaaaggaagagtatgagtattcaacatttccgtgtcgcccttattcccttttttgcggc
attttgccttcctgtttttgctcacccagaaacgctggtgaaagtaaaagatgctgaagatc
agttgggtgcacgagtgggttacatcgaactggatctcaacagcggtaagatccttgagagt
tttcgccccgaagaacgttttccaatgatgagcacttttaaagttctgctatgtggcgcggt
attatcccgtattgacgccgggcaagagcaactcggtcgccgcatacactattctcagaatg
acttggttgagtactcaccagtcacagaaaagcatcttacggatggcatgacagtaagagaa
ttatgcagtgctgccataaccatgagtgataacactgcggccaacttacttctgacaacgat
cggaggaccgaaggagctaaccgcttttttgcacaacatgggggatcatgtaactcgccttg
atcgttgggaaccggagctgaatgaagccataccaaacgacgagcgtgacaccacgatgcct
gtagcaatggcaacaacgttgcgcaaactattaactggcgaactacttactctagcttcccg
gcaacaattaatagactggatggaggcggataaagttgcaggaccacttctgcgctcggccc
ttccggctggctggtttattgctgataaatctggagccggtgagcgtgggtctcgcggtatc
attgcagcactggggccagatggtaagccctcccgtatcgtagttatctacacgacggggag
tcaggcaactatggatgaacgaaatagacagatcgctgagataggtgcctcactgattaagc
attggtaactgtcagaccaagtttactcatatatactttagattgatttaaaacttcatttt
taatttaaaaggatctaggtgaagatcctttttgataatctcatgaccaaaatcccttaacg
tgagttttcgttccactgagcgtcagaccccgtagaaaagatcaaaggatcttcttgagatc
ctttttttctgcgcgtaatctgctgcttgcaaacaaaaaaaccaccgctaccagcggtggtt
tgtttgccggatcaagagctaccaactctttttccgaaggtaactggcttcagcagagcgca
gataccaaatactgtccttctagtgtagccgtagttaggccaccacttcaagaactctgtag
caccgcctacatacctcgctctgctaatcctgttaccagtggctgctgccagtggcgataag

FIG. 4H

```
tcgtgtcttaccgggttggactcaagacgatagttaccggataaggcgcagcggtcgggctg
aacggggggttcgtgcacacagcccagcttggagcgaacgacctacaccgaactgagatacc
tacagcgtgagcattgagaaagcgccacgcttcccgaagggagaaaggcggacaggtatccg
gtaagcggcagggtcggaacaggagagcgcacgagggagcttccagggggaaacgcctggta
tctttatagtcctgtcgggtttcgccacctctgacttgagcgtcgatttttgtgatgctcgt
caggggggcggagcctatggaaaaacgccagcaacgcggcctttttacggttcctggccttt
tgctggccttttgctcacatgttctttcctgcgttatcccctgattctgtggataaccgtat
taccgcctttgagtgagctgataccgctcgccgcagccgaacgaccgagcgcagcgagtcag
tgagcgaggaagcggaagagcgcccaatacgcaaaccgcctctccccgcgcgttggccgatt
cattaatgcagctggcacgacaggtttcccgactggaaagcgggcagtgagcgcaacgcaat
taatgtgagttagctcactcattaggcaccccaggctttacactttatgcttccggctcgta
tgttgtgtggaattgtgagcggataacaatttcacacaggaaacagctatgaccatgattac
gccaagcttacgcgtcctggcattatgcccagtacatgaccttatgggactttcctacttgg
cagtacatctacgtattagtcatcgctattaccatggtgatgcggttttggcagtacatcaa
tgggcgtggatagcggtttgactcacggggatttccaagtctccaccccattgacgtcaatg
ggagtttgttttggcaccaaaatcaacgggactttccaaaatgtcgtaacaactccgcccca
ttgacgcaaatgggcggtaggcgtgtacggtgggaggtctatataagcagagctcgtttagt
gaaccgtgg
```

FIG. 5A pcDIMer-N nt 1358 - 2935: N ORF MeV Schwarz (1578 nt = 525 aa + stop codon)

```
agcttgcatgcctgcaggtcaattccctggcattatgcccagtacatgaccttatgggactt
tcctacttggcagtacatctacgtattagtcatcgctattaccatggtgatgcggttttggc
agtacatcaatgcgcgtggataccggtttgactcacggggatttccaagtctccaccccatt
cacgtcaatgggagtttgttttggcaccaaaatcaacgggactttccaaaatgtcgtaacaa
ctccgccccattgacgcaaatgggcggtaggcgtgtacggtgggaggtctatataagcagag
ctcgtttagtgaaccgtcagatcgcctggagacgccatccacgctgttttgacctccataga
agacaccgggaccgatccagcctggggatctagcctccgcggccgggaacggtgcattggaa
cgcggattccccgtgccaagagtgacgtaagtaccgcctatagagtctataggcccaccccc
ttggcttcttatgcatgctatactgtttttggcttggggtctatacacccccgcttcctcat
gttataggtgatggtatagcttagcctataggtgtgggttattgaccattattgaccactcc
cctattggtgacgatactttccattactaatccataacatggctctttgccacaactctctt
tattggctatatgccaatacactgtccttcagagactgacacggactctgtatttttacagg
atggggtctcatttattatttacaaattcacatatacaacaccaccgtccccagtgcccgca
gtttttattaaacataacgtgggatctccacgcgaatctcgggtacgtgttccggacatggg
ctcttctccggtagcggcggagctcctacatccgagccctgctcccatgcctccagcgactc
atggtcgctcggcagctccttgctcctaacagtggaggccagacttaggcacagcacgatgc
ccaccaccaccagtgtgccgcacaaggccgtggcggtagggtatgtgtctgaaaatgagctc
ggggagcgggcttgcaccgctgacgcatttggaagacttaaggcagcggcagaagaagatgc
aggcagctgagttgttgtgttctgataagagtcagaggtaactcccgttgcggtgctgttaa
cggtggagggcagtgtagtctgagcagtactcgttgctgccgcgcgcgccaccagacataat
agctgacagactaacagactgttcctttccatgggtcttttctgcagtcaccgtccttgaca
cgatcggatcccgggtacctctagaagatctgatatcgtcgacctcgaggccaccatggcca
cactttaaggagcttagcattgttcaaaagaaacaaggacaaaccacccattacatcagga
tccggtggagccatcagaggaatcaaacacattattatagtaccaatccctggagattcctc
aattaccactcgatccagacttctggaccggttggtgaggttaattggaaacccggatgtga
gcgggcccaaactaacaggggcactaataggtatattatccttatttgtggagtctccaggt
caattgattcagaggatcaccgatgaccctgacgttagcataaggctgttagaggttgtcca
gagtgaccagtcacaatctggccttaccttcgcatcaagaggtaccaacatggaggatgagg
cggaccaatacttttcacatgatgatccaattagtagtgatcaatccaggttcggatggttc
gggaacaaggaaatctcagatattgaagtgcaagaccctgagggattcaacatgattctggg
taccatcctagcccaaatttgggtcttgctcgcaaaggcggttacggccccagacacggcag
ctgattcggagctaagaaggtggataaagtacacccaacaaagaagggtagttggtgaattt
agattggagagaaaatggttggatgtggtgaggaacaggattgccgaggacctctccttacg
ccgattcatggtcgctctaatcctggatatcaagagaacacccggaaacaaacccaggattg
ctgaaatgatatgtgacattgatacatatatcgtagaggcaggattagccagttttatcctg
actattaagtttgggatagaaactatgtatcctgctcttggactgcatgaatttgctggtga
gttatccacacttgagtccttgatgaacctttaccagcaaatgggggaaactgcaccctaca
tggtaatcctggagaactcaattcagaacaagttcagtgcaggatcataccctctgctctgg
agctatgccatgggagtaggagtggaacttgaaaactccatgggaggtttgaactttggccg
atcttactttgatccagcatattttagattagggcaagagatggtaaggaggtcagctggaa
aggtcagttccacattggcatctgaactcggtatcactgccgaggatgcaaggcttgtttca
gagattgcaatgcatactactgaggacaagatcagtagagcggttggacccagacaagccca
agtatcatttctacacggtgatcaaagtgagaatgagctaccgagattgggggcaaggaag
ataggagggtcaaacagagtcgaggagaagccagggagagctacagagaaaccgggcccagc
```

FIG. 5B agagcaagtgatgcgagagctgcccatcttccaaccggcacacccctagacattgacactgc
aacggagtccagccaagatccgcaggacagtcgaaggtcagctgacgccctgcttaggctgc
aagccatggcaggaatctcggaagaacaaggctcagacacggacacccctatagtgtacaat
gacagaaatcttctagactaggtgcgagaggccgagggccagaacaacatccgcctaccatc
catcattctcgaggaattctagatcccacgtcactattgtatactctatattatactctatg
ttatactctgtaatcctactcaataaacgtgtcacgcctgtgaaaccgtactaagtctcccg
tgtcttcttatcaccatcaggtgacatcctcgcccaggctgtcaatcatgccggtatcgatt
ccagtagcaccggccccacgctgacaacccactcttgcagcgttagcagcgcccctcttaac
aagccgacccccaccagcgtcgcggttactaacactcctctccccgacctgcagcccaagct
ctagagggccctattctatagtgtcacctaaatgctagagctcgctgatcagcctcgactgt
gccttctagttgccagccatctgttgtttgcccctcccccgtgccttccttgaccctggaag
gtgccactcccactgtcctttcctaataaaatgaggaaattgcatcgcattgtctgagtagg
tgtcattctattctggggggtggggtggggcaggacagcaagggggaggattgggaagacaa
tagcaggcatgctggggatgcggtgggctctatggcttctgaggcggaaagaaccagctggg
gctctagggggtatccccacgcgccctgtagcggcgcattaagcgcggcgggtgtggtggtt
acgcgcagcgtgaccgctacacttgccagcgccctagcgcccgctcctttcgctttcttccc
ttcctttctcgccacgttcgccggctttccccgtcaagctctaaatcggggcatccctttag
ggttccgatttagtgctttacggcacctcgaccccaaaaaacttgattagggtgatggttca
cgtagtgggccatcgccctgatagacggtttttcgccctttgacgttggagtccacgttctt
taatagtggactcttgttccaaactggaacaacactcaaccctatctcggtctattcttttg
atttataagggattttggggatttcggcctattggttaaaaaatgagctgatttaacaaaaa
tttaacgcgaattaattctgtggaatgtgtgtcagttagggtgtggaaagtccccaggctcc
ccaggcaggcagaagtatgcaaagcatgcatctcaattagtcagcaaccaggtgtggaaagt
ccccaggctccccagcaggcagaagtatgcaaagcatgcatctcaattagtcagcaaccata
gtcccgcccctaactccgcccatcccgcccctaactccgcccagttccgcccattctccgcc
ccatggctgactaattttttttatttatgcagaggccgaggccgcctctgcctctgagctat
tccagaagtagtgaggaggcttttttggaggcctaggcttttgcaaaaagctcccgggagct
tgtatatccattttcggatctgatcaagagacaggatgaggatcgtttcgcatgattgaaca
agatggattgcacgcaggttctccggccgcttgggtggagaggctattcggctatgactggg
cacaacagacaatcggctgctctgatgccgccgtgttccggctgtcagcgcaggggcgcccg
gttctttttgtcaagaccgacctgtccggtgccctgaatgaactgcaggacgaggcagcgcg
gctatcgtggctggccacgacgggcgttccttgcgcagctgtgctcgacgttgtcactgaag
cgggaagggactggctgctattgggcgaagtgccggggcaggatctcctgtcatctcacctt
gctcctgccgagaaagtatccatcatggctgatgcaatgcggcggctgcatacgcttgatcc
ggctacctgcccattcgaccaccaagcgaaacatcgcatcgagcgagcacgtactcggatgg
aagccggtcttgtcgatcaggatgatctggacgaagagcatcaggggctcgcgccagccgaa
ctgttcgccaggctcaaggcgcgcatgcccgacggcgaggatctcgtcgtgacccatggcga
tgcctgcttgccgaatatcatggtggaaaatggccgcttttctggattcatcgactgtggcc
ggctgggtgtggcggaccgctatcaggacatagcgttggctacccgtgatattgctgaagag
cttggcggcgaatgggctgaccgcttcctcgtgctttacggtatcgccgctcccgattcgca
gcgcatcgccttctatcgccttcttgacgagttcttctgagcgggactctggggttcgaaat
gaccgaccaagcgacgcccaacctgccatcacgagatttcgattccaccgccgccttctatg
aaaggttgggcttcggaatcgttttccgggacgccggctggatgatcctccagcgcggggat
ctcatgctggagttcttcgcccaccccaacttgtttattgcagcttataatggttacaaata
aagcaatagcatcacaaatttcacaaataaagcatttttttcactgcattctagttgtggtt
tgtccaaactcatcaatgtatcttatcatgtctgtataccgtcgacctctagctagagcttg
gcgtaatcatggtcatagctgtttcctgtgtgaaattgttatccgctcacaattccacacaa
catacgagccggaagcataaagtgtaaagcctggggtgcctaatgagtgagctaactcacat
taattgcgttgcgctcactgcccgctttccagtcgggaaacctgtcgtgccagctgcattaa
tgaatcggccaacgcgcggggagaggcggtttgcgtattgggcgctcttccgcttcctcgct

FIG. 5C

```
cactgactcgctgcgctcggtcgttcggctgcggcgagcggtatcagctcactcaaaggcgg
taatacggttatccacagaatcaggggataacgcaggaaagaacatgtgagcaaaaggccag
caaaaggccaggaaccgtaaaaaggccgcgttgctggcgtttttccataggctccgcccccc
tgacgagcatcacaaaaatcgacgctcaagtcagaggtggcgaaacccgacaggactataaa
gataccaggcgtttccccctggaagctccctcgtgcgctctcctgttccgaccctgccgctt
accggatacctgtccgcctttctcccttcgggaagcgtggcgctttctcaatgctcacgctg
taggtatctcagttcggtgtaggtcgttcgctccaagctgggctgtgtgcacgaaccccccg
ttcagcccgaccgctgcgccttatccggtaactatcgtcttgagtccaacccggtaagacac
gacttatcgccactggcagcagccactggtaacaggattagcagagcgaggtatgtaggcgg
tgctacagagttcttgaagtggtggcctaactacggctacactagaaggacagtatttggta
tctgcgctctgctgaagccagttaccttcggaaaaagagttggtagctcttgatccggcaaa
caaaccaccgctggtagcggtggtttttttgtttgcaagcagcagattacgcgcagaaaaaa
aggatctcaagaagatcctttgatcttttctacggggtctgacgctcagtggaacgaaaact
cacgttaagggattttggtcatgagattatcaaaaaggatcttcacctagatccttttaaat
taaaaatgaagttttaaatcaatctaaagtatatatgagtaaacttggtctgacagttacca
atgcttaatcagtgaggcacctatctcagcgatctgtctatttcgttcatccatagttgcct
gactccccgtcgtgtagataactacgatacgggagggcttaccatctggccccagtgctgca
atgataccgcgagacccacgctcaccggctccagatttatcagcaataaaccagccagccgg
aagggccgagcgcagaagtggtcctgcaactttatccgcctccatccagtctattaattgtt
gccgggaagctagagtaagtagttcgccagttaatagtttgcgcaacgttgttgccattgct
acaggcatcgtggtgtcacgctcgtcgtttggtatggcttcattcagctccggttcccaacg
atcaaggcgagttacatgatcccccatgttgtgcaaaaaagcggttagctccttcggtcctc
cgatcgttgtcagaagtaagttggccgcagtgttatcactcatggttatggcagcactgcat
aattctcttactgtcatgccatccgtaagatgcttttctgtgactggtgagtactcaaccaa
gtcattctgagaatagtgtatgcggcgaccgagttgctcttgcccggcgtcaatacgggata
ataccgcgccacatagcagaactttaaaagtgctcatcattggaaaacgttcttcggggcga
aaactctcaaggatcttaccgctgttgagatccagttcgatgtaacccactcgtgcacccaa
ctgatcttcagcatcttttactttcaccagcgtttctgggtgagcaaaaacaggaaggcaaa
atgccgcaaaaaagggaataagggcgacacggaaatgttgaatactcatactcttcctttt
caatattattgaagcatttatcagggttattgtctcatgagcggatacatatttgaatgtat
ttagaaaaataaacaaataggggttccgcgcacatttccccgaaaagtgccacctgacgtcg
acggatcgggagatc
```

FIG. 6A pcDIMer-P nt 1358 - 2881: P ORF MeV Schwarz (1524 nt = 507 aa + stop codon)

```
agcttgcatgcctgcaggtcaattccctggcattatgcccagtacatgaccttatgggactt
tcctacttggcagtacatctacgtattagtcatcgctattaccatggtgatgcggttttggc
agtacatcaatgcgcgtggataccggtttgactcacggggatttccaagtctccaccccatt
cacgtcaatgggagtttgttttggcaccaaaatcaacgggactttccaaaatgtcgtaacaa
ctccgccccattgacgcaaatgggcggtaggcgtgtacggtgggaggtctatataagcagag
ctcgtttagtgaaccgtcagatcgcctggagacgccatccacgctgttttgacctccataga
agacaccgggaccgatccagcctggggatctagcctccgcggccgggaacggtgcattggaa
cgcggattccccgtgccaagagtgacgtaagtaccgcctatagagtctataggcccaccccc
ttggcttcttatgcatgctatactgtttttggcttggggtctatacacccccgcttcctcat
gttataggtgatggtatagcttagcctataggtgtgggttattgaccattattgaccactcc
cctattggtgacgatactttccattactaatccataacatggctctttgccacaactctctt
tattggctatatgccaatacactgtccttcagagactgacacggactctgtatttttacagg
atggggtctcatttattatttacaaattcacatatacaacaccaccgtccccagtgcccgca
gtttttattaaacataacgtgggatctccacgcgaatctcgggtacgtgttccggacatggg
ctcttctccggtagcggcggagctcctacatccgagccctgctcccatgcctccagcgactc
atggtcgctcggcagctccttgctcctaacagtggaggccagacttaggcacagcacgatgc
ccaccaccaccagtgtgccgcacaaggccgtggcggtagggtatgtgtctgaaaatgagctc
ggggagcgggcttgcaccgctgacgcatttggaagacttaaggcagcggcagaagaagatgc
aggcagctgagttgttgtgttctgataagagtcagaggtaactcccgttgcggtgctgttaa
cggtggagggcagtgtagtctgagcagtactcgttgctgccgcgcgcgccaccagacataat
agctgacagactaacagactgttcctttccatgggtcttttctgcagtcaccgtccttgaca
cgatcggatcccgggtacctctagaagatctgatatcgtcgacctcgaggccaccatggcag
aagagcaggcacgccatgtcaaaaacggactggaatgcatccgggctctcaaggccgagccc
atcggctcactggccatcgaggaagctatggcagcatggtcagaaatatcagacaacccagg
acaggagcgagccacctgcagggaagagaaggcaggcagttcgggtctcagcaaaccatgcc
tctcagcaattggatcaactgaaggcggtgcacctcgcatccgcggtcagggacctggagag
agcgatgacgacgctgaaactttgggaatcccccaagaaatctccaggcatcaagcactgg
gttacagtgttattacgtttatgatcacagcggtgaagcggttaagggaatccaagatgctg
actctatcatggttcaatcaggccttgatggtgatagcaccctctcaggaggagacaatgaa
tctgaaaacagcgatgtggatattggcgaacctgataccgagggatatgctatcactgaccg
gggatctgctcccatctctatggggttcagggcttctgatgttgaaactgcagaaggagggg
agatccacgagctcctgagactccaatccagaggcaacaactttccgaagcttgggaaaact
ctcaatgttcctccgcccccggaccccggtagggccagcacttccgggacacccattaaaaa
gggcacagacgcgagattagcctcatttggaacggagatcgcgtctttattgacaggtggtg
caacccaatgtgctcgaaagtcaccctcggaaccatcagggccaggtgcacctgcggggaat
gtccccgagtgtgtgagcaatgccgcactgatacaggagtggacacccgaatctggtaccac
aatctccccgagatcccagaataatgaagaaggggggagactattatgatgatgagctgttct
ctgatgtccaagatattaaaacagccttggccaaaatacacgaggataatcagaagataatc
tccaagctagaatcactgctgttattgaagggagaagttgagtcaattaagaagcagatcaa
caggcaaaatatcagcatatccaccctggaaggacacctctcaagcatcatgatcgccattc
ctggacttgggaaggatcccaacgaccccactgcagatgtcgaaatcaatcccgacttgaaa
cccatcataggcagagattcaggccgagcactggccgaagttctcaagaaacccgttgccag
ccgacaactccaaggaatgacaaatggacggaccagttccagaggacagctgctgaaggaat
ttcagctaaagccgatcgggaaaaagatgagctcagccgtcgggtttgttcctgacaccggc
cctgcatcacgcagtgtaatccgctccattataaaatccagccggctagaggaggatcggaa
```

FIG. 6B gcgttacctgatgactctccttgatgatatcaaaggagccaatgatcttgccaagttccacc
agatgctgatgaagataataatgaagtagctacagctcaacttacctgccaaccccatgcca
gtcgacccaactagtacaacctaaatcctcgaggaattctagatcccacgtcactattgtat
actctatattatactctatgttatactctgtaatcctactcaataaacgtgtcacgcctgtg
aaaccgtactaagtctcccgtgtcttcttatcaccatcaggtgacatcctcgcccaggctgt
caatcatgccggtatcgattccagtagcaccggccccacgctgacaacccactcttgcagcg
ttagcagcgcccctcttaacaagccgaccccccaccagcgtcgcggttactaacactcctctc
cccgacctgcagcccaagctctagagggccctattctatagtgtcacctaaatgctagagct
cgctgatcagcctcgactgtgccttctagttgccagccatctgttgtttgcccctcccccgt
gccttccttgaccctggaaggtgccactcccactgtcctttcctaataaaatgaggaaattg
catcgcattgtctgagtaggtgtcattctattctggggggtggggtggggcaggacagcaag
ggggaggattgggaagacaatagcaggcatgctggggatgcggtgggctctatggcttctga
ggcggaaagaaccagctggggctctagggggtatccccacgcgccctgtagcggcgcattaa
gcgcggcgggtgtggtggttacgcgcagcgtgaccgctacacttgccagcgccctagcgccc
gctcctttcgctttcttcccttcctttctcgccacgttcgccggctttccccgtcaagctct
aaatcggggcatccctttagggttccgatttagtgctttacggcacctcgaccccaaaaaac
ttgattagggtgatggttcacgtagtgggccatcgccctgatagacggtttttcgccctttg
acgttggagtccacgttctttaatagtggactcttgttccaaactggaacaacactcaaccc
tatctcggtctattcttttgatttataagggattttggggatttcggcctattggttaaaaa
atgagctgatttaacaaaaatttaacgcgaattaattctgtggaatgtgtgtcagttagggt
gtggaaagtccccaggctccccaggcaggcagaagtatgcaaagcatgcatctcaattagtc
agcaaccaggtgtggaaagtccccaggctccccagcaggcagaagtatgcaaagcatgcatc
tcaattagtcagcaaccatagtcccgcccctaactccgcccatcccgcccctaactccgccc
agttccgcccattctccgccccatggctgactaattttttttatttatgcagaggccgaggc
cgcctctgcctctgagctattccagaagtagtgaggaggcttttttggaggcctaggctttt
gcaaaaagctcccgggagcttgtatatccattttcggatctgatcaagagacaggatgagga
tcgtttcgcatgattgaacaagatggattgcacgcaggttctccggccgcttgggtggagag
gctattcggctatgactgggcacaacagacaatcggctgctctgatgccgccgtgttccggc
tgtcagcgcaggggcgcccggttctttttgtcaagaccgacctgtccggtgccctgaatgaa
ctgcaggacgaggcagcgcggctatcgtggctggccacgacgggcgttccttgcgcagctgt
gctcgacgttgtcactgaagcgggaagggactggctgctattgggcgaagtgccggggcagg
atctcctgtcatctcaccttgctcctgccgagaaagtatccatcatggctgatgcaatgcgg
cggctgcatacgcttgatccggctacctgcccattcgaccaccaagcgaaacatcgcatcga
gcgagcacgtactcggatggaagccggtcttgtcgatcaggatgatctggacgaagagcatc
aggggctcgcgccagccgaactgttcgccaggctcaaggcgcgcatgcccgacggcgaggat
ctcgtcgtgacccatggcgatgcctgcttgccgaatatcatggtggaaaatggccgcttttc
tggattcatcgactgtggccggctgggtgtggcggaccgctatcaggacatagcgttggcta
cccgtgatattgctgaagagcttggcggcgaatgggctgaccgcttcctcgtgctttacggt
atcgccgctcccgattcgcagcgcatcgccttctatcgccttcttgacgagttcttctgagc
gggactctggggttcgaaatgaccgaccaagcgacgcccaacctgccatcacgagatttcga
ttccaccgccgccttctatgaaaggttgggcttcggaatcgttttccgggacgccggctgga
tgatcctccagcgcggggatctcatgctggagttcttcgcccaccccaacttgtttattgca
gcttataatggttacaaataaagcaatagcatcacaaatttcacaaataaagcatttttttc
actgcattctagttgtggtttgtccaaactcatcaatgtatcttatcatgtctgtataccgt
cgacctctagctagagcttggcgtaatcatggtcatagctgtttcctgtgtgaaattgttat
ccgctcacaattccacacaacatacgagccggaagcataaagtgtaaagcctggggtgccta
atgagtgagctaactcacattaattgcgttgcgctcactgcccgctttccagtcgggaaacc
tgtcgtgccagctgcattaatgaatcggccaacgcgcggggagaggcggtttgcgtattggg
cgctcttccgcttcctcgctcactgactcgctgcgctcggtcgttcggctgcggcgagcggt
atcagctcactcaaaggcggtaatacggttatccacagaatcaggggataacgcaggaaaga

FIG. 6C acatgtgagcaaaaggccagcaaaaggccaggaaccgtaaaaaggccgcgttgctggcgttt
ttccataggctccgcccccctgacgagcatcacaaaaatcgacgctcaagtcagaggtggcg
aaacccgacaggactataaagataccaggcgtttccccctggaagctccctcgtgcgctctc
ctgttccgaccctgccgcttaccggatacctgtccgcctttctcccttcgggaagcgtggcg
ctttctcaatgctcacgctgtaggtatctcagttcggtgtaggtcgttcgctccaagctggg
ctgtgtgcacgaaccccccgttcagcccgaccgctgcgccttatccggtaactatcgtcttg
agtccaacccggtaagacacgacttatcgccactggcagcagccactggtaacaggattagc
agagcgaggtatgtaggcggtgctacagagttcttgaagtggtggcctaactacggctacac
tagaaggacagtatttggtatctgcgctctgctgaagccagttaccttcggaaaaagagttg
gtagctcttgatccggcaaacaaaccaccgctggtagcggtggtttttttgtttgcaagcag
cagattacgcgcagaaaaaaaggatctcaagaagatcctttgatcttttctacggggtctga
cgctcagtggaacgaaaactcacgttaagggattttggtcatgagattatcaaaaaggatct
tcacctagatccttttaaattaaaaatgaagttttaaatcaatctaaagtatatatgagtaa
acttggtctgacagttaccaatgcttaatcagtgaggcacctatctcagcgatctgtctatt
tcgttcatccatagttgcctgactccccgtcgtgtagataactacgatacgggagggcttac
catctggccccagtgctgcaatgataccgcgagacccacgctcaccggctccagatttatca
gcaataaaccagccagccggaagggccgagcgcagaagtggtcctgcaactttatccgcctc
catccagtctattaattgttgccgggaagctagagtaagtagttcgccagttaatagtttgc
gcaacgttgttgccattgctacaggcatcgtggtgtcacgctcgtcgtttggtatggcttca
ttcagctccggttcccaacgatcaaggcgagttacatgatcccccatgttgtgcaaaaaagc
ggttagctccttcggtcctccgatcgttgtcagaagtaagttggccgcagtgttatcactca
tggttatggcagcactgcataattctcttactgtcatgccatccgtaagatgcttttctgtg
actggtgagtactcaaccaagtcattctgagaatagtgtatgcggcgaccgagttgctcttg
cccggcgtcaatacgggataataccgcgccacatagcagaactttaaaagtgctcatcattg
gaaaacgttcttcggggcgaaaactctcaaggatcttaccgctgttgagatccagttcgatg
taacccactcgtgcacccaactgatcttcagcatcttttactttcaccagcgtttctgggtg
agcaaaaacaggaaggcaaaatgccgcaaaaaagggaataagggcgacacggaaatgttgaa
tactcatactcttcctttttcaatattattgaagcatttatcagggttattgtctcatgagc
ggatacatatttgaatgtatttagaaaaataaacaaataggggttccgcgcacatttccccg
aaaagtgccacctgacgtcgacggatcgggagatc

FIG. 7A pcDIMer-L nt 1358 - 7909: L ORF MeV Schwarz (6552 nt = 2183 aa + stop codon)

agcttgcatgcctgcaggtcaattccctggcattatgcccagtacatgaccttatgggactt
tcctacttggcagtacatctacgtattagtcatcgctattaccatggtgatgcggttttggc
agtacatcaatgcgcgtggataccggtttgactcacggggatttccaagtctccaccccatt
cacgtcaatgggagtttgttttggcaccaaaatcaacgggactttccaaaatgtcgtaacaa
ctccgccccattgacgcaaatgggcggtaggcgtgtacggtgggaggtctatataagcagag
ctcgtttagtgaaccgtcagatcgcctggagacgccatccacgctgttttgacctccataga
agacaccgggaccgatccagcctggggatctagcctccgcggccgggaacggtgcattggaa
cgcggattccccgtgccaagagtgacgtaagtaccgcctatagagtctataggcccaccccc
ttggcttcttatgcatgctatactgtttttggcttggggtctatacacccccgcttcctcat
gttataggtgatggtatagcttagcctataggtgtgggttattgaccattattgaccactcc
cctattggtgacgatactttccattactaatccataacatggctctttgccacaactctctt
tattggctatatgccaatacactgtccttcagagactgacacggactctgtatttttacagg
atggggtctcatttattatttacaaattcacatatacaacaccaccgtccccagtgcccgca
gtttttattaaacataacgtgggatctccacgcgaatctcgggtacgtgttccggacatggg
ctcttctccggtagcggcggagctcctacatccgagccctgctcccatgcctccagcgactc
atggtcgctcggcagctccttgctcctaacagtggaggccagacttaggcacagcacgatgc
ccaccaccaccagtgtgccgcacaaggccgtggcggtagggtatgtgtctgaaaatgagctc
ggggagcgggcttgcaccgctgacgcatttggaagacttaaggcagcggcagaagaagatgc
aggcagctgagttgttgtgttctgataagagtcagaggtaactcccgttgcggtgctgttaa
cggtggagggcagtgtagtctgagcagtactcgttgctgccgcgcgcgccaccagacataat
agctgacagactaacagactgttcctttccatgggtcttttctgcagtcaccgtccttgaca
cgatcggatcccgggtacctctagaagatctgatatcgtcgacctcgacgccaccatggact
cgctatctgtcaaccagatcttataccctgaagttcacctagatagcccgatagttaccaat
aagatagtagccatcctggagtatgctcgagtccctcacgcttacagcctggaggaccctac
actgtgtcagaacatcaagcaccgcctaaaaaacggattttccaaccaaatgattataaaca
atgtggaagttgggaatgtcatcaagtccaagcttaggagttatccggcccactctcatatt
ccatatccaaattgtaatcaggatttatttaacatagaagacaaagagtcaacgaggaagat
ccgtgaactcctcaaaaaggggaattcgctgtactccaaagtcagtgataaggttttccaat
gcttaagggacactaactcacggcttggcctaggctccgaattgagggaggacatcaaggag
aaagttattaacttgggagtttacatgcacagctcccagtggtttgagccctttctgttttg
gtttacagtcaagactgagatgaggtcagtgattaaatcacaaacccatacttgccatagga
ggagacacacacctgtattcttcactggtagttcagttgagttgctaatctctcgtgacctt
gttgctataatcagtaaagagtctcaacatgtatattacctgacatttgaactggttttgat
gtattgtgatgtcatagaggggaggttaatgacagagaccgctatgactattgatgctaggt
atacagagcttctaggaagagtcagatacatgtggaaactgatagatggtttcttccctgca
ctcgggaatccaacttatcaaattgtagccatgctggagcctctttcacttgcttacctgca
gctgagggatataacagtagaactcagaggtgctttccttaaccactgctttactgaaatac
atgatgttcttgaccaaaacgggttttctgatgaaggtacttatcatgagttaactgaagct
ctagattacattttcataactgatgacatacatctgacaggggagatttctcatttttcag
aagtttcggccaccccagacttgaagcagtaacggctgctgaaaatgttaggaaatacatga
atcagcctaaagtcattgtgtatgagactctgatgaaaggtcatgccatatttgtggaatc
ataatcaacggctatcgtgacaggcacggaggcagttggccaccgctgaccctcccctgca
tgctgcagacacaatccggaatgctcaagcttcaggtgaagggttaacacatgagcagtgcg
ttgataactggaaatcttttgctggagtgaaatttggctgctttatgcctcttagcctggat
agtgatctgacaatgtacctaaaggacaaggcacttgctgctctccaaagggaatgggattc

FIG. 7B agtttacccgaaagagttcctgcgttacgaccctcccaagggaaccgggtcacggaggcttg
tagatgttttccttaatgattcgagctttgacccatatgatgtgataatgtatgttgtaagt
ggagcttacctccatgaccctgagttcaacctgtcttacagcctgaaagaaaggagatcaa
ggaaacaggtagacttttgctaaaatgacttacaaaatgagggcatgccaagtgattgctg
aaaatctaatctcaaacgggattggcaaatattttaaggacaatgggatggccaaggatgag
cacgatttgactaaggcactccacactctagctgtctcaggagtccccaaagatctcaaaga
aagtcacaggggggggccagtcttaaaacctactcccgaagcccagtccacacaagtacca
ggaacgtgagagcagcaaaagggtttatagggttccctcaagtaattcggcaggaccaagac
actgatcatccggagaatatggaagcttacgagacagtcagtgcatttatcacgactgatct
caagaagtactgccttaattggagatatgagaccatcagcttgtttgcacagaggctaaatg
agatttacggattgccctcatttttccagtggctgcataagaggcttgagacctctgtcctg
tatgtaagtgaccctcattgcccccccgaccttgacgcccatatcccgttatataaagtccc
caatgatcaaatcttcattaagtaccctatgggaggtatagaagggtattgtcagaagctgt
ggaccatcagcaccattccctatctatacctggctgcttatgagagcggagtaaggattgct
tcgttagtgcaaggggacaatcagaccatagccgtaacaaaaagggtacccagcacatggcc
ctacaaccttaagaaacgggaagctgctagagtaactagagattactttgtaattcttaggc
aaaggctacatgatattggccatcacctcaaggcaaatgagacaattgtttcatcacatttt
tttgtctattcaaaaggaatatattatgatgggctacttgtgtcccaatcactcaagagcat
cgcaagatgtgtattctggtcagagactatagttgatgaaacaagggcagcatgcagtaata
ttgctacaacaatggctaaaagcatcgagagaggttatgaccgttaccttgcatattccctg
aacgtcctaaaagtgatacagcaaattctgatctctcttggcttcacaatcaattcaaccat
gacccgggatgtagtcatacccctcctcacaaacaacgacctcttaataaggatggcactgt
tgcccgctcctattgggggatgaattatctgaatatgagcaggctgtttgtcagaaacatc
ggtgatccagtaacatcatcaattgctgatctcaagagaatgattctcgcctcactaatgcc
tgaagagaccctccatcaagtaatgacacaacaaccggggactcttcattcctagactggg
ctagcgacccttactcagcaaatcttgtatgtgtccagagcatcactagactcctcaagaac
ataactgcaaggtttgtcctgatccatagtccaaacccaatgttaaaaggattattccatga
tgacagtaaagaagaggacgagggactggcggcattcctcatggacaggcatattatagtac
ctagggcagctcatgaaatcctggatcatagtgtcacaggggcaagagagtctattgcaggc
atgctggataccacaaaaggcttgattcgagccagcatgaggaaggggggttaacctctcg
agtgataaccagattgtccaattatgactatgaacaattcagagcagggatggtgctattga
caggaagaaagagaaatgtcctcattgacaaagagtcatgttcagtgcagctggcgagagct
ctaagaagccatatgtgggcgaggctagctcgaggacggcctatttacggccttgaggtccc
tgatgtactagaatctatgcgaggccaccttattcggcgtcatgagacatgtgtcatctgcg
agtgtggatcagtcaactacggatggtttttgtcccctcgggttgccaactggatgatatt
gacaaggaaacatcatccttgagagtcccatatattggttctaccactgatgagagaacaga
catgaagcttgccttcgtaagagccccaagtcgatccttgcgatctgctgttagaatagcaa
cagtgtactcatgggcttacggtgatgatgatagctcttggaacgaagcctggttgttggct
aggcaaagggccaatgtgagcctggaggagctaagggtgatcactcccatctcaacttcgac
taatttagcgcataggttgagggatcgtagcactcaagtgaaatactcaggtacatcccttg
tccgagtggcgaggtataccacaatctccaacgacaatctctcatttgtcatatcagataag
aaggttgatactaactttatataccaacaaggaatgcttctagggttgggtgttttagaaac
attgtttcgactcgagaaagataccggatcatctaacacggtattacatcttcacgtcgaaa
cagattgttgcgtgatcccgatgatagatcatcccaggatacccagctcccgcaagctagag
ctgagggcagagctatgtaccaacccattgatatatgataatgcacctttaattgacagaga
tgcaacaaggctatacacccagagccataggaggcaccttgtggaatttgttacatggtcca
caccccaactatatcacattttagctaagtccacagcactatctatgattgacctggtaaca
aaatttgagaaggaccatatgaatgaaatttcagctctcataggggatgacgatatcaatag
tttcataactgagtttctgctcatagagccaagattattcactatctacttgggccagtgtg
cggccatcaattgggcatttgatgtacattatcatagaccatcagggaaatatcagatgggt

FIG. 7C gagctgttgtcatcgttcctttctagaatgagcaaaggagtgtttaaggtgcttgtcaatgc
tctaagccacccaaagatctacaagaaattctggcattgtggtattatagagcctatccatg
gtccttcacttgatgctcaaaacttgcacacaactgtgtgcaacatggtttacacatgctat
atgacctacctcgacctgttgttgaatgaagagttagaagagttcacatttctcttgtgtga
aagcgacgaggatgtagtaccggacagattcgacaacatccaggcaaaacacttatgtgttc
tggcagatttgtactgtcaaccagggacctgcccaccaattcgaggtctaagaccggtagag
aaatgtgcagttctaaccgaccatatcaaggcagaggctatgttatctccagcaggatcttc
gtggaacataaatccaattattgtagaccattactcatgctctctgacttatctccggcgag
gatcgatcaaacagataagattgagagttgatccaggattcattttcgacgccctcgctgag
gtaaatgtcagtcagccaaagatcggcagcaacaacatctcaaatatgagcatcaaggcttt
cagacccccacacgatgatgttgcaaaattgctcaaagatatcaacacaagcaagcacaatc
ttcccatttcagggggcaatctcgccaattatgaaatccatgctttccgcagaatcgggttg
aactcatctgcttgctacaaagctgttgagatatcaacattaattaggagatgccttgagcc
aggggaggacggcttgttcttgggtgagggatcgggttctatgttgatcacttataaagaga
tacttaaactaaacaagtgcttctataatagtggggtttccgccaattctagatctggtcaa
agggaattagcaccctatccctccgaagttggccttgtcgaacacagaatgggagtaggtaa
tattgtcaaagtgctctttaacgggaggcccgaagtcacgtgggtaggcagtgtagattgct
tcaatttcatagttagtaatatccctacctctagtgtggggtttatccattcagatatagag
accttgcctgacaaagatactatagagaagctagaggaattggcagccatcttatcgatggc
tctgctcctgggcaaaataggatcaatactggtgattaagcttatgcctttcagcggggatt
ttgttcagggatttataagttatgtagggtctcattatagagaagtgaaccttgtataccct
agatacagcaacttcatctctactgaatcttatttggttatgacagatctcaaggctaaccg
gctaatgaatcctgaaaagattaagcagcagataattgaatcatctgtgaggacttcacctg
gacttataggtcacatcctatccattaagcaactaagctgcatacaagcaattgtgggagac
gcagttagtagaggtgatatcaatcctactctgaaaaaacttacacctatagagcaggtgct
gatcaattgcgggttggcaattaacggacctaagctgtgcaaagaattgatccaccatgatg
ttgcctcagggcaagatggattgcttaattctatactcatcctctacagggagttggcaaga
ttcaaagacaaccaaagaagtcaacaagggatgttccacgcttaccccgtattggtaagtag
caggcaacgagaacttatatctaggatcacccgcaaattctgggggcacattcttctttact
ccgggaacaaaaagttgataaataagtttatccagaatctcaagtccggctatctgatacta
gacttacaccagaatatcttcgttaagaatctatccaagtcagagaaacagattattatgac
gggggtttgaaacgtgagtgggtttttaaggtaacagtcaaggagaccaaagaatggtata
agttagtcggatacagtgccctgattaaggactaattggttgaactccggaaccctaatcct
gccctaggtggttaggcattatttgcagaattctagatcccacgtcactattgtatactcta
tattatactctatgttatactctgtaatcctactcaataaacgtgtcacgcctgtgaaaccg
tactaagtctcccgtgtcttcttatcaccatcaggtgacatcctcgcccaggctgtcaatca
tgccggtatcgattccagtagcaccggccccacgctgacaacccactcttgcagcgttagca
gcgcccctcttaacaagccgacccccaccagcgtcgcggttactaacactcctctccccgac
ctgcagcccaagctctagagggccctattctatagtgtcacctaaatgctagagctcgctga
tcagcctcgactgtgccttctagttgccagccatctgttgtttgcccctcccccgtgccttc
cttgaccctggaaggtgccactcccactgtcctttcctaataaaatgaggaaattgcatcgc
attgtctgagtaggtgtcattctattctggggggtggggtggggcaggacagcaagggggag
gattgggaagacaatagcaggcatgctggggatgcggtgggctctatggcttctgaggcgga
aagaaccagctggggctctagggggtatccccacgcgccctgtagcggcgcattaagcgcgg
cgggtgtggtggttacgcgcagcgtgaccgctacacttgccagcgccctagcgcccgctcct
ttcgctttcttcccttcctttctcgccacgttcgccggctttccccgtcaagctctaaatcg
ggcatccctttagggttccgatttagtgctttacggcacctcgaccccaaaaaacttgatt
agggtgatggttcacgtagtgggccatcgccctgatagacggtttttcgccctttgacgttg
gagtccacgttctttaatagtggactcttgttccaaactggaacaacactcaaccctatctc
ggtctattcttttgatttataagggattttggggatttcggcctattggttaaaaaatgagc

FIG. 7D

```
tgatttaacaaaaatttaacgcgaattaattctgtggaatgtgtgtcagttagggtgtggaa
agtccccaggctccccaggcaggcagaagtatgcaaagcatgcatctcaattagtcagcaac
caggtgtggaaagtccccaggctccccagcaggcagaagtatgcaaagcatgcatctcaatt
agtcagcaaccatagtcccgcccctaactccgcccatcccgcccctaactccgcccagttcc
gcccattctccgccccatggctgactaattttttttatttatgcagaggccgaggccgcctc
tgcctctgagctattccagaagtagtgaggaggcttttttggaggcctaggcttttgcaaaa
agctcccgggagcttgtatatccattttcggatctgatcaagagacaggatgaggatcgttt
cgcatgattgaacaagatggattgcacgcaggttctccggccgcttgggtggagaggctatt
cggctatgactgggcacaacagacaatcggctgctctgatgccgccgtgttccggctgtcag
cgcaggggcgcccggttctttttgtcaagaccgacctgtccggtgccctgaatgaactgcag
gacgaggcagcgcggctatcgtggctggccacgacgggcgttccttgcgcagctgtgctcga
cgttgtcactgaagcgggaagggactggctgctattgggcgaagtgccggggcaggatctcc
tgtcatctcaccttgctcctgccgagaaagtatccatcatggctgatgcaatgcggcggctg
catacgcttgatccggctacctgcccattcgaccaccaagcgaaacatcgcatcgagcgagc
acgtactcggatggaagccggtcttgtcgatcaggatgatctggacgaagagcatcaggggc
tcgcgccagccgaactgttcgccaggctcaaggcgcgcatgcccgacggcgaggatctcgtc
gtgacccatggcgatgcctgcttgccgaatatcatggtggaaaatggccgcttttctggatt
catcgactgtggccggctgggtgtggcggaccgctatcaggacatagcgttggctacccgtg
atattgctgaagagcttggcggcgaatgggctgaccgcttcctcgtgctttacggtatcgcc
gctcccgattcgcagcgcatcgccttctatcgccttcttgacgagttcttctgagcgggact
ctggggttcgaaatgaccgaccaagcgacgcccaacctgccatcacgagatttcgattccac
cgccgccttctatgaaaggttgggcttcggaatcgttttccgggacgccggctggatgatcc
tccagcgcggggatctcatgctggagttcttcgcccaccccaacttgtttattgcagcttat
aatggttacaaataaagcaatagcatcacaaatttcacaaataaagcatttttttcactgca
ttctagttgtggtttgtccaaactcatcaatgtatcttatcatgtctgtataccgtcgacct
ctagctagagcttggcgtaatcatggtcatagctgtttcctgtgtgaaattgttatccgctc
acaattccacacaacatacgagccggaagcataaagtgtaaagcctggggtgcctaatgagt
gagctaactcacattaattgcgttgcgctcactgcccgctttccagtcgggaaacctgtcgt
gccagctgcattaatgaatcggccaacgcgcggggagaggcggtttgcgtattgggcgctct
tccgcttcctcgctcactgactcgctgcgctcggtcgttcggctgcggcgagcggtatcagc
tcactcaaaggcggtaatacggttatccacagaatcaggggataacgcaggaaagaacatgt
gagcaaaaggccagcaaaaggccaggaaccgtaaaaaggccgcgttgctggcgtttttccat
aggctccgcccccctgacgagcatcacaaaaatcgacgctcaagtcagaggtggcgaaaccc
gacaggactataaagataccaggcgtttccccctggaagctccctcgtgcgctctcctgttc
cgaccctgccgcttaccggatacctgtccgcctttctcccttcgggaagcgtggcgctttct
caatgctcacgctgtaggtatctcagttcggtgtaggtcgttcgctccaagctgggctgtgt
gcacgaaccccccgttcagcccgaccgctgcgccttatccggtaactatcgtcttgagtcca
acccggtaagacacgacttatcgccactggcagcagccactggtaacaggattagcagagcg
aggtatgtaggcggtgctacagagttcttgaagtggtggcctaactacggctacactagaag
gacagtatttggtatctgcgctctgctgaagccagttaccttcggaaaaagagttggtagct
cttgatccggcaaacaaaccaccgctggtagcggtggtttttttgtttgcaagcagcagatt
acgcgcagaaaaaaaggatctcaagaagatcctttgatcttttctacggggtctgacgctca
gtggaacgaaaactcacgttaagggattttggtcatgagattatcaaaaaggatcttcacct
agatccttttaaattaaaaatgaagttttaaatcaatctaaagtatatatgagtaaacttgg
tctgacagttaccaatgcttaatcagtgaggcacctatctcagcgatctgtctatttcgttc
atccatagttgcctgactccccgtcgtgtagataactacgatacgggagggcttaccatctg
gccccagtgctgcaatgataccgcgagacccacgctcaccggctccagatttatcagcaata
aaccagccagccggaagggccgagcgcagaagtggtcctgcaactttatccgcctccatcca
gtctattaattgttgccgggaagctagagtaagtagttcgccagttaatagtttgcgcaacg
ttgttgccattgctacaggcatcgtggtgtcacgctcgtcgtttggtatggcttcattcagc
```

FIG. 7E tccggttcccaacgatcaaggcgagttacatgatcccccatgttgtgcaaaaaagcggttag
ctccttcggtcctccgatcgttgtcagaagtaagttggccgcagtgttatcactcatggtta
tggcagcactgcataattctcttactgtcatgccatccgtaagatgcttttctgtgactggt
gagtactcaaccaagtcattctgagaatagtgtatgcggcgaccgagttgctcttgcccggc
gtcaatacgggataataccgcgccacatagcagaactttaaaagtgctcatcattggaaaac
gttcttcggggcgaaaactctcaaggatcttaccgctgttgagatccagttcgatgtaaccc
actcgtgcacccaactgatcttcagcatcttttactttcaccagcgtttctgggtgagcaaa
aacaggaaggcaaaatgccgcaaaaaagggaataagggcgacacggaaatgttgaatactca
tactcttcctttttcaatattattgaagcatttatcagggttattgtctcatgagcggatac
atatttgaatgtatttagaaaaataaacaaataggggttccgcgcacatttccccgaaaagt
gccacctgacgtcgacggatcgggagatc RBE
TFK-1
HuCCT1
viability (% control)
5-FC [log mM]
control
Id-SCD MOI 0.01
Id-SCD MOI 0.1
Id-SCD MOI 1

FIG. 8B

RBE

| 5-FC | control | MOI 0.01 | MOI 0.1 | MOI 1 |
|---|---|---|---|---|
| 0 | 100.00 | 112.35 | 85.27 | 41.90 |
| 0.0001 | 109.83 | 118.46 | 73.62 | 37.70 |
| 0.001 | 110.54 | 108.68 | 45.03 | 27.18 |
| 0.01 | 107.05 | 91.61 | 25.56 | 10.36 |
| 0.1 | 101.41 | 69.78 | 11.91 | 1.51 |
| 1 | 92.62 | 56.72 | 9.08 | 1.94 |

TFK-1

| 5-FC | control | MOI 0.01 | MOI 0.1 | MOI 1 |
|---|---|---|---|---|
| 0 | 100.00 | 83.05 | 47.97 | 13.61 |
| 0.0001 | 100.03 | 77.25 | 32.41 | 8.74 |
| 0.001 | 101.18 | 69.85 | 21.43 | 6.42 |
| 0.01 | 100.83 | 51.79 | 13.35 | 5.24 |
| 0.1 | 95.16 | 33.38 | 6.76 | 3.92 |
| 1 | 94.60 | 15.83 | 2.75 | 2.70 |

HuCCT1

| 5-FC | control | MOI 0.01 | MOI 0.1 | MOI 1 |
|---|---|---|---|---|
| 0 | 100.00 | 89.26 | 71.27 | 47.98 |
| 0.0001 | 98.55 | 95.65 | 76.40 | 44.87 |
| 0.001 | 97.64 | 93.53 | 64.04 | 27.78 |
| 0.01 | 96.01 | 80.94 | 39.96 | 21.98 |
| 0.1 | 96.95 | 51.17 | 17.00 | 5.21 |
| 1 | 90.08 | 33.41 | 2.68 | 1.43 |

RBE
relative LDH release
100
Triton
75
50
25
0
0
$10^{-4}$
$10^{-3}$
$10^{-2}$
$10^{-1}$
$10^{0}$
5-FC [mM]
control
MOI 0.01
MOI 0.1
MOI 1
TFK-1
relative LDH release
100
Triton
75
50
25
0
0
$10^{-4}$
$10^{-3}$
$10^{-2}$
$10^{-1}$
$10^{0}$
5-FC [mM]
control
MOI 0.01
MOI 0.1
MOI 1
HuCCT1
relative LDH release
100
Triton
75
50
25
0
0
$10^{-4}$
$10^{-3}$
$10^{-2}$
$10^{-1}$
$10^{0}$
5-FC [mM]
control
MOI 0.01
MOI 0.1
MOI 1

FIG. 10B

SAS

| 5-FC | control | MOI 0.01 | MOI 0.1 | MOI 1 |
|---|---|---|---|---|
| 0 | 100.00 | 122.22 | 112.75 | 101.55 |
| 0.0001 | 124.51 | 147.54 | 127.69 | 84.64 |
| 0.001 | 130.56 | 147.65 | 114.36 | 45.82 |
| 0.01 | 129.65 | 140.91 | 79.77 | 35.27 |
| 0.1 | 130.95 | 104.41 | 52.75 | 23.72 |
| 1 | 105.35 | 84.26 | 40.10 | 17.44 |

HTB-43 FaDu

| 5-FC | control | MOI 0.01 | MOI 0.1 | MOI 1 |
|---|---|---|---|---|
| 0 | 100.00 | 84.96 | 76.55 | 33.43 |
| 0.0001 | 116.65 | 94.74 | 83.10 | 39.22 |
| 0.001 | 115.59 | 86.81 | 74.80 | 29.12 |
| 0.01 | 115.42 | 91.38 | 52.71 | 16.48 |
| 0.1 | 114.71 | 68.53 | 29.39 | 9.25 |
| 1 | 102.32 | 36.96 | 18.29 | 5.71 |

FIG. 11B

| HTB-43 FaDu | | | | | SAS | | | | |
|---|---|---|---|---|---|---|---|---|---|
| 5-FC | control | MOI 0.01 | MOI 0.1 | MOI 1 | 5-FC | control | MOI 0.01 | MOI 0.1 | MOI 1 |
| 0 | 5.21 | 4.99 | 7.72 | 16.40 | 0 | 4.97 | 4.31 | 6.30 | 17.65 |
| 0.0001 | 3.06 | 2.85 | 5.44 | 10.29 | 0.0001 | 2.86 | 3.28 | 2.87 | 15.63 |
| 0.001 | 2.82 | 2.55 | 5.77 | 9.33 | 0.001 | 2.35 | 2.83 | 2.84 | 20.98 |
| 0.01 | 2.32 | 2.86 | 6.33 | 15.28 | 0.01 | 2.21 | 2.57 | 4.62 | 27.94 |
| 0.1 | 3.69 | 5.01 | 9.28 | 23.26 | 0.1 | 2.34 | 3.52 | 6.81 | 36.13 |
| 1 | 4.19 | 12.06 | 15.02 | 36.48 | 1 | 3.22 | 6.19 | 10.26 | 37.72 |

A 673
cell mass (%of control)
200
150
100
50
0
0
0.0001
0.001
0.01
0.1
1
5-FC [mM]
MOCK
MOI 0.01
MOI 0.1
MOI 1
BRZ
cell mass [% of control]
SRH
% cell mass of control

| 5-FC | control | MOI 0,01 | MOI 0.1 | MOI 1 |
|---|---|---|---|---|
| 0 | 100.00 | 62.90 | 30.46 | 3.88 |
| 0.0001 | 124.63 | 69.80 | 28.06 | 3.73 |
| 0.001 | 118.90 | 70.17 | 13.83 | 2.41 |
| 0.01 | 120.45 | 45.01 | 8.12 | 3.14 |
| 0.1 | 118.41 | 25.78 | 3.52 | 1.78 |
| 1 | 108.66 | 17.93 | 2.64 | 2.39 |

BRZ

| 5-FC | control | MOI 0.01 | MOI 0.1 | MOI 1 |
|---|---|---|---|---|
| 0 | 100.00 | 94.02 | 85.64 | 24.64 |
| 0.0001 | 97.08 | 95.68 | 83.49 | 28.30 |
| 0.001 | 96.60 | 97.67 | 80.17 | 22.26 |
| 0.01 | 99.55 | 92.16 | 63.81 | 17.90 |
| 0.1 | 98.34 | 90.63 | 35.95 | 12.91 |
| 1 | 94.72 | 75.29 | 25.75 | 9.00 |

SRH

| 5-FC | control | MOI 0.01 | MOI 0.1 | MOI 1 |
|---|---|---|---|---|
| 0 | 100.00 | 108.37 | 100.90 | 89.80 |
| 0.0001 | 108.46 | 123.06 | 116.04 | 96.24 |
| 0.001 | 109.91 | 123.13 | 108.19 | 83.86 |
| 0.01 | 114.29 | 116.24 | 110.56 | 62.09 |
| 0.1 | 117.06 | 121.99 | 73.92 | 52.01 |
| 1 | 106.57 | 90.65 | 53.43 | 44.59 |

A 673
% LDH release
90
80
70
60
50
40
30
20
10
0
0
0.0001
0.001
0.01
0.1
1
5-FC [mM]
MOCK
MOI 0.01
MOI 0.1
MOI 1
SRH
% LDH release
5-FC (mM)
MOCK
MOI 0.01
MOI 0.1
MOI 1

FIG. 13B

| A 673 | | | | | SRH | | | | |
|---|---|---|---|---|---|---|---|---|---|
| 5-FC | control | MOI 0.01 | MOI 0.1 | MOI 1 | 5-FC | control | MOI 0.01 | MOI 0.1 | MOI 1 |
| 0 | 11.52 | 9.12 | 20.72 | 53.89 | 0 | 14.64 | 10.98 | 19.49 | 22.90 |
| 0.0001 | 4.39 | 6.73 | 12.28 | 40.86 | 0.0001 | 8.59 | 10.07 | 11.21 | 18.43 |
| 0.001 | 4.42 | 6.37 | 10.72 | 44.62 | 0.001 | 6.55 | 8.62 | 10.65 | 21.91 |
| 0.01 | 3.33 | 4.93 | 18.52 | 53.52 | 0.01 | 6.34 | 7.38 | 10.78 | 22.64 |
| 0.1 | 3.69 | 10.22 | 21.94 | 74.71 | 0.1 | 13.65 | 9.42 | 17.34 | 27.86 |
| 1 | 5.12 | 16.01 | 37.49 | 80.47 | 1 | 8.05 | 16.84 | 25.07 | 31.23 |

| 5-FC | control | MOI 0.1 | MOI 1 | MOI 10 |
|---|---|---|---|---|
| 0 | 100.00 | 83.90 | 71.73 | 32.26 |
| 0.0001 | 106.35 | 92.90 | 75.01 | 31.76 |
| 0.001 | 106.30 | 87.21 | 64.26 | 23.31 |
| 0.01 | 111.73 | 80.18 | 48.34 | 22.31 |
| 0.1 | 109.28 | 56.45 | 39.55 | 15.64 |
| 1 | 107.08 | 44.07 | 36.48 | 10.81 |

CCS
cell mass (%of control)
140
130
120
110
100
90
80
70
60
50
40
30
20
10
0
0
0.0001
0.001
0.01
0.1
1
5-FC [mM]
MOCK
MOI 0.1
MOI 1
MOI 10
LM
cell mass (% of control)
0
0.0001
0.001
0.01
0.1
1.0
5-FC [mM]
MOCK
MOI 0.1
MOI 1
MOI 10

FIG. 15B

| LM | | | | | CCS | | | | |
|---|---|---|---|---|---|---|---|---|---|
| 5-FC | control | MOI 0.1 | MOI 1 | MOI 10 | 5-FC | control | MOI 0.1 | MOI 1 | MOI 10 |
| 0 | 100.00 | 99.75 | 75.41 | 26.68 | 0 | 100.00 | 105.29 | 94.73 | 50.04 |
| 0.0001 | 110.92 | 109.42 | 75.58 | 19.10 | 0.0001 | 110.26 | 115.57 | 103.50 | 56.67 |
| 0.001 | 118.08 | 106.01 | 51.44 | 7.93 | 0.001 | 119.40 | 118.08 | 99.57 | 41.23 |
| 0.01 | 118.36 | 81.25 | 22.82 | 5.79 | 0.01 | 120.31 | 107.84 | 64.13 | 26.07 |
| 0.1 | 115.34 | 37.63 | 16.96 | 4.71 | 0.1 | 117.63 | 72.38 | 43.60 | 17.27 |
| 1 | 103.00 | 20.20 | 5.59 | 2.09 | 1 | 115.72 | 45.22 | 21.35 | 8.07 |

STO
cell mass (% of control)
5-FC [mM]
MOCK
MOI 0.01
MOI 0.1
MOI 1
ZAF
Cell mass (%of control)
5-FC [mM]
MOCK
MOI 0.01
MOI 0.1
MOI 1
KD
cell mass (% of control)
5-FC [mM]
MOCK
MOI 0.01
MOI 0.1
MOI 1

FIG. 16B

ZAF

| 5-FC | control | MOI 0.01 | MOI 0.1 | MOI 1 |
|---|---|---|---|---|
| 0 | 99.92 | 102.19 | 51.36 | 12.64 |
| 0.0001 | 106.79 | 98.75 | 54.55 | 6.01 |
| 0.001 | 111.00 | 103.62 | 47.79 | 5.39 |
| 0.01 | 108.04 | 71.75 | 15.92 | 1.97 |
| 0.1 | 114.76 | 38.10 | 5.71 | 1.08 |
| 1 | 105.84 | 26.66 | 3.38 | 1.24 |

STO

| 5-FC | control | MOI 0.01 | MOI 0.1 | MOI 1 |
|---|---|---|---|---|
| 0 | 100.00 | 89.47 | 66.29 | 23.53 |
| 0.0001 | 118.38 | 104..52 | 70.59 | 24.92 |
| 0.001 | 107.95 | 100.76 | 61.99 | 18.46 |
| 0.01 | 115.28 | 92.52 | 41.69 | 10.93 |
| 0.1 | 115.60 | 56.72 | 20.27 | 6.34 |
| 1 | 110.65 | 33.31 | 13.69 | 5.88 |

KD

| 5-FC | control | MOI 0.01 | MOI 0.1 | MOI 1 |
|---|---|---|---|---|
| 0 | 100.00 | 93.33 | 43.65 | 5.89 |
| 0.0001 | 107.06 | 96.33 | 43.66 | 4.77 |
| 0.001 | 105.86 | 90.88 | 27.11 | 3.20 |
| 0.01 | 108.86 | 71.89 | 20.16 | 3.15 |
| 0.1 | 107.89 | 44.46 | 14.72 | 2.99 |
| 1 | 104.54 | 25.,59 | 10.26 | 2.20 |

FIG. 17A
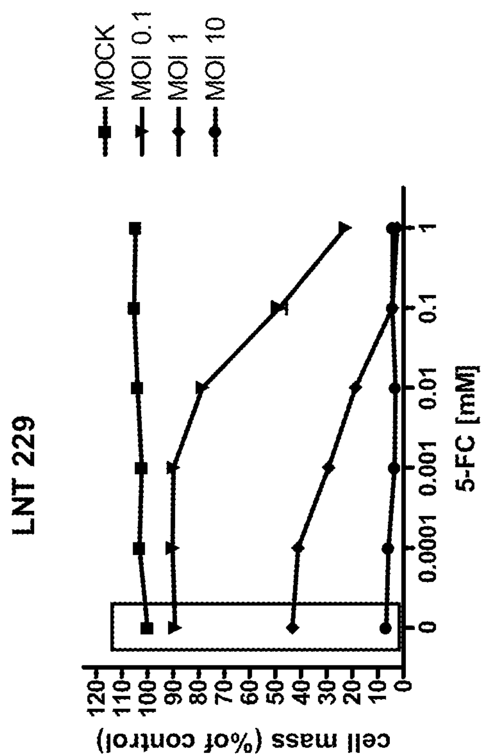
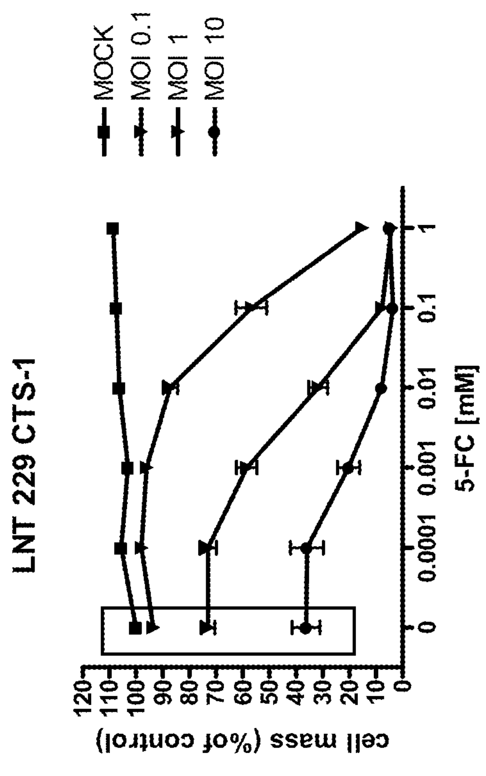

FIG. 17B

LNT 229

| 5-FC | control | MOI 0.1 | MOI 1 | MOI 10 |
|---|---|---|---|---|
| 0 | 100.00 | 89.35 | 43.51 | 6.79 |
| 0.0001 | 103.18 | 90.30 | 41.21 | 5.84 |
| 0.001 | 102.32 | 89.94 | 29.37 | 3.49 |
| 0.01 | 103.93 | 78.49 | 18.76 | 3.19 |
| 0.1 | 105.24 | 48.50 | 4.35 | 4.29 |
| 1 | 104.76 | 22.70 | 2.59 | 4.17 |

LNT 229 CTS-1

| 5-FC | control | MOI 0.1 | MOI 1 | MOI 10 |
|---|---|---|---|---|
| 0 | 100.00 | 93.55 | 73.07 | 36.29 |
| 0.0001 | 105.58 | 98.10 | 73.09 | 36.00 |
| 0.001 | 103.02 | 96.18 | 58.57 | 20.31 |
| 0.01 | 106.34 | 87.12 | 31.76 | 7.90 |
| 0.1 | 107.32 | 56.77 | 7.78 | 3.76 |
| 1 | 108.52 | 15.21 | 4.23 | 5.01 |

| 5-FC | control | MOI 0.1 | MOI 1 | MOI 10 |
|---|---|---|---|---|
| 0 | 100.00 | 100.61 | 66.89 | 7.78 |
| 0.0001 | 101.78 | 100.29 | 66.99 | 8.87 |
| 0.001 | 105.74 | 97.77 | 40.18 | 5.07 |
| 0.01 | 104.95 | 71.13 | 12.20 | 3.41 |
| 0.1 | 103.62 | 32.49 | 3.69 | 4.17 |
| 1 | 104.71 | 13.19 | 3.45 | 4.00 |

LN 18 Apoptosis resistant

| 5-FC | control | MOI 0.1 | MOI 1 | MOI 10 |
|---|---|---|---|---|
| 0 | 100.00 | 106.54 | 78.31 | 21.79 |
| 0.0001 | 104.10 | 107.26 | 82.75 | 22.26 |
| 0.001 | 106.21 | 101.39 | 67.85 | 15.34 |
| 0.01 | 109.17 | 95.91 | 42.64 | 10.47 |
| 0.1 | 109.98 | 69.32 | 23.56 | 11.25 |
| 1 | 101.87 | 52.57 | 17.38 | 8.95 |

ACHN
HOP-62
M14
no 5-FC
5-FC [1 mM]
cell mass (% of control)
MOI
MOCK
0.1
1
10
0
10
20
30
40
50
60
70
80
90
100
110
120

FIG. 19B

ACHN

| 5-FC | control | MOI 0.1 | MOI 1 | MOI 10 |
|---|---|---|---|---|
| 0 | 100.00 | 93.63 | 79.79 | 42.91 |
| 1 | 96.38 | 41.95 | 14.62 | 1.89 |

HOP-62

| 5-FC | control | MOI 0.1 | MOI 1 | MOI 10 |
|---|---|---|---|---|
| 0 | 100.00 | 95.50 | 83.74 | 50.50 |
| 1 | 103.08 | 32.71 | 13.50 | 9.55 |

M14

| 5-FC | control | MOI 0.1 | MOI 1 | MOI 10 |
|---|---|---|---|---|
| 0 | 100.00 | 96.22 | 84.30 | 41.96 |
| 1 | 106.23 | 40.71 | 24.12 | 15.06 |

KM12
HCT-15
cell mass (% of control)
MOI
MOCK
0.1
1
10
no 5-FC
5-FC [1 mM]
5-FC [1mM]

FIG. 20B

| KM12 | | | | | HCT-15 | | | | |
|---|---|---|---|---|---|---|---|---|---|
| 5-FC | control | MOI 0.1 | MOI 1 | MOI 10 | 5-FC | control | MOI 0.1 | MOI 1 | MOI 10 |
| 0 | 100.00 | 100.65 | 86.91 | 29.73 | 0 | 100.00 | 110.12 | 98.41 | 85.13 |
| 1 | 99.34 | 45.75 | 5.98 | 1.76 | 1 | 94.77 | 68.66 | 34.54 | 1.71 |

FIG. 21

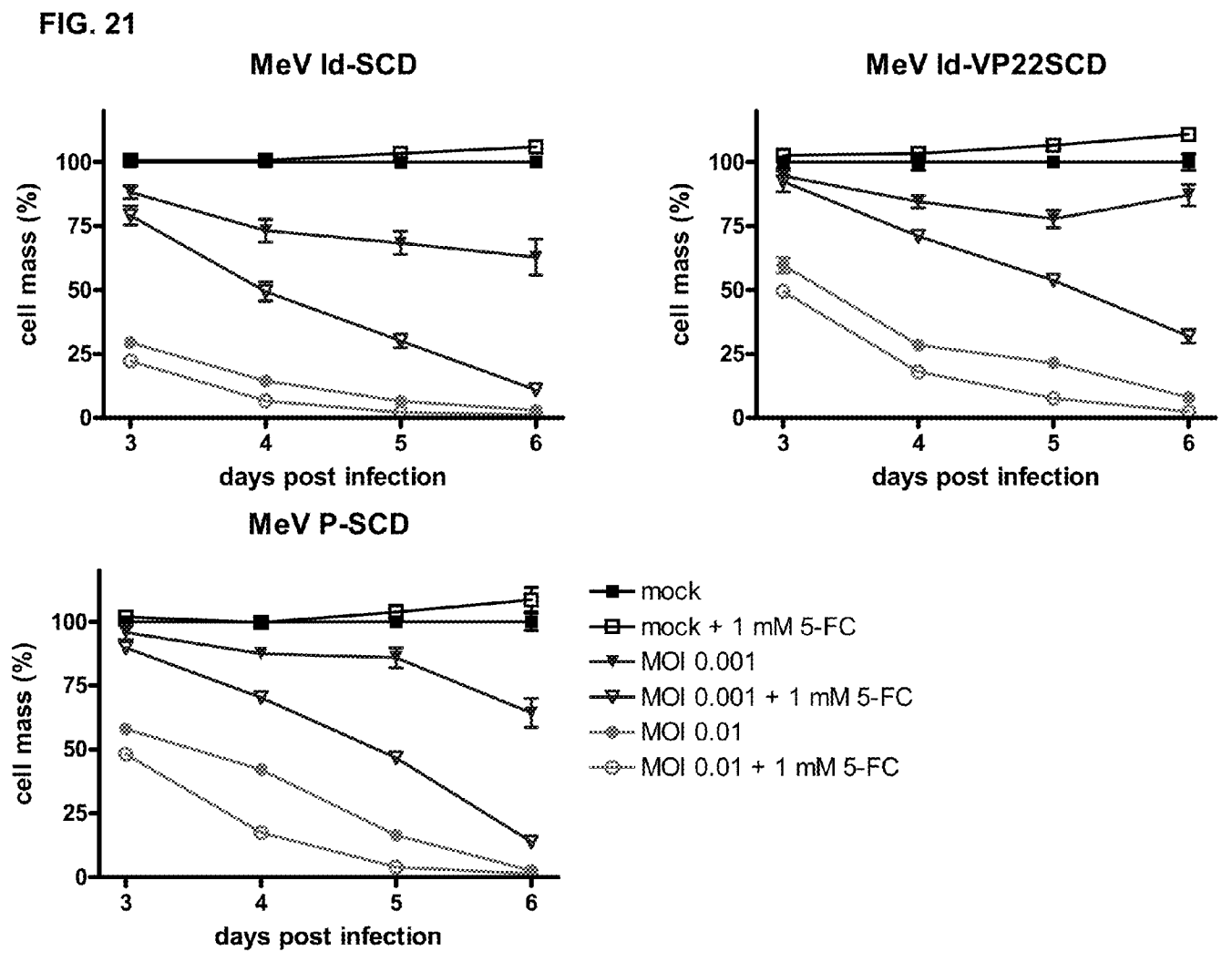

MeV Id-SCD cell mass (%)

100
75
50
25
0

3 4 5 6 days post infection

MeV Id-VP22SCD cell mass (%)

100
75
50
25
0

3 4 5 6 days post infection

MeV P-SCD cell mass (%)

100
75
50
25
0

3 4 5 6 days post infection mock
mock + 1 mM 5-FC
MOI 0.001
MOI 0.001 + 1 mM 5-FC
MOI 0.01
MOI 0.01 + 1 mM 5-FC MeV Id-SCD
MeV P-SCD
MeV Id-VP22SCD
cell mass (%)
100
75
50
25
0
days post infection
3
4
5
6
mock
mock + 1 mM 5-FC
MOI 0.001
MOI 0.001 + 1 mM 5-FC
MOI 0.01
MOI 0.01 + 1 mM 5-FC

FIG. 23

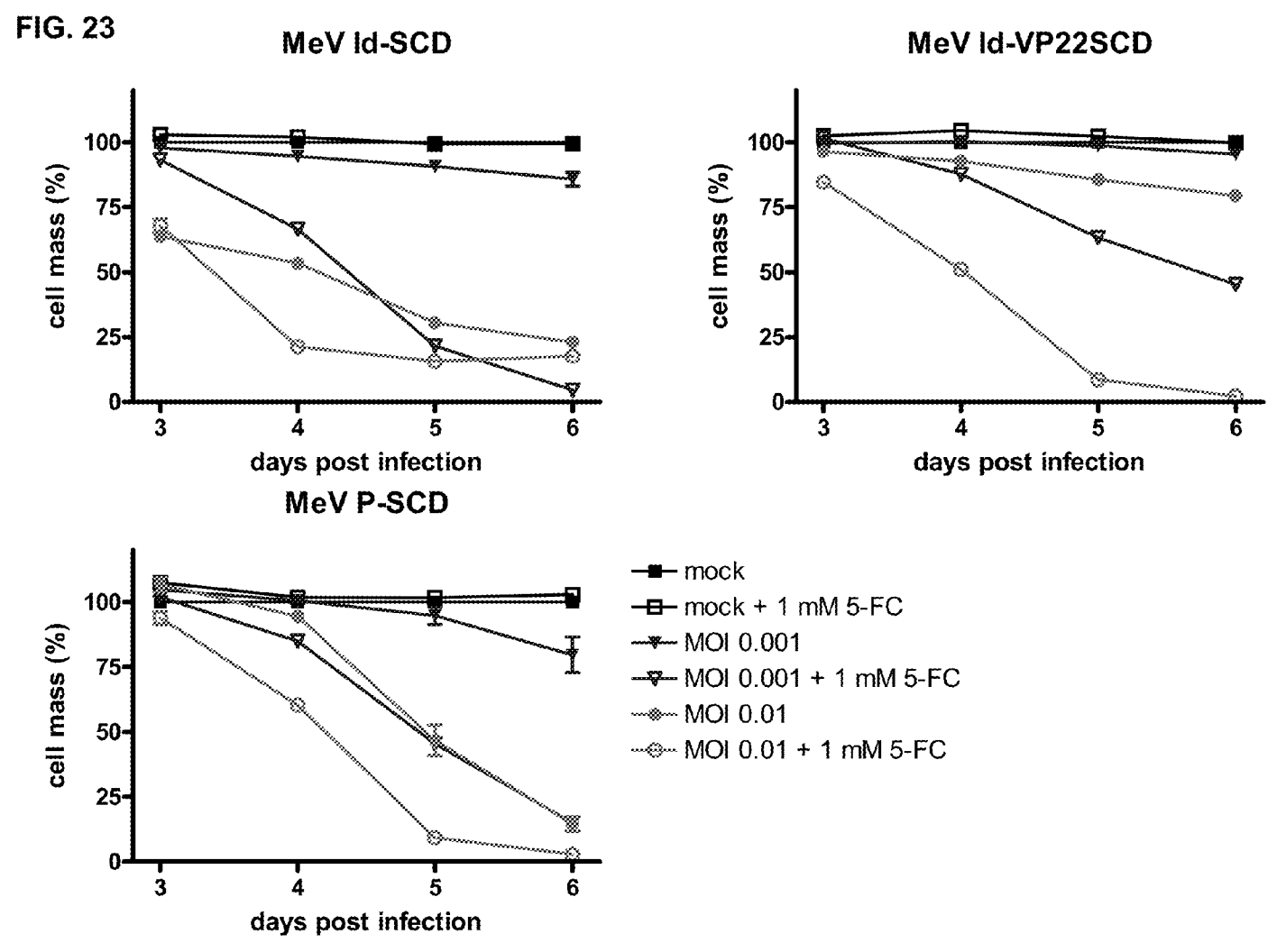

MeV Id-SCD

MeV Id-VP22SCD

MeV P-SCD cell mass (%)

100
75
50
25
0

3
4
5
6 days post infection mock
mock + 1 mM 5-FC
MOI 0.001
MOI 0.001 + 1 mM 5-FC
MOI 0.01
MOI 0.01 + 1 mM 5-FC

| Treatment | control | 5-FC only | MeV Id SCD | MeV Id-SCD + 5-FC | MeV Id-VP22SCD | MeV Id-VP22SCD + 5-FC | MeV P-SCD | MeV P-SCD + 5-FC |
|---|---|---|---|---|---|---|---|---|
| median survival [d] | 35 | 32 | 82.5 | 61.5 | 55.5 | 52 | 49 | 60 |

A
SCD
N
P
M
F
H
L
B
VP22SCD
N
P
M
F
H
L
C
N
P
SCD
M
F
H
L

FIG. 28A pMerV2 P-SCD (coding for MeV P-SCD)

```
accaaacaaagttgggtaaggatagttcaatcaatgatcatcttctagtgcacttaggatt
caagatcctattatcagggacaagagcaggattagggatatccgagatggccacactttta
aggagcttagcattgttcaaaagaaacaaggacaaaccacccattacatcaggatccggtg
gagccatcagaggaatcaaacacattattatagtaccaatccctggagattcctcaattac
cactcgatccagacttctggaccggttggtgaggttaattggaaacccggatgtgagcggg
cccaaactaacaggggcactaataggtatattatccttatttgtggagtctccaggtcaat
tgattcagaggatcaccgatgaccctgacgttagcataaggctgttagaggttgtccagag
tgaccagtcacaatctggccttaccttcgcatcaagaggtaccaacatggaggatgaggcg
gaccaatacttttcacatgatgatccaattagtagtgatcaatccaggttcggatggttcg
ggaacaaggaaatctcagatattgaagtgcaagaccctgagggattcaacatgattctggg
taccatcctagcccaaatttgggtcttgctcgcaaaggcggttacggccccagacacggca
gctgattcggagctaagaaggtggataaagtacacccaacaaagaagggtagttggtgaat
ttagattggagagaaaatggttggatgtggtgaggaacaggattgccgaggacctctcctt
acgccgattcatggtcgctctaatcctggatatcaagagaacacccggaaacaaacccagg
attgctgaaatgatatgtgacattgatacatatatcgtagaggcaggattagccagtttta
tcctgactattaagtttgggatagaaactatgtatcctgctcttggactgcatgaatttgc
tggtgagttatccacacttgagtccttgatgaacctttaccagcaaatgggggaaactgca
ccctacatggtaatcctggagaactcaattcagaacaagttcagtgcaggatcataccctc
tgctctggagctatgccatgggagtaggagtggaacttgaaaactccatgggaggtttgaa
ctttggccgatcttactttgatccagcatattttagattagggcaagagatggtaaggagg
tcagctggaaaggtcagttccacattggcatctgaactcggtatcactgccgaggatgcaa
ggcttgtttcagagattgcaatgcatactactgaggacaagatcagtagagcggttggacc
cagacaagcccaagtatcatttctacacggtgatcaaagtgagaatgagctaccgagattg
gggggcaaggaagataggagggtcaaacagagtcgaggagaagccagggagagctacagag
aaaccgggcccagcagagcaagtgatgcgagagctgcccatcttccaaccggcacacccct
agacattgacactgcaacggagtccagccaagatccgcaggacagtcgaaggtcagctgac
gccctgcttaggctgcaagccatggcaggaatctcggaagaacaaggctcagacacggaca
cccctatagtgtacaatgacagaaatcttctagactaggtgcgagaggccgagggccagaa
caacatccgcctaccatccatcattgttataaaaaacttaggaaccaggtccacacagccg
ccagcccatcaaccatccactcccacgattggagccaatggcagaagagcaggcacgccat
gtcaaaaacggactggaatgcatccgggctctcaaggccgagcccatcggctcactggcca
tcgaggaagctatggcagcatggtcagaaatatcagacaacccaggacaggagcgagccac
ctgcagggaagagaaggcaggcagttcgggtctcagcaaaccatgcctctcagcaattgga
tcaactgaaggcggtgcacctcgcatccgcggtcagggacctggagagagcgatgacgacg
ctgaaactttgggaatcccccaagaaatctccaggcatcaagcactgggttacagtgtta
ttacgtttatgatcacagcggtgaagcggttaagggaatccaagatgctgactctatcatg
gttcaatcaggccttgatggtgatagcaccctctcaggaggagacaatgaatctgaaaaca
gcgatgtggatattggcgaacctgataccgagggatatgctatcactgaccggggatctgc
```

FIG. 28B tcccatctctatggggttcagggcttctgatgttgaaactgcagaaggaggggagatccac
gagctcctgagactccaatccagaggcaacaactttccgaagcttgggaaaactctcaatg
ttcctccgcccccggaccccggtagggccagcacttccgggacacccattaaaagggcac
agacgcgagattagcctcatttggaacggagatcgcgtctttattgacaggtggtgcaacc
caatgtgctcgaaagtcaccctcggaaccatcagggccaggtgcacctgcggggaatgtcc
ccgagtgtgtgagcaatgccgcactgatacaggagtggacacccgaatctggtaccacaat
ctccccgagatcccagaataatgaagaaggggagactattatgatgatgagctgttctct
gatgtccaagatattaaaacagccttggccaaaatacacgaggataatcagaagataatct
ccaagctagaatcactgctgttattgaagggagaagttgagtcaattaagaagcagatcaa
caggcaaaatatcagcatatccaccctggaaggacacctctcaagcatcatgatcgccatt
cctggacttgggaaggatcccaacgaccccactgcagatgtcgaaatcaatcccgacttga
aacccatcataggcagagattcaggccgagcactggccgaagttctcaagaaacccgttgc
cagccgacaactccaaggaatgacaaatggacggaccagttccagaggacagctgctgaag
gaatttcagctaaagccgatcgggaaaaagatgagctcagccgtcgggtttgttcctgaca
ccggccctgcatcacgcagtgtaatccgctccattataaaatccagccggctagaggagga
tcggaagcgttacctgatgactctccttgatgatatcaaaggagccaatgatcttgccaag
ttccaccagatgctgatgaagataataatgaagtagctacagctcaacttacctgccaacc
ccatgccagtcgacccaactagtcctccatcattgttataaaaaacttaggaaccaggtcc
atacaccgtacgctcgaggcgcgtgccaccatggtgacaggggaatggcaagcaagtggg
atcagaagggtatggacattgcctatgaggaggcggccttaggttacaaagagggtggtgt
tcctattggcggatgtcttatcaataacaaagacggaagtgttctcggtcgtggtcacaac
atgagatttcaaaagggatccgccacactacatggtgagatctccactttggaaaactgtg
ggagattagagggcaaagtgtacaaagataccactttgtatacgacgctgtctccatgcga
catgtgtacaggtgccatcatcatgtatggtattccacgctgtgttgtcggtgagaacgtt
aatttcaaaagtaagggcgagaaatatttacaaactagaggtcacgaggttgttgttgttg
acgatgagaggtgtaaaaagatcatgaaacaatttatcgatgaaagacctcaggattggtt
tgaagatattggtgaggcttcggaaccatttaagaacgtctacttgctacctcaaacaaac
caattgctgggtttgtacaccatcatcagaaataagaatacaactagacctgatttcattt
tctactccgatagaatcatcagattgttggttgaagaaggtttgaaccatctacctgtgca
aaagcaaattgtggaaactgacaccaacgaaaacttcgaaggtgtctcattcatgggtaaa
atctgtggtgtttccattgtcagagctggtgaatcgatggagcaaggattaagagactgtt
gtaggtctgtgcgtatcggtaaaattttaattcaaagggacgaggagactgctttaccaaa
gttattctacgaaaaattaccagaggatatatctgaaaggtatgtcttcctattagaccca
atgctggccaccggtggtagtgctatcatggctacagaagtcttgattaagagaggtgtta
agccagagagaatttacttcttaaacctaatctgtagtaaggaagggattgaaaaatacca
tgccgccttcccagaggtcagaattgttactggtgccctcgacagaggtctagatgaaaac
aagtatctagttccagggttgggtgactttggtgacagatactactgtgtttaaacgcgcg
acgtctagtacaacctaaatccattataaaaaacttaggagcaaagtgattgcctcccaag
gtccacaatgacagagacctacgacttcgacaagtcggcatgggacatcaaagggtcgatc
gctccgatacaacccaccacctacagtgatggcaggctggtgccccaggtcagagtcatag
atcctggtctaggcgacaggaaggatgaatgctttatgtacatgtttctgctggggggttgt
tgaggacagcgattccctagggcctccaatcgggcgagcatttgggttcctgcccttaggt
gttggcagatccacagcaaagcccgaaaaactcctcaaagaggccactgagcttgacatag
ttgttagacgtacagcagggctcaatgaaaaactggtgttctacaacaacaccccactaac
tctcctcacaccttggagaaaggtcctaacaacagggagtgtcttcaacgcaaaccaagtg

FIG. 28C tgcaatgcggttaatctgataccgctcgataccccgcagaggttccgtgttgtttatatga
gcatcacccgtctttcggataacgggtattacaccgttcctagaagaatgctggaattcag
atcggtcaatgcagtggccttcaacctgctggtgacccttaggattgacaaggcgataggc
cctgggaagatcatcgacaatacagagcaacttcctgaggcaacatttatggtccacatcg
ggaacttcaggagaaagaagagtgaagtctactctgccgattattgcaaaatgaaaatcga
aaagatgggcctggtttttgcacttggtgggataggggcaccagtcttcacattagaagc
acaggcaaaatgagcaagactctccatgcacaactcgggttcaagaagaccttatgttacc
cgctgatggatatcaatgaagaccttaatcgattactctggaggagcagatgcaagatagt
aagaatccaggcagttttgcagccatcagttcctcaagaattccgcatttacgacgacgtg
atcataaatgatgaccaaggactattcaaagttctgtagaccgtagtgcccagcaatgccc
gaaaacgacccccctcacaatgacagccagaaggcccggacaaaaaagcccccctccgaaag
actccacggaccaagcgagaggccagccagcagccgacggcaagcgcgaacaccaggcggc
cccagcacagaacagccctgacacaaggccaccaccagccaccccaatctgcatcctcctc
gtgggacccccgaggaccaacccccaaggctgcccccgatccaaaccaccaaccgcatccc
caccacccccgggaaagaaacccccagcaattggaaggcccctcccccctcttcctcaacac
aagaactccacaaccgaaccgcacaagcgaccgaggtgacccaaccgcaggcatccgactc
cctagacagatcctctctccccggcaaactaaacaaaacttagggccaaggaacatacaca
cccaacagaacccagaccccggcccacggcgccgcgcccccaaccccccgacaaccagaggg
agcccccaaccaatcccgccggctcccccggtgcccacaggcagggacaccaacccccgaa
cagacccagcacccaaccatcgacaatccaagacgggggggcccccccaaaaaaaggcccc
caggggccgacagccagcaccgcgaggaagcccacccaccccacacacgaccacggcaacc
aaaccagaacccagaccaccctgggccaccagctcccagactcggccatcaccccgcagaa
aggaaaggccacaacccgcgcaccccagccccgatccggcggggagccacccaacccgaac
cagcacccaagagcgatccccgaaggacccccgaaccgcaaaggacatcagtatcccacag
cctctccaagtcccccggtctcctcctcttctcgaagggaccaaaagatcaatccaccaca
cccgacgacactcaactccccacccctaaaggagacaccgggaatcccagaatcaagactc
atccaatgtccatcatgggtctcaaggtgaacgtctctgccatattcatggcagtactgtt
aactctccaaacacccaccggtcaaatccattggggcaatctctctaagataggggtggta
ggaataggaagtgcaagctacaaagttatgactcgttccagccatcaatcattagtcataa
aattaatgcccaatataactctcctcaataactgcacgagggtagagattgcagaatacag
gagactactgagaacagttttggaaccaattagagatgcacttaatgcaatgacccagaat
ataagaccggttcagagtgtagcttcaagtaggagacacaagagatttgcgggagtagtcc
tggcaggtgcggccctaggcgttgccacagctgctcagataacagccggcattgcacttca
ccagtccatgctgaactctcaagccatcgacaatctgagagcgagcctggaaactactaat
caggcaattgagacaatcagacaagcagggcaggagatgatattggctgttcagggtgtcc
aagactacatcaataatgagctgataccgtctatgaaccaactatcttgtgatttaatcgg
ccagaagctcgggctcaaattgctcagatactatacagaaatcctgtcattatttggcccc
agtttacgggaccccatatctgcggagatatctatccaggctttgagctatgcgcttggag
gagacatcaataaggtgttagaaaagctcggatacagtggaggtgatttactgggcatctt
agagagcggaggaataaaggcccggataactcacgtcgacacagagtcctacttcattgtc
ctcagtatagcctatccgacgctgtccgagattaagggggtgattgtccaccggctagagg
gggtctcgtacaacataggctctcaagagtggtataccactgtgcccaagtatgttgcaac
ccaagggtaccttatctcgaattttgatgagtcatcgtgtactttcatgccagaggggact
gtgtgcagccaaaatgccttgtacccgatgagtcctctgctccaagaatgcctccggggt
acaccaagtcctgtgctcgtacactcgtatccgggtcttttgggaaccggttcattttatc

FIG. 28D acaagggaacctaatagccaattgtgcatcaatcctttgcaagtgttacacaacaggaacg
atcattaatcaagaccctgacaagatcctaacatacattgctgccgatcactgcccggtag
tcgaggtgaacggcgtgaccatccaagtcgggagcaggaggtatccagacgctgtgtactt
gcacagaattgacctcggtcctcccatatcattggagaggttggacgtagggacaaatctg
gggaatgcaattgctaagttggaggatgccaaggaattgttggagtcatcggaccagatat
tgaggagtatgaaaggtttatcgagcactagcatagtctacatcctgattgcagtgtgtct
tggagggttgatagggatccccgctttaatatgttgctgcaggggcgttgtaacaaaaag
ggagaacaagttggtatgtcaagaccaggcctaaagcctgatcttacgggaacatcaaaat
cctatgtaaggtcgctctgatcctctacaactcttgaaacacaaatgtcccacaagtctcc
tcttcgtcatcaagcaaccaccgcacccagcatcaagcccacctgaaattatctccggctt
ccctctggccgaacaatatcggtagttaatcaaaacttagggtgcaagatcatccacaatg
tcaccacaacgagaccggataaatgccttctacaaagataacccccatcccaagggaagta
ggatagtcattaacagagaacatcttatgattgatagaccttatgttttgctggctgttct
gtttgtcatgtttctgagcttgatcgggttgctagccattgcaggcattagacttcatcgg
gcagccatctacaccgcagagatccataaaagcctcagcaccaatctagatgtaactaact
caatcgagcatcaggtcaaggacgtgctgacaccactcttcaaaatcatcggtgatgaagt
gggcctgaggacacctcagagattcactgacctagtgaaattaatctctgacaagattaaa
ttccttaatccggatagggagtacgacttcagagatctcacttggtgtatcaacccgccag
agagaatcaaattggattatgatcaatactgtgcagatgtggctgctgaagagctcatgaa
tgcattggtgaactcaactctactggagaccagaacaaccaatcagttcctagctgtctca
aagggaaactgctcagggcccactacaatcagaggtcaattctcaaacatgtcgctgtccc
tgttagacttgtatttaggtcgaggttacaatgtgtcatctatagtcactatgacatccca
gggaatgtatggggggaacttacctagtggaaaagcctaatctgagcagcaaaaggtcagag
ttgtcacaactgagcatgtaccgagtgtttgaagtaggtgttatcagaaatccgggtttgg
gggctccggtgttccatatgacaaactatcttgagcaaccagtcagtaatgatctcagcaa
ctgtatggtggctttgggggagctcaaactcgcagccctttgtcacggggaagattctatc
acaattccctatcagggatcagggaaaggtgtcagcttccagctcgtcaagctaggtgtct
ggaaatccccaaccgacatgcaatcctgggtccccttatcaacggatgatccagtgataga
caggctttacctctcatctcacagaggtgttatcgctgacaatcaagcaaaatgggctgtc
ccgacaacacgaacagatgacaagttgcgaatggagacatgcttccaacaggcgtgtaagg
gtaaaatccaagcactctgcgagaatcccgagtgggcaccattgaaggataacaggattcc
ttcatacggggtcttgtctgttgatctgagtctgacagttgagcttaaaatcaaaattgct
tcgggattcgggccattgatcacacacggttcagggatggacctatacaaatccaaccaca
acaatgtgtattggctgactatcccgccaatgaagaacctagccttaggtgtaatcaacac
attggagtggataccgagattcaaggttagtccctacctcttcactgtcccaattaaggaa
gcaggcgaagactgccatgccccaacatacctacctgcggaggtggatggtgatgtcaaac
tcagttccaatctggtgattctacctggtcaagatctccaatatgttttggcaacctacga
tacttccagggttgaacatgctgtggtttattacgtttacagcccaagccgctcattttct
tacttttatccttttaggttgcctataaaggggtccccatcgaattacaagtggaatgct
tcacatgggaccaaaaactctggtgccgtcacttctgtgtgcttgcggactcagaatctgg
tggacatatcactcactctgggatggtgggcatgggagtcagctgcacagtcacccgggaa
gatggaaccaatcgcagatagggctgctagtgaaccaatcacatgatgtcacccagacatc
aggcatacccactagtgtgaaatagacatcagaattaagaaaaacgtagggtccaagtggt
tccccgttatggactcgctatctgtcaaccagatcttataccctgaagttcacctagatag
cccgatagttaccaataagatagtagccatcctggagtatgctcgagtccctcacgcttac

FIG. 28E agcctggaggaccctacactgtgtcagaacatcaagcaccgcctaaaaacggattttcca
accaaatgattataaacaatgtggaagttgggaatgtcatcaagtccaagcttaggagtta
tccggcccactctcatattccatatccaaattgtaatcaggatttatttaacatagaagac
aaagagtcaacgaggaagatccgtgaactcctcaaaaaggggaattcgctgtactccaaag
tcagtgataaggttttccaatgcttaagggacactaactcacggcttggcctaggctccga
attgagggaggacatcaaggagaaagttattaacttgggagtttacatgcacagctcccag
tggtttgagccctttctgttttggtttacagtcaagactgagatgaggtcagtgattaaat
cacaaacccatacttgccataggaggagacacacacctgtattcttcactggtagttcagt
tgagttgctaatctctcgtgaccttgttgctataatcagtaaagagtctcaacatgtatat
tacctgacatttgaactggttttgatgtattgtgatgtcatagaggggaggttaatgacag
agaccgctatgactattgatgctaggtatacagagcttctaggaagagtcagatacatgtg
gaaactgatagatggtttcttccctgcactcgggaatccaacttatcaaattgtagccatg
ctggagcctctttcacttgcttacctgcagctgagggatataacagtagaactcagaggtg
ctttccttaaccactgctttactgaaatacatgatgttcttgaccaaaacgggttttctga
tgaaggtacttatcatgagttaactgaagctctagattacattttcataactgatgacata
catctgacaggggagatttctcatttttcagaagtttcggccaccccagacttgaagcag
taacggctgctgaaaatgttaggaaatacatgaatcagcctaaagtcattgtgtatgagac
tctgatgaaaggtcatgccatattttgtggaatcataatcaacggctatcgtgacaggcac
ggaggcagttggccaccgctgaccctcccccctgcatgctgcagacacaatccggaatgctc
aagcttcaggtgaagggttaacacatgagcagtgcgttgataactggaaatcttttgctgg
agtgaaatttggctgctttatgcctcttagcctggatagtgatctgacaatgtacctaaag
gacaaggcacttgctgctctccaaagggaatgggattcagtttacccgaaagagttcctgc
gttacgaccctcccaagggaaccgggtcacggaggcttgtagatgttttccttaatgattc
gagctttgacccatatgatgtgataatgtatgttgtaagtggagcttacctccatgaccct
gagttcaacctgtcttacagcctgaaagaaaaggagatcaaggaaacaggtagacttttg
ctaaaatgacttacaaaatgagggcatgccaagtgattgctgaaaatctaatctcaaacgg
gattggcaaatattttaaggacaatgggatggccaaggatgagcacgatttgactaaggca
ctccacactctagctgtctcaggagtccccaaagatctcaaagaaagtcacaggggggggc
cagtcttaaaaacctactcccgaagcccagtccacacaagtaccaggaacgtgagagcagc
aaaagggtttatagggttccctcaagtaattcggcaggaccaagacactgatcatccggag
aatatggaagcttacgagacagtcagtgcatttatcacgactgatctcaagaagtactgcc
ttaattggagatatgagaccatcagcttgtttgcacagaggctaaatgagatttacggatt
gccctcatttttccagtggctgcataagaggcttgagacctctgtcctgtatgtaagtgac
cctcattgccccccgaccttgacgcccatatcccgttatataaagtccccaatgatcaaa
tcttcattaagtaccctatgggaggtatagaagggtattgtcagaagctgtggaccatcag
caccattccctatctatacctggctgcttatgagagcggagtaaggattgcttcgttagtg
caaggggacaatcagaccatagccgtaacaaaaagggtacccagcacatggccctacaacc
ttaagaaacgggaagctgctagagtaactagagattactttgtaattcttaggcaaaggct
acatgatattggccatcacctcaaggcaaatgagacaattgtttcatcacatttttttgtc
tattcaaaaggaatatattatgatgggctacttgtgtcccaatcactcaagagcatcgcaa
gatgtgtattctggtcagagactatagttgatgaaacaagggcagcatgcagtaatattgc
tacaacaatggctaaaagcatcgagagaggttatgaccgttaccttgcatattccctgaac
gtcctaaaagtgatacagcaaattctgatctctcttggcttcacaatcaattcaaccatga
cccgggatgtagtcatacccctcctcacaaacaacgacctcttaataaggatggcactgtt
gcccgctcctattgggggatgaattatctgaatatgagcaggctgtttgtcagaaacatc

FIG. 28F ggtgatccagtaacatcatcaattgctgatctcaagagaatgattctcgcctcactaatgc
ctgaagagaccctccatcaagtaatgacacaacaaccggggggactcttcattcctagactg
ggctagcgacccttactcagcaaatcttgtatgtgtccagagcatcactagactcctcaag
aacataactgcaaggtttgtcctgatccatagtccaaacccaatgttaaaaggattattcc
atgatgacagtaaagaagaggacgagggactggcggcattcctcatggacaggcatattat
agtacctagggcagctcatgaaatcctggatcatagtgtcacaggggcaagagagtctatt
gcaggcatgctggataccacaaaaggcttgattcgagccagcatgaggaaggggggttaa
cctctcgagtgataaccagattgtccaattatgactatgaacaattcagagcagggatggt
gctattgacaggaagaaagagaaatgtcctcattgacaaagagtcatgttcagtgcagctg
gcgagagctctaagaagccatatgtgggcgaggctagctcgaggacggcctatttacggcc
ttgaggtccctgatgtactagaatctatgcgaggccaccttattcggcgtcatgagacatg
tgtcatctgcgagtgtggatcagtcaactacggatggtttttgtcccctcgggttgccaa
ctggatgatattgacaaggaaacatcatccttgagagtcccatatattggttctaccactg
atgagagaacagacatgaagcttgccttcgtaagagccccaagtcgatccttgcgatctgc
tgttagaatagcaacagtgtactcatgggcttacggtgatgatgatagctcttggaacgaa
gcctggttgttggctaggcaaagggccaatgtgagcctggaggagctaagggtgatcactc
ccatctcaacttcgactaatttagcgcataggttgagggatcgtagcactcaagtgaaata
ctcaggtacatcccttgtccgagtggcgaggtataccacaatctccaacgacaatctctca
tttgtcatatcagataagaaggttgatactaactttatataccaacaaggaatgcttctag
ggttgggtgttttagaaacattgtttcgactcgagaaagataccggatcatctaacacggt
attacatcttcacgtcgaaacagattgttgcgtgatcccgatgatagatcatcccaggata
cccagctcccgcaagctagagctgagggcagagctatgtaccaacccattgatatatgata
atgcacctttaattgacagagatgcaacaaggctatacacccagagccataggaggcacct
tgtggaatttgttacatggtccacaccccaactatatcacattttagctaagtccacagca
ctatctatgattgacctggtaacaaaatttgagaaggaccatatgaatgaaatttcagctc
tcataggggatgacgatatcaatagtttcataactgagtttctgctcatagagccaagatt
attcactatctacttgggccagtgtgcggccatcaattgggcatttgatgtacattatcat
agaccatcagggaaatatcagatgggtgagctgttgtcatcgttcctttctagaatgagca
aaggagtgtttaaggtgcttgtcaatgctctaagccacccaaagatctacaagaaattctg
gcattgtggtattatagagcctatccatggtccttcacttgatgctcaaaacttgcacaca
actgtgtgcaacatggtttacacatgctatatgacctacctcgacctgttgttgaatgaag
agttagaagagttcacatttctcttgtgtgaaagcgacgaggatgtagtaccggacagatt
cgacaacatccaggcaaaacacttatgtgttctggcagatttgtactgtcaaccagggacc
tgcccaccaattcgaggtctaagaccggtagagaaatgtgcagttctaaccgaccatatca
aggcagaggctatgttatctccagcaggatcttcgtggaacataaatccaattattgtaga
ccattactcatgctctctgacttatctccggcgaggatcgatcaaacagataagattgaga
gttgatccaggattcattttcgacgccctcgctgaggtaaatgtcagtcagccaaagatcg
gcagcaacaacatctcaaatatgagcatcaaggctttcagacccccacacgatgatgttgc
aaaattgctcaaagatatcaacacaagcaagcacaatcttcccatttcaggggcaatctc
gccaattatgaaatccatgctttccgcagaatcgggttgaactcatctgcttgctacaaag
ctgttgagatatcaacattaattaggagatgccttgagccaggggaggacggcttgttctt
gggtgagggatcgggttctatgttgatcacttataaagagatacttaaactaaacaagtgc
ttctataatagtggggtttccgccaattctagatctggtcaaagggaattagcaccctatc
cctccgaagttggccttgtcgaacacagaatgggagtaggtaatattgtcaaagtgctctt
taacgggaggcccgaagtcacgtgggtaggcagtgtagattgcttcaatttcatagttagt

FIG. 28G aatatccctacctctagtgtggggtttatccattcagatatagagaccttgcctgacaaag
atactatagagaagctagaggaattggcagccatcttatcgatggctctgctcctgggcaa
aataggatcaatactggtgattaagcttatgcctttcagcggggattttgttcagggattt
ataagttatgtagggtctcattatagagaagtgaaccttgtataccctagatacagcaact
tcatctctactgaatcttatttggttatgacagatctcaaggctaaccggctaatgaatcc
tgaaaagattaagcagcagataattgaatcatctgtgaggacttcacctggacttataggt
cacatcctatccattaagcaactaagctgcatacaagcaattgtgggagacgcagttagta
gaggtgatatcaatcctactctgaaaaaacttacacctatagagcaggtgctgatcaattg
cgggttggcaattaacggacctaagctgtgcaaagaattgatccaccatgatgttgcctca
gggcaagatggattgcttaattctatactcatcctctacagggagttggcaagattcaaag
acaaccaaagaagtcaacaagggatgttccacgcttaccccgtattggtaagtagcaggca
acgagaacttatatctaggatcacccgcaaattctggggggcacattcttctttactccggg
aacaaaaagttgataaataagtttatccagaatctcaagtccggctatctgatactagact
tacaccagaatatcttcgttaagaatctatccaagtcagagaaacagattattatgacggg
gggtttgaaacgtgagtgggtttttaaggtaacagtcaaggagaccaaagaatggtataag
ttagtcggatacagtgccctgattaaggactaattggttgaactccggaaccctaatcctg
ccctaggtggttaggcattatttgcaatatattaaagaaaactttgaaaatacgaagtttc
tattcccagctttgtctggtggccggcatggtcccagcctcctcgctggcgccggctgggc
aacattccgaggggaccgtcccctcggtaatggcgaatgggacgcggccggtcgatcgacg
atccggctgctaacaaagcccgaaaggaagctgagttggctgctgccaccgctgagcaata
actagcataaccccttggggcctctaaacgggtcttgaggggttttttgctgaaaggagga
actatatccggatcgagatcaattctgtgagcgtatggcaaacgaaggaaaaatagttata
gtagccgcactcgatgggacatttcaacgtaaaccgtttaataatatttgaatcttattc
cattatctgaaatggtggtaaaactaactgctgtgtgtatgaaatgctttaaggaggcttc
cttttctaaacgattgggtgaggaaaccgagatagaaataataggaggtaatgatatgtat
caatcggtgtgtagaaagtgttacatcgactcataatattatatttttatctaaaaaact
aaaaataaacattgattaaattttaatataatacttaaaaatggatgttgtgtcgttagat
aaaccgtttatgtattttgaggaaattgataatgagttagattacgaaccagaaagtgcaa
atgaggtcgcaaaaaaactgccgtatcaaggacagttaaaactattactaggagaattatt
ttttcttagtaagttacagcgacacggtatattagatggtgccaccgtagtgtatatagga
tctgctcccggtacacatatacgttatttgagagatcatttctataatttaggagtgatcc
cgaaaggaagctgagttggctgctgccaccgctgagcaataactagcataaccccttgggg
cctctaaacgggtcttgaggggttttttgctgaaaggaggaacgcgcctgatgcggtattt
tctccttacgcatctgtgcggtatttcacaccgcatatatggtgcactctcagtacaatct
gctctgatgccgcatagttaagccagccccgacacccgccaacacccgctgacgcgccctg
acgggcttgtctgctcccggcatccgcttacagacaagctgtgaccgtctccgggagctgc
atgtgtcagaggttttcaccgtcatcaccgaaacgcgcgagacgaaagggcctcgtgatac
gcctatttttataggttaatgtcatgataataatggtttcttagacgtcaggtggcacttt
tcggggaaatgtgcgcggaacccctatttgtttatttttctaaatacattcaaatatgtat
ccgctcatgagacaataaccctgataaatgcttcaataatattgaaaaaggaagagtatga
gtattcaacatttccgtgtcgcccttattcccttttttgcggcattttgccttcctgtttt
tgctcacccagaaacgctggtgaaagtaaaagatgctgaagatcagttgggtgcacgagtg
ggttacatcgaactggatctcaacagcggtaagatccttgagagttttcgccccgaagaac
gttttccaatgatgagcacttttaaagttctgctatgtggcgcggtattatcccgtattga
cgccgggcaagagcaactcggtcgccgcatacactattctcagaatgacttggttgagtac

FIG. 28H tcaccagtcacagaaaagcatcttacggatggcatgacagtaagagaattatgcagtgctg
ccataaccatgagtgataacactgcggccaacttacttctgacaacgatcggaggaccgaa
ggagctaaccgcttttttgcacaacatgggggatcatgtaactcgccttgatcgttgggaa
ccggagctgaatgaagccataccaaacgacgagcgtgacaccacgatgcctgtagcaatgg
caacaacgttgcgcaaactattaactggcgaactacttactctagcttcccggcaacaatt
aatagactggatggaggcggataaagttgcaggaccacttctgcgctcggcccttccggct
ggctggtttattgctgataaatctggagccggtgagcgtgggtctcgcggtatcattgcag
cactggggccagatggtaagccctcccgtatcgtagttatctacacgacggggagtcaggc
aactatggatgaacgaaatagacagatcgctgagataggtgcctcactgattaagcattgg
taactgtcagaccaagtttactcatatatactttagattgatttaaaacttcatttttaat
ttaaaaggatctaggtgaagatcctttttgataatctcatgaccaaaatcccttaacgtga
gttttcgttccactgagcgtcagaccccgtagaaaagatcaaaggatcttcttgagatcct
ttttttctgcgcgtaatctgctgcttgcaaacaaaaaaaccaccgctaccagcggtggttt
gtttgccggatcaagagctaccaactctttttccgaaggtaactggcttcagcagagcgca
gataccaaatactgtccttctagtgtagccgtagttaggccaccacttcaagaactctgta
gcaccgcctacatacctcgctctgctaatcctgttaccagtggctgctgccagtggcgata
agtcgtgtcttaccgggttggactcaagacgatagttaccggataaggcgcagcggtcggg
ctgaacggggggttcgtgcacacagcccagcttggagcgaacgacctacaccgaactgaga
tacctacagcgtgagcattgagaaagcgccacgcttcccgaagggagaaaggcggacaggt
atccggtaagcggcagggtcggaacaggagagcgcacgagggagcttccagggggaaacgc
ctggtatctttatagtcctgtcgggtttcgccacctctgacttgagcgtcgatttttgtga
tgctcgtcaggggggcggagcctatggaaaaacgccagcaacgcggcctttttacggttcc
tggccttttgctggccttttgctcacatgttctttcctgcgttatcccctgattctgtgga
taaccgtattaccgcctttgagtgagctgataccgctcgccgcagccgaacgaccgagcgc
agcgagtcagtgagcgaggaagcggaagagcgcccaatacgcaaaccgcctctccccgcgc
gttggccgattcattaatgcagctggcacgacaggtttcccgactggaaagcgggcagtga
gcgcaacgcaattaatgtgagttagctcactcattaggcaccccaggctttacactttatg
cttccggctcgtatgttgtgtggaattgtgagcggataacaatttcacacaggaaacagct
atgaccatgattacgccaagcttacgcgtgtaatacgactcactataggg

FIG. 29A pc3MerV2 ld-VP22SCD (coding for MeV ld-VP22SCD)

accaaacaaagttgggtaaggatagttcaatcaatgatcatcttctagtgcacttaggatt
caagatcctattatcagggacaagagcaggattagggatatctcgaggcgcgtgccaccat
gacctctcgccgctccgtgaagtcgggtccgcgggaggttccgcgcgatgagtacgaggat
ctgtactacaccccgtcttcaggtatggcgagtcccgatagtccgcctgacacctcccgcc
gtggcgccctacagacacgctcgcgccagaggggcgaggtccgtttcgtccagtacgacga
gtcggattatgccctctacgggggctcgtcatccgaagacgacgaacacccggaggtcccc
cggacgcggcgtcccgtttccggggcggttttgtccggcccggggcctgcgcgggcgcctc
cgccacccgctgggtccggaggggccggacgcacacccaccaccgcccccgggcccccg
aacccagcgggtggcgactaaggcccccgcggccccggcggcggagaccacccgcggcagg
aaatcggcccagccagaatccgccgcactcccagacgcccccgcctcgacggcgccaaccc
gatccaagacacccgcgcaggggctggccagaaagctgcactttagcaccgccccccaaa
ccccgacgcgccatggacccccgggtggccggctttaacaagcgcgtcttctgcgccgcg
gtcgggcgcctggcggccatgcatgcccggatggcggcggtccagctctgggacatgtcgc
gtccgcgcacagacgaagacctcaacgaactccttggcatcaccaccatccgcgtgacggt
ctgcgagggcaaaaacctgcttcagcgcgccaacgagttggtgaatccagacgtggtgcag
gacgttgacgcggccacggcgactcgagggcgttctgcggcgtcgcgccccaccgagcgac
ctcgagccccagcccgctccgcttctcgccccagacggcccgtcgaggatatcgccaccat
ggtgacaggggaatggcaagcaagtgggatcagaagggtatggacattgcctatgaggag
gcggccttaggttacaaagagggtggtgttcctattggcggatgtcttatcaataacaaag
acggaagtgttctcggtcgtggtcacaacatgagatttcaaaagggatccgccacactaca
tggtgagatctccactttggaaaactgtgggagattagagggcaaagtgtacaaagatacc
actttgtatacgacgctgtctccatgcgacatgtgtacaggtgccatcatcatgtatggta
ttccacgctgtgttgtcggtgagaacgttaatttcaaaagtaagggcgagaaatatttaca
aactagaggtcacgaggttgttgttgttgacgatgagaggtgtaaaaagatcatgaaacaa
tttatcgatgaaagacctcaggattggtttgaagatattggtgaggcttcggaaccattta
agaacgtctacttgctacctcaaacaaaccaattgctgggtttgtacaccatcatcagaaa
taagaatacaactagacctgatttcattttctactccgatagaatcatcagattgttggtt
gaagaaggtttgaaccatctacctgtgcaaaagcaaattgtggaaactgacaccaacgaaa
acttcgaaggtgtctcattcatgggtaaaatctgtggtgtttccattgtcagagctggtga
atcgatggagcaaggattaagagactgttgtaggtctgtgcgtatcggtaaaattttaatt
caaagggacgaggagactgctttaccaaagttattctacgaaaaattaccagaggatatat
ctgaaaggtatgtcttcctattagacccaatgctggccaccggtggtagtgctatcatggc
tacagaagtcttgattaagagaggtgttaagccagagagaatttacttcttaaacctaatc
tgtagtaaggaagggattgaaaaataccatgccgccttcccagaggtcagaattgttactg
gtgccctcgacagaggtctagatgaaaacaagtatctagttccagggttgggtgactttgg
tgacagatactactgtgtttaataaacgcgccatccatcattgttataaaaacttaggat
tcaagatcctattatcagggacaagagcaggattagggatatccgagatggccacactttt
aaggagcttagcattgttcaaaagaaacaaggacaaaccacccattacatcaggatccggt
ggagccatcagaggaatcaaacacattattatagtaccaatccctggagattcctcaatta
ccactcgatccagacttctggaccggttggtgaggttaattggaaacccggatgtgagcgg
gcccaaactaacaggggcactaataggtatattatccttatttgtggagtctccaggtcaa
ttgattcagaggatcaccgatgaccctgacgttagcataaggctgttagaggttgtccaga
gtgaccagtcacaatctggccttaccttcgcatcaagaggtaccaacatggaggatgaggc

FIG. 29B ggaccaatacttttcacatgatgatccaattagtagtgatcaatccaggttcggatggttc
gggaacaaggaaatctcagatattgaagtgcaagaccctgagggattcaacatgattctgg
gtaccatcctagcccaaatttgggtcttgctcgcaaaggcggttacggccccagacacggc
agctgattcggagctaagaaggtggataaagtacacccaacaaagaagggtagttggtgaa
tttagattggagagaaaatggttggatgtggtgaggaacaggattgccgaggacctctcct
tacgccgattcatggtcgctctaatcctggatatcaagagaacacccggaaacaaacccag
gattgctgaaatgatatgtgacattgatacatatatcgtagaggcaggattagccagtttt
atcctgactattaagtttgggatagaaactatgtatcctgctcttggactgcatgaatttg
ctggtgagttatccacacttgagtccttgatgaacctttaccagcaaatgggggaaactgc
accctacatggtaatcctggagaactcaattcagaacaagttcagtgcaggatcataccct
ctgctctggagctatgccatgggagtaggagtggaacttgaaaactccatgggaggtttga
actttggccgatcttactttgatccagcatattttagattagggcaagagatggtaaggag
gtcagctggaaaggtcagttccacattggcatctgaactcggtatcactgccgaggatgca
aggcttgtttcagagattgcaatgcatactactgaggacaagatcagtagagcggttggac
ccagacaagcccaagtatcatttctacacggtgatcaaagtgagaatgagctaccgagatt
ggggggcaaggaagataggagggtcaaacagagtcgaggagaagccagggagagctacaga
gaaaccgggcccagcagagcaagtgatgcgagagctgcccatcttccaaccggcacacccc
tagacattgacactgcaacggagtccagccaagatccgcaggacagtcgaaggtcagctga
cgccctgcttaggctgcaagccatggcaggaatctcggaagaacaaggctcagacacggac
acccctatagtgtacaatgacagaaatcttctagactaggtgcgagaggccgagggccaga
acaacatccgcctaccatccatcattgttataaaaaacttaggaaccaggtccacacagcc
gccagcccatcaaccatccactcccacgattggagccaatggcagaagagcaggcacgcca
tgtcaaaaacggactggaatgcatccgggctctcaaggccgagcccatcggctcactggcc
atcgaggaagctatggcagcatggtcagaaatatcagacaacccaggacaggagcgagcca
cctgcagggaagagaaggcaggcagttcgggtctcagcaaaccatgcctctcagcaattgg
atcaactgaaggcggtgcacctcgcatccgcggtcagggacctggagagagcgatgacgac
gctgaaactttgggaatccccccaagaaatctccaggcatcaagcactgggttacagtgtt
attacgtttatgatcacagcggtgaagcggttaagggaatccaagatgctgactctatcat
ggttcaatcaggccttgatggtgatagcaccctctcaggaggagacaatgaatctgaaaac
agcgatgtggatattggcgaacctgataccgagggatatgctatcactgaccggggatctg
ctcccatctctatggggttcagggcttctgatgttgaaactgcagaaggaggggagatcca
cgagctcctgagactccaatccagaggcaacaactttccgaagcttgggaaaactctcaat
gttcctccgcccccggaccccggtagggccagcacttccgggacacccattaaaaagggca
cagacgcgagattagcctcatttggaacggagatcgcgtctttattgacaggtggtgcaac
ccaatgtgctcgaaagtcaccctcggaaccatcagggccaggtgcacctgcggggaatgtc
cccgagtgtgtgagcaatgccgcactgatacaggagtggacacccgaatctggtaccacaa
tctccccgagatcccagaataatgaagaaggggagactattatgatgatgagctgttctc
tgatgtccaagatattaaaacagccttggccaaaatacacgaggataatcagaagataatc
tccaagctagaatcactgctgttattgaagggagaagttgagtcaattaagaagcagatca
acaggcaaaatatcagcatatccaccctggaaggacacctctcaagcatcatgatcgccat
tcctggacttgggaaggatcccaacgaccccactgcagatgtcgaaatcaatcccgacttg
aaacccatcataggcagagattcaggccgagcactggccgaagttctcaagaaacccgttg
ccagccgacaactccaaggaatgacaaatggacggaccagttccagaggacagctgctgaa
ggaatttcagctaaagccgatcgggaaaaagatgagctcagccgtcgggtttgttcctgac
accggccctgcatcacgcagtgtaatccgctccattataaaatccagccggctagaggagg

FIG. 29C atcggaagcgttacctgatgactctccttgatgatatcaaaggagccaatgatcttgccaa
gttccaccagatgctgatgaagataataatgaagtagctacagctcaacttacctgccaac
cccatgccagtcgacccaactagtacaacctaaatccattataaaaacttaggagcaaag
tgattgcctcccaaggtccacaatgacagagacctacgacttcgacaagtcggcatgggac
atcaaagggtcgatcgctccgatacaacccaccacctacagtgatggcaggctggtgcccc
aggtcagagtcatagatcctggtctaggcgacaggaaggatgaatgctttatgtacatgtt
tctgctggggttgttgaggacagcgattccctagggcctccaatcgggcgagcatttggg
ttcctgcccttaggtgttggcagatccacagcaaagcccgaaaaactcctcaaagaggcca
ctgagcttgacatagttgttagacgtacagcagggctcaatgaaaaactggtgttctacaa
caacaccccactaactctcctcacaccttggagaaaggtcctaacaacagggagtgtcttc
aacgcaaaccaagtgtgcaatgcggttaatctgataccgctcgataccccgcagaggttcc
gtgttgtttatatgagcatcacccgtctttcggataacgggtattacaccgttcctagaag
aatgctggaattcagatcggtcaatgcagtggccttcaacctgctggtgacccttaggatt
gacaaggcgataggccctgggaagatcatcgacaatacagagcaacttcctgaggcaacat
ttatggtccacatcgggaacttcaggagaaagaagagtgaagtctactctgccgattattg
caaaatgaaaatcgaaaagatgggcctggtttttgcacttggtgggataggggcaccagt
cttcacattagaagcacaggcaaaatgagcaagactctccatgcacaactcgggttcaaga
agaccttatgttacccgctgatggatatcaatgaagaccttaatcgattactctggaggag
cagatgcaagatagtaagaatccaggcagttttgcagccatcagttcctcaagaattccgc
atttacgacgacgtgatcataaatgatgaccaaggactattcaaagttctgtagaccgtag
tgcccagcaatgcccgaaaacgacccccctcacaatgacagccagaaggcccggacaaaaa
agcccccctccgaaagactccacggaccaagcgagaggccagccagcagccgacggcaagcg
cgaacaccaggcggccccagcacagaacagccctgacacaaggccaccaccagccacccca
atctgcatcctcctcgtgggacccccgaggaccaacccccaaggctgcccccgatccaaac
caccaaccgcatccccaccacccccgggaaagaaacccccagcaattggaaggcccctccc
cctcttcctcaacacaagaactccacaaccgaaccgcacaagcgaccgaggtgacccaacc
gcaggcatccgactccctagacagatcctctctccccggcaaactaaacaaaacttagggc
caaggaacatacacacccaacagaacccagaccccggcccacggcgccgcgcccccaaccc
ccgacaaccagagggagcccccaaccaatcccgccggctcccccggtgcccacaggcaggg
acaccaacccccgaacagacccagcacccaaccatcgacaatccaagacgggggggccccc
ccaaaaaaaggcccccaggggccgacagccagcaccgcgaggaagcccacccaccccacac
acgaccacggcaaccaaaccagaacccagaccaccctgggccaccagctcccagactcggc
catcaccccgcagaaaggaaaggccacaacccgcgcaccccagccccgatccggcggggag
ccacccaacccgaaccagcacccaagagcgatccccgaaggacccccgaaccgcaaaggac
atcagtatcccacagcctctccaagtcccccggtctcctcctcttctcgaagggaccaaaa
gatcaatccaccacacccgacgacactcaactccccacccctaaaggagacaccgggaatc
ccagaatcaagactcatccaatgtccatcatgggtctcaaggtgaacgtctctgccatatt
catggcagtactgttaactctccaaacacccaccggtcaaatccattggggcaatctctct
aagataggggtggtaggaataggaagtgcaagctacaaagttatgactcgttccagccatc
aatcattagtcataaaattaatgcccaatataactctcctcaataactgcacgagggtaga
gattgcagaatacaggagactactgagaacagttttggaaccaattagagatgcacttaat
gcaatgacccagaatataagaccggttcagagtgtagcttcaagtaggagacacaagagat
ttgcgggagtagtcctggcaggtgcggccctaggcgttgccacagctgctcagataacagc
cggcattgcacttcaccagtccatgctgaactctcaagccatcgacaatctgagagcgagc
ctggaaactactaatcaggcaattgagacaatcagacaagcagggcaggagatgatattgg

FIG. 29D ctgttcagggtgtccaagactacatcaataatgagctgataccgtctatgaaccaactatc
ttgtgatttaatcggccagaagctcgggctcaaattgctcagatactatacagaaatcctg
tcattatttggccccagtttacgggaccccatatctgcggagatatctatccaggctttga
gctatgcgcttggaggagacatcaataaggtgttagaaaagctcggatacagtggaggtga
tttactgggcatcttagagagcggaggaataaaggcccggataactcacgtcgacacagag
tcctacttcattgtcctcagtatagcctatccgacgctgtccgagattaaggggggtgattg
tccaccggctagaggggtctcgtacaacataggctctcaagagtggtataccactgtgcc
caagtatgttgcaacccaagggtaccttatctcgaattttgatgagtcatcgtgtactttc
atgccagaggggactgtgtgcagccaaaatgccttgtacccgatgagtcctctgctccaag
aatgcctccggggggtacaccaagtcctgtgctcgtacactcgtatccgggtcttttgggaa
ccggttcattttatcacaaggaacctaatagccaattgtgcatcaatcctttgcaagtgt
tacacaacaggaacgatcattaatcaagaccctgacaagatcctaacatacattgctgccg
atcactgcccggtagtcgaggtgaacggcgtgaccatccaagtcgggagcaggaggtatcc
agacgctgtgtacttgcacagaattgacctcggtcctcccatatcattggagaggttggac
gtagggacaaatctggggaatgcaattgctaagttggaggatgccaaggaattgttggagt
catcggaccagatattgaggagtatgaaaggtttatcgagcactagcatagtctacatcct
gattgcagtgtgtcttggagggttgatagggatccccgctttaatatgttgctgcagggg
cgttgtaacaaaaagggagaacaagttggtatgtcaagaccaggcctaaagcctgatctta
cgggaacatcaaaatcctatgtaaggtcgctctgatcctctacaactcttgaaacacaaat
gtcccacaagtctcctcttcgtcatcaagcaaccaccgcacccagcatcaagcccacctga
aattatctccggcttccctctggccgaacaatatcggtagttaatcaaaacttagggtgca
agatcatccacaatgtcaccacaacgagaccggataaatgccttctacaaagataaccccc
atcccaagggaagtaggatagtcattaacagagaacatcttatgattgatagaccttatgt
tttgctggctgttctgtttgtcatgtttctgagcttgatcgggttgctagccattgcaggc
attagacttcatcgggcagccatctacaccgcagagatccataaaagcctcagcaccaatc
tagatgtaactaactcaatcgagcatcaggtcaaggacgtgctgacaccactcttcaaaat
catcggtgatgaagtgggcctgaggacacctcagagattcactgacctagtgaaattaatc
tctgacaagattaaattccttaatccggatagggagtacgacttcagagatctcacttggt
gtatcaacccgccagagagaatcaaattggattatgatcaatactgtgcagatgtggctgc
tgaagagctcatgaatgcattggtgaactcaactctactggagaccagaacaaccaatcag
ttcctagctgtctcaaagggaaactgctcagggcccactacaatcagaggtcaattctcaa
acatgtcgctgtccctgttagacttgtatttaggtcgaggttacaatgtgtcatctatagt
cactatgacatcccagggaatgtatggggggaacttacctagtggaaaagcctaatctgagc
agcaaaaggtcagagttgtcacaactgagcatgtaccgagtgtttgaagtaggtgttatca
gaaatccgggtttggggggctccggtgttccatatgacaaactatcttgagcaaccagtcag
taatgatctcagcaactgtatggtggctttgggggagctcaaactcgcagccctttgtcac
ggggaagattctatcacaattccctatcagggatcagggaaaggtgtcagcttccagctcg
tcaagctaggtgtctggaaatccccaaccgacatgcaatcctgggtccccttatcaacgga
tgatccagtgatagacaggctttacctctcatctcacagaggtgttatcgctgacaatcaa
gcaaaatgggctgtcccgacaacacgaacagatgacaagttgcgaatggagacatgcttcc
aacaggcgtgtaagggtaaaatccaagcactctgcgagaatcccgagtgggcaccattgaa
ggataacaggattccttcatacggggtcttgtctgttgatctgagtctgacagttgagctt
aaaatcaaaattgcttcgggattcgggccattgatcacacacggttcagggatggacctat
acaaatccaaccacaacaatgtgtattggctgactatcccgccaatgaagaacctagcctt
aggtgtaatcaacacattggagtggataccgagattcaaggttagtccctacctcttcact

FIG. 29E

```
gtcccaattaaggaagcaggcgaagactgccatgccccaacatacctacctgcggaggtgg
atggtgatgtcaaactcagttccaatctggtgattctacctggtcaagatctccaatatgt
tttggcaacctacgatacttccagggttgaacatgctgtggtttattacgtttacagccca
agccgctcattttcttacttttatcctttttaggttgcctataaaggggggtccccatcgaat
tacaagtggaatgcttcacatgggaccaaaaactctggtgccgtcacttctgtgtgcttgc
ggactcagaatctggtggacatatcactcactctgggatggtgggcatgggagtcagctgc
acagtcacccgggaagatggaaccaatcgcagatagggctgctagtgaaccaatcacatga
tgtcacccagacatcaggcatacccactagtgtgaaatagacatcagaattaagaaaaacg
tagggtccaagtggttccccgttatggactcgctatctgtcaaccagatcttataccctga
agttcacctagatagcccgatagttaccaataagatagtagccatcctggagtatgctcga
gtccctcacgcttacagcctggaggaccctacactgtgtcagaacatcaagcaccgcctaa
aaaacggattttccaaccaaatgattataaacaatgtggaagttgggaatgtcatcaagtc
caagcttaggagttatccggcccactctcatattccatatccaaattgtaatcaggattta
tttaacatagaagacaaagagtcaacgaggaagatccgtgaactcctcaaaaaggggaatt
cgctgtactccaaagtcagtgataaggttttccaatgcttaagggacactaactcacggct
tggcctaggctccgaattgagggaggacatcaaggagaaagttattaacttgggagtttac
atgcacagctcccagtggtttgagccctttctgttttggtttacagtcaagactgagatga
ggtcagtgattaaatcacaaacccatacttgccataggaggagacacacacctgtattctt
cactggtagttcagttgagttgctaatctctcgtgaccttgttgctataatcagtaaagag
tctcaacatgtatattacctgacatttgaactggttttgatgtattgtgatgtcatagagg
ggaggttaatgacagagaccgctatgactattgatgctaggtatacagagcttctaggaag
agtcagatacatgtggaaactgatagatggtttcttccctgcactcgggaatccaacttat
caaattgtagccatgctggagcctctttcacttgcttacctgcagctgagggatataacag
tagaactcagaggtgctttccttaaccactgctttactgaaatacatgatgttcttgacca
aaacgggttttctgatgaaggtacttatcatgagttaactgaagctctagattacattttc
ataactgatgacatacatctgacaggggagattttctcatttttcagaagtttcggccacc
ccagacttgaagcagtaacggctgctgaaaatgttaggaaatacatgaatcagcctaaagt
cattgtgtatgagactctgatgaaaggtcatgccatattttgtggaatcataatcaacggc
tatcgtgacaggcacggaggcagttggccaccgctgaccctcccccctgcatgctgcagaca
caatccggaatgctcaagcttcaggtgaagggttaacacatgagcagtgcgttgataactg
gaaatctttgctggagtgaaatttggctgctttatgcctcttagcctggatagtgatctg
acaatgtacctaaaggacaaggcacttgctgctctccaaagggaatgggattcagtttacc
cgaaagagttcctgcgttacgaccctcccaagggaaccgggtcacggaggcttgtagatgt
tttccttaatgattcgagctttgacccatatgatgtgataatgtatgttgtaagtggagct
tacctccatgaccctgagttcaacctgtcttacagcctgaaagaaaaggagatcaaggaaa
caggtagacttttgctaaaatgacttacaaaatgagggcatgccaagtgattgctgaaaa
tctaatctcaaacgggattggcaaatattttaaggacaatgggatggccaaggatgagcac
gatttgactaaggcactccacactctagctgtctcaggagtccccaaagatctcaaagaaa
gtcacagggggggccagtcttaaaaacctactcccgaagcccagtccacacaagtaccag
gaacgtgagagcagcaaaagggtttatagggttccctcaagtaattcggcaggaccaagac
actgatcatccggagaatatggaagcttacgagacagtcagtgcatttatcacgactgatc
tcaagaagtactgccttaattggagatatgagaccatcagcttgtttgcacagaggctaaa
tgagatttacggattgccctcatttttccagtggctgcataagaggcttgagacctctgtc
ctgtatgtaagtgaccctcattgcccccccgaccttgacgcccatatcccgttatataaag
tccccaatgatcaaatcttcattaagtaccctatgggaggtatagaagggtattgtcagaa
```

FIG. 29F gctgtggaccatcagcaccattccctatctatacctggctgcttatgagagcggagtaagg
attgcttcgttagtgcaaggggacaatcagaccatagccgtaacaaaaaggtacccagca
catggccctacaaccttaagaaacgggaagctgctagagtaactagagattactttgtaat
tcttaggcaaaggctacatgatattggccatcacctcaaggcaaatgagacaattgtttca
tcacatttttttgtctattcaaaaggaatatattatgatgggctacttgtgtcccaatcac
tcaagagcatcgcaagatgtgtattctggtcagagactatagttgatgaaacaagggcagc
atgcagtaatattgctacaacaatggctaaaagcatcgagagaggttatgaccgttacctt
gcatattccctgaacgtcctaaaagtgatacagcaaattctgatctctcttggcttcacaa
tcaattcaaccatgacccgggatgtagtcatacccctcctcacaaacaacgacctcttaat
aaggatggcactgttgcccgctcctattgggggatgaattatctgaatatgagcaggctg
tttgtcagaaacatcggtgatccagtaacatcatcaattgctgatctcaagagaatgattc
tcgcctcactaatgcctgaagagaccctccatcaagtaatgacacaacaaccggggactc
ttcattcctagactgggctagcgacccttactcagcaaatcttgtatgtgtccagagcatc
actagactcctcaagaacataactgcaaggtttgtcctgatccatagtccaaacccaatgt
taaaaggattattccatgatgacagtaaagaagaggacgagggactggcggcattcctcat
ggacaggcatattatagtacctagggcagctcatgaaatcctggatcatagtgtcacaggg
gcaagagagtctattgcaggcatgctggataccacaaaaggcttgattcgagccagcatga
ggaaggggggttaacctctcgagtgataaccagattgtccaattatgactatgaacaatt
cagagcagggatggtgctattgacaggaagaaagagaaatgtcctcattgacaaagagtca
tgttcagtgcagctggcgagagctctaagaagccatatgtgggcgaggctagctcgaggac
ggcctatttacggccttgaggtccctgatgtactagaatctatgcgaggccaccttattcg
gcgtcatgagacatgtgtcatctgcgagtgtggatcagtcaactacggatggtttttgtc
ccctcgggttgccaactggatgatattgacaaggaaacatcatccttgagagtcccatata
ttggttctaccactgatgagagaacagacatgaagcttgccttcgtaagagccccaagtcg
atccttgcgatctgctgttagaatagcaacagtgtactcatgggcttacggtgatgatgat
agctcttggaacgaagcctggttgttggctaggcaaagggccaatgtgagcctggaggagc
taagggtgatcactcccatctcaacttcgactaatttagcgcataggttgagggatcgtag
cactcaagtgaaatactcaggtacatcccttgtccgagtggcgaggtataccacaatctcc
aacgacaatctctcatttgtcatatcagataagaaggttgatactaactttatataccaac
aaggaatgcttctagggttgggtgttttagaaacattgtttcgactcgagaaagataccgg
atcatctaacacggtattacatcttcacgtcgaaacagattgttgcgtgatcccgatgata
gatcatcccaggatacccagctcccgcaagctagagctgagggcagagctatgtaccaacc
cattgatatatgataatgcacctttaattgacagagatgcaacaaggctatacacccagag
ccataggaggcaccttgtggaatttgttacatggtccacaccccaactatatcacattta
gctaagtccacagcactatctatgattgacctggtaacaaaatttgagaaggaccatatga
atgaaatttcagctctcataggggatgacgatatcaatagtttcataactgagtttctgct
catagagccaagattattcactatctacttgggccagtgtgcggccatcaattgggcattt
gatgtacattatcatagaccatcagggaaatatcagatgggtgagctgttgtcatcgttcc
tttctagaatgagcaaaggagtgtttaaggtgcttgtcaatgctctaagccacccaaagat
ctacaagaaattctggcattgtggtattatagagcctatccatggtccttcacttgatgct
caaaacttgcacacaactgtgtgcaacatggtttacacatgctatatgacctacctcgacc
tgttgttgaatgaagagttagaagagttcacatttctcttgtgtgaaagcgacgaggatgt
agtaccggacagattcgacaacatccaggcaaaacacttatgtgttctggcagatttgtac
tgtcaaccagggacctgcccaccaattcgaggtctaagaccggtagagaaatgtgcagttc
taaccgaccatatcaaggcagaggctatgttatctccagcaggatcttcgtggaacataaa

FIG. 29G tccaattattgtagaccattactcatgctctctgacttatctccggcgaggatcgatcaaa
cagataagattgagagttgatccaggattcattttcgacgccctcgctgaggtaaatgtca
gtcagccaaagatcggcagcaacaacatctcaaatatgagcatcaaggctttcagaccccc
acacgatgatgttgcaaaattgctcaaagatatcaacacaagcaagcacaatcttcccatt
tcagggggcaatctcgccaattatgaaatccatgctttccgcagaatcgggttgaactcat
ctgcttgctacaaagctgttgagatatcaacattaattaggagatgccttgagccagggga
ggacggcttgttcttgggtgagggatcgggttctatgttgatcacttataaagagatactt
aaactaaacaagtgcttctataatagtggggtttccgccaattctagatctggtcaaaggg
aattagcaccctatccctccgaagttggccttgtcgaacacagaatgggagtaggtaatat
tgtcaaagtgctctttaacgggaggcccgaagtcacgtgggtaggcagtgtagattgcttc
aatttcatagttagtaatatccctacctctagtgtggggtttatccattcagatatagaga
ccttgcctgacaaagatactatagagaagctagaggaattggcagccatcttatcgatggc
tctgctcctgggcaaaataggatcaatactggtgattaagcttatgcctttcagcggggat
tttgttcagggatttataagttatgtagggtctcattatagagaagtgaaccttgtatacc
ctagatacagcaacttcatctctactgaatcttatttggttatgacagatctcaaggctaa
ccggctaatgaatcctgaaaagattaagcagcagataattgaatcatctgtgaggacttca
cctggacttataggtcacatcctatccattaagcaactaagctgcatacaagcaattgtgg
gagacgcagttagtagaggtgatatcaatcctactctgaaaaaacttacacctatagagca
ggtgctgatcaattgcgggttggcaattaacggacctaagctgtgcaaagaattgatccac
catgatgttgcctcagggcaagatggattgcttaattctatactcatcctctacagggagt
tggcaagattcaaagacaaccaaagaagtcaacaaggatgttccacgcttaccccgtatt
ggtaagtagcaggcaacgagaacttatatctaggatcacccgcaaattctgggggcacatt
cttctttactccgggaacaaaaagttgataaataagtttatccagaatctcaagtccggct
atctgatactagacttacaccagaatatcttcgttaagaatctatccaagtcagagaaaca
gattattatgacgggggtttgaaacgtgagtgggtttttaaggtaacagtcaaggagacc
aaagaatggtataagttagtcggatacagtgccctgattaaggactaattggttgaactcc
ggaaccctaatcctgccctaggtggttaggcattatttgcaatatattaaagaaaactttg
aaaatacgaagtttctattcccagctttgtctggtggccggcatggtcccagcctcctcgc
tggcgccggctgggcaacattccgaggggaccgtcccctcggtaatggcgaatgggacgcg
gccggtcgatcgacgatccggctgctaacaaagcccgaaaggaagctgagttggctgctgc
caccgctgagcaataactagcataaccccttggggcctctaaacgggtcttgaggggtttt
ttgctgaaaggaggaactatatccggatcgagatcaattctgtgagcgtatggcaaacgaa
ggaaaaatagttatagtagccgcactcgatgggacatttcaacgtaaaccgtttaataata
ttttgaatcttattccattatctgaaatggtggtaaaactaactgctgtgtgtatgaaatg
ctttaaggaggcttccttttctaaacgattgggtgaggaaaccgagatagaaataatagga
ggtaatgatatgtatcaatcggtgtgtagaaagtgttacatcgactcataatattatattt
tttatctaaaaaactaaaaataaacattgattaaattttaatataatacttaaaaatggat
gttgtgtcgttagataaaccgtttatgtattttgaggaaattgataatgagttagattacg
aaccagaaagtgcaaatgaggtcgcaaaaaaactgccgtatcaaggacagttaaaactatt
actaggagaattatttttttcttagtaagttacagcgacacggtatattagatggtgccacc
gtagtgtatataggatctgctcccggtacacatatacgttatttgagagatcatttctata
atttaggagtgatcccgaaaggaagctgagttggctgctgccaccgctgagcaataactag
cataaccccttggggcctctaaacgggtcttgaggggtttttttgctgaaaggaggaacgcg
cctgatgcggtattttctccttacgcatctgtgcggtatttcacaccgcatatatggtgca
ctctcagtacaatctgctctgatgccgcatagttaagccagccccgacacccgccaacacc

FIG. 29H cgctgacgcgccctgacgggcttgtctgctcccggcatccgcttacagacaagctgtgacc
gtctccgggagctgcatgtgtcagaggttttcaccgtcatcaccgaaacgcgcgagacgaa
agggcctcgtgatacgcctatttttataggttaatgtcatgataataatggtttcttagac
gtcaggtggcacttttcggggaaatgtgcgcggaacccctatttgtttatttttctaaata
cattcaaatatgtatccgctcatgagacaataaccctgataaatgcttcaataatattgaa
aaaggaagagtatgagtattcaacatttccgtgtcgcccttattcccttttttgcggcatt
ttgccttcctgtttttgctcacccagaaacgctggtgaaagtaaaagatgctgaagatcag
ttgggtgcacgagtgggttacatcgaactggatctcaacagcggtaagatccttgagagtt
ttcgccccgaagaacgttttccaatgatgagcacttttaaagttctgctatgtggcgcggt
attatcccgtattgacgccgggcaagagcaactcggtcgccgcatacactattctcagaat
gacttggttgagtactcaccagtcacagaaaagcatcttacggatggcatgacagtaagag
aattatgcagtgctgccataaccatgagtgataacactgcggccaacttacttctgacaac
gatcggaggaccgaaggagctaaccgcttttttgcacaacatgggggatcatgtaactcgc
cttgatcgttgggaaccggagctgaatgaagccataccaaacgacgagcgtgacaccacga
tgcctgtagcaatggcaacaacgttgcgcaaactattaactggcgaactacttactctagc
ttcccggcaacaattaatagactggatggaggcggataaagttgcaggaccacttctgcgc
tcggcccttccggctggctggtttattgctgataaatctggagccggtgagcgtgggtctc
gcggtatcattgcagcactggggccagatggtaagccctcccgtatcgtagttatctacac
gacggggagtcaggcaactatggatgaacgaaatagacagatcgctgagataggtgcctca
ctgattaagcattggtaactgtcagaccaagtttactcatatatactttagattgatttaa
aacttcatttttaatttaaaaggatctaggtgaagatcctttttgataatctcatgaccaa
aatcccttaacgtgagttttcgttccactgagcgtcagaccccgtagaaaagatcaaagga
tcttcttgagatcctttttttctgcgcgtaatctgctgcttgcaaacaaaaaaaccaccgc
taccagcggtggtttgtttgccggatcaagagctaccaactctttttccgaaggtaactgg
cttcagcagagcgcagataccaaatactgtccttctagtgtagccgtagttaggccaccac
ttcaagaactctgtagcaccgcctacatacctcgctctgctaatcctgttaccagtggctg
ctgccagtggcgataagtcgtgtcttaccgggttggactcaagacgatagttaccggataa
ggcgcagcggtcgggctgaacggggggttcgtgcacacagcccagcttggagcgaacgacc
tacaccgaactgagatacctacagcgtgagcattgagaaagcgccacgcttcccgaaggga
gaaaggcggacaggtatccggtaagcggcagggtcggaacaggagagcgcacgagggagct
tccagggggaaacgcctggtatctttatagtcctgtcgggtttcgccacctctgacttgag
cgtcgatttttgtgatgctcgtcaggggggcggagcctatggaaaaacgccagcaacgcgg
cctttttacggttcctggccttttgctggccttttgctcacatgttctttcctgcgttatc
ccctgattctgtggataaccgtattaccgcctttgagtgagctgataccgctcgccgcagc
cgaacgaccgagcgcagcgagtcagtgagcgaggaagcggaagagcgcccaatacgcaaac
cgcctctccccgcgcgttggccgattcattaatgcagctggcacgacaggtttcccgactg
gaaagcgggcagtgagcgcaacgcaattaatgtgagttagctcactcattaggcaccccag
gctttacactttatgcttccggctcgtatgttgtgtggaattgtgagcggataacaatttc
acacaggaaacagctatgaccatgattacgccaagcttacgcgtcctggcattatgcccag
tacatgaccttatgggactttcctacttggcagtacatctacgtattagtcatcgctatta
ccatggtgatgcggttttggcagtacatcaatgggcgtggatagcggtttgactcacgggg
atttccaagtctccaccccattgacgtcaatgggagtttgttttggcaccaaaatcaacgg
gactttccaaaatgtcgtaacaactccgccccattgacgcaaatgggcggtaggcgtgtac
ggtgggaggtctatataagcagagctcgtttagtgaaccgtgg

ONCOLYTIC MEASLES VIRUS

FIELD OF THE INVENTION

The present invention pertains to a pharmaceutical composition comprising a recombinant measles virus comprising a suicide gene for use in the treatment of malignant cells with primary or secondary resistances against an oncolytic measles virus without suicide gene activity. Further, the present invention pertains to a recombinant measles virus based on the genome of measles vaccine strain Schwarz comprising a suicide gene, which comprises a fusion of yeast cytosine deaminase and yeast uracil phosphoribosyltransferase, to a method and a kit for preparing the recombinant measles virus as claimed herein.

BACKGROUND OF THE INVENTION

Despite significant progress in the past, for example in the development of chemotherapeutics, antibody-based therapies, tumor vaccination, and radiation therapy, there is still an urgent and unmet need for the development of novel therapeutics and therapeutic approaches for the treatment of tumors and related malignant diseases.

While gene therapy approaches have substantial promise for such treatments, and while anti-tumoral results have been observed in different gene therapy models, certain limitations, particularly in the transfer of genes of interest to the tumor cells, have hampered the further development of such approaches.

In the past, it had occasionally been observed that natural infections or vaccinations with measles virus resulted in spontaneous tumor remissions, particularly in hematological malignancies, such as leukemias, resulting in the identification of the oncolytic potential of measles virus.

Measles virus is an enveloped, single-stranded, negative-sense paramyxo-virus of the genus *Morbillivirus* that is causing the infectious measles disease, an infection of the respiratory system. The genome of the measles virus contains six genes encoding eight proteins: the nucleocapsid (N), phospho- (P), matrix (M), fusion (F), hemagglutinin (H) and large (L) proteins, and two accessory proteins, termed C and V. The virus enters the target cells via pH-independent membrane fusion. The H and F proteins are involved in receptor binding and membrane fusion, respectively. Entry of measles virus into cells occurs via interaction of the surface H glycoprotein with the two known receptors for measles virus: CD46, which is ubiquitously present on nucleated primate cells, but is frequently over-expressed in tumors, and the signaling lymphocyte-activation molecule (SLAM) that is primarily located on B- and T-cells. CD46 is a membrane-associated complement regulatory protein that protects human cells against autologous complement lysis by acting as a cofactor in the proteolytic inactivation of C3b and C4b complement products, thus providing protection for tumor cells against complement-mediated lysis. Receptor recognition by the H protein leads to conformational changes of the F protein resulting in fusion with target cell membranes and subsequent viral entry. Infected cells, including tumor cells, express the viral F and H proteins on the cell surface. Recognition of the viral receptor in neighboring infected or uninfected cells similarly triggers cell-to-cell fusion. Therefore, the typical cytopathic effect of measles virus is the formation of giant mononuclear cell aggregates (syncytia).

Most of the measles virus preparations used for measles vaccines or for the research on oncolytic measles virus are based on an attenuated live measles virus derived from the so-called Edmonston vaccine strain, an isolate originally obtained in 1954, which was used to create the Edmonston-Enders cell line, and based on that, Edmonston A and B seed lines by serial passages on human cells and subsequent adaptation to chicken embryo fibroblastic (CEF) cells. Use of the originally developed live attenuated vaccine based on the Edmonston B lineage had to be stopped due to its high reactogenicity. By further attenuation of the Edmonston lines Edmonston-Enders and Edmonston A and B, additional measles derivatives were developed (Edmonston-Enders: AIK-C, Edmonston Zagreb; Edmonston A: Schwarz; Edmonston B: Moraten).

Despite the progress that has been made since the discovery of the oncolytic potential of measles virus, which is summarized in a recent review article (Msaouel, P., Dispenzieri, A., and Galanis, E., Clinical testing of engineered oncolytic measles virus strains in the treatment of cancer: An overview, Curr Opin Mol Ther. 2009; 11: 43-53), no therapeutic product based on oncolytic measles virus has yet reached the market, a fact that may, at least in part, be due to the potential of wild-type viruses to cause serious side effects, and particularly technical limitations in manufacturing virus preparations of high purity for clinical use. While the expanding knowledge of the biology of measles virus, as well as the development of a reverse genetics system that allows rescue of recombinant measles virus strains and viral engineering, have opened new opportunities for the development of measles virus as therapeutic in cancer treatment, there are still several limitations in the constructs that are presently in use.

For example, many of the research and development programs that are currently being pursued are based on the work of Martin Billeter and colleagues (Radecke, F., Spielhofer, P., Schneider, H., Kaelin, K., Huber, M., Dötsch, K, Christiansen, G., and Billeter, M., Rescue of measles viruses from cloned DNA. EMBO Journal 14 (1995) 5773-5784; WO 97/06270). Subsequently, it was shown that the sequence of the cloned viral genome deviated from the Edmonston B sequence, being closer to the wild-type Edmonston strain and having substitutions being related to the Edmonston subgroup (Parks et al., J. Virol. 75 (2001) 910-920; Parks et al., J. Virol. 75 (2001) 921-933).

Furthermore, measles virus preparations are currently rescued from cell lines not being approved for vaccine production like chicken embryo fibroblastic (CEF) cells or 293 human embryonic kidney cells, both complicating and thereby increasing the costs for the large-scale production of recombinant measles virus particles in conformity with GMP requirements.

Additionally, it has been shown that, for example, tumors derived from certain cell lines (eg, RPMI 8226 and HT1080) were resistant to treatment with oncolytic measles virus despite repeated virus injections (Peng K W, Facteau S, Wegman T, O'Kane D, Russell S J. Non-invasive in vivo monitoring of trackable viruses expressing soluble marker peptides. Nat Med. (2002); 8:527-31).

Therefore, there remains a continuous need for an improved pharmaceutical composition comprising a recombinant measles virus for use in the treatment of a malignant cells and improved methods for the generation of such pharmaceutical compositions and recombinant measles virus.

OBJECTS OF THE INVENTION

Accordingly, in view of the problems of the prior art, a first object of the present invention is to provide an improved pharmaceutical composition comprising a recombinant measles virus with oncolytic activity against tumors that are resistant to measles virus of the prior art.

The second object of the present invention is an improved pharmaceutical composition comprising a recombinant measles virus having a viral genome corresponding to the genome of established attenuated live measles vaccines.

The third object of the present invention is a safer and cheaper method for rescuing recombinant measles virus for use in the treatment of malignant cells.

SUMMARY OF THE INVENTION

These and other objects are solved by a pharmaceutical composition comprising a recombinant measles virus comprising a suicide gene for use in the treatment of malignant cells with primary or secondary resistances against an oncolytic measles virus without suicide gene activity.

The invention of a recombinant measles virus encoding a suicide gene for use in the treatment of malignant cells with primary or secondary resistances against an oncolytic measles virus without suicide gene activity enables a much more efficient treatment of solid tumors which concomitantly allows the employment of a reduced number of infectious measles virus particles without any loss in anti-tumor efficiency. Thereby, costs of virotherapeutic therapy can be reduced significantly.

In another aspect, the present invention relates to a recombinant measles virus based on measles vaccine strain Schwarz comprising a suicide gene, which comprises a fusion of a cytosine deaminase, particularly yeast cytosine deaminase, and a uracil phosphoribosyltransferase, particularly yeast uracil phosphoribosyltransferase, particularly wherein said suicide gene comprises a sequence according to SEQ-ID NO. 2.

In another aspect, the present invention relates to a method of treatment of malignant cells with primary or secondary resistances against an oncolytic measles virus without suicide gene activity, comprising the step of administering a recombinant measles virus comprising a suicide gene according to the present invention to a patient in need thereof.

In another aspect, the present invention relates to a method for generating the recombinant measles virus according to the present invention, comprising the step of (a) cloning (i) the genome of measles vaccine strain Schwarz, and (ii) a suicide gene, which comprises a fusion of a cytosine deaminase, particularly yeast cytosine deaminase, and a uracil phosphoribosyltransferase, particularly yeast uracil phosphoribosyltransferase, into a plasmid under the control of an RNA polymerase II promoter.

In yet another aspect, the present invention relates to a kit comprising (a) a plasmid comprising (i) the genome of measles vaccine strain Schwarz, and (ii) a suicide gene, which comprises a fusion of a cytosine deaminase, particularly yeast cytosine deaminase, and a uracil phosphoribosyltransferase, particularly yeast uracil phosphoribosyltransferase, under the control of an RNA polymerase II promoter, particularly wherein said suicide gene comprises a sequence according to SEQ-ID No. 2, particularly wherein the plasmid has the sequence according to SEQ-ID No. 4 SEQ-ID No. 8, or SEQ-ID No. 9, more particularly SEQ-ID No. 4;

(b) at least one plasmid comprising measles virus helper genes N, P and L, in form of single genes, each under the control of an RNA polymerase II promoter.

FIGURES

FIG. 1 shows the genetic sequence of measles vaccine strain Schwarz (SEQ-ID NO. 1).

FIG. 2 shows genetic sequence of fusion of yeast cytosine deaminase and yeast uracil phosphoribosyltransferase (with linker sequence) (SEQ-ID NO. 2).

FIG. 3 shows the complete genetic sequence of the plasmid pc3MerV2 Id-Trka coding for the basic recombinant measles virus engineered from the MeV Schwarz strain without any transgenes but with additional transcription cassette (SEQ-ID NO. 3).

FIG. 4 shows the genetic sequence of vector pc3MerV2 Id-SCD (coding for MeV Id-SCD) (SEQ-ID NO. 4).

FIG. 5 shows the genetic sequence of the helper plasmid required for the expression of the N gene (SEQ-ID No. 5), which is based on the CMV promoter variant construct pc3, encompassing CMV promoter nucleotides from −301 until −1 (+1 being defined as transcription initiation site) plus three nucleotides (TGG) additionally inserted after position −1:

nt 1358-2935: N ORF of MeV Schwarz (1578 nt=525 aa+stop codon)

FIG. 6 shows the genetic sequence of the helper plasmid required for the expression of the P gene (SEQ-ID No. 6), which is based on the CMV promoter variant construct pc3:

nt 1358-2881: P ORF of MeV Schwarz (1524 nt=507 aa+stop codon)

FIG. 7 shows the genetic sequence of the helper plasmid required for the expression of the L gene (SEQ-ID No. 7), which is based on the CMV promoter variant construct pc3:

nt 1358-7909: L ORF of MeV Schwarz (6552 nt=2183 aa+stop codon)

Figure 8A:
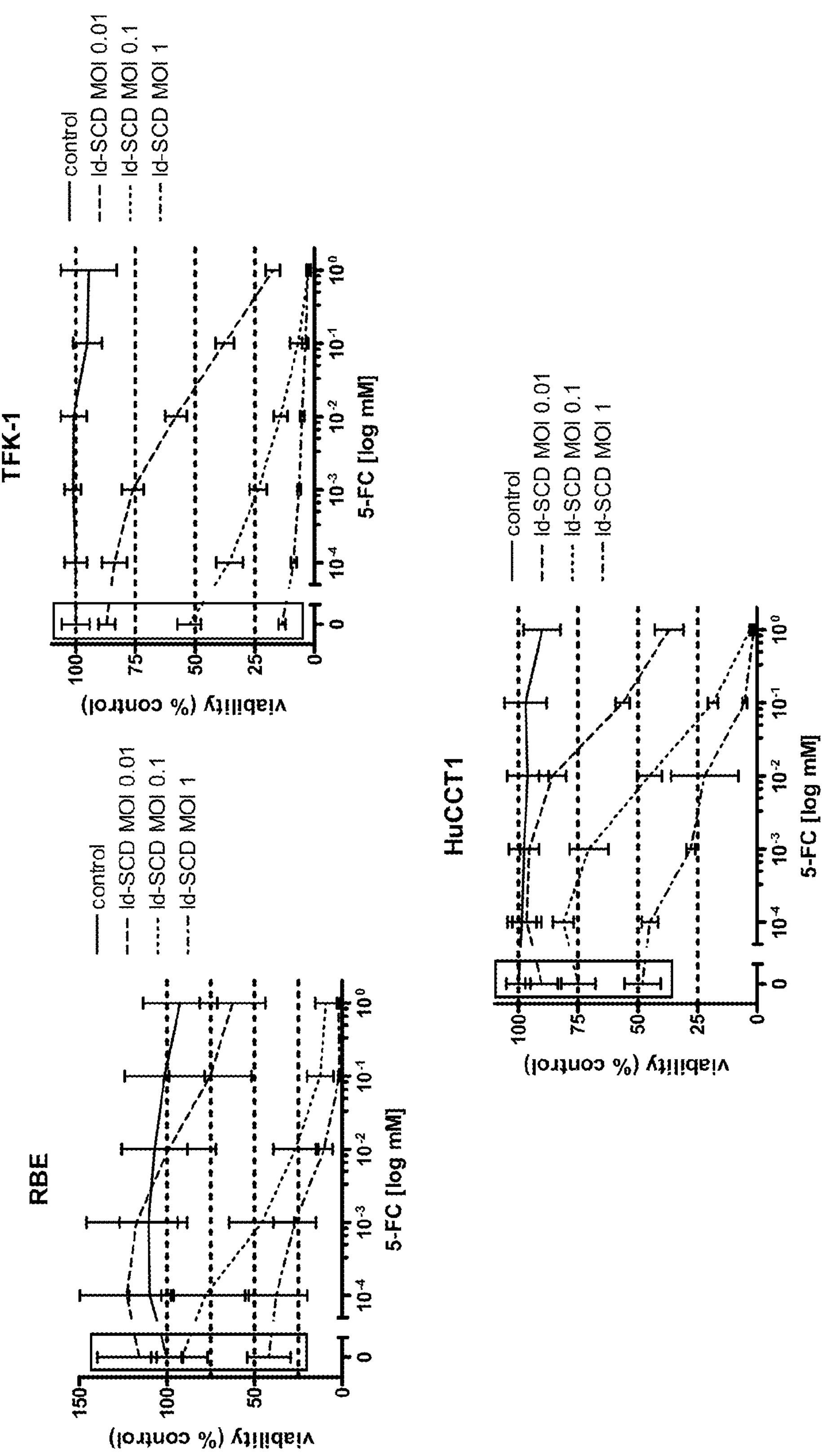

FIG. 8 shows the results of an SRB proliferation assay of HuCCT1, RBE, and TFK-1 cells (human cholangiocarcinoma cells) treated with viral particles rescued from the plasmid pc3MerV2 Id-SCD (Id-SCD) and incubated with prodrug 5-FC.

Figure 9:
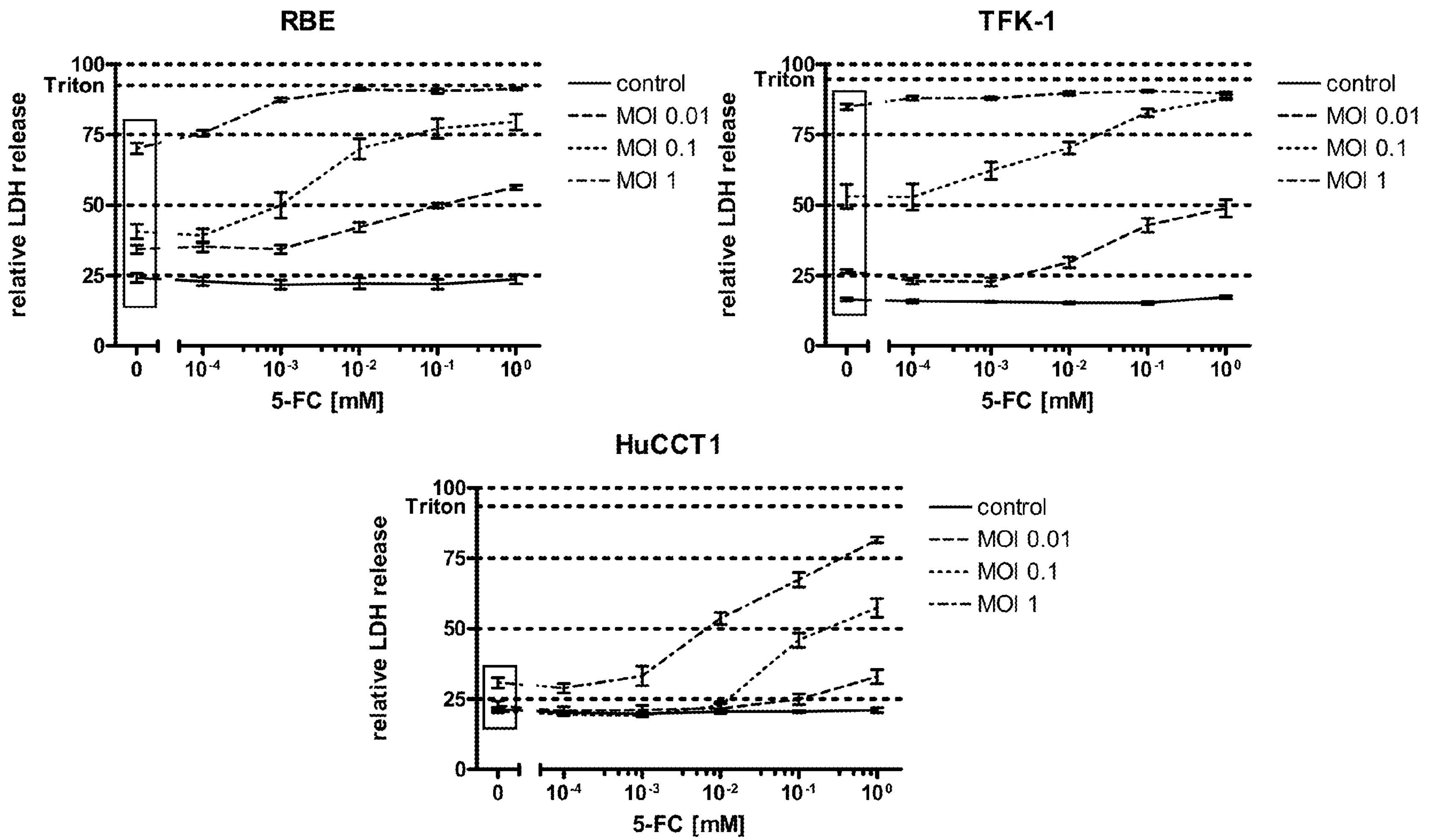

FIG. 9 shows the results of an LDH release assay of HuCCT1, RBE, and TFK-1 cells (human cholangiocarcinoma cells) treated with viral particles rescued from the plasmid pc3MerV2 Id-SCD (Id-SCD).

Figure 10A:
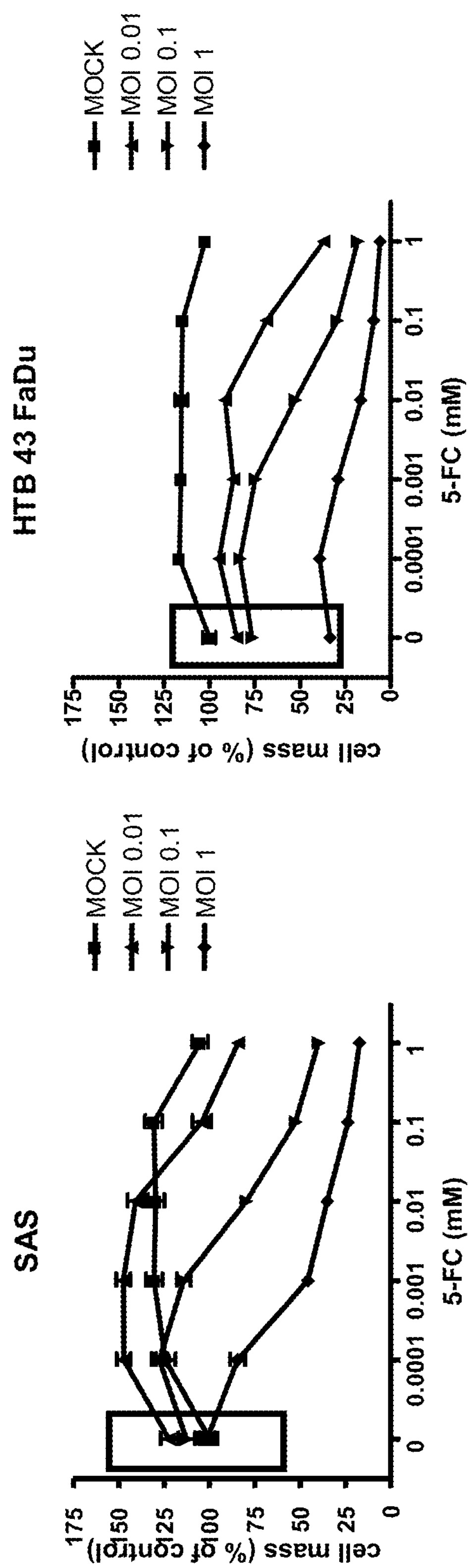

FIG. 10 shows the results of an SRB proliferation assay of SAS and HTB-43 FaDu cells (human Head & Neck (H&N) cancer cells) treated with viral particles rescued from the plasmid pc3MerV2 Id-SCD (Id-SCD).

Figure 11A:
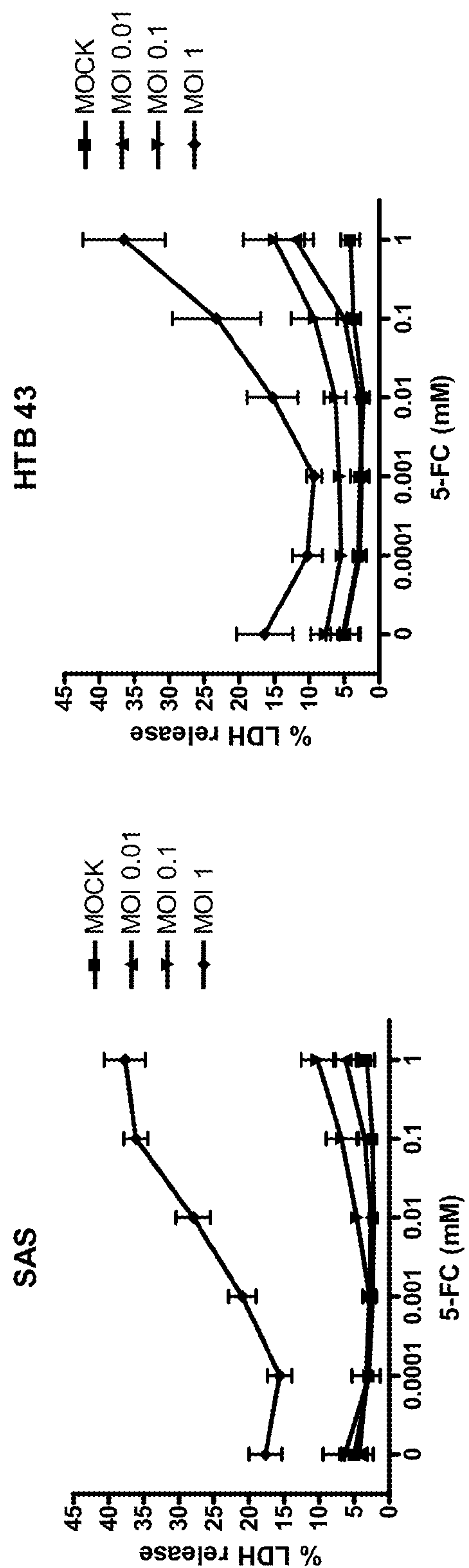

FIG. 11 shows the results of an LDH release assay of SAS and HTB-43 FaDu cells (human H&N cancer cells) treated with viral particles rescued from the plasmid pc3MerV2 Id-SCD (Id-SCD).

Figure 12A:
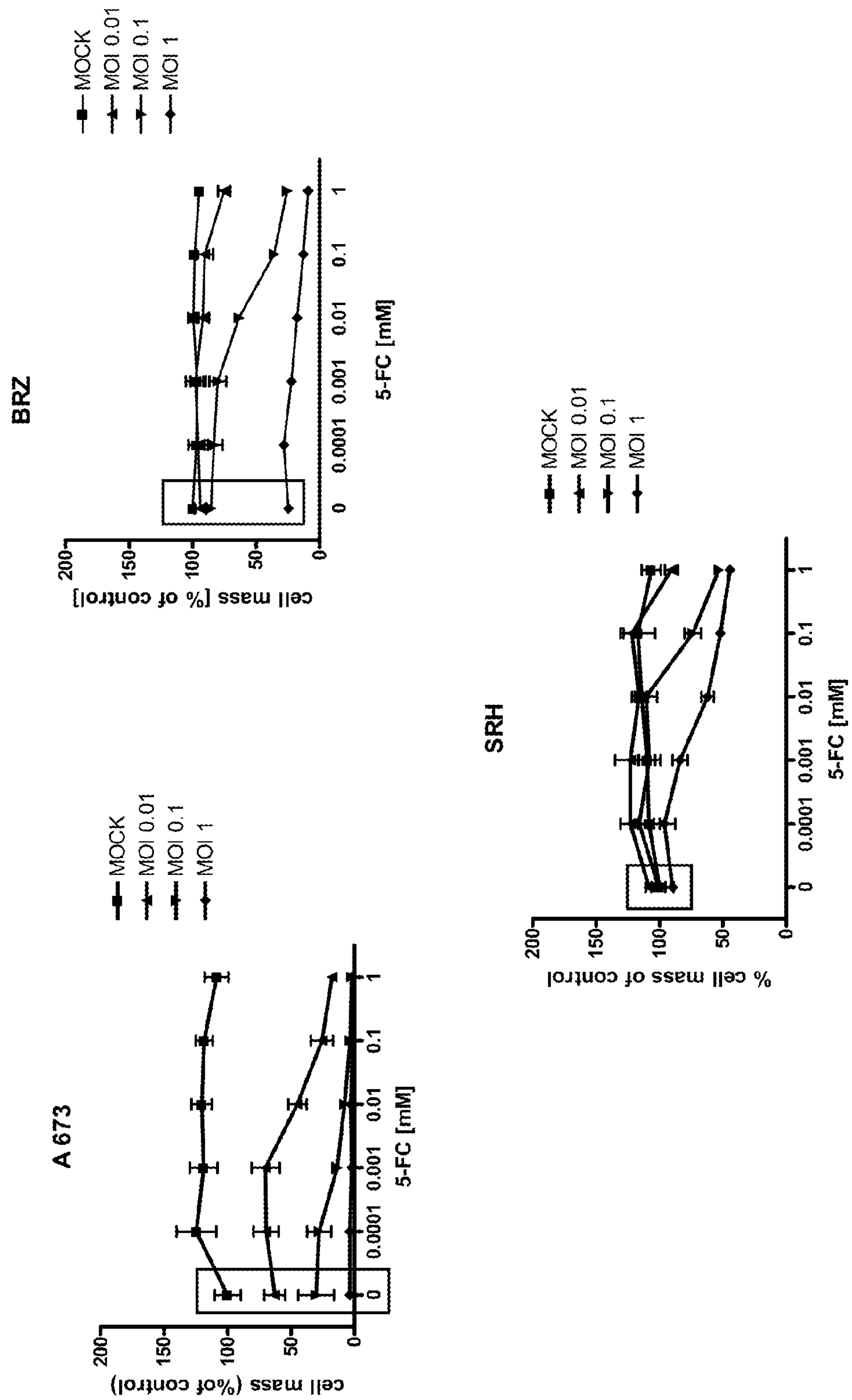

FIG. 12 shows the results of an SRB proliferation assay of A 673, BRZ, and SRH cells (human sarcoma cells) treated with viral particles rescued from the plasmid pc3MerV2 Id-SCD (Id-SCD).

Figure 13A:
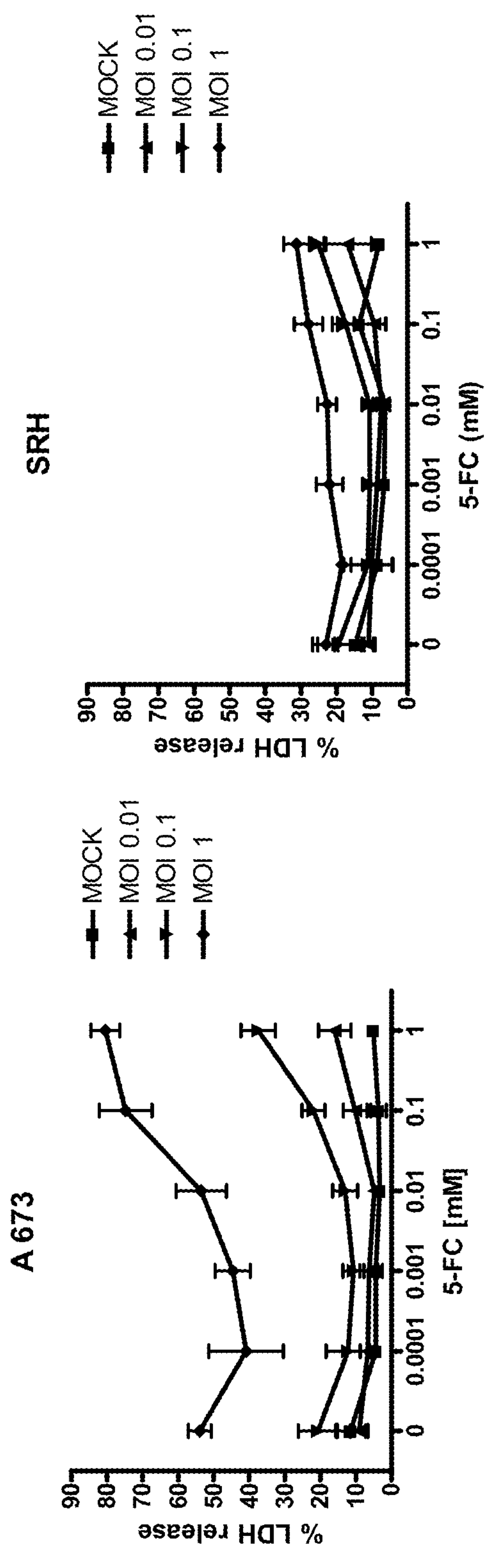

FIG. 13 shows the results of an LDH release assay of A 673 and SRH cells (human sarcoma cells) treated with viral particles rescued from pc3MerV2 Id-SCD (Id-SCD).

Figure 14:
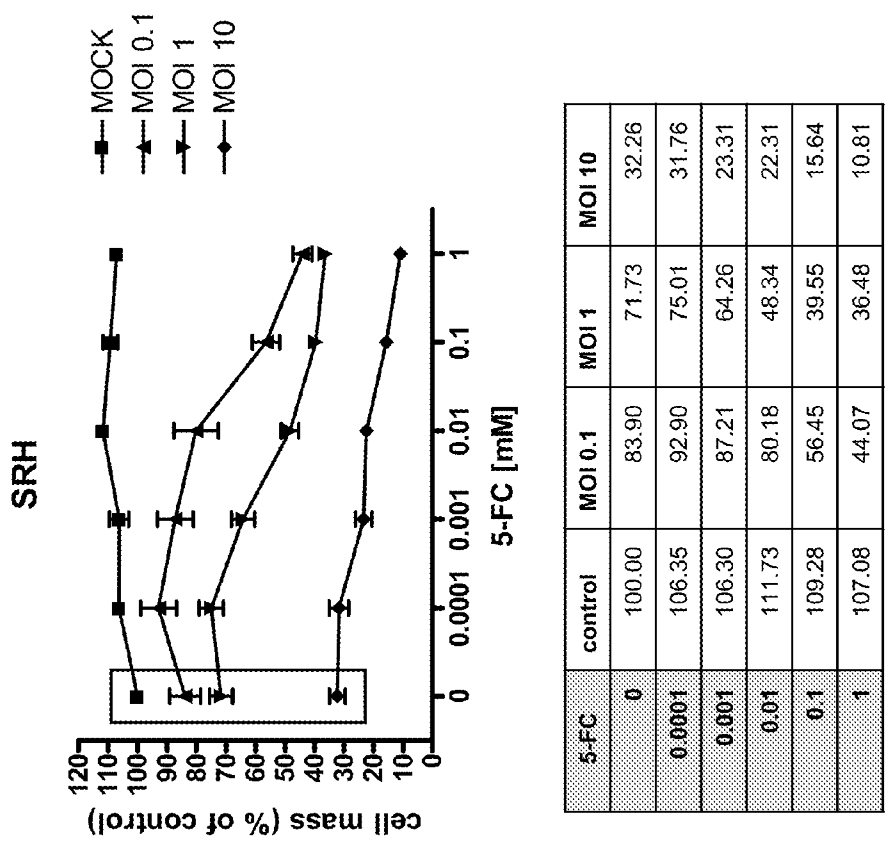

FIG. 14 shows the results of an SRB proliferation assay of SRH cells treated with viral particles rescued from the plasmid pc3MerV2 Id-SCD (Id-SCD).

Figure 15A:
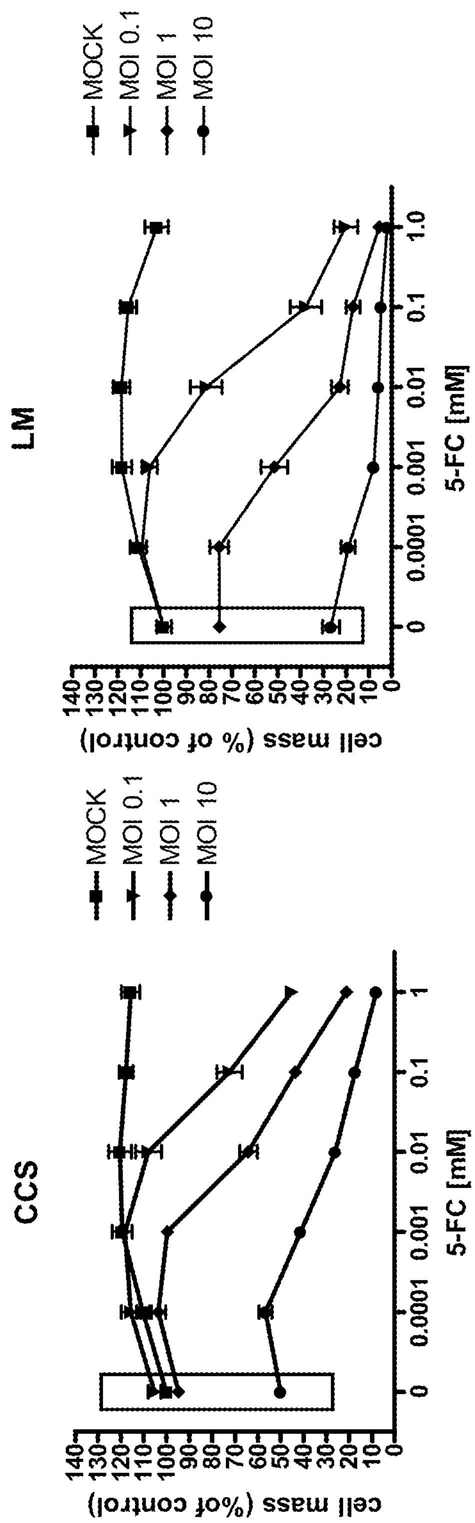

FIG. 15 shows the results of an SRB proliferation assay of sarcoma tumor cells (cell lines CCS, LM) treated with viral particles rescued from the plasmid pc3MerV2 Id-SCD (Id-SCD).

Figure 16A:
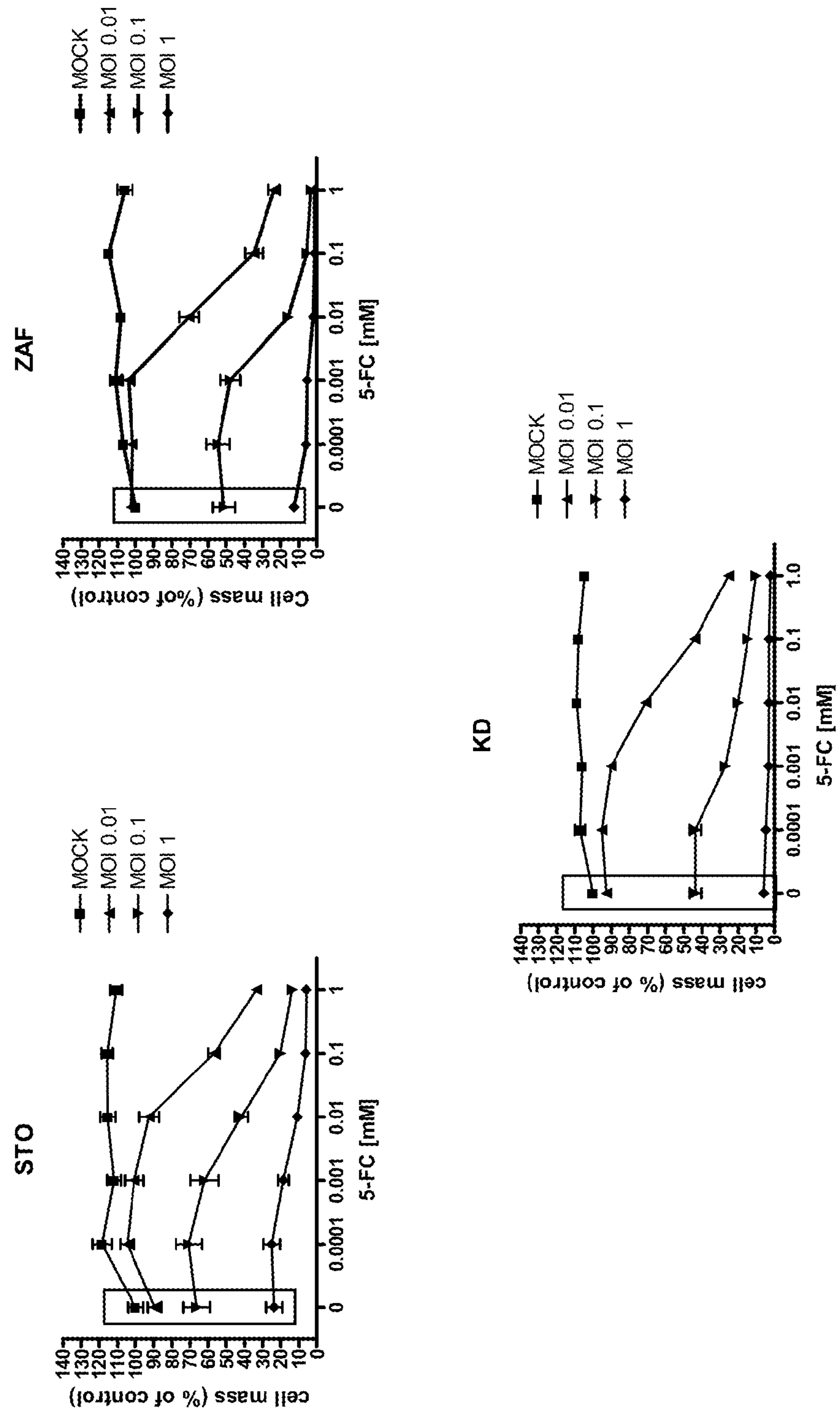

FIG. 16 shows the results of an SRB proliferation assay of sarcoma tumor cells (cell lines STO, ZAF, KD) treated with viral particles rescued from the plasmid pc3MerV2 Id-SCD (Id-SCD).

FIG. 17 shows the results of an SRB proliferation assay of glioblastoma tumor cells (cell lines LNT 229, LNT 229 CTS-1) treated with viral particles rescued from the plasmid pc3MerV2 Id-SCD (Id-SCD).

Figure 18A:
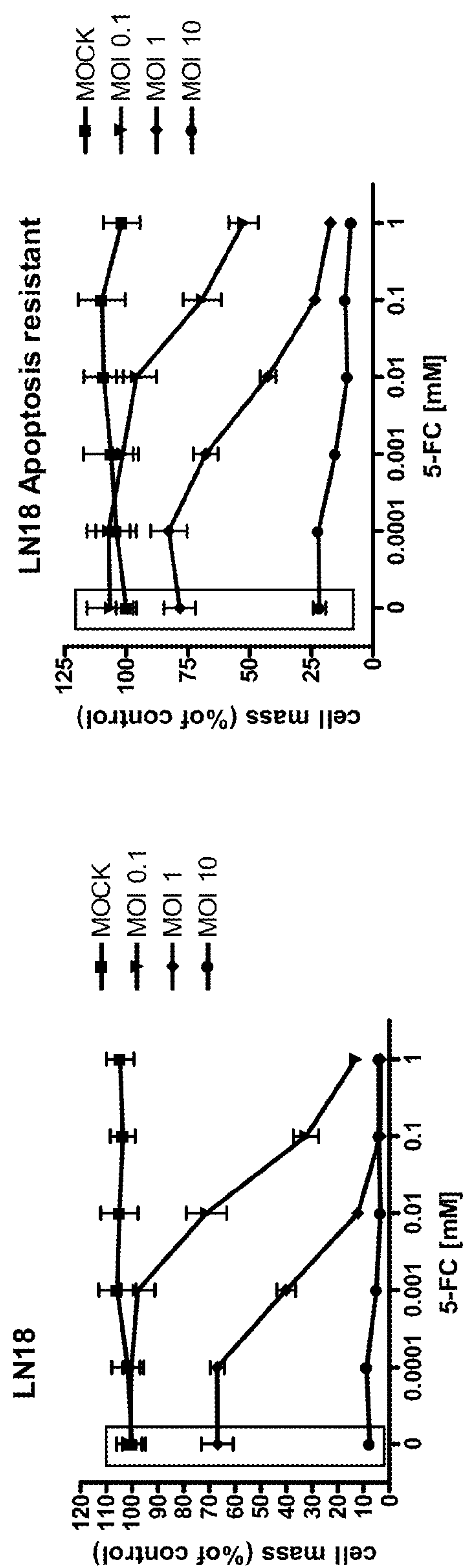

FIG. 18 shows the results of an SRB proliferation assay of glioblastoma tumor cells (cell lines LN 18, LN 18 Apoptosis resistant) treated with viral particles rescued from the plasmid pc3MerV2 Id-SCD (Id-SCD).

Figure 19A:
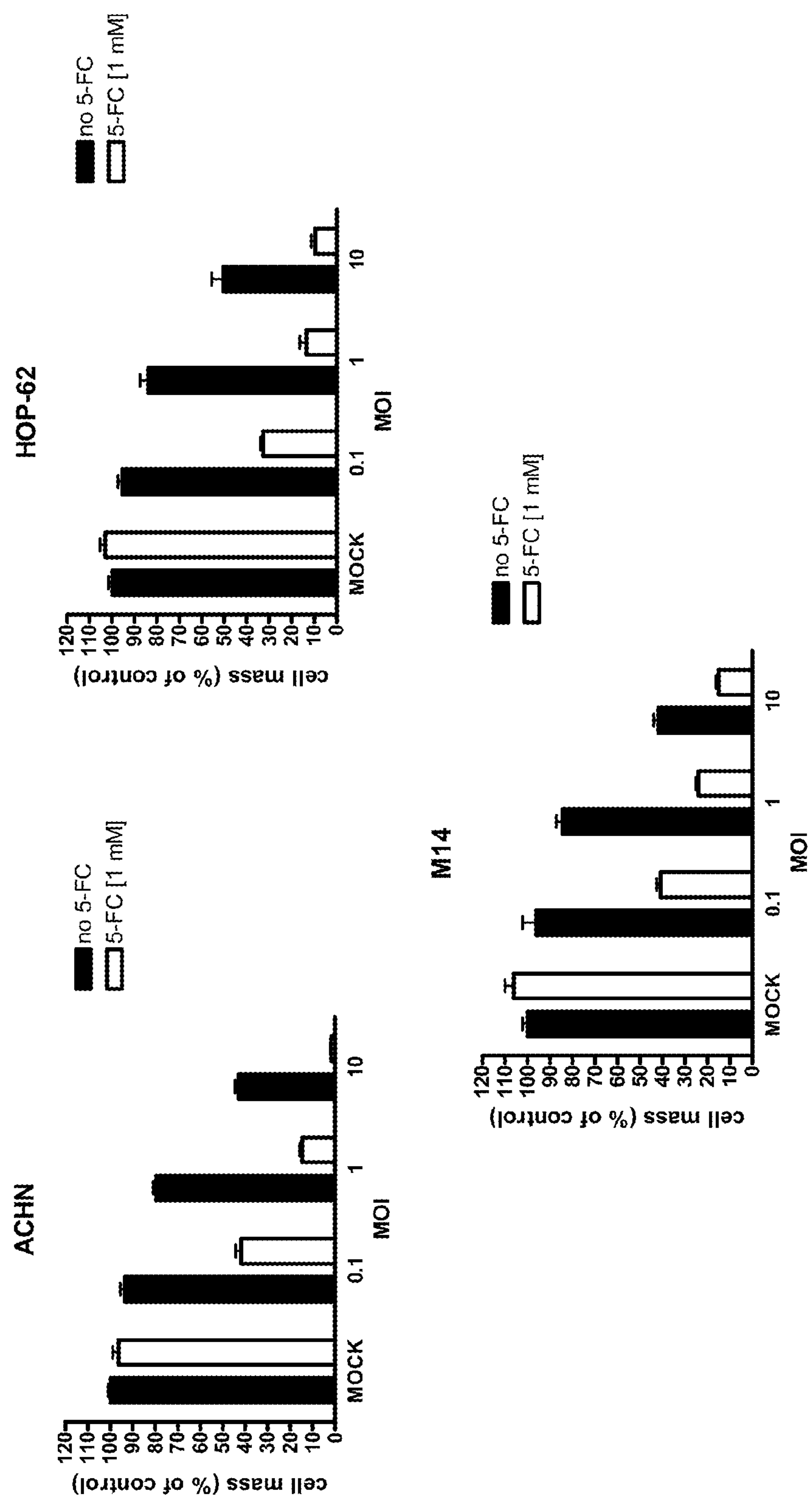

FIG. 19 shows the results of an SRB proliferation assay of renal cell carcinoma (ACHN), pulmonary adenocarcinoma (HOP-62) and melanoma (M14) tumor cells treated with viral particles rescued from the plasmid pc3MerV2 Id-SCD (Id-SCD).

Figure 20A:
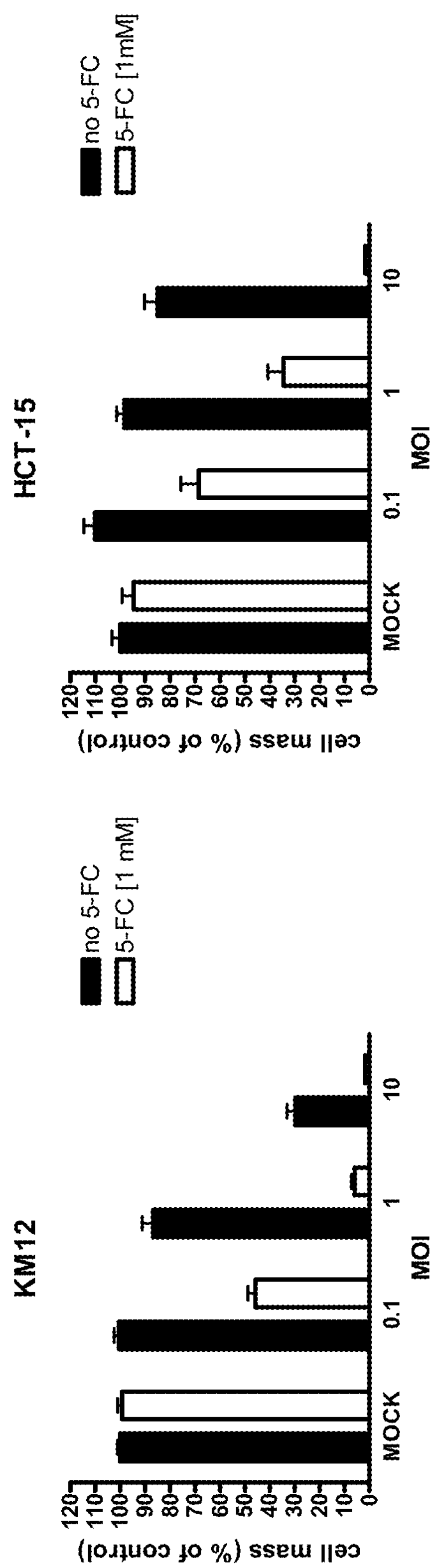

FIG. 20 shows the results of an SRB proliferation assay of colonic adenocarcinoma tumor cells (cell lines KM-12, HCT-15) treated with viral particles rescued from the plasmid pc3MerV2 Id-SCD (Id-SCD).

FIG. 21 shows the effect of three different armed MeV vectors on Hep3B human hepatocellular carcinoma cells (vectors pc3MerV2 Id-SCD, pc3MerV2 Id-VP22SCD, and pMerV2 P-SCD); all experiments were performed in quadruplicates; experiments were repeated three times; values: mean+SEM.

Figure 22:
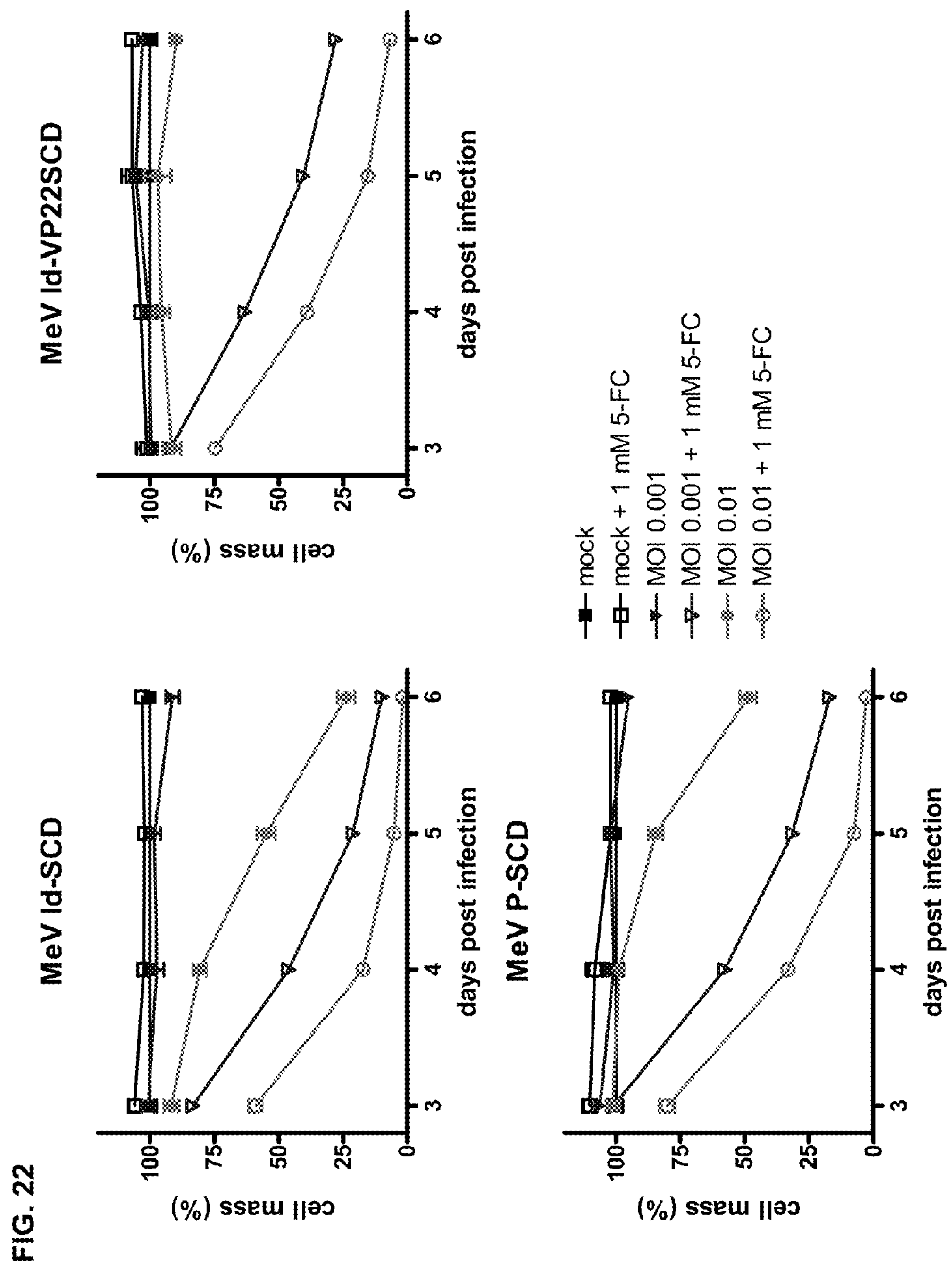

FIG. 22 shows the effect of three different armed MeV vectors on HepG2 human hepatocellular carcinoma cells (vectors pc3MerV2 Id-SCD, pc3MerV2 Id-VP22SCD, and pMerV2 P-SCD); all experiments were performed in quadruplicates; experiments were repeated three times; values: mean+SEM.

FIG. 23 shows the effect of three different armed MeV vectors on PLC/PRF/5 human hepatocellular carcinoma cells (vectors pc3MerV2 Id-SCD, pc3MerV2 Id-VP22SCD, and pMerV2 P-SCD); all experiments were performed in quadruplicates; experiments were repeated three times; values: mean+SEM.

Figure 24:
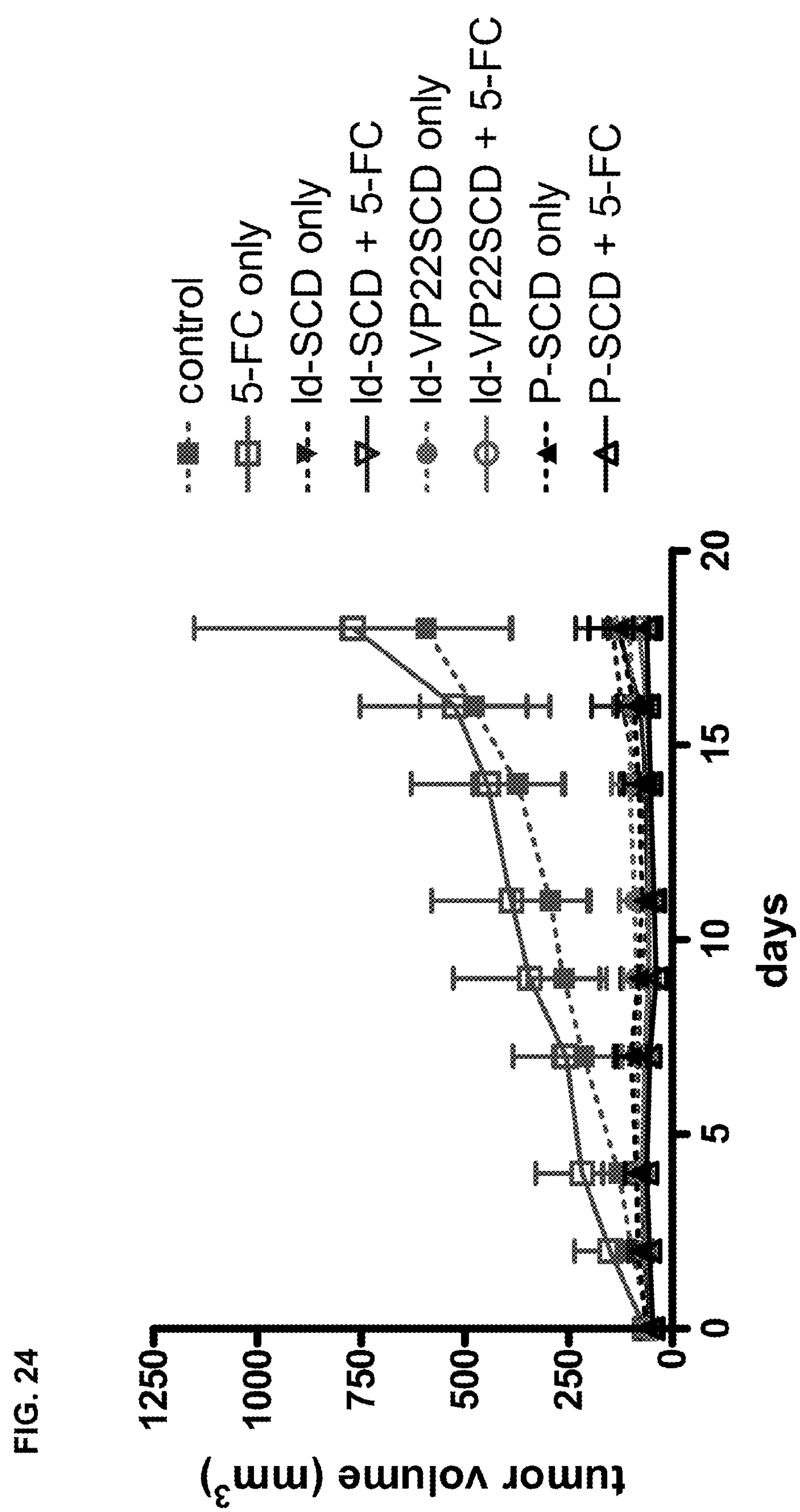

FIG. 24 shows the results of a determination of tumor volumes in a xenograft animal HCC tumor model (Hep3B model).

Figure 25:
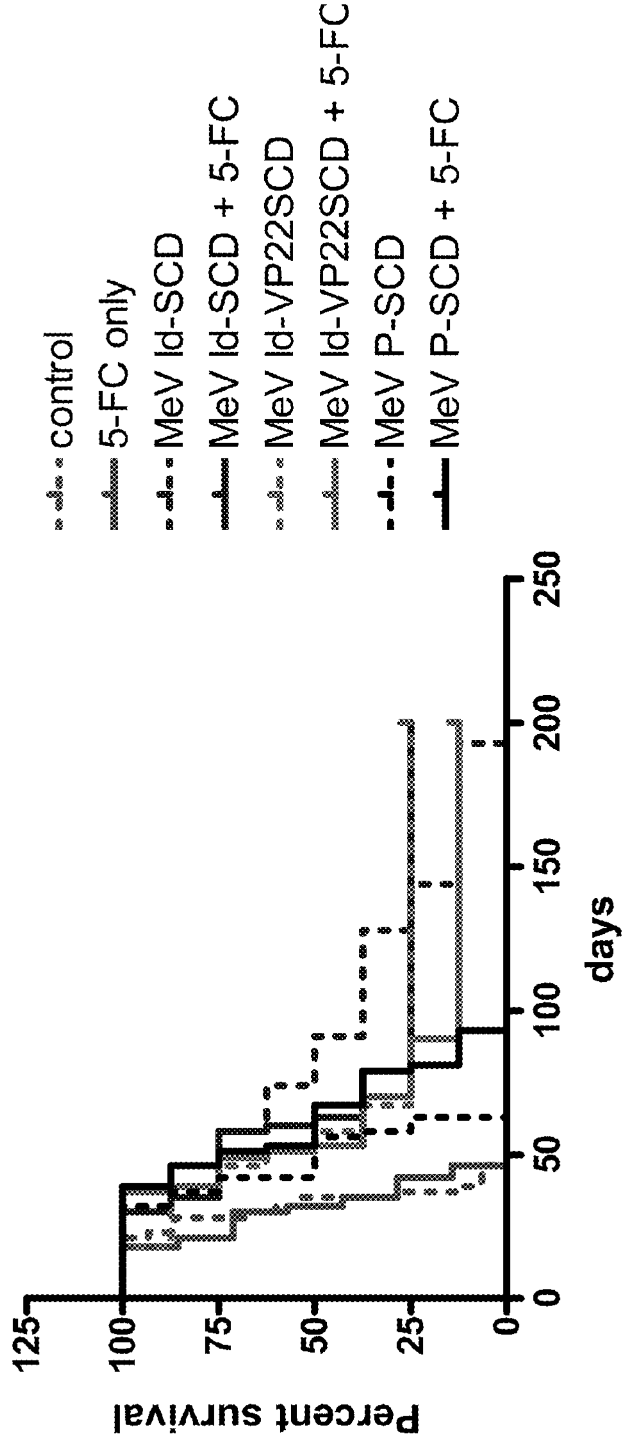

FIG. 25 shows the results of a determination of survival data in a xenograft animal HCC tumor model (Hep3B model).

Figure 26:
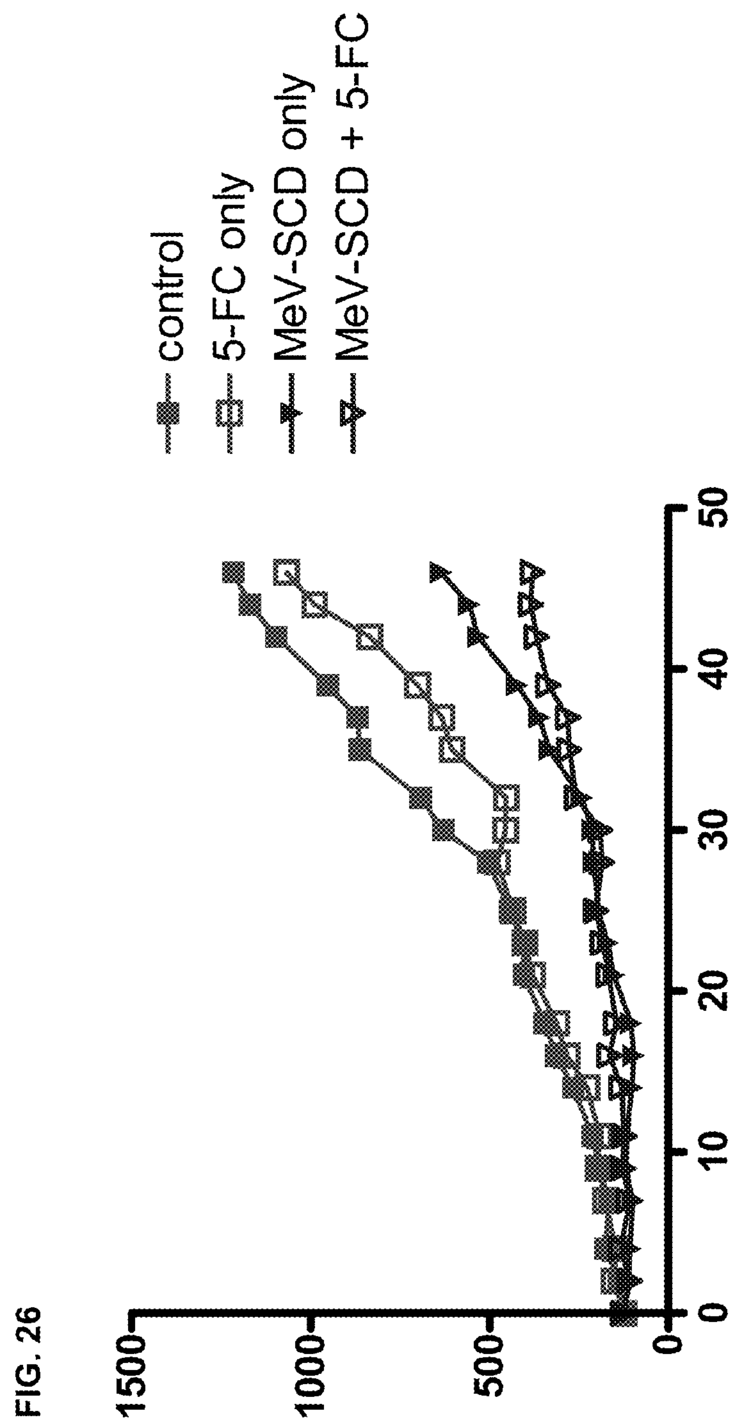

FIG. 26 shows the results of a determination of tumor volumes in a xenograft animal CC tumor model (TFK-1 model).

Figure 27:
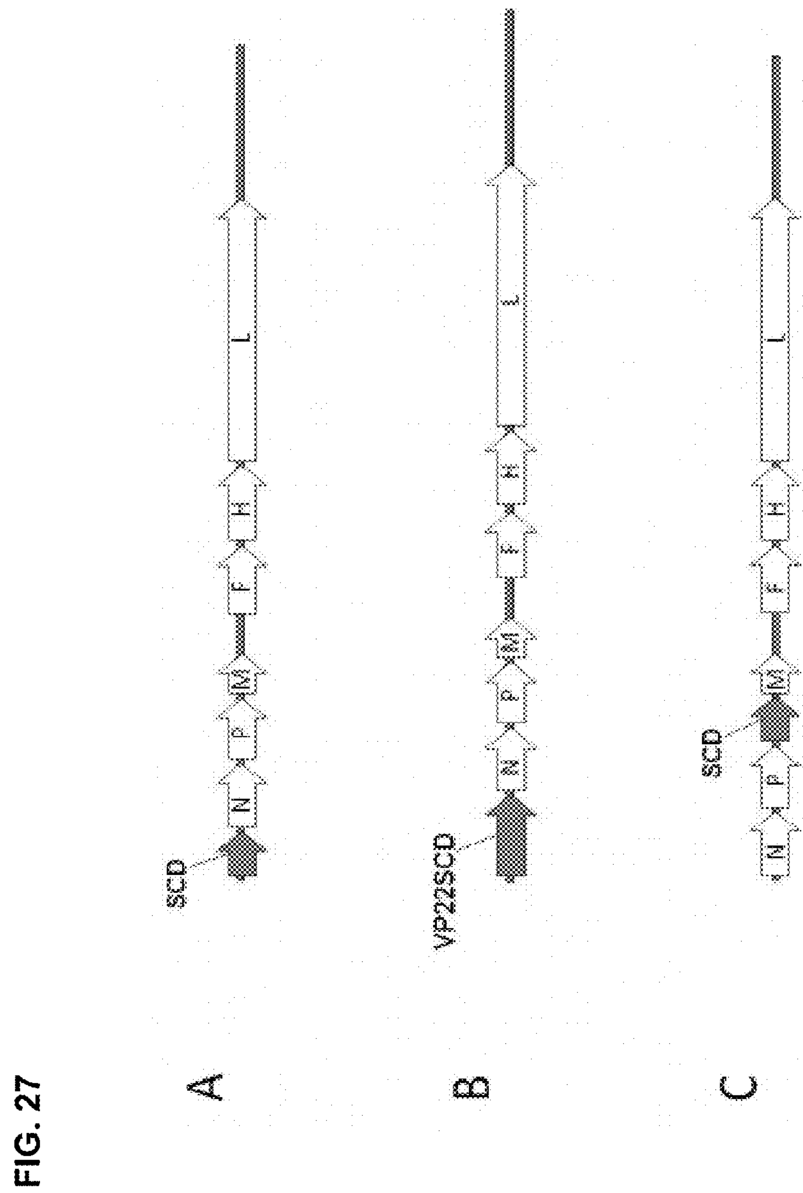

FIG. 27 shows a schematic overview of viral cDNAs and the respective viral vectors. Plasmids (A) pc3MerV21d-SCD (20,841 bp), (B) pc3MerV2 Id-VP22SCD (21,759 bp), and (C) pMerV2 P-SCD (20,546 bp) are shown. Open reading frames are displayed as arrows (viral genes in white, transgenes in dark). Nontranslated regions and the plasmid backbone are depicted as straight lines. N: Nucleocapsid protein, P: Phosphoprotein, M: Matrix protein, F: Fusion protein, H: Hemagglutinin, L: Large protein, SCD: Super-cytosine deaminase, VP22SCD: Fusion of SCD and the herpes simplex virus protein VP22.

FIG. 28 shows the genetic sequence of vector pMerV2 P-SCD (coding for MeV P-SCD) (SEQ-ID NO. 8).

FIG. 29 shows the genetic sequence of vector pc3MerV2 Id-VP22SCD (coding for MeV Id-VP22SCD) (SEQ-ID NO. 9).

DETAILED DESCRIPTION OF THE INVENTION

The present invention relates to a pharmaceutical composition comprising a recombinant measles virus comprising a suicide gene for use in the treatment of malignant cells with primary or secondary resistances against an oncolytic measles virus without suicide gene activity.

The terms "comprise" and "contain" within the meaning of the invention introduce a non-exhaustive list of features. Likewise, the word "one" is to be understood in the sense of "at least one".

In the context of the present invention, the term "suicide gene" refers to a gene, the expression of which in a host cell causes or results in a reduced viability of such host cells. In particular settings, the suicide gene will cause a cell to kill itself through apoptosis. In certain such settings, expression of the suicide gene will result in an enzyme, which catalyzes the generation of a cytotoxic drug from a non-toxic prodrug.

In a particular embodiment of the pharmaceutical composition according to the present invention, the malignant cells are identified by performing the following step:

(a) determining the percentage of living cells in a population of cells derived from said malignant cells 72 h, or preferably 96 h, after infecting said population with the oncolytic measles virus at a multiplicity of infection of 1, wherein a percentage of 40% or more of living cells in said population, particularly 50% or more, more particularly 60% or more, is indicative for said malignant cells being primarily or secondarily resistant against an oncolytic measles virus without suicide gene activity.

In a particular embodiment, the recombinant measles virus is based on measles vaccine strain Schwarz.

A description of the measles vaccine strain Schwarz, including its full genomic sequence and its comparison with other vaccine strains, can be found in Tillieux et al. (Tillieux, S. L., Halseyb, W. S., Satheb, G. M., and Vassilev, V. Comparative analysis of the complete nucleotide sequences of measles, mumps, and rubella strain genomes contained in Priorix-Tetra™ and ProQuad™ live attenuated combined vaccines. Vaccine 27 (2009) 2265-2273).

In a particular embodiment, the oncolytic measles virus without suicide gene activity is from measles vaccine strain Schwarz. More particularly, the oncolytic measles virus without suicide gene activity has a sequence according to SEQ-ID No. 1 (see FIG. 1).

In the context of the present invention, the term "has a sequence according to SEQ-ID No. 1" depends on the context given and refers to either the DNA sequence as depicted in SEQ-ID No. 1 (cDNA of measles virus particles from the Schwarz strain), or to the corresponding RNA sequence, as found packaged in the viral particle rescued from a vector comprising such cDNA sequence.

In a particular embodiment of the pharmaceutical composition according to the present invention, the suicide gene comprises a cytosine deaminase, particularly yeast cytosine deaminase.

Cytosine deaminases, particularly yeast cytosine deaminase, and their use as prodrug-converting enzyme in cancer gene therapy has been discussed and examined in various publications (see, for example: Kievit, E., Nyati, M. K., Ng, E., Stegman, L. D., Parsels, J., Ross, B. D., Rehemtulla, A., Lawrence, T. S. Yeast cytosine deaminase improves radiosensitization and bystander effect by 5-fluoro-cytosine of human colorectal cancer xenografts. Cancer Res. 60 (2000) 6649-55).

In a particular embodiment, the suicide gene further comprises a uracil phosphoribosyltransferase, particularly yeast uracil phosphoribosyltransferase.

It could be shown that the concomitant expression of a cytosine deaminase and a uracil phosphoribosyltransferase improves the enzymatic conversion of 5-fluorocytosine to cytotoxic metabolites (Tiraby M, Cazaux C, Baron M, Drocourt D, Reynes J P, Tiraby G. FEMS Microbiol Lett. 167 (1998) 41-9).

More particularly, the suicide gene comprises a fusion of a cytosine deaminase, particularly yeast cytosine deaminase, and a uracil phosphoribosyltransferase, particularly yeast uracil phosphoribosyltransferase, called SCD (SuperCD).

The use of a fusion gene comprising a cytosine deaminase and a uracil phosphoribosyltransferase has been described for an adenoviral system (Erbs, P., Regulier, E., Kintz, J., Leroy, P., Poitevin, Y., Exinger, F., Jund, R., and Mehtali, M. In vivo cancer gene therapy by adenovirus-mediated transfer of a bifunctional yeast cytosine deaminase/uracil phosphoribosyltransferase fusion gene. Cancer Res. 60 (2000) 3813-22).

Most particularly, the suicide gene comprises a sequence according to SEQ-ID NO. 2 (see FIG. 2).

In the context of the present invention, the term "comprises a sequence according to SEQ-ID No. . . . " depends on the context given and refers to either the DNA sequence as depicted in said SEQ-ID No., or to the corresponding RNA sequence, as found packaged in the viral particle rescued from a vector comprising such DNA sequence.

In a particular embodiment, the recombinant measles virus comprises an RNA sequence corresponding to SEQ-ID No. 3 (see FIG. 3), SEQ-ID No. 4 (see FIG. 4), SEQ-ID No. 8 (see FIG. 28), or SEQ-ID No. 9 (see FIG. 29), particularly SEQ-ID No. 4.

In a particular embodiment of the pharmaceutical composition according to said the present invention, the malignant cells are additionally non-responsive to chemotherapeutics and/or radiation therapy.

In a particular embodiment, the malignant cells are selected from the list of: malignant cells from cholangiocarcinoma, head and neck cancer, and sarcoma.

In a particular embodiment, the pharmaceutical composition is for use in a treatment, which is a repeated treatment, particularly every week, or every two weeks, or every three weeks, or every four weeks, employing such a recombinant measles virus comprising a suicide gene for use in the treatment of malignant cells with primary or secondary resistances against an oncolytic measles virus without suicide gene activity.

Recently, employment of a clinical regime of repetitive application of a recombinant measles virus without suicide gene activity (every 4 weeks for up to 6 cycles) has demonstrated that serum anti-measles antibody levels at baseline and on study completion remained stable both in blood and in peritoneal fluid as compared with baseline, indicating a lack of significant boost to the humoral immune response (Galanis E, Hartmann L C, Cliby W A, Long H J, Peethambaram P P, Barrette B A, Kaur J S, Haluska P J Jr, Aderca I, Zollman P J, Sloan J A, Keeney G, Atherton P J, Podratz K C, Dowdy S C, Stanhope C R, Wilson T O, Federspiel M J, Peng K W, Russell S J. Cancer Res. 2010; 70(3):875-82). Therefore, repetitive application of recombinant measles viruses was found to be feasible in the treatment of cancer patients.

In another aspect, the present invention relates to a recombinant measles virus based on measles vaccine strain Schwarz encoding a suicide gene, which comprises a fusion of a cytosine deaminase, particularly a yeast cytosine deaminase, and a uracil phosphoribosyltransferase, particularly a yeast uracil phosphoribosyltransferase.

In a particular embodiment of the recombinant measles virus according to the present invention, the suicide gene comprises a sequence according to SEQ-ID NO. 2 (see FIG. 2).

In a particular embodiment, the recombinant measles virus comprises an RNA sequence according to SEQ-ID No. 3 (see FIG. 3), SEQ-ID No. 4 (see FIG. 4), SEQ-ID No. 8 (see FIG. 28), or SEQ-ID No. 9 (see FIG. 29), particularly SEQ-ID No. 4.

In another aspect, the present invention relates to a method of treatment of malignant cells with primary or secondary resistances against an oncolytic measles virus without suicide gene activity, comprising the step of administering a recombinant measles virus comprising a suicide gene according to the present invention to a patient in need thereof.

In certain embodiments of that aspect of the invention, the treatment is the treatment of a cholangiocarcinoma, head and neck cancer, or sarcoma.

In certain embodiment, the method of treatment is a repeated treatment, particularly every week, or every two weeks, or every three weeks, or every four weeks.

In another aspect, the present invention relates to a method for generating the recombinant measles virus according to the present invention, comprising the step of (a) cloning (i) the genome of measles vaccine strain Schwarz, and (ii) a suicide gene, into a plasmid under the control of an RNA polymerase II promoter.

The use of the RNA polymerase II promoter system for the efficient expression of antigenomic RNA (cRNA) from cDNA of Mononegavirales has been shown for Borna disease virus (BDV) and measles virus (Martin, A., Staeheli, P., and Schneider, U. RNA Polymerase II-Controlled Expression of Antigenomic RNA Enhances the Rescue Efficacies of Two Different Members of the Mononegavirales Independently of the Site of Viral Genome Replication, J. Virol. 80 (2006) 5708-5715).

In a particular embodiment of the method according to the present invention, the suicide gene comprises a cytosine deaminase, particularly yeast cytosine deaminase.

In another particular embodiment, the suicide gene further comprises a uracil phosphoribosyltransferase, particularly yeast uracil phosphoribosyltransferase.

In another particular embodiment, the suicide gene comprises a fusion of a cytosine deaminase, particularly yeast cytosine deaminase, and a uracil phosphoribosyltransferase, particularly yeast uracil phosphoribosyltransferase.

In a particular embodiment of the method according to the present invention, the suicide gene comprises a sequence according to SEQ-ID NO. 2 (see FIG. 2).

In a particular embodiment, the method further comprises the step of (b) cloning measles virus helper genes N, P and L, each under the control of an RNA polymerase II promoter, into at least one vector.

In a particular embodiment, the viral helper genes N, P and L, are each cloned into a separate vector under the control of an RNA polymerase II promoter, particularly a plasmid vector, resulting in (i) a plasmid encoding the measles virus helper gene N, (ii) a plasmid encoding the measles virus helper gene P, and (iii) a plasmid encoding the measles virus helper gene L.

Thus, such embodiment relates to a method comprising the steps of (b) cloning measles virus helper genes N under the control of an RNA polymerase II promoter, into a first vector, particularly a plasmid vector;

(c) cloning measles virus helper gene P under the control of an RNA polymerase II promoter into a second vector, particularly a plasmid vector;

(d) cloning measles virus helper gene L under the control of an RNA polymerase II promoter into a third vector, particularly a plasmid vector.

In a particular embodiment, steps (a) and/or (b), or (a) and/or (b) to (d), further comprise the step of removing putative splicing sequences from said genome and/or said helper genes.

In a particular embodiment, step (a) results in the plasmid having the sequence according to SEQ-ID No. 4 (see FIG. 4), SEQ-ID No. 8 (see FIG. 28), or SEQ-ID No. 9 (see FIG. 29), particularly SEQ-ID No. 4.

20. In a particular embodiment, steps (b) to (d) result in plasmids having the sequences according to SEQ-ID No. 5, SEQ-ID No. 6, and SEQ-ID No. 7 (see FIGS. 5 to 7).

In a particular embodiment, the method according to the present invention further comprises the step of (e) transfecting host cells with plasmids of steps (a) and (b), particularly host cells from a certified cell line approved for vaccine production, particularly from Vero or MRC-5 cell lines.

One of the most important factors for the production of live viral vaccines is their genetic stability. Genetic stability includes questions related to the potential reversion of the vaccine strain to more virulent forms, the recombination with other viral sequences to produce potentially pathogenic viruses, and any genetic drift that could result in decrease of immunogenicity and efficacy. In various cases it has been shown that propagation of live vaccine strains in Vero and MRC-5 cell lines maintains genetic stability of the vaccine strains (see, for example, Laassri M, Meseda C A, Williams O, Merchlinsky M, Weir J P, Chumakov K., Microarray assay for evaluation of the genetic stability of modified vaccinia virus Ankara B5R gene. J. Med. Virol. 79 (2007) 791-802).

In a particular embodiment, the method further comprises the step of (f) rescuing recombinant measles virus from the host cell transfected in step (e).

In another aspect, the present invention relates to a kit comprising (a) a plasmid comprising (i) the genome of measles vaccine strain Schwarz, and (ii) a suicide gene, which comprises a fusion of a cytosine deaminase, particularly yeast cytosine deaminase, and a uracil phosphoribosyltransferase, particularly yeast uracil phosphoribosyltransferase, under the control of an RNA polymerase II promoter, particularly wherein said suicide gene comprises a sequence according to SEQ-ID No. 2 (see FIG. 2), particularly wherein the plasmid has the sequence according to SEQ-ID No. 4 (see FIG. 4) SEQ-ID No. 8 (see FIG. 28), or SEQ-ID No. 9 (see FIG. 29), more particularly SEQ-ID No. 4;

(b) at least one plasmid comprising measles virus helper genes N, P, and L, each in form of a single gene under the control of an RNA polymerase II promoter.

In a particular embodiment of the kit according to the present invention, the viral helper genes N, P, and L, are each cloned into a separate plasmid, each under the control of an RNA polymerase II promoter particularly wherein the plasmids have the sequences according to SEQ-ID No. 5, SEQ-ID No. 6, and SEQ-ID No. 7 (see FIGS. 5 to 7).

The invention is now described with reference to the following examples. These examples are provided for the purpose of illustration only and the invention should not be construed as being limited to these examples, but rather should be construed to encompass any and all variations which become evident as a result of the teaching provided herein. The following materials and methods are provided with respect to the subsequent examples but do not limit a multiplicity of materials and methodologies encompassed by the present invention.

EXAMPLES

Example 1

Preparation of MeV cDNA Plasmid Vector pc3MerV2 Id-Trka (SEQ-ID NO. 3)

Preparation of the measles virus cDNA vector was performed essentially as described recently (Inoue K, Shoji Y, Kurane I, Iijima T, Sakai T, Morimoto K. J Virol Methods. 2003; 107:229-36; Martin A, Staeheli P, Schneider U. J Virol. 2006; 80:5708-15), but with the following important modifications.

- initially, it was unclear (i) which sequence parts/segments of the widely used cytomegalovirus (CMV) RNA polymerase II (Pol II) promoter had to be considered as optimal when employed for the rescue and amplification of recombinant measles virus vectors and (ii) which of the different CMV virus genomes described in GenBank (M60321, M21295) should be used for the generation of a CMV-based minimal promoter; therefore, a systematic analysis on different minimal CMV-derived promoter constructs had to be undertaken first; the results of this study revealed that the promoter variant construct pc3, encompassing CMV promoter nucleotides from −301 until −1 (+1 being defined as transcription initiation site) plus three nucleotides (TGG) additionally inserted after position −1, gave an optimal yield in both viral rescue and virus amplification;
- this very short version of the cytomegalovirus-derived promoter, exhibiting only 301 plus 3 nucleotides (nt), provides the further advantage of shortening the overall length of the plasmid containing the recombinant measles virus vector genome, which enhances efficiency of plasmid replication;
- furthermore, lack of intron sequences in the minimal pc3 CMV promoter (301 nt+3 nt) hinders the direction of mRNAs to the splicing machinery before mRNA export from the nucleus; a thereby reduced splicing efficiency improves both measles virus rescue and amplification;
- in addition, purposeful incorporation of a 3' placed hepatitis delta virus (HDV) ribozyme was used to exactly process the 3'-end of all transcripts.

The sequence of pc3MerV2 Id-Trka (see FIG. 1) can be described as follows with reference to the position of the nucleotides (nt); UTR—untranslated region; ORF—open reading frame:

- nt 1-55: MeV leader sequence
- nt 56-66: gene start for transgene transcription (gene start sequence obtained from the MeV N gene)
- nt 67-103: 5'-UTR (5'-UTR sequence obtained from the MeV N gene)
- nt 103-108: cloning site, exhibiting recognition site for restriction endonuclease XhoI (C'TCGAG)
- nt 109-114: cloning site, exhibiting recognition sites for restriction endonuclease Paul (G'CGCGC) or AscI (GG'CGCGCC); both recognition site represent unique sites being present only once in the complete vector sequence
- nt 115-126: 3'-UTR derived from MeV N gene
- nt 127-136: gene end for transgene transcription (obtained from the MeV N gene)
- nt 140-150: gene start of MeV N
- nt 192-1769: N ORF (1578 nt=525 aa+stop codon)
- nt 1891-3414: P ORF (1524 nt=507 aa+stop codon)

nt 2036-2043: 3'-cloning site, exhibiting recognition site for restriction endonuclease SdaI (CCTGCA'GG), unique site being present only once in the complete vector sequence
nt 1913-2473: C ORF (non-structural gene; 561 nt=186 aa+stop codon)
nt 2575-2582: A5G3 editing box; single nucleotide (G) insertion after nt 2580
nt 1891-2789: V trans-frame ORF after mRNA editing (non-structural gene; 900 nt=299 aa+stop codon)
nt 3522-4529: M ORF (1008 nt=335 aa+stop codon)
nt 5533-7194: F ORF (1662 nt=553 aa+stop codon)
nt 7355-9208: H ORF (1854 nt=617 aa+stop codon)
nt 9318-15869: L ORF (6552 nt=2183 aa+stop codon)
nt 15942-15978: MeV trailer sequence (37 nt)

Example 2

Preparation of MeV Id-SCD (Id-SCD) Plasmid Vector pc3MerV2 Id-SCD (SEQ-ID NO. 4)

For generation of the recombinant MeV Id-SCD (Id-SCD) measles virus vector, plasmid pUC-SCD, encoding the SCD suicide fusion gene, was digested with restriction endonuclease MluI and the fragment containing the open reading frame of the SCD suicide fusion gene was ligated into basic vector pc3MerV2 Id-Trka (derivative of parental vector pc3 encompassing the optimized (shortened and modified) CMV RNA polymerase II (Pol II) promoter) which had been linearized with restriction endonuclease AscI. The correct integration of the fragment was verified by restriction digest and sequencing. Infectious viral particles were successfully produced by the subsequent rescue procedure.

pc3MerV2 Id-SCD (SEQ-ID NO. 4). The sequence of pc3MerV2 Id-SCD (see FIG. 2) can be described as follows with reference to the position of the nt:

nt 1-55: MeV leader sequence
nt 56-66: gene start for transgene transcription (gene start sequence obtained from the MeV N gene)
nt 67-103: 5'-UTR (5'-UTR sequence obtained from the MeV N gene)
nt 103-108: cloning site, exhibiting recognition site for restriction endonuclease XhoI (C'TCGAG)
nt 109-114: cloning site, exhibiting recognition sites for restriction endonuclease PauI (G'CGCGC) or AscI (GG'CGCGCC); both recognition site represent unique sites being present only once in the complete vector sequence
nt 121-1242: SCD ORF (1122 nt=373 aa+stop codon)
nt 1243-1248: cloning sites, exhibiting recognition sites for restriction endonucleases MluI (A'CGCGT)+PauI (A'CGCGC)
nt 1249-1260: 3'-UTR
nt 1262-1270: gene end for transgene transcription (obtained from the MeV N gene)
nt 1274-1284: gene start of MeV N
nt 1326-2903: N ORF (1578 nt=525 aa+stop codon)
nt 3025-4548: P ORF (1524 nt=507 aa+stop codon)
nt 3047-3607: C ORF (non-structural gene; 561 nt=186 aa+stop codon)
nt 3709-3716: A5G3 editing box; single nucleotide (G) insertion after nt 2580
nt 3025-3923: V trans-frame ORF after mRNA editing (non-structural gene; 900 nt=299 aa+stop codon)
nt 4656-5663: M ORF (1008 nt=335 aa+stop codon)
nt 6667-8328: F ORF (1662 nt=553 aa+stop codon)
nt 8489-10342: H ORF (1854 nt=617 aa+stop codon)
nt 10452-17003: L ORF (6552 nt=2183 aa+stop codon)
nt 17076-17112: MeV trailer sequence (37 nt)

Example 3

Preparation of Helper Plasmids (SEQ-ID NOs. 5 to 7)

Preparation of helper plasmids carrying either the N, the P, or the L gene, respectively, was performed essentially as described recently (Martin A, Staeheli P, Schneider U. J Virol. 2006; 80:5708-15), but with the following important modifications:

as a result of a systematic analysis of different minimal CMV-derived promoter constructs the promoter variant construct pc3, being found to give an optimal yield in both viral rescue and virus amplification, was employed also for the helper plasmid generation;
lack of intron sequences in the minimal pc3 CMV promoter (301 nt+3 nt) hinders the direction of mRNAs to the splicing machinery before mRNA export from the nucleus; a thereby reduced splicing efficiency improves both measles virus rescue and amplification;
in addition, purposeful incorporation of a 3' placed hepatitis delta virus (HDV) ribozyme was used to exactly process the 3'-end of all transcripts.
finally, this promoter variant pc3 was found not only to enable efficient Pol II-mediated transcription of the N, the P, and the L gene of measles virus, but transcripts of the N, the P, and the L gene of measles virus are also efficiently exported from the nucleus without abundant splicing of cryptic splice sites.

Example 4

Rescue of Measles Virus Particles from MeV Id-SCD (Id-SCD) Vector

On day 0, Vero cells (ATCC CCL-81) were seeded in a 6-well plate at a density of $4\times10^5$ cells/well. On day 1, the Vero cells were transfected using the following transfection conditions 200 μl DMEM medium were pipetted into a 1.5 ml tube. Then, the following amounts of plasmid DNA were added:

| Plasmid | Amount [μg] |
|---|---|
| pcDI-DsRed | 0.1 |
| pcDIMER-N | 0.5 |
| pcDIMER-P | 0.1 |
| pcDIMER-L | 0.5 |
| MeV full length plasmid | 5.0 |

After mixing, the mixture was spun down and 18.6 μl FuGene HD (Roche) (i.e. 3 μl FuGene/1 μg DNA) were added directly into the liquid. After vortexing, the mixture was spun down. The reaction mixture was incubated for 25 min at room temperature.

The cells were washed two times with PBS. After addition of 1.8 ml DMEM+2% FCS+PS, the transfection mixture was added drop wise to the cells, and the plate was swirled.

The cell culture was incubated at 37° C. and 5% $CO_2$.

On days 2 and 3, the medium was changed (1 ml DMEM+2% FCS+PS).

When syncytia appeared (approx. at day 4), the Vero cells were plated in 10 cm dishes for overlay (one confluent T75 in 10 ml, seed approximately 0.5 ml per dish).

On the next day, an overlay was done by scraping rescue cells in medium, pipetting up and drop wise down on Vero cells.

When syncytia appeared (approx. 1 day post overlay), $3\times10^5$ Vero cells were plated in a 6-well plate for passage 0 of virus (P.0).

On the next day syncytia were picked (2-3 per construct). Medium was removed from the 10 cm dish and 5-10 μl medium were pipetted directly onto a syncytium. By pipetting up and down and by scraping, the syncytium was dislodged and pipetted on the fresh Vero cells in a 6-well plate.

When syncytia appeared, cells were scraped into medium and stored at −80° C. (=P.0).

As a result of our procedure employing these plasmids encoding (a) the genome of measles vaccine strain Schwarz, and a suicide gene, which comprises a fusion of yeast cytosine deaminase and yeast uracil phosphoribosyltransferase,
(b) the measles virus helper gene N,
(c) the measles virus helper gene P,
(d) the measles virus helper gene L, each under the control of an RNA polymerase II promoter, a maximum of 16.000 infectious spots (syncytia) could be achieved at passage 1 (P.1), which is much higher when compared with the results expressing the same genomes and transgenes under the control of bacteriophage T7 RNA polymerase, yielding only a maximum of 8.800 infectious spots (syncytia) at P.1. Thus, it has been demonstrated that usage of the CMV-derived RNA polymerase II promoter system results in a highly efficient production of infectious recombinant measles virus particles.

Example 5

SRB Proliferation Assay of HuCCT1, RBE, and TFK-1 Cells

FIG. 8 shows the results of an SRB proliferation assay of HuCCT1, RBE, and TFK-1 cells (human cholangiocarcinoma cells) treated with MeV Id-SCD viral particles rescued from the plasmid pc3MerV2 Id-SCD (Id-SCD) and incubated with prodrug 5-FC.

In general, for the SRB proliferation assay, cells were seeded on day 0. and infected after 24 h with either 0.001, 0.01, 0.1, 1 or 10 MOI (see the individual experiments and/or accompanying Figures) of viral particles, and in the case of prodrug treatment, 5-FC was added 3 h post infection. The SRB assay was performed 96 h post infection.

When RBE or TFK-1 cells were infected with MeV Id-SCD at a multiplicity of infection of 1 (M01 1) and then cultivated without the addition of the prodrug 5-FC, the loss in cell mass after 96 h (as measured by the SRB proliferation assay) was calculated to be in the range of 58% (RBE) or 86% (TFK-1) in comparison to non-infected control cells (set to a cell mass of 100%), respectively (values encircled by the rectangle placed on the left hand side of the graphics); in contrast.

HuCCT1 cells being infected with MeV Id-SCD (MOI 1) and then cultivated without the addition of the prodrug 5-FC demonstrated a loss in cell mass after 96 h only in the range of 42% in comparison to non-infected control cells (set to a cell mass of 100%). Thereby, HuCCT1 cells display a primary resistance to measles virus of the prior art (no employment of an additional suicide gene function). However, when MeV Id-SCD (MOI 1)-infected HuCCT1 cells were cultivated with the addition of the prodrug 5-FC (ranging from $10^{-4}$ to $10^{0}$ mM) a loss in cell mass after 96 h was demonstrated in a range of up to 99% in comparison to non-infected control cells (set to a cell mass of 100%). Thus it was shown, that a primary resistance to measles virus of the prior art (no employment of an additional suicide gene function) of HuCCT1 cells could be overcome through usage of the SCD suicide gene function which catalyzes the generation of a cytotoxic drug (5-FU and derivatives) from a non-toxic prodrug (5-FC).

Example 6

LDH Release Assay of HuCCT1, RBE, and TFK-1 Cells

FIG. 9 shows the results of an LDH release assay of HuCCT1, RBE, and TFK-1 cells (human cholangiocarcinoma cells) treated with MeV Id-SCD viral particles rescued from the plasmid pc3MerV2 Id-SCD (Id-SCD) and incubated with prodrug 5-FC.

When RBE or TFK-1 cells were infected with MeV Id-SCD at MOI 1 and then cultivated without the addition of the prodrug 5-FC, the release of the enzyme LDH (here used as a surrogate parameter for loss of cell integrity) after 96 h (as measured by the LDH release assay) was calculated to be in the range of 70% (RBE) or 85% (TFK-1) in comparison to non-infected control cells being completely lysed by treatment with the detergent Triton X-100 (set to a LDH release of 100%), respectively (values encircled by the rectangle placed on the left hand side of the graphics).

In contrast, HuCCT1 cells being infected with MeV Id-SCD (MOI 1) and then cultivated without the addition of the prodrug 5-FC demonstrated a release of the enzyme LDH after 96 h only in the range of 31% in comparison to non-infected control cells, respectively. Thereby, it again was demonstrated that HuCCT1 cells display a primary resistance to measles virus of the prior art (no employment of an additional suicide gene function). However, when MeV Id-SCD (MOI 1)-infected HuCCT1 cells were cultivated with the addition of the prodrug 5-FC (ranging from $10^{-4}$ to $10^{0}$ mM) a highly significant increase in the release of the enzyme LDH after 96 h was demonstrated in a range of up to 82% in comparison to non-infected control cells (set to a cell mass of 100%), respectively.

Thus it again was shown, that a primary resistance to measles virus of the prior art (no employment of an additional suicide gene function) of HuCCT1 cells could be overcome through usage of the SCD suicide gene function.

Example 7

SRB Proliferation Assay of SAS and HTB-43 FaDu Cells

FIG. 10 shows the results of an SRB proliferation assay of SAS and HTB-43 FaDu cells (human Head & Neck (H&N) cancer cells) treated with MeV Id-SCD viral particles rescued from the plasmid pc3MerV2 Id-SCD (Id-SCD) and incubated with prodrug 5-FC.

When HTB-43 FaDu cells were infected with MeV Id-SCD at MOI 1 and then cultivated without the addition of the prodrug 5-FC, the loss in cell mass after 96 h was calculated to be in the range of 66% in comparison to non-infected control cells (values encircled by the rectangle placed on the left hand side of the graphics).

In contrast, SAS cells infected with MeV Id-SCD (M01 1) and then cultivated without the addition of the prodrug 5-FC demonstrated no loss in cell mass at all (0%) after 96 h in comparison to non-infected control cells. Thereby, SAS cells display a primary resistance to measles virus of the prior art (no employment of an additional suicide gene function). However, when MeV Id-SCD (MOI 1)-infected SAS cells were cultivated with the addition of the prodrug 5-FC (ranging from $10^{-4}$ to $10^{0}$ mM) a loss in cell mass after 96 h was demonstrated in the range of up to 83% in comparison to non-infected control cells, respectively.

Thus it was shown, that a primary resistance to measles virus of the prior art (no employment of an additional suicide gene function) of SAS cells could be overcome through usage of the SCD suicide gene function.

Example 8

LDH Release Assay of SAS and HTB-43 FaDu Cells

FIG. 11 shows the results of an LDH release assay of SAS and HTB-43 FaDu cells (human H&N cancer cells) treated with MeV Id-SCD viral particles rescued from the plasmid pc3MerV2 Id-SCD (Id-SCD) and incubated with prodrug 5-FC.

When HTB-43 FaDu cells were infected with MeV Id-SCD at MOI 1 and then cultivated without the addition of the prodrug 5-FC, the release of the enzyme LDH after 96 h was calculated to be in the range of 16% in comparison to non-infected control cells being completely lysed by treatment with the detergent Triton X-100, respectively (values encircled by the rectangle placed on the left hand side of the graphics).

SAS cells being infected with MeV Id-SCD (MOI 1) and then cultivated without the addition of the prodrug 5-FC demonstrated a release of the enzyme LDH after 96 h only in the range of 18% in comparison to non-infected control cells, respectively. However, when MeV Id-SCD (MOI 1)-infected SAS cells were cultivated with the addition of the prodrug 5-FC (ranging from 10E-4 to 10E0 mM) a strong increase in the release of the enzyme LDH after 96 h was demonstrated in a range of up to 38% in comparison to non-infected control cells (set to a cell mass of 100%).

Thus it again was shown, that a primary resistance to measles virus of the prior art (no employment of an additional suicide gene function) of SAS cells could be overcome through usage of the SCD suicide gene function.

Example 9

SRB Proliferation Assay of A 673, BRZ, and SRH Cells

FIG. 12 shows the results of an SRB proliferation assay of A 673, BRZ, and SRH cells (human sarcoma cells) treated with MeV Id-SCD viral particles rescued from the plasmid pc3MerV2 Id-SCD (Id-SCD) and incubated with prodrug 5-FC.

When A 673 or BRZ cells were infected with MeV Id-SCD at MOI 1 and then cultivated without the addition of the prodrug 5-FC, the loss in cell mass after 96 h was calculated to be in the range of 96% or 75%, respectively, in comparison to non-infected control cells (values encircled by the rectangle placed on the left hand side of the graphics).

In contrast, SRH cells being infected with MeV Id-SCD (MOI 1) and then cultivated without the addition of the prodrug 5-FC demonstrated a loss in cell mass after 96 h only in the range of 10% in comparison to non-infected control cells. Thereby, SRH cells display a primary resistance to measles virus of the prior art (no employment of an additional suicide gene function). However, when MeV Id-SCD-infected SRH cells (MOI 1) were cultivated with the addition of the prodrug 5-FC (ranging from $10^{-4}$ to $10^{0}$ mM) a loss in cell mass after 96 h was demonstrated in the range of up to 55% in comparison to non-infected control cells.

Thus it was shown, that a primary resistance to measles virus of the prior art (no employment of an additional suicide gene function) of SAS cells could be significantly improved, but not yet overcome under the chosen conditions (MOI 1) through usage of the SCD suicide gene function.

Example 10

LDH Release Assay of A 673 and SRH Cells

FIG. 13 shows the results of an LDH release assay of A 673 and SRH cells (human sarcoma cells) treated with MeV Id-SCD viral particles rescued from pc3MerV2 Id-SCD (Id-SCD) and incubated with prodrug 5-FC.

When A 673 cells were infected with MeV Id-SCD at MOI 1 and then cultivated without the addition of the prodrug 5-FC, the release of the enzyme LDH after 96 h was calculated to be in the range of 54% in comparison to non-infected control cells being completely lysed by treatment with the detergent Triton X-100 (values encircled by the rectangle placed on the left hand side of the graphics).

SRH cells being infected with MeV Id-SCD (MOI 1) and then cultivated without the addition of the prodrug 5-FC demonstrated a release of the enzyme LDH after 96 h only in the range of 23% in comparison to non-infected control cells. Of note, when MeV Id-SCD (MOI 1)-infected SRH cells were cultivated with the addition of the prodrug 5-FC (ranging from $10^{-4}$ to $10^{0}$ mM) an increase in the release of the enzyme LDH of 31% after 96 h was demonstrated in comparison to non-infected control cells (set to a cell mass of 100%).

Thus it was shown, that a primary resistance to measles virus of the prior art (no employment of an additional suicide gene function) of SRH cells could not yet be sufficiently overcome under the chosen conditions (MOI 1) through usage of the SCD suicide gene function.

Example 11

SRB Proliferation Assay of SRH Cells

FIG. 14 shows the results of an SRB proliferation assay of SRH cells treated with MeV Id-SCD viral particles rescued from the plasmid pc3MerV2 Id-SCD (Id-SCD) at an elevated MOI of 10 (usually, a MOI of 1 is used; here increase in "viral load" was employed to overcome phenomena of resistance observed at MOI 1 in the presence of the prodrug 5-FC).

SRH cells being infected with MeV Id-SCD at MOI 10 and then cultivated without the addition of the prodrug 5-FC demonstrated a loss in cell mass after 96 h in the range of now 68% in comparison to non-infected control cells, which is significantly improved in comparison to the results obtained at MOI 1, at which only 28% of loss in cell mass was obtained in comparison to non-infected control cells. Furthermore, when MeV Id-SCD (MOI 10)-infected SRH cells were cultivated with the addition of the prodrug 5-FC (ranging from 10-4 to $10^{0}$ mM) a loss in cell mass after 96 h was demonstrated in the range of up to 89% in comparison to non-infected control cells.

Thus it was shown, that a primary resistance to measles virus of the prior art (no employment of an additional suicide gene function) of SRH cells could be overcome under the chosen conditions (MOI 10) through additional usage of the SCD suicide gene function.

Example 12

SRB Proliferation Assay of Sarcoma Tumor Cells (Cell Lines CCS, LM)

FIG. 15 shows the results of an SRB proliferation assay of sarcoma tumor cells (cell lines CCS, LM) treated with viral particles rescued from the plasmid pc3MerV2 Id-SCD (Id-SCD) and incubated with prodrug 5-FC.

CCS or LM cells infected with vector MeV Id-SCD at MOI 1 and then cultivated without the addition of the prodrug 5-FC demonstrated a loss in cell mass after 96 h in the range of 5% or 25%, respectively, in comparison to non-infected control cells (values encircled by the rectangle placed on the left hand side of the graphics). Thus, both CCS and LM cells display a primary resistance to measles virus of the prior art (no employment of an additional suicide gene function). However, when MeV Id-SCD-infected CCS or LM cells (MOI 1) were cultivated with the addition of the prodrug 5-FC (ranging from $10^{-4}$ to $10^{0}$ mM) a loss in cell mass after 96 h was demonstrated in the range of up to 79% or 94%, respectively, in comparison to non-infected control cells.

Thus it was shown, that a primary resistance to measles virus of the prior art (no employment of an additional suicide gene function) of CCS and LM cells could be strongly improved, and in the case of LM cells almost fully overcome under the chosen conditions (MOI 1) through usage of the SCD suicide gene function.

Example 13

SRB Proliferation Assay of Sarcoma Tumor Cells (Cell Lines STO, ZAF, KD)

FIG. 16 shows the results of an SRB proliferation assay of sarcoma tumor cells (cell lines STO, ZAF, KD) treated with MeV Id-SCD viral particles rescued from the plasmid pc3MerV2 Id-SCD (Id-SCD) and incubated with prodrug 5-FC.

When STO, ZAF, or KD cells were infected with MeV Id-SCD at MOI 1 and then cultivated without the addition of the prodrug 5-FC, the loss in cell mass after 96 h was calculated to be in the range of 76%, 87% or 94%, respectively, in comparison to non-infected control cells (values encircled by the rectangle placed on the left hand side of the graphics).

Thus, STO, ZAF, or KD cells do not display a primary resistance to measles virus of the prior art (no employment of an additional suicide gene function). When MeV Id-SCD-infected STO, ZAF, or KD cells (MOI 1) were cultivated with the addition of the prodrug 5-FC (ranging from $10^{-4}$ to $10^{0}$ mM) a loss in cell mass after 96 h was demonstrated in the range of up to 94%, 99%, or 98%, respectively, in comparison to non-infected control cells.

Example 14

SRB Proliferation Assay of Sarcoma Tumor Cells (Cell Lines CCS, LM)

FIG. 17 shows the results of an SRB proliferation assay of glioblastoma tumor cells (cell lines LNT 229, LNT 229 CTS-1) treated with MeV Id-SCD viral particles rescued from the plasmid pc3MerV2 Id-SCD (Id-SCD) and incubated with prodrug 5-FC.

LNT 229 or LNT 229 CTS-1 cells infected with MeV Id-SCD at MOI 1 and then cultivated without the addition of the prodrug 5-FC demonstrated a loss in cell mass after 96 h in the range of 56% or 27%, respectively, in comparison to non-infected control cells (values encircled by the rectangle placed on the left hand side of the graphics). Thus, both LNT 229 or LNT 229 CTS-1 cells display a primary resistance to measles virus of the prior art (no employment of an additional suicide gene function). However, when MeV Id-SCD-infected LNT 229 or LNT 229 CTS-1 cells (MOI 1) were cultivated with the addition of the prodrug 5-FC (ranging from $10^{-4}$ to $10^{0}$ mM) a loss in cell mass after 96 h was demonstrated in the range of up to 97% or 96%, respectively, in comparison to non-infected control cells.

Thus it was shown, that a primary resistance to measles virus of the prior art (no employment of an additional suicide gene function) of LNT 229 or LNT 229 CTS-1 cells could be almost fully overcome under the chosen conditions (MOI 1) through usage of the SCD suicide gene function.

Example 15

SRB Proliferation Assay of Glioblastoma Tumor Cells (Cell Lines LN 18, LN 18 Apoptosis Resistant)

FIG. 18 shows the results of an SRB proliferation assay of glioblastoma tumor cells (cell lines LN 18, LN 18 Apoptosis resistant) treated with MeV Id-SCD viral particles rescued from the plasmid pc3MerV2 Id-SCD (Id-SCD) and incubated with prodrug 5-FC.

LN 18 or LN 18 Apoptosis resistant cells infected with MeV Id-SCD at MOI 1 and then cultivated without the addition of the prodrug 5-FC demonstrated a loss in cell mass after 96 h in the range of 33% or 22%, respectively, in comparison to non-infected control cells (values encircled by the rectangle placed on the left hand side of the graphics). Thus, both LN 18 or LN 18 Apoptosis resistant cells display a primary resistance to measles virus of the prior art (no employment of an additional suicide gene function). However, when MeV Id-SCD-infected LN 18 or LN 18 Apoptosis resistant cells (MOI 1) were cultivated with the addition of the prodrug 5-FC (ranging from $10^{-4}$ to $10^{0}$ mM) a loss in cell mass after 96 h was demonstrated in the range of up to 97% or 83%, respectively, in comparison to non-infected control cells.

Thus it was shown, that a primary resistance to measles virus of the prior art (no employment of an additional suicide gene function) of LN 18 or LN 18 Apoptosis resistant cells could be strongly improved, and in the case of LN 18 cells almost fully overcome under the chosen conditions (MOI 1) through usage of the SCD suicide gene function.

Example 16

SRB Proliferation Assay of Renal Cell Carcinoma (ACHN), Pulmonary Adenocarcinoma (HOP-62) and Melanoma (M14) Tumor Cells FIG. 19 shows the results of an SRB proliferation assay of renal cell carcinoma (ACHN), pulmonary adenocarcinoma (HOP-62) and melanoma (M14) tumor cells treated with MeV Id-SCD viral particles rescued from the plasmid pc3MerV2 Id-SCD (Id-SCD) and incubated with prodrug 5-FC.

ACHN, HOP-62, or M14 cells infected with MeV Id-SCD at MOI 1 and then cultivated without the addition of the prodrug 5-FC demonstrated a loss in cell mass after 96 h in the range of 20%, 16%, or 16%, respectively, in comparison to non-infected control cells. Thus, ACHN, HOP-62, and M14 cells display a primary resistance to measles virus of the prior art (no employment of an additional suicide gene function). However, when MeV Id-SCD-infected ACHN, HOP-62, or M14 cells (MOI 1) were cultivated with the addition of 1 mM prodrug 5-FC, a loss in cell mass after 96 h was demonstrated in the range of up to 85%, 86% or 76%, respectively, in comparison to non-infected control cells.

Thus it was shown, that a primary resistance to measles virus of the prior art (no employment of an additional suicide gene function) of ACHN, HOP-62, and M14 cells could be strongly improved under the chosen conditions (MOI 1) through usage of the SCD suicide gene function.

Example 17

SRB Proliferation Assay of Colonic Adenocarcinoma Tumor Cells (Cell Lines KM-12, HCT-15)

FIG. 20 shows the results of an SRB proliferation assay of colonic adenocarcinoma tumor cells (cell lines KM-12, HCT-15) treated with viral particles rescued from the plasmid pc3MerV2 Id-SCD (Id-SCD) and incubated with prodrug 5-FC.

KM-12 or HCT-15 cells infected with vector MeV Id-SCD at MOI 1 and then cultivated without the addition of the prodrug 5-FC demonstrated a loss in cell mass after 96 h in the range of 13% or 2%, respectively, in comparison to non-infected control cells (values encircled by the rectangle placed on the left hand side of the graphics). Thus, both KM-12 and HCT-15 cells display a primary resistance to measles virus of the prior art (no employment of an additional suicide gene function). However, when MeV Id-SCD-infected KM-12 or HCT-15 cells (MOI 1) were cultivated with the addition of 1 mM prodrug 5-FC, a loss in cell mass after 96 h was demonstrated in the range of up to 94% or 65%, respectively, in comparison to non-infected control cells.

Thus it was shown, that a primary resistance to measles virus of the prior art (no employment of an additional suicide gene function) of KM-12 or HCT-15 cells could be strongly improved, and in the case of KM-12 cells almost fully overcome under the chosen conditions (MOI 1) through usage of the SCD suicide gene function.

Example 18

Construction of Alternative Viral Vectors

Three vectors differing in their suicide gene array concerning the (i) positioning within the Measles virus genome as well as (ii) their context of SCD gene expression (here in the context of a fusion gene; i.e. with the Herpes simplex virus type 1 (HSV-1) tegument protein VP22 which mediates the function of protein spreading of fusion proteins) were constructed (see FIG. 27).

As the genome position at which a transgene is inserted in the Measles virus genome effects both viral replication and transgene expression, we compared two versions of positioning of the super-cytosine deaminase (SCD) transgene. Genome position one for SCD in vector pc3MerV2 Id-SCD, genome position three for SCD in vector pMerV2 P-SCD.

Additionally, a third vector, vector pc3MerV2 Id-VP22SCD, was constructed and compared with the other two vectors. At genome position one, this vector pc3MerV2 Id-VP22SCD expresses a fusion of the SCD transgene with the Herpes simplex virus type 1 (HSV-1) tegument protein VP22 gene, which mediates the function of protein spreading of fusion proteins (here: VP22SCD) from expressing cells to neighboring cells, which have not been infected hitherto with this MeV Id-VP22SCD viral particles rescued from vector pc3MerV2 Id-VP22SCD, thus making it a promising tool for compensation of inadequate primary vector transfer efficiencies.

DETAILS of the construction of pc3MerV2 Id-VP22SCD: To newly generate a third armed measles vaccine virus (MeV Id-VP22SCD) the plasmid pc3MerV2 Id-Trka was used as the starting basis. This plasmid codes for the viral cDNA with 100% identity to the vaccine strain Schwarz and contains an empty additional transcription unit (ATU, or Trka, transcription cassette) between the leader sequence and the N-gene. This additional transcription unit contains all regulatory sequences needed for expression of a transgene from the viral genome. The gene-start and the gene-end sequence and the nontranslated regions are identical to those from the N gene. Transgenes can be inserted via restriction enzyme sites XhoI or PauI.

The open reading frame (ORF) for VP22SCD was derived from the plasmid pUC29-VP22SCD. Since this ORF contains two SalI restriction sites and as further cloning steps in the MeV full length construct would be most likely carried out via SalI, these restriction sites had to be removed first by site-directed mutagenesis. As the ORF was already flanked by MluI sites which produces termini identical to those produced by PauI, and as the MluI-MluI fragment derived from this plasmid already contained the correct number of nucleotides to produce a MeV genome according to the rule of six, it was possible to insert this fragment into the MeV cDNA after removal of the SalI sites without any further modification. Thus, the cloning strategy was composed of three steps:

Removal of the SalI sites by site-directed mutagenesis
Insertion of VP22SCD into pc3MerV2 Id-Trka
Rescue of the virus Removal of the SalI sites: Two rounds of a single-site mutagenesis were applied. In the first round, the SalI site at position 802 was successfully removed, as shown by restriction analysis. The produced plasmid was then digested by DpnI and amplified in XL-1 blue supercompetent bacteria and was used as a template for the second round of mutagenesis, where the site at position 1127 was removed, as shown again by restriction analysis. Removal of both sites as well as the correct sequence of the ORF was verified by sequencing. The resulting plasmid was named pUC29-VP22SCD_w/oSalI.

Insertion of VP22SCD into pc3MerV2 Id-Trka: The recipient plasmid pc3MerV2 Id-Trka was digested with PauI. To avoid mechanical shearing of the ~20 kb plasmid, the linearized plasmid was not gel-purified. The restriction enzyme was heat-inactivated and the DNA fragment was dephosphorylated and subjected directly to ligation. pUC29-VP22SCD_w/oSalI was digested with MluI, gel-purified and subjected to ligation. Successful insertion of the transgene was shown by HindIII-digest and by sequencing. The resulting plasmid was named pc3MerV2 Id-VP22SCD.

Example 19

Comparison of Alternative Viral Vectors

The three different viral vectors synthesized as described in Example 18 were compared with the aim to identify the most effective one (see FIGS. 21 to 23).

FIG. 21 shows the effect of viral particles MeV Id-SCD, MeV Id-VP22SCD, and MeV P-SCD on Hep3B human hepatocellular carcinoma cells.

Hep3B cells were infected at an MOI of 0.001 or 0.01 with viral particles rescued from pc3MerV2 Id-SCD, pMerV2 P-SCD, and pc3MerV2 Id-VP22SCD, and tumor cell mass was determined either in the presence of 1 mM or the absence of 5-FC over time.

As can be seen, viral particles rescued from pc3MerV2 Id-SCD exhibited a drastically higher oncolytic potential even in the absence of 5-FC in the case of an MOI of 0.01, and led to an almost complete loss of tumor cell mass after 6 days even in the case of an MOI of 0.001 in the presence of 5-FC.

FIG. 22 shows the effect of viral particles rescued from vectors pc3MerV2 Id-SCD, pMerV2 P-SCD, and pc3MerV2 Id-VP22SCD on HepG2 human hepatocellular carcinoma cells.

HepG2 cells were infected at an MOI of 0.001 or 0.01 with viral particles rescued from pc3MerV2 Id-SCD, pMerV2 P-SCD, and pc3MerV2 Id-VP22SCD, and tumor cell mass was determined either in the presence of 1 mM or the absence of 5-FC over time.

As can be seen, MeV Id-SCD viral particles exhibited a substantially higher oncolytic potential even in the absence of 5-FC in the case of an MOI of 0.01, and led to a substantially higher loss of tumor cell mass after 6 days even in the case of an MOI of 0.001 in the presence of 5-FC.

FIG. 23 shows the effect of viral particles rescued from vectors pc3MerV2 Id-SCD, pMerV2 P-SCD, and pc3MerV2 Id-VP22SCD on PLC/PRF/5 human hepatocellular carcinoma cells.

PLC/PRF/5 cells were infected at an MOI of 0.001 or 0.01 with viral particles rescued from vectors pc3MerV2 Id-SCD, pMerV2 P-SCD, and pc3MerV2 Id-VP22SCD, and tumor cell mass was determined either in the presence of 1 mM or the absence of 5-FC over time.

As can be seen, viral particles rescued from vector pc3MerV2 Id-SCD exhibited a substantially higher oncolytic potential even in the absence of 5-FC in the case of an MOI of 0.01, and led to a substantially higher loss of tumor cell mass after 6 days even in the case of an MOI of 0.001 in the presence of 5-FC.

Thus, surprisingly it was found that the positioning of the SCD suicide gene within the Measles virus genome as well as the context of SCD gene expression had a strong influence of the oncolytic activity of the viral particles, with particles from vector pc3MerV2 Id-SCD being substantially better than particles rescued from vectors pMerV2 P-SCD, and pc3MerV2 Id-VP22SCD.

Example 20

In Vivo Characterization of Armed Vectors in Xenograft Animal Tumor Models

To test the armed vectors pc3MerV2 Id-SCD, pMerV2 P-SCD, and pc3MerV2 Id-VP22SCD in vivo, a murine xenograft model of human HCC was applied. As measles virus does not infect murine cells, it is not possible to use a murine model with syngeneic tumors to test vectors without special modifications of the surface glycoproteins.

To compare the armed vectors, a mouse model of subcutaneously grown Hep3B tumors was chosen. This decision was based on the facts (i) that Hep3B can be efficiently infected by MeV and support MeV replication at high levels, (ii) that in Hep3B, the conversion of 5-FC into 5-FU is fast and efficient and (iii) that over an incubation of 1-4 days after addition of the prodrug to infected cells, an increasing gap between the treatment with virus alone and the combination treatment can be observed. Additionally, a mouse model of Hep3B has been described before (Blechacz B, Splinter P L, Greiner S, Myers R, Peng K W, Federspiel M J, Russell S J, LaRusso N F. Hepatology. December 2006; 44(6):1465-77) with a high engraftment ratio (80%, personal communication with Boris Blechacz, Mayo Clinic, Rochester, Minn., USA). In contrast, this ratio is much lower in PLC/PRF/5 (60%) and in HepG2, both determined in our laboratory.

For this in vivo experiment, six week old nude mice received subcutaneous injections of 100 μl cell suspension containing $10^6$ Hep3B cells in PBS. As expected, the cells grafted in 80% of the mice, although the duration between tumor cell implantation and appearance of the tumors was found to be quite heterogeneous. The tumors were very well vascularized and appeared blue through the nude skin of the mice. After the tumors had grown to a diameter of approximately 5 mm, the mice received five intratumoral injections of the respective virus (MeV Id-SCD, MeV Id-VP22SCD or MeV P-SCD) with $2*10^6$ pfu per injection and one injection daily (total dose: 107 pfu). Control groups were treated with medium only. On the following seven days, the mice received 500 mg/kg bodyweight 5-FC in PBS intraperitoneally. Tumor volume and weight of the animals were determined three times a week.

To ensure that the above described treatment schedule does not lead to toxicities, mice were monitored daily and weight was determined three times a week. The combinatorial treatment (MeV-SCD+5-FC) did neither lead to any visible changes in the behavior of the animals, nor did they show reactions like enhanced sensitivity to touch. The skin of the mice looked healthy, no changes in their movement or feeding behaviors were observed and their weight remained stable.

Treatment of tumor-bearing mice with the suicide gene therapy both reduces tumor volume and extends survival significantly.

As a result of the in vivo testing, a strong oncolytic effect of either of the viruses could be documented. As expected, the administration of the prodrug alone had no effect: 5-FC injection in virus-treated mice did not lead to an altered outcome compared to the treatment with virus alone, but importantly it also did not inhibit the virus-mediated effects by early abrogation of virus replication. Additionally, no significant oncolytic differences were observed between the three vectors. In this experimental setting, the direct effect of oncolytic measles vaccine virus seems to be highly effective, so that the additional application of 5-FC does not lead to an enhanced oncolysis or to any survival benefits. Survival of the mice was significantly improved by all treatments compared to the controls. The median survival of control-treated mice was 35 days and that of mice treated with 5-FC only was 32 days (see FIG. 24). All mice from these groups had to be sacrificed before day 50. In contrast, the median survival in the treatment groups ranged between 49 days (MeV P-SCD only) and 82.5 days (MeV Id-SCD only) (see FIG. 24). The mice from both groups treated with MeV P-SCD were sacrificed before day 100, whereas six mice from the other treatment groups survived tumor-free more than 150 days (1 mouse each for MeV Id-SCD only and MeV Id-VP22SCD+5-FC; two mice each for MeV Id-SCD+5-FC and for MeV Id-VP22SCD only). Some mice from different treatment groups developed a visible and palpable secondary tumor inside the peritoneal cavity. As this was considered a treatment failure, these mice were not excluded from the statistical analysis.

In all treatment groups, tumors with different growth behaviors were observed. Some tumors grew very quickly and reached the defined endpoint of >2000 $mm^3$ around day 30 after initiation of treatment which was similar to control-treated mice. Several other mice had a retarded tumor growth, with a low tumor volume in the first weeks after treatment initiation, but eventually, their tumors reinitiated growing and reached the endpoint volume. Some other tumors completely disappeared and mice were tumor-free for more than 195 days. This differential behavior is shown exemplarily for both MeV Id-SCD treatment groups. Also, some tumors had an oscillating growth behavior, which was probably due to virus replication reducing tumor volume, followed by growth of remaining tumor cells, offering the virus a new basis for replication, leading again to oncolysis and remission of the tumor. This shrinking and growing of the tumor was accompanied by the loss and regaining of tumor vascularization as detected by the blue color shimmering through the skin of the mice. In the example shown here, the tumor ultimately disappeared at day 91. This oscillating growth was considered as a first hint for a long-term virus replication in tumors.

Similar results were obtained with additional xenograft animal models (HepG2 human hepatocellular carcinoma cells, and PLC/PRF/5 human hepatocellular carcinoma cells): see FIGS. 25 and 26, respectively.

Sequence Listing:

SEQ-ID NO. 1: genetic sequence of measles vaccine strain Schwarz (see FIG. 1)

SEQ-ID NO. 2: genetic sequence of fusion of yeast cytosine deaminase and yeast uracil phosphoribosyltransferase (with linker sequence) (see FIG. 2)

SEQ-ID NO. 3: genetic sequence of basic recombinant measles virus without any trangenes but insertion cassettes (see FIG. 3)

SEQ-ID NO. 4: genetic sequence of vector pc3MerV2 Id-SCD (see FIG. 4)

SEQ-ID No. 5: genetic sequence of helper plasmid required for the expression of the N gene (see FIG. 5)

SEQ-ID No. 6: genetic sequence of helper plasmid required for the expression of the P gene (see FIG. 6)

SEQ-ID No. 7: genetic sequence of helper plasmid required for the expression of the L gene (see FIG. 7)

SEQ-ID No. 8: genetic sequence of vector pMerV2 P-SCD, (see FIG. 28)

SEQ-ID No. 9: genetic sequence of vector pc3MerV2 Id-VP22SCD (see FIG. 29)

The invention claimed is:

1. A pharmaceutical composition comprising a recombinant measles virus comprising a suicide gene for treating malignant cells with primary or secondary resistances against an oncolytic measles virus without suicide gene activity, wherein said recombinant measles virus is from measles vaccine strain Schwarz, wherein said suicide gene comprises a fusion of a cytosine deaminase and a uracil phosphoribosyltransferase, and wherein said recombinant measles virus comprises an RNA sequence according to SEQ-ID No. 4, SEQ-ID No. 8, or SEQ-ID No. 9.

2. The pharmaceutical composition according to claim 1, wherein said malignant cells are identified by performing the following step:

(a) determining the percentage of living cells in a population of cells derived from said malignant cells 72 h, or 96 h, after infecting said population with the oncolytic measles virus at a multiplicity of infection of 1, wherein a percentage of 40% or more of living cells in said population is indicative for said malignant cells being primarily or secondarily resistant to an oncolytic measles virus without suicide gene activity.

3. The pharmaceutical composition according to claim 1, wherein said oncolytic measles virus without suicide gene activity comprises a sequence according to SEQ-ID No. 1.

4. The pharmaceutical composition according to claim 1, wherein said cytosine deaminase comprises yeast cytosine deaminase.

5. The pharmaceutical composition according to claim 4, wherein said uracil phosphoribosyltransferase comprises yeast uracil phosphoribosyltransferase.

6. The pharmaceutical composition according to claim 5, wherein said suicide gene comprises a sequence according to SEQ-ID NO. 2.

7. The pharmaceutical composition according to claim 1, wherein said malignant cells are additionally non-responsive to chemotherapeutics and/or radiation therapy.

8. The pharmaceutical composition according to claim 1, wherein said malignant cells are selected from the list of: malignant cells from cholangiocarcinoma, head and neck cancer, hepatocellular carcinoma, and sarcoma.

9. The pharmaceutical composition according to any one of claims 1 to 8, wherein said treatment is a repeated treatment.

10. A recombinant measles virus from measles vaccine strain Schwarz encoding a suicide gene comprising a fusion of a cytosine deaminase and a uracil phosphoribosyltransferase, wherein said recombinant measles virus comprises an RNA sequence according to SEQ-ID No. 4, SEQ-ID No. 8, or SEQ-ID No. 9.

11. A method for generating the recombinant measles virus according to claim 10, comprising the step of (a) cloning (i) the genome of measles vaccine strain Schwarz, and (ii) a suicide gene comprising a fusion of a cytosine deaminase, and a uracil phosphoribosyltransferase, into a plasmid under the control of an RNA polymerase II promoter;

wherein step (a) results in the plasmid having the sequence according to SEQ-ID No. 4, SEQ-ID No. 8, or SEQ-ID No. 9.

12. The method according to claim 11, wherein said suicide gene comprises a sequence according to SEQ-ID NO. 2.

13. The method according to claim 11, further comprising the step of (b) cloning measles virus helper genes N, P and L, each under the control of an RNA polymerase II promoter, into at least one vector.

14. The method according to claim 13, wherein the viral helper genes N, P and L are each cloned into a separate vector.

15. The method according to claim 14, wherein step (b) comprises the steps of (ba) cloning measles virus helper gene N under the control of an RNA polymerase II promoter, into a first vector;

(bb) cloning measles virus helper gene P under the control of an RNA polymerase II promoter into a second vector;

(bc) cloning measles virus helper gene L under the control of an RNA polymerase II promoter into a third vector.

16. The method according to claim 15, wherein step (a), (ba), (bb) and/or (bc), further comprise the step of removing putative splicing sequences from said genome and/or any of said helper genes.

17. The method according to claim 15, wherein steps (ba) to (bc) result in plasmids having the sequences according to SEQ-ID No. 5, SEQ-ID No. 6, and SEQ-ID No. 7.

18. The method according to any one of claims 13-16 or 17, further comprising the step of (c) transfecting host cells with plasmids of steps (a) and (b), or (a) and (ba) to (bc).

19. The method according to claim 18, further comprising the step of (d) rescuing recombinant measles virus from the host cell transformed in step (c).

20. A kit comprising (a) a plasmid comprising (i) the genome of measles vaccine strain Schwarz, and (ii) a suicide gene comprising a fusion of a cytosine deaminase and a uracil phosphoribosyltransferase under the control of an RNA polymerase II promoter;

(b) at least one plasmid comprising the measles virus helper genes N, P and L, each in form of a single gene under the control of an RNA polymerase II promoter;

wherein the plasmid has the sequence according to SEQ-ID No. 4, SEQ-ID No. 8, or SEQ-ID No. 9.

21. The kit according to claim 20, wherein the viral helper genes N, P and L are each cloned into a separate plasmid.

22. The kit according to claim 20, wherein said cytosine deaminase is a yeast cytosine deaminase.

23. The kit according to claim 22, wherein said uracil phosphoribosyltransferase is a yeast uracil phosphoribosyltransferase.

24. The kit according to claim 23, wherein said suicide gene comprises a sequence according to SEQ-ID NO. 2.

25. The kit according to claim 20, wherein the plasmid has the sequence according to SEQ-ID No. 4.

26. The pharmaceutical composition according to claim 1, wherein said recombinant measles virus comprises an RNA sequence according to SEQ-ID No. 4.

27. The pharmaceutical composition claim according to claim 1, wherein the malignant cells are selected from human carcinoma and human sarcoma.

28. The recombinant measles virus according to claim 10, wherein said cytosine deaminase comprises yeast cytosine deaminase.

29. The recombinant measles virus according to claim 28, wherein said uracil phosphoribosyltransferase comprises yeast uracil phosphoribosyltransferase.

30. The recombinant measles virus according to claim 10, wherein said suicide gene comprises a sequence according to SEQ-ID NO. 2.

31. The recombinant measles virus according to claim 10, wherein said recombinant measles virus comprises an RNA sequence according to SEQ-ID No. 4.

32. The pharmaceutical composition according to claim 2, wherein a percentage of 50% or more of living cells in said population is indicative for said malignant cells being primarily or secondarily resistant to an oncolytic measles virus without suicide gene activity.

33. The pharmaceutical composition according to claim 2, wherein a percentage of 60% or more of living cells in said population is indicative for said malignant cells being primarily or secondarily resistant to an oncolytic measles virus without suicide gene activity.

34. The kit according to claim 21, wherein the plasmids have the sequences according to SEQ-ID No. 5, SEQ-ID No. 6, and SEQ-ID No. 7.

35. The pharmaceutical composition according to claim 9, wherein said treatment is repeated every week, every two weeks, every three weeks, or every four weeks.

36. The method according to claim 11, wherein the cytosine deaminase is yeast cytosine deaminase.

37. The method according to claim 11, wherein the uracil phosphoribosyltransferase is yeast uracil phosphoribosyltransferase.

38. The method according to claim 11, wherein step (a) results in the plasmid having the sequence according to SEQ-ID No. 4.

39. The method according to claim 13, wherein the viral helper genes N, P and L are each cloned into a separate plasmid vector.

40. The method according to claim 15, wherein the first vector is a plasmid vector, wherein the second vector is a plasmid vector, and wherein the third vector is a plasmid vector.

41. The method according to claim 18, wherein the host cells are from a certified cell line approved for vaccine production.

42. The method according to claim 18, wherein the host cells are from Vero or MRC-5 cell lines.

* * * * *

SEQUENCE LISTING

<160> NUMBER OF SEQ ID NOS: 9

<210> SEQ ID NO 1
<211> LENGTH: 15894
<212> TYPE: DNA
<213> ORGANISM: measles virus

<400> SEQUENCE: 1
accaaacaaa gttgggtaag gatagttcaa tcaatgatca tcttctagtg cacttaggat 60
tcaagatcct attatcaggg acaagagcag gattagggat atccgagatg gccacacttt 120
taaggagctt agcattgttc aaaagaaaca aggacaaacc acccattaca tcaggatccg 180
gtggagccat cagaggaatc aaacacatta ttatagtacc aatccctgga gattcctcaa 240
ttaccactcg atccagactt ctggaccggt tggtgaggtt aattggaaac ccggatgtga 300
gcgggcccaa actaacaggg gcactaatag gtatattatc cttatttgtg gagtctccag 360
gtcaattgat tcagaggatc accgatgacc ctgacgttag cataaggctg ttagaggttg 420
tccagagtga ccagtcacaa tctggcctta ccttcgcatc aagaggtacc aacatggagg 480
atgaggcgga ccaatacttt tcacatgatg atccaattag tagtgatcaa tccaggttcg 540
gatggttcgg gaacaaggaa atctcagata ttgaagtgca agaccctgag ggattcaaca 600
tgattctggg taccatccta gcccaaattt gggtcttgct cgcaaaggcg gttacggccc 660
cagacacggc agctgattcg gagctaagaa ggtggataaa gtacacccaa caaagaaggg 720
tagttggtga atttagattg gagagaaaat ggttggatgt ggtgaggaac aggattgccg 780
aggacctctc cttacgccga ttcatggtcg ctctaatcct ggatatcaag agaacacccg 840
gaaacaaacc caggattgct gaaatgatat gtgacattga tacatatatc gtagaggcag 900
gattagccag ttttatcctg actattaagt ttgggataga aactatgtat cctgctcttg 960
gactgcatga atttgctggt gagttatcca cacttgagtc cttgatgaac ctttaccagc 1020 aaatgggggga aactgcaccc tacatggtaa tcctggagaa ctcaattcag aacaagttca 1080
gtgcaggatc ataccctctg ctctggagct atgccatggg agtaggagtg gaacttgaaa 1140
actccatggg aggtttgaac tttggccgat cttactttga tccagcatat tttagattag 1200

```
ggcaagagat ggtaaggagg tcagctggaa aggtcagttc cacattggca tctgaactcg   1260

gtatcactgc cgaggatgca aggcttgttt cagagattgc aatgcatact actgaggaca   1320

agatcagtag agcggttgga cccagacaag cccaagtatc atttctacac ggtgatcaaa   1380

gtgagaatga gctaccgaga ttgggggca aggaagatag gagggtcaaa cagagtcgag   1440

gagaagccag ggagagctac agagaaaccg ggcccagcag agcaagtgat gcgagagctg   1500

cccatcttcc aaccggcaca cccctagaca ttgacactgc aacggagtcc agccaagatc   1560

cgcaggacag tcgaaggtca gctgacgccc tgcttaggct gcaagccatg gcaggaatct   1620

cggaagaaca aggctcagac acggacaccc ctatagtgta caatgacaga aatcttctag   1680

actaggtgcg agaggccgag ggccagaaca acatccgcct accatccatc attgttataa   1740

aaaacttagg aaccaggtcc acacagccgc cagcccatca accatccact cccacgattg   1800

gagccaatgg cagaagagca ggcacgccat gtcaaaaacg gactggaatg catccgggct   1860

ctcaaggccg agcccatcgg ctcactggcc atcgaggaag ctatggcagc atggtcagaa   1920

atatcagaca acccaggaca ggagcgagcc acctgcaggg aagagaaggc aggcagttcg   1980

ggtctcagca aaccatgcct ctcagcaatt ggatcaactg aaggcggtgc acctcgcatc   2040

cgcggtcagg gacctggaga gagcgatgac gacgctgaaa ctttgggaat ccccccaaga   2100

aatctccagg catcaagcac tgggttacag tgttattacg tttatgatca cagcggtgaa   2160

gcggttaagg gaatccaaga tgctgactct atcatggttc aatcaggcct tgatggtgat   2220

agcaccctct caggaggaga caatgaatct gaaaacagcg atgtggatat tggcgaacct   2280

gataccgagg gatatgctat cactgaccgg ggatctgctc ccatctctat ggggttcagg   2340

gcttctgatg ttgaaactgc agaaggaggg gagatccacg agctcctgag actccaatcc   2400

agaggcaaca actttccgaa gcttgggaaa actctcaatg ttcctccgcc cccggacccc   2460

ggtagggcca gcacttccgg gacacccatt aaaaagggca cagacgcgag attagcctca   2520

tttggaacgg agatcgcgtc tttattgaca ggtggtgcaa cccaatgtgc tcgaaagtca   2580

ccctcggaac catcagggcc aggtgcacct gcggggaatg tccccgagtg tgtgagcaat   2640

gccgcactga tacaggagtg gacacccgaa tctggtacca caatctcccc gagatcccag   2700

aataatgaag aagggggaga ctattatgat gatgagctgt tctctgatgt ccaagatatt   2760

aaaacagcct tggccaaaat acacgaggat aatcagaaga taatctccaa gctagaatca   2820

ctgctgttat tgaagggaga agttgagtca attaagaagc agatcaacag gcaaaatatc   2880

agcatatcca ccctggaagg acacctctca agcatcatga tcgccattcc tggacttggg   2940

aaggatccca acgaccccac tgcagatgtc gaaatcaatc ccgacttgaa acccatcata   3000

ggcagagatt caggccgagc actggccgaa gttctcaaga aacccgttgc cagccgacaa   3060

ctccaaggaa tgacaaatgg acggaccagt tccagaggac agctgctgaa ggaatttcag   3120

ctaaagccga tcgggaaaaa gatgagctca gccgtcgggt ttgttcctga caccggccct   3180

gcatcacgca gtgtaatccg ctccattata aaatccagcc ggctagagga ggatcggaag   3240

cgttacctga tgactctcct tgatgatatc aaaggagcca atgatcttgc caagttccac   3300

cagatgctga tgaagataat aatgaagtag ctacagctca acttacctgc caaccccatg   3360

ccagtcgacc caactagtac aacctaaatc cattataaaa aacttaggag caaagtgatt   3420

gcctcccaag gtccacaatg acagagacct acgacttcga caagtcggca tgggacatca   3480

aagggtcgat cgctccgata caacccacca cctacagtga tggcaggctg gtgccccagg   3540
```

```
tcagagtcat agatcctggt ctaggcgaca ggaaggatga atgctttatg tacatgtttc   3600
tgctgggggt tgttgaggac agcgattccc tagggcctcc aatcgggcga gcatttgggt   3660
tcctgccctt aggtgttggc agatccacag caaagcccga aaaactcctc aaagaggcca   3720
ctgagcttga catagttgtt agacgtacag cagggctcaa tgaaaaactg gtgttctaca   3780
acaacacccc actaactctc ctcacacctt ggagaaaggt cctaacaaca gggagtgtct   3840
tcaacgcaaa ccaagtgtgc aatgcggtta atctgatacc gctcgatacc ccgcagaggt   3900
tccgtgttgt ttatatgagc atcacccgtc tttcggataa cgggtattac accgttccta   3960
gaagaatgct ggaattcaga tcggtcaatg cagtggcctt caacctgctg gtgaccctta   4020
ggattgacaa ggcgataggc cctgggaaga tcatcgacaa tacagagcaa cttcctgagg   4080
caacatttat ggtccacatc gggaacttca ggagaaagaa gagtgaagtc tactctgccg   4140
attattgcaa aatgaaaatc gaaaagatgg gcctggtttt tgcacttggt gggatagggg   4200
gcaccagtct tcacattaga agcacaggca aaatgagcaa gactctccat gcacaactcg   4260
ggttcaagaa gaccttatgt tacccgctga tggatatcaa tgaagacctt aatcgattac   4320
tctggaggag cagatgcaag atagtaagaa tccaggcagt tttgcagcca tcagttcctc   4380
aagaattccg catttacgac gacgtgatca taaatgatga ccaaggacta ttcaaagttc   4440
tgtagaccgt agtgcccagc aatgcccgaa aacgaccccc ctcacaatga cagccagaag   4500
gcccggacaa aaaagccccc tccgaaagac tccacggacc aagcgagagg ccagccagca   4560
gccgacggca agcgcgaaca ccaggcggcc ccagcacaga acagccctga cacaaggcca   4620
ccaccagcca ccccaatctg catcctcctc gtgggacccc cgaggaccaa cccccaaggc   4680
tgcccccgat ccaaaccacc aaccgcatcc ccaccacccc cgggaaagaa acccccagca   4740
attggaaggc ccctccccct cttcctcaac acaagaactc cacaaccgaa ccgcacaagc   4800
gaccgaggtg acccaaccgc aggcatccga ctccctagac agatcctctc tccccggcaa   4860
actaaacaaa acttagggcc aaggaacata cacacccaac agaacccaga ccccggccca   4920
cggcgccgcg cccccaaccc ccgacaacca gagggagccc ccaaccaatc ccgccggctc   4980
ccccggtgcc cacaggcagg gacaccaacc cccgaacaga cccagcaccc aaccatcgac   5040
aatccaagac ggggggggccc ccccaaaaaa aggcccccag gggccgacag ccagcaccgc   5100
gaggaagccc acccacccca cacacgacca cggcaaccaa accagaaccc agaccaccct   5160
gggccaccag ctcccagact cggccatcac cccgcagaaa ggaaaggcca caacccgcgc   5220
accccagccc cgatccggcg gggagccacc caacccgaac cagcacccaa gagcgatccc   5280
cgaaggaccc ccgaaccgca aaggacatca gtatcccaca gcctctccaa gtcccccggt   5340
ctcctcctct tctcgaaggg accaaaagat caatccacca cacccgacga cactcaactc   5400
cccaccccta aaggagacac cgggaatccc agaatcaaga ctcatccaat gtccatcatg   5460
ggtctcaagg tgaacgtctc tgccatattc atggcagtac tgttaactct ccaaacaccc   5520
accggtcaaa tccattgggg caatctctct aagatagggg tggtaggaat aggaagtgca   5580
agctacaaag ttatgactcg ttccagccat caatcattag tcataaaatt aatgcccaat   5640
ataactctcc tcaataactg cacgaggtta gagattgcag aatacaggag actactgaga   5700
acagttttgg aaccaattag agatgcactt aatgcaatga cccagaatat aagaccggtt   5760
cagagtgtag cttcaagtag gagacacaag agatttgcgg gagtagtcct ggcaggtgcg   5820
gccctaggcg ttgccacagc tgctcagata acagccggca ttgcacttca ccagtccatg   5880
ctgaactctc aagccatcga caatctgaga gcgagcctgg aaactactaa tcaggcaatt   5940
```

```
gagacaatca gacaagcagg gcaggagatg atattggctg ttcagggtgt ccaagactac   6000
atcaataatg agctgatacc gtctatgaac caactatctt gtgatttaat cggccagaag   6060
ctcgggctca aattgctcag atactataca gaaatcctgt cattatttgg ccccagttta   6120
cgggacccca tatctgcgga gatatctatc caggctttga gctatgcgct tggaggagac   6180
atcaataagg tgttagaaaa gctcggatac agtggaggtg atttactggg catcttagag   6240
agcggaggaa taaaggcccg gataactcac gtcgacacag agtcctactt cattgtcctc   6300
agtatagcct atccgacgct gtccgagatt aagggggtga ttgtccaccg gctagagggg   6360
gtctcgtaca acataggctc tcaagagtgg tataccactg tgcccaagta tgttgcaacc   6420
caagggtacc ttatctcgaa ttttgatgag tcatcgtgta ctttcatgcc agaggggact   6480
gtgtgcagcc aaaatgcctt gtacccgatg agtcctctgc tccaagaatg cctccggggg   6540
tacaccaagt cctgtgctcg tacactcgta tccgggtctt ttgggaaccg gttcatttta   6600
tcacaaggga acctaatagc caattgtgca tcaatccttt gcaagtgtta cacaacagga   6660
acgatcatta atcaagaccc tgacaagatc ctaacataca ttgctgccga tcactgcccg   6720
gtagtcgagg tgaacggcgt gaccatccaa gtcgggagca ggaggtatcc agacgctgtg   6780
tacttgcaca gaattgacct cggtcctccc atatcattgg agaggttgga cgtagggaca   6840
aatctgggga atgcaattgc taagttggag gatgccaagg aattgttgga gtcatcggac   6900
cagatattga ggagtatgaa aggtttatcg agcactagca tagtctacat cctgattgca   6960
gtgtgtcttg gagggttgat agggatcccc gctttaatat gttgctgcag ggggcgttgt   7020
aacaaaaagg gagaacaagt tggtatgtca agaccaggcc taaagcctga tcttacggga   7080
acatcaaaat cctatgtaag gtcgctctga tcctctacaa ctcttgaaac acaaatgtcc   7140
cacaagtctc ctcttcgtca tcaagcaacc accgcaccca gcatcaagcc cacctgaaat   7200
tatctccggc ttccctctgg ccgaacaata tcggtagtta atcaaaactt agggtgcaag   7260
atcatccaca atgtcaccac aacgagaccg gataaatgcc ttctacaaag ataaccccca   7320
tcccaaggga agtaggatag tcattaacag agaacatctt atgattgata gaccttatgt   7380
tttgctggct gttctgtttg tcatgtttct gagcttgatc gggttgctag ccattgcagg   7440
cattagactt catcgggcag ccatctacac cgcagagatc cataaaagcc tcagcaccaa   7500
tctagatgta actaactcaa tcgagcatca ggtcaaggac gtgctgacac cactcttcaa   7560
aatcatcggt gatgaagtgg gcctgaggac acctcagaga ttcactgacc tagtgaaatt   7620
aatctctgac aagattaaat tccttaatcc ggatagggag tacgacttca gagatctcac   7680
ttggtgtatc aacccgccag agagaatcaa attggattat gatcaatact gtgcagatgt   7740
ggctgctgaa gagctcatga atgcattggt gaactcaact ctactggaga ccagaacaac   7800
caatcagttc ctagctgtct caaagggaaa ctgctcaggg cccactacaa tcagaggtca   7860
attctcaaac atgtcgctgt ccctgttaga cttgtattta ggtcgaggtt acaatgtgtc   7920
atctatagtc actatgacat cccagggaat gtatggggga acttacctag tggaaaagcc   7980
taatctgagc agcaaaaggt cagagttgtc acaactgagc atgtaccgag tgtttgaagt   8040
aggtgttatc agaaatccgg gtttgggggc tccggtgttc catatgacaa actatcttga   8100
gcaaccagtc agtaatgatc tcagcaactg tatggtggct ttgggggagc tcaaactcgc   8160
agccctttgt cacggggaag attctatcac aattccctat cagggatcag ggaaaggtgt   8220
cagcttccag ctcgtcaagc taggtgtctg gaaatcccca accgacatgc aatcctgggt   8280
```

```
ccccttatca acggatgatc cagtgataga caggctttac ctctcatctc acagaggtgt   8340
tatcgctgac aatcaagcaa aatgggctgt cccgacaaca cgaacagatg acaagttgcg   8400
aatggagaca tgcttccaac aggcgtgtaa gggtaaaatc caagcactct gcgagaatcc   8460
cgagtgggca ccattgaagg ataacaggat tccttcatac ggggtcttgt ctgttgatct   8520
gagtctgaca gttgagctta aaatcaaaat tgcttcggga ttcgggccat tgatcacaca   8580
cggttcaggg atggacctat acaaatccaa ccacaacaat gtgtattggc tgactatccc   8640
gccaatgaag aacctagcct taggtgtaat caacacattg gagtggatac cgagattcaa   8700
ggttagtccc tacctcttca ctgtcccaat taaggaagca ggcgaagact gccatgcccc   8760
aacataccta cctgcggagg tggatggtga tgtcaaactc agttccaatc tggtgattct   8820
acctggtcaa gatctccaat atgttttggc aacctacgat acttccaggg ttgaacatgc   8880
tgtggtttat tacgtttaca gcccaagccg ctcattttct tacttttatc cttttaggtt   8940
gcctataaag gggggtcccca tcgaattaca agtggaatgc ttcacatggg accaaaaact   9000
ctggtgccgt cacttctgtg tgcttgcgga ctcagaatct ggtggacata tcactcactc   9060
tgggatggtg ggcatgggag tcagctgcac agtcacccgg gaagatggaa ccaatcgcag   9120
atagggctgc tagtgaacca atcacatgat gtcacccaga catcaggcat acccactagt   9180
gtgaaataga catcagaatt aagaaaaacg tagggtccaa gtggttcccc gttatggact   9240
cgctatctgt caaccagatc ttataccctg aagttcacct agatagcccg atagttacca   9300
ataagatagt agccatcctg gagtatgctc gagtccctca cgcttacagc ctggaggacc   9360
ctacactgtg tcagaacatc aagcaccgcc taaaaaacgg attttccaac caaatgatta   9420
taaacaatgt ggaagttggg aatgtcatca agtccaagct taggagttat ccggcccact   9480
ctcatattcc atatccaaat tgtaatcagg atttatttaa catagaagac aaagagtcaa   9540
cgaggaagat ccgtgaactc ctcaaaaagg ggaattcgct gtactccaaa gtcagtgata   9600
aggttttcca atgcttaagg gacactaact cacggcttgg cctaggctcc gaattgaggg   9660
aggacatcaa ggagaaagtt attaacttgg gagtttacat gcacagctcc cagtggtttg   9720
agccctttct gttttggttt acagtcaaga ctgagatgag gtcagtgatt aaatcacaaa   9780
cccatacttg ccataggagg agacacacac ctgtattctt cactggtagt tcagttgagt   9840
tgctaatctc tcgtgacctt gttgctataa tcagtaaaga gtctcaacat gtatattacc   9900
tgacatttga actggttttg atgtattgtg atgtcataga ggggaggtta atgacagaga   9960
ccgctatgac tattgatgct aggtatacag agcttctagg aagagtcaga tacatgtgga  10020
aactgataga tggtttcttc cctgcactcg ggaatccaac ttatcaaatt gtagccatgc  10080
tggagcctct ttcacttgct tacctgcagc tgagggatat aacagtagaa ctcagaggtg  10140
ctttccttaa ccactgcttt actgaaatac atgatgttct tgaccaaaac gggttttctg  10200
atgaaggtac ttatcatgag ttaactgaag ctctagatta cattttcata actgatgaca  10260
tacatctgac aggggagatt ttctcatttt tcagaagttt cggccacccc agacttgaag  10320
cagtaacggc tgctgaaaat gttaggaaat acatgaatca gcctaaagtc attgtgtatg  10380
agactctgat gaaaggtcat gccatatttt gtggaatcat aatcaacggc tatcgtgaca  10440
ggcacggagg cagttggcca ccgctgaccc tccccctgca tgctgcagac acaatccgga  10500
atgctcaagc ttcaggtgaa gggttaacac atgagcagtg cgttgataac tggaaatctt  10560
ttgctggagt gaaatttggc tgctttatgc ctcttagcct ggatagtgat ctgacaatgt  10620
acctaaagga caaggcactt gctgctctcc aaagggaatg ggattcagtt tacccgaaag  10680
```

```
agttcctgcg ttacgaccct cccaagggaa ccgggtcacg gaggcttgta gatgttttcc  10740

ttaatgattc gagctttgac ccatatgatg tgataatgta tgttgtaagt ggagcttacc  10800

tccatgaccc tgagttcaac ctgtcttaca gcctgaaaga aaaggagatc aaggaaacag  10860

gtagactttt tgctaaaatg acttacaaaa tgagggcatg ccaagtgatt gctgaaaatc  10920

taatctcaaa cgggattggc aaatatttta aggacaatgg gatggccaag gatgagcacg  10980

atttgactaa ggcactccac actctagctg tctcaggagt ccccaaagat ctcaaagaaa  11040

gtcacagggg ggggccagtc ttaaaaacct actcccgaag cccagtccac acaagtacca  11100

ggaacgtgag agcagcaaaa gggtttatag ggttccctca agtaattcgg caggaccaag  11160

acactgatca tccggagaat atggaagctt acgagacagt cagtgcattt atcacgactg  11220

atctcaagaa gtactgcctt aattggagat atgagaccat cagcttgttt gcacagaggc  11280

taaatgagat ttacggattg ccctcatttt tccagtggct gcataagagg cttgagacct  11340

ctgtcctgta tgtaagtgac cctcattgcc cccccgacct tgacgcccat atcccgttat  11400

ataaagtccc caatgatcaa atcttcatta agtaccctat gggaggtata gaagggtatt  11460

gtcagaagct gtggaccatc agcaccattc cctatctata cctggctgct tatgagagcg  11520

gagtaaggat tgcttcgtta gtgcaagggg acaatcagac catagccgta acaaaaaggg  11580

tacccagcac atggccctac aaccttaaga aacgggaagc tgctagagta actagagatt  11640

actttgtaat tcttaggcaa aggctacatg atattggcca tcacctcaag gcaaatgaga  11700

caattgtttc atcacatttt tttgtctatt caaaaggaat atattatgat gggctacttg  11760

tgtcccaatc actcaagagc atcgcaagat gtgtattctg gtcagagact atagttgatg  11820

aaacaagggc agcatgcagt aatattgcta caacaatggc taaaagcatc gagagaggtt  11880

atgaccgtta ccttgcatat tccctgaacg tcctaaaagt gatacagcaa attctgatct  11940

ctcttggctt cacaatcaat tcaaccatga cccgggatgt agtcataccc ctcctcacaa  12000

acaacgacct cttaataagg atggcactgt tgcccgctcc tattgggggg atgaattatc  12060

tgaatatgag caggctgttt gtcagaaaca tcggtgatcc agtaacatca tcaattgctg  12120

atctcaagag aatgattctc gcctcactaa tgcctgaaga gaccctccat caagtaatga  12180

cacaacaacc gggggactct tcattcctag actgggctag cgacccttac tcagcaaatc  12240

ttgtatgtgt ccagagcatc actagactcc tcaagaacat aactgcaagg tttgtcctga  12300

tccatagtcc aaacccaatg ttaaaaggat tattccatga tgacagtaaa gaagaggacg  12360

agggactggc ggcattcctc atggacaggc atattatagt acctagggca gctcatgaaa  12420

tcctggatca tagtgtcaca ggggcaagag agtctattgc aggcatgctg gataccacaa  12480

aaggcttgat tcgagccagc atgaggaagg gggggttaac ctctcgagtg ataaccagat  12540

tgtccaatta tgactatgaa caattcagag cagggatggt gctattgaca ggaagaaaga  12600

gaaatgtcct cattgacaaa gagtcatgtt cagtgcagct ggcgagagct ctaagaagcc  12660

atatgtgggc gaggctagct cgaggacggc ctatttacgg ccttgaggtc cctgatgtac  12720

tagaatctat gcgaggccac cttattcggc gtcatgagac atgtgtcatc tgcgagtgtg  12780

gatcagtcaa ctacggatgg ttttttgtcc cctcgggttg ccaactggat gatattgaca  12840

aggaaacatc atccttgaga gtcccatata ttggttctac cactgatgag agaacagaca  12900

tgaagcttgc cttcgtaaga gccccaagtc gatccttgcg atctgctgtt agaatagcaa  12960

cagtgtactc atgggcttac ggtgatgatg atagctcttg gaacgaagcc tggttgttgg  13020
```

```
ctaggcaaag ggccaatgtg agcctggagg agctaagggt gatcactccc atctcaactt  13080
cgactaattt agcgcatagg ttgagggatc gtagcactca agtgaaatac tcaggtacat  13140
cccttgtccg agtggcgagg tataccacaa tctccaacga caatctctca tttgtcatat  13200
cagataagaa ggttgatact aactttatat accaacaagg aatgcttcta gggttgggtg  13260
ttttagaaac attgtttcga ctcgagaaag ataccggatc atctaacacg gtattacatc  13320
ttcacgtcga aacagattgt tgcgtgatcc cgatgataga tcatcccagg atacccagct  13380
cccgcaagct agagctgagg gcagagctat gtaccaaccc attgatatat gataatgcac  13440
ctttaattga cagagatgca acaaggctat acacccagag ccataggagg caccttgtgg  13500
aatttgttac atggtccaca ccccaactat atcacatttt agctaagtcc acagcactat  13560
ctatgattga cctggtaaca aaatttgaga aggaccatat gaatgaaatt tcagctctca  13620
taggggatga cgatatcaat agtttcataa ctgagtttct gctcatagag ccaagattat  13680
tcactatcta cttgggccag tgtgcggcca tcaattgggc atttgatgta cattatcata  13740
gaccatcagg gaaatatcag atgggtgagc tgttgtcatc gttcctttct agaatgagca  13800
aaggagtgtt taaggtgctt gtcaatgctc taagccaccc aaagatctac aagaaattct  13860
ggcattgtgg tattatagag cctatccatg gtccttcact tgatgctcaa aacttgcaca  13920
caactgtgtg caacatggtt tacacatgct atatgaccta cctcgacctg ttgttgaatg  13980
aagagttaga agagttcaca tttctcttgt gtgaaagcga cgaggatgta gtaccggaca  14040
gattcgacaa catccaggca aaacacttat gtgttctggc agatttgtac tgtcaaccag  14100
ggacctgccc accaattcga ggtctaagac cggtagagaa atgtgcagtt ctaaccgacc  14160
atatcaaggc agaggctatg ttatctccag caggatcttc gtggaacata aatccaatta  14220
ttgtagacca ttactcatgc tctctgactt atctccggcg aggatcgatc aaacagataa  14280
gattgagagt tgatccagga ttcattttcg acgccctcgc tgaggtaaat gtcagtcagc  14340
caaagatcgg cagcaacaac atctcaaata tgagcatcaa ggctttcaga cccccacacg  14400
atgatgttgc aaaattgctc aaagatatca acacaagcaa gcacaatctt cccatttcag  14460
ggggcaatct cgccaattat gaaatccatg ctttccgcag aatcgggttg aactcatctg  14520
cttgctacaa agctgttgag atatcaacat taattaggag atgccttgag ccaggggagg  14580
acggcttgtt cttgggtgag ggatcgggtt ctatgttgat cacttataaa gagatactta  14640
aactaaacaa gtgcttctat aatagtgggg tttccgccaa ttctagatct ggtcaaaggg  14700
aattagcacc ctatccctcc gaagttggcc ttgtcgaaca cagaatggga gtaggtaata  14760
ttgtcaaagt gctctttaac gggaggcccg aagtcacgtg ggtaggcagt gtagattgct  14820
tcaatttcat agttagtaat atccctacct ctagtgtggg gtttatccat tcagatatag  14880
agaccttgcc tgacaaagat actatagaga agctagagga attggcagcc atcttatcga  14940
tggctctgct cctgggcaaa ataggatcaa tactggtgat taagcttatg cctttcagcg  15000
gggattttgt tcagggattt ataagttatg tagggtctca ttatagagaa gtgaaccttg  15060
tataccctag atacagcaac ttcatctcta ctgaatctta tttggttatg acagatctca  15120
aggctaaccg gctaatgaat cctgaaaaga ttaagcagca gataattgaa tcatctgtga  15180
ggacttcacc tggacttata ggtcacatcc tatccattaa gcaactaagc tgcatacaag  15240
caattgtggg agacgcagtt agtagaggtg atatcaatcc tactctgaaa aaacttacac  15300
ctatagagca ggtgctgatc aattgcgggt tggcaattaa cggacctaag ctgtgcaaag  15360
aattgatcca ccatgatgtt gcctcagggc aagatggatt gcttaattct atactcatcc  15420
```

```
tctacaggga gttggcaaga ttcaaagaca accaaagaag tcaacaaggg atgttccacg  15480

cttaccccgt attggtaagt agcaggcaac gagaacttat atctaggatc acccgcaaat  15540

tctgggggca cattcttctt tactccggga acaaaaagtt gataaataag tttatccaga  15600

atctcaagtc cggctatctg atactagact tacaccagaa tatcttcgtt aagaatctat  15660

ccaagtcaga gaaacagatt attatgacgg ggggtttgaa acgtgagtgg gtttttaagg  15720

taacagtcaa ggagaccaaa gaatggtata agttagtcgg atacagtgcc ctgattaagg  15780

actaattggt tgaactccgg aaccctaatc ctgccctagg tggttaggca ttatttgcaa  15840

tatattaaag aaaactttga aaatacgaag tttctattcc cagctttgtc tggt        15894
```

```
<210> SEQ ID NO 2
<211> LENGTH: 1122
<212> TYPE: DNA
<213> ORGANISM: Artificial
<220> FEATURE:
<223> OTHER INFORMATION: fusion of yeast cytosine deaminase and yeast
      uracil phosphoribosyltransferase

<400> SEQUENCE: 2

atggtgacag gggggaatggc aagcaagtgg gatcagaagg gtatggacat tgcctatgag     60

gaggcggcct taggttacaa agagggtggt gttcctattg gcggatgtct tatcaataac    120

aaagacggaa gtgttctcgg tcgtggtcac aacatgagat ttcaaaaggg atccgccaca    180

ctacatggtg agatctccac tttggaaaac tgtgggagat tagagggcaa agtgtacaaa    240

gataccactt tgtatacgac gctgtctcca tgcgacatgt gtacaggtgc catcatcatg    300

tatggtattc cacgctgtgt tgtcggtgag aacgttaatt tcaaaagtaa gggcgagaaa    360

tatttacaaa ctagaggtca cgaggttgtt gttgttgacg atgagaggtg taaaaagatc    420

atgaaacaat ttatcgatga aagacctcag gattggtttg aagatattgg tgaggcttcg    480

gaaccattta agaacgtcta cttgctacct caaacaaacc aattgctggg tttgtacacc    540

atcatcagaa ataagaatac aactagacct gatttcattt tctactccga tagaatcatc    600

agattgttgg ttgaagaagg tttgaaccat ctacctgtgc aaaagcaaat tgtggaaact    660

gacaccaacg aaaacttcga aggtgtctca ttcatgggta aaatctgtgg tgtttccatt    720

gtcagagctg gtgaatcgat ggagcaagga ttaagagact gttgtaggtc tgtgcgtatc    780

ggtaaaattt taattcaaag ggacgaggag actgctttac caaagttatt ctacgaaaaa    840

ttaccagagg atatatctga aaggtatgtc ttcctattag acccaatgct ggccaccggt    900

ggtagtgcta tcatggctac agaagtcttg attaagagag gtgttaagcc agagagaatt    960

tacttcttaa acctaatctg tagtaaggaa gggattgaaa aataccatgc cgccttccca   1020

gaggtcagaa ttgttactgg tgccctcgac agaggtctag atgaaaacaa gtatctagtt   1080

ccagggttgg gtgactttgg tgacagatac tactgtgttt aa                      1122
```

```
<210> SEQ ID NO 3
<211> LENGTH: 19707
<212> TYPE: DNA
<213> ORGANISM: Artificial
<220> FEATURE:
<223> OTHER INFORMATION: plasmid DNA

<400> SEQUENCE: 3

accaaacaaa gttgggtaag gatagttcaa tcaatgatca tcttctagtg cacttaggat     60

tcaagatcct attatcaggg acaagagcag gattagggat atctcgaggc gcgccatcca    120
```

```
tcattgttat aaaaaactta ggattcaaga tcctattatc agggacaaga gcaggattag    180
ggatatccga gatggccaca cttttaagga gcttagcatt gttcaaaaga aacaaggaca    240
aaccacccat tacatcagga tccggtggag ccatcagagg aatcaaacac attattatag    300
taccaatccc tggagattcc tcaattacca ctcgatccag acttctggac cggttggtga    360
ggttaattgg aaacccggat gtgagcgggc ccaaactaac aggggcacta ataggtatat    420
tatccttatt tgtggagtct ccaggtcaat tgattcagag gatcaccgat gaccctgacg    480
ttagcataag gctgttagag gttgtccaga gtgaccagtc acaatctggc cttaccttcg    540
catcaagagg taccaacatg gaggatgagg cggaccaata cttttcacat gatgatccaa    600
ttagtagtga tcaatccagg ttcggatggt tcgggaacaa ggaaatctca gatattgaag    660
tgcaagaccc tgagggattc aacatgattc tgggtaccat cctagcccaa atttgggtct    720
tgctcgcaaa ggcggttacg gccccagaca cggcagctga ttcggagcta agaaggtgga    780
taaagtacac ccaacaaaga agggtagttg gtgaatttag attggagaga aaatggttgg    840
atgtggtgag gaacaggatt gccgaggacc tctccttacg ccgattcatg gtcgctctaa    900
tcctggatat caagagaaca cccggaaaca aacccaggat tgctgaaatg atatgtgaca    960
ttgatacata tatcgtagag gcaggattag ccagttttat cctgactatt aagtttggga   1020
tagaaactat gtatcctgct cttggactgc atgaatttgc tggtgagtta tccacacttg   1080
agtccttgat gaacctttac cagcaaatgg gggaaactgc accctacatg gtaatcctgg   1140
agaactcaat tcagaacaag ttcagtgcag gatcataccc tctgctctgg agctatgcca   1200
tgggagtagg agtggaactt gaaaactcca tgggaggttt gaactttggc cgatcttact   1260
ttgatccagc atattttaga ttagggcaag agatggtaag gaggtcagct ggaaaggtca   1320
gttccacatt ggcatctgaa ctcggtatca ctgccgagga tgcaaggctt gtttcagaga   1380
ttgcaatgca tactactgag gacaagatca gtagagcggt tggacccaga caagcccaag   1440
tatcatttct acacggtgat caaagtgaga atgagctacc gagattgggg ggcaaggaag   1500
ataggagggt caaacagagt cgaggagaag ccagggagag ctacagagaa accgggccca   1560
gcagagcaag tgatgcgaga gctgcccatc ttccaaccgg cacaccccta gacattgaca   1620
ctgcaacgga gtccagccaa gatccgcagg acagtcgaag gtcagctgac gccctgctta   1680
ggctgcaagc catggcagga atctcggaag aacaaggctc agacacggac acccctatag   1740
tgtacaatga cagaaatctt ctagactagg tgcgagaggc cgagggccag aacaacatcc   1800
gcctaccatc catcattgtt ataaaaaact taggaaccag gtccacacag ccgccagccc   1860
atcaaccatc cactcccacg attggagcca atggcagaag agcaggcacg ccatgtcaaa   1920
aacggactgg aatgcatccg ggctctcaag gccgagccca tcggctcact ggccatcgag   1980
gaagctatgg cagcatggtc agaaatatca gacaacccag gacaggagcg agccacctgc   2040
agggaagaga aggcaggcag ttcgggtctc agcaaaccat gcctctcagc aattggatca   2100
actgaaggcg gtgcacctcg catccgcggt cagggacctg gagagagcga tgacgacgct   2160
gaaactttgg gaatcccccc aagaaatctc caggcatcaa gcactgggtt acagtgttat   2220
tacgtttatg atcacagcgg tgaagcggtt aagggaatcc aagatgctga ctctatcatg   2280
gttcaatcag gccttgatgg tgatagcacc ctctcaggag gagacaatga atctgaaaac   2340
agcgatgtgg atattggcga acctgatacc gagggatatg ctatcactga ccggggatct   2400
gctcccatct ctatggggtt cagggcttct gatgttgaaa ctgcagaagg aggggagatc   2460
```

-continued

```
cacgagctcc tgagactcca atccagaggc aacaactttc cgaagcttgg gaaaactctc   2520
aatgttcctc cgcccccgga ccccggtagg gccagcactt ccgggacacc cattaaaaag   2580
ggcacagacg cgagattagc ctcatttgga acggagatcg cgtctttatt gacaggtggt   2640
gcaacccaat gtgctcgaaa gtcaccctcg gaaccatcag ggccaggtgc acctgcgggg   2700
aatgtccccg agtgtgtgag caatgccgca ctgatacagg agtggacacc cgaatctggt   2760
accacaatct ccccgagatc ccagaataat gaagaagggg gagactatta tgatgatgag   2820
ctgttctctg atgtccaaga tattaaaaca gccttggcca aaatacacga ggataatcag   2880
aagataatct ccaagctaga atcactgctg ttattgaagg gagaagttga gtcaattaag   2940
aagcagatca acaggcaaaa tatcagcata tccaccctgg aaggacacct ctcaagcatc   3000
atgatcgcca ttcctggact tgggaaggat cccaacgacc ccactgcaga tgtcgaaatc   3060
aatcccgact tgaaacccat cataggcaga gattcaggcc gagcactggc cgaagttctc   3120
aagaaacccg ttgccagccg acaactccaa ggaatgacaa atggacggac cagttccaga   3180
ggacagctgc tgaaggaatt tcagctaaag ccgatcggga aaaagatgag ctcagccgtc   3240
gggtttgttc ctgacaccgg ccctgcatca cgcagtgtaa tccgctccat tataaaatcc   3300
agccggctag aggaggatcg gaagcgttac ctgatgactc tccttgatga tatcaaagga   3360
gccaatgatc ttgccaagtt ccaccagatg ctgatgaaga taataatgaa gtagctacag   3420
ctcaacttac ctgccaaccc catgccagtc gacccaacta gtacaaccta aatccattat   3480
aaaaaactta ggagcaaagt gattgcctcc caaggtccac aatgacagag acctacgact   3540
tcgacaagtc ggcatgggac atcaaagggt cgatcgctcc gatacaaccc accacctaca   3600
gtgatggcag gctggtgccc caggtcagag tcatagatcc tggtctaggc gacaggaagg   3660
atgaatgctt tatgtacatg tttctgctgg gggttgttga ggacagcgat tccctagggc   3720
ctccaatcgg gcgagcattt gggttcctgc ccttaggtgt tggcagatcc acagcaaagc   3780
ccgaaaaact cctcaaagag gccactgagc ttgacatagt tgttagacgt acagcagggc   3840
tcaatgaaaa actggtgttc tacaacaaca ccccactaac tctcctcaca ccttggagaa   3900
aggtcctaac aacagggagt gtcttcaacg caaaccaagt gtgcaatgcg gttaatctga   3960
taccgctcga taccccgcag aggttccgtg ttgtttatat gagcatcacc cgtctttcgg   4020
ataacgggta ttacaccgtt cctagaagaa tgctggaatt cagatcggtc aatgcagtgg   4080
ccttcaacct gctggtgacc cttaggattg acaaggcgat aggccctggg aagatcatcg   4140
acaatacaga gcaacttcct gaggcaacat ttatggtcca catcgggaac ttcaggagaa   4200
agaagagtga agtctactct gccgattatt gcaaaatgaa aatcgaaaag atgggcctgg   4260
tttttgcact tggtgggata gggggcacca gtcttcacat tagaagcaca ggcaaaatga   4320
gcaagactct ccatgcacaa ctcgggttca agaagacctt atgttacccg ctgatggata   4380
tcaatgaaga ccttaatcga ttactctgga ggagcagatg caagatagta agaatccagg   4440
cagttttgca gccatcagtt cctcaagaat tccgcattta cgacgacgtg atcataaatg   4500
atgaccaagg actattcaaa gttctgtaga ccgtagtgcc cagcaatgcc cgaaaacgac   4560
ccccctcaca atgacagcca gaaggcccgg acaaaaaagc cccctccgaa agactccacg   4620
gaccaagcga gaggccagcc agcagccgac ggcaagcgcg aacaccaggc ggccccagca   4680
cagaacagcc ctgacacaag gccaccacca gccaccccaa tctgcatcct cctcgtggga   4740
cccccgagga ccaaccccca aggctgcccc cgatccaaac caccaaccgc atccccacca   4800
cccccgggaa agaaaccccc agcaattgga aggcccctcc ccctcttcct caacacaaga   4860
```

```
actccacaac cgaaccgcac aagcgaccga ggtgacccaa ccgcaggcat ccgactccct   4920
agacagatcc tctctccccg gcaaactaaa caaaacttag ggccaaggaa catacacacc   4980
caacagaacc cagaccccgg cccacggcgc cgcgccccca acccccgaca accagaggga   5040
gcccccaacc aatcccgccg gctcccccgg tgcccacagg cagggacacc aacccccgaa   5100
cagacccagc acccaaccat cgacaatcca agacgggggg gcccccccaa aaaaaggccc   5160
ccaggggccg acagccagca ccgcgaggaa gcccacccac cccacacacg accacggcaa   5220
ccaaaccaga acccagacca ccctgggcca ccagctccca gactcggcca tcaccccgca   5280
gaaaggaaag gccacaaccc gcgcacccca gccccgatcc ggcggggagc cacccaaccc   5340
gaaccagcac ccaagagcga tccccgaagg acccccgaac cgcaaaggac atcagtatcc   5400
cacagcctct ccaagtcccc cggtctcctc ctcttctcga agggaccaaa agatcaatcc   5460
accacacccg acgacactca actccccacc cctaaaggag acaccgggaa tcccagaatc   5520
aagactcatc caatgtccat catgggtctc aaggtgaacg tctctgccat attcatggca   5580
gtactgttaa ctctccaaac acccaccggt caaatccatt ggggcaatct ctctaagata   5640
ggggtggtag gaataggaag tgcaagctac aaagttatga ctcgttccag ccatcaatca   5700
ttagtcataa aattaatgcc caatataact ctcctcaata actgcacgag ggtagagatt   5760
gcagaataca ggagactact gagaacagtt ttggaaccaa ttagagatgc acttaatgca   5820
atgacccaga atataagacc ggttcagagt gtagcttcaa gtaggagaca caagagattt   5880
gcgggagtag tcctggcagg tgcggcccta ggcgttgcca cagctgctca gataacagcc   5940
ggcattgcac ttcaccagtc catgctgaac tctcaagcca tcgacaatct gagagcgagc   6000
ctggaaacta ctaatcaggc aattgagaca atcagacaag cagggcagga gatgatattg   6060
gctgttcagg gtgtccaaga ctacatcaat aatgagctga taccgtctat gaaccaacta   6120
tcttgtgatt taatcggcca gaagctcggg ctcaaattgc tcagatacta tacagaaatc   6180
ctgtcattat ttggccccag tttacgggac cccatatctg cggagatatc tatccaggct   6240
ttgagctatg cgcttggagg agacatcaat aaggtgttag aaaagctcgg atacagtgga   6300
ggtgatttac tgggcatctt agagagcgga ggaataaagg cccggataac tcacgtcgac   6360
acagagtcct acttcattgt cctcagtata gcctatccga cgctgtccga gattaagggg   6420
gtgattgtcc accggctaga gggggtctcg tacaacatag gctctcaaga gtggtatacc   6480
actgtgccca agtatgttgc aacccaaggg taccttatct cgaattttga tgagtcatcg   6540
tgtactttca tgccagaggg gactgtgtgc agccaaaatg ccttgtaccc gatgagtcct   6600
ctgctccaag aatgcctccg gggtacacc aagtcctgtg ctcgtacact cgtatccggg   6660
tcttttggga accggttcat tttatcacaa gggaacctaa tagccaattg tgcatcaatc   6720
ctttgcaagt gttacacaac aggaacgatc attaatcaag accctgacaa gatcctaaca   6780
tacattgctg ccgatcactg cccggtagtc gaggtgaacg gcgtgaccat ccaagtcggg   6840
agcaggaggt atccagacgc tgtgtacttg cacagaattg acctcggtcc tcccatatca   6900
ttggagaggt tggacgtagg gacaaatctg gggaatgcaa ttgctaagtt ggaggatgcc   6960
aaggaattgt tggagtcatc ggaccagata ttgaggagta tgaaaggttt atcgagcact   7020
agcatagtct acatcctgat tgcagtgtgt cttggagggt tgatagggat ccccgcttta   7080
atatgttgct gcagggggcg ttgtaacaaa aagggagaac aagttggtat gtcaagacca   7140
ggcctaaagc ctgatcttac gggaacatca aaatcctatg taaggtcgct ctgatcctct   7200
```

```
acaactcttg aaacacaaat gtcccacaag tctcctcttc gtcatcaagc aaccaccgca   7260

cccagcatca agcccacctg aaattatctc cggcttccct ctggccgaac aatatcggta   7320

gttaatcaaa acttagggtg caagatcatc cacaatgtca ccacaacgag accggataaa   7380

tgccttctac aaagataacc cccatcccaa gggaagtagg atagtcatta acagagaaca   7440

tcttatgatt gatagacctt atgttttgct ggctgttctg tttgtcatgt ttctgagctt   7500

gatcgggttg ctagccattg caggcattag acttcatcgg gcagccatct acaccgcaga   7560

gatccataaa agcctcagca ccaatctaga tgtaactaac tcaatcgagc atcaggtcaa   7620

ggacgtgctg acaccactct tcaaaatcat cggtgatgaa gtgggcctga ggacacctca   7680

gagattcact gacctagtga aattaatctc tgacaagatt aaattcctta atccggatag   7740

ggagtacgac ttcagagatc tcacttggtg tatcaacccg ccagagagaa tcaaattgga   7800

ttatgatcaa tactgtgcag atgtggctgc tgaagagctc atgaatgcat tggtgaactc   7860

aactctactg gagaccagaa caaccaatca gttcctagct gtctcaaagg gaaactgctc   7920

agggcccact acaatcagag gtcaattctc aaacatgtcg ctgtccctgt tagacttgta   7980

tttaggtcga ggttacaatg tgtcatctat agtcactatg acatcccagg gaatgtatgg   8040

gggaacttac ctagtggaaa agcctaatct gagcagcaaa aggtcagagt tgtcacaact   8100

gagcatgtac cgagtgtttg aagtaggtgt tatcagaaat ccgggtttgg gggctccggt   8160

gttccatatg acaaactatc ttgagcaacc agtcagtaat gatctcagca actgtatggt   8220

ggctttgggg gagctcaaac tcgcagccct ttgtcacggg gaagattcta tcacaattcc   8280

ctatcaggga tcagggaaag gtgtcagctt ccagctcgtc aagctaggtg tctggaaatc   8340

cccaaccgac atgcaatcct gggtcccctt atcaacggat gatccagtga tagacaggct   8400

ttacctctca tctcacagag gtgttatcgc tgacaatcaa gcaaaatggg ctgtcccgac   8460

aacacgaaca gatgacaagt tgcgaatgga gacatgcttc caacaggcgt gtaagggtaa   8520

aatccaagca ctctgcgaga atcccgagtg ggcaccattg aaggataaca ggattccttc   8580

atacggggtc ttgtctgttg atctgagtct gacagttgag cttaaaatca aaattgcttc   8640

gggattcggg ccattgatca cacacggttc agggatggac ctatacaaat ccaaccacaa   8700

caatgtgtat tggctgacta tcccgccaat gaagaaccta gccttaggtg taatcaacac   8760

attggagtgg ataccgagat tcaaggttag tccctacctc ttcactgtcc caattaagga   8820

agcaggcgaa gactgccatg ccccaacata cctacctgcg gaggtggatg gtgatgtcaa   8880

actcagttcc aatctggtga ttctacctgg tcaagatctc caatatgttt tggcaaccta   8940

cgatacttcc agggttgaac atgctgtggt ttattacgtt tacagcccaa gccgctcatt   9000

ttcttacttt tatccttta ggttgcctat aaagggggtc cccatcgaat tacaagtgga   9060

atgcttcaca tgggaccaaa aactctggtg ccgtcacttc tgtgtgcttg cggactcaga   9120

atctggtgga catatcactc actctgggat ggtgggcatg ggagtcagct gcacagtcac   9180

ccgggaagat ggaaccaatc gcagataggg ctgctagtga accaatcaca tgatgtcacc   9240

cagacatcag gcatacccac tagtgtgaaa tagacatcag aattaagaaa aacgtagggt   9300

ccaagtggtt ccccgttatg gactcgctat ctgtcaacca gatcttatac cctgaagttc   9360

acctagatag cccgatagtt accaataaga tagtagccat cctggagtat gctcgagtcc   9420

ctcacgctta cagcctggag gaccctacac tgtgtcagaa catcaagcac cgcctaaaaa   9480

acggattttc caaccaaatg attataaaca atgtggaagt tgggaatgtc atcaagtcca   9540

agcttaggag ttatccggcc cactctcata ttccatatcc aaattgtaat caggatttat   9600
```

```
ttaacataga agacaaagag tcaacgagga agatccgtga actcctcaaa aaggggaatt   9660
cgctgtactc caaagtcagt gataaggttt tccaatgctt aagggacact aactcacggc   9720
ttggcctagg ctccgaattg agggaggaca tcaaggagaa agttattaac ttgggagttt   9780
acatgcacag ctcccagtgg tttgagccct ttctgttttg gtttacagtc aagactgaga   9840
tgaggtcagt gattaaatca caaacccata cttgccatag gaggagacac acacctgtat   9900
tcttcactgg tagttcagtt gagttgctaa tctctcgtga ccttgttgct ataatcagta   9960
aagagtctca acatgtatat tacctgacat ttgaactggt tttgatgtat tgtgatgtca  10020
tagaggggag gttaatgaca gagaccgcta tgactattga tgctaggtat acagagcttc  10080
taggaagagt cagatacatg tggaaactga tagatggttt cttccctgca ctcgggaatc  10140
caacttatca aattgtagcc atgctggagc ctctttcact tgcttacctg cagctgaggg  10200
atataacagt agaactcaga ggtgctttcc ttaaccactg ctttactgaa atacatgatg  10260
ttcttgacca aaacgggttt tctgatgaag gtacttatca tgagttaact gaagctctag  10320
attacatttt cataactgat gacatacatc tgacagggga gattttctca tttttcagaa  10380
gtttcggcca ccccagactt gaagcagtaa cggctgctga aaatgttagg aaatacatga  10440
atcagcctaa agtcattgtg tatgagactc tgatgaaagg tcatgccata ttttgtggaa  10500
tcataatcaa cggctatcgt gacaggcacg gaggcagttg gccaccgctg accctccccc  10560
tgcatgctgc agacacaatc cggaatgctc aagcttcagg tgaagggtta acacatgagc  10620
agtgcgttga taactggaaa tcttttgctg gagtgaaatt tggctgcttt atgcctctta  10680
gcctggatag tgatctgaca atgtacctaa aggacaaggc acttgctgct ctccaaaggg  10740
aatgggattc agtttacccg aaagagttcc tgcgttacga ccctcccaag ggaaccgggt  10800
cacggaggct tgtagatgtt ttccttaatg attcgagctt tgacccatat gatgtgataa  10860
tgtatgttgt aagtggagct tacctccatg accctgagtt caacctgtct tacagcctga  10920
aagaaaagga gatcaaggaa acaggtagac tttttgctaa aatgacttac aaaatgaggg  10980
catgccaagt gattgctgaa aatctaatct caaacgggat tggcaaatat tttaaggaca  11040
atgggatggc caaggatgag cacgatttga ctaaggcact ccacactcta gctgtctcag  11100
gagtccccaa agatctcaaa gaaagtcaca ggggggggcc agtcttaaaa acctactccc  11160
gaagcccagt ccacacaagt accaggaacg tgagagcagc aaaagggttt atagggttcc  11220
ctcaagtaat tcggcaggac caagacactg atcatccgga gaatatggaa gcttacgaga  11280
cagtcagtgc atttatcacg actgatctca agaagtactg ccttaattgg agatatgaga  11340
ccatcagctt gtttgcacag aggctaaatg agatttacgg attgccctca tttttccagt  11400
ggctgcataa gaggcttgag acctctgtcc tgtatgtaag tgaccctcat tgcccccccg  11460
accttgacgc ccatatcccg ttatataaag tccccaatga tcaaatcttc attaagtacc  11520
ctatgggagg tatagaaggg tattgtcaga agctgtggac catcagcacc attccctatc  11580
tatacctggc tgcttatgag agcggagtaa ggattgcttc gttagtgcaa ggggacaatc  11640
agaccatagc cgtaacaaaa agggtaccca gcacatggcc ctacaacctt aagaaacggg  11700
aagctgctag agtaactaga gattactttg taattcttag gcaaaggcta catgatattg  11760
gccatcacct caaggcaaat gagacaattg tttcatcaca ttttttttgtc tattcaaaag  11820
gaatatatta tgatgggcta cttgtgtccc aatcactcaa gagcatcgca agatgtgtat  11880
tctggtcaga gactatagtt gatgaaacaa gggcagcatg cagtaatatt gctacaacaa  11940
```

```
tggctaaaag catcgagaga ggttatgacc gttaccttgc atattccctg aacgtcctaa  12000
aagtgataca gcaaattctg atctctcttg gcttcacaat caattcaacc atgacccggg  12060
atgtagtcat accccctcctc acaaacaacg acctcttaat aaggatggca ctgttgcccg  12120
ctcctattgg ggggatgaat tatctgaata tgagcaggct gtttgtcaga aacatcggtg  12180
atccagtaac atcatcaatt gctgatctca agagaatgat tctcgcctca ctaatgcctg  12240
aagagaccct ccatcaagta atgacacaac aaccggggga ctcttcattc ctagactggg  12300
ctagcgaccc ttactcagca aatcttgtat gtgtccagag catcactaga ctcctcaaga  12360
acataactgc aaggtttgtc ctgatccata gtccaaaccc aatgttaaaa ggattattcc  12420
atgatgacag taaagaagag gacgagggac tggcggcatt cctcatggac aggcatatta  12480
tagtacctag ggcagctcat gaaatcctgg atcatagtgt cacaggggca agagagtcta  12540
ttgcaggcat gctggatacc acaaaaggct tgattcgagc cagcatgagg aagggggggt  12600
taacctctcg agtgataacc agattgtcca attatgacta tgaacaattc agagcaggga  12660
tggtgctatt gacaggaaga aagagaaatg tcctcattga caaagagtca tgttcagtgc  12720
agctggcgag agctctaaga agccatatgt gggcgaggct agctcgagga cggcctattt  12780
acggccttga ggtccctgat gtactagaat ctatgcgagg ccaccttatt cggcgtcatg  12840
agacatgtgt catctgcgag tgtggatcag tcaactacgg atggtttttt gtcccctcgg  12900
gttgccaact ggatgatatt gacaaggaaa catcatcctt gagagtccca tatattggtt  12960
ctaccactga tgagagaaca gacatgaagc ttgccttcgt aagagcccca agtcgatcct  13020
tgcgatctgc tgttagaata gcaacagtgt actcatgggc ttacggtgat gatgatagct  13080
cttggaacga agcctggttg ttggctaggc aaagggccaa tgtgagcctg gaggagctaa  13140
gggtgatcac tcccatctca acttcgacta atttagcgca taggttgagg gatcgtagca  13200
ctcaagtgaa atactcaggt acatcccttg tccgagtggc gaggtatacc acaatctcca  13260
acgacaatct ctcatttgtc atatcagata agaaggttga tactaacttt atataccaac  13320
aaggaatgct tctagggttg ggtgttttag aaacattgtt tcgactcgag aaagataccg  13380
gatcatctaa cacggtatta catcttcacg tcgaaacaga ttgttgcgtg atcccgatga  13440
tagatcatcc caggataccc agctcccgca agctagagct gagggcagag ctatgtacca  13500
acccattgat atatgataat gcacctttaa ttgacagaga tgcaacaagg ctatacaccc  13560
agagccatag gaggcacctt gtggaatttg ttacatggtc cacaccccaa ctatatcaca  13620
ttttagctaa gtccacagca ctatctatga ttgacctggt aacaaaattt gagaaggacc  13680
atatgaatga aatttcagct ctcatagggg atgacgatat caatagtttc ataactgagt  13740
ttctgctcat agagccaaga ttattcacta tctacttggg ccagtgtgcg gccatcaatt  13800
gggcatttga tgtacattat catagaccat cagggaaata tcagatgggt gagctgttgt  13860
catcgttcct ttctagaatg agcaaaggag tgtttaaggt gcttgtcaat gctctaagcc  13920
acccaaagat ctacaagaaa ttctggcatt gtggtattat agagcctatc catggtcctt  13980
cacttgatgc tcaaaacttg cacacaactg tgtgcaacat ggtttacaca tgctatatga  14040
cctacctcga cctgttgttg aatgaagagt tagaagagtt cacatttctc ttgtgtgaaa  14100
gcgacgagga tgtagtaccg gacagattcg acaacatcca ggcaaaacac ttatgtgttc  14160
tggcagattt gtactgtcaa ccagggacct gcccaccaat tcgaggtcta agaccggtag  14220
agaaatgtgc agttctaacc gaccatatca aggcagaggc tatgttatct ccagcaggat  14280
cttcgtggaa cataaatcca attattgtag accattactc atgctctctg acttatctcc  14340
```

```
ggcgaggatc gatcaaacag ataagattga gagttgatcc aggattcatt ttcgacgccc  14400
tcgctgaggt aaatgtcagt cagccaaaga tcggcagcaa caacatctca aatatgagca  14460
tcaaggcttt cagacccccca cacgatgatg ttgcaaaatt gctcaaagat atcaacacaa  14520
gcaagcacaa tcttcccatt tcagggggca atctcgccaa ttatgaaatc catgctttcc  14580
gcagaatcgg gttgaactca tctgcttgct acaaagctgt tgagatatca acattaatta  14640
ggagatgcct tgagccaggg gaggacggct tgttcttggg tgagggatcg ggttctatgt  14700
tgatcactta taaagagata cttaaactaa acaagtgctt ctataatagt ggggtttccg  14760
ccaattctag atctggtcaa agggaattag caccctatcc ctccgaagtt ggccttgtcg  14820
aacacagaat gggagtaggt aatattgtca aagtgctctt taacgggagg cccgaagtca  14880
cgtgggtagg cagtgtagat tgcttcaatt tcatagttag taatatccct acctctagtg  14940
tggggtttat ccattcagat atagagacct tgcctgacaa agatactata gagaagctag  15000
aggaattggc agccatctta tcgatggctc tgctcctggg caaaatagga tcaatactgg  15060
tgattaagct tatgcctttc agcggggatt ttgttcaggg atttataagt tatgtagggt  15120
ctcattatag agaagtgaac cttgtatacc ctagatacag caacttcatc tctactgaat  15180
cttatttggt tatgacagat ctcaaggcta accggctaat gaatcctgaa aagattaagc  15240
agcagataat tgaatcatct gtgaggactt cacctggact tataggtcac atcctatcca  15300
ttaagcaact aagctgcata caagcaattg tgggagacgc agttagtaga ggtgatatca  15360
atcctactct gaaaaaactt acacctatag agcaggtgct gatcaattgc gggttggcaa  15420
ttaacggacc taagctgtgc aaagaattga tccaccatga tgttgcctca gggcaagatg  15480
gattgcttaa ttctatactc atcctctaca gggagttggc aagattcaaa gacaaccaaa  15540
gaagtcaaca agggatgttc cacgcttacc ccgtattggt aagtagcagg caacgagaac  15600
ttatatctag gatcacccgc aaattctggg ggcacattct tctttactcc gggaacaaaa  15660
agttgataaa taagtttatc cagaatctca agtccggcta tctgatacta gacttacacc  15720
agaatatctt cgttaagaat ctatccaagt cagagaaaca gattattatg acggggggtt  15780
tgaaacgtga gtgggttttt aaggtaacag tcaaggagac caaagaatgg tataagttag  15840
tcggatacag tgccctgatt aaggactaat tggttgaact ccggaaccct aatcctgccc  15900
taggtggtta ggcattattt gcaatatatt aaagaaaact ttgaaaatac gaagtttcta  15960
ttcccagctt tgtctggtgg ccggcatggt cccagcctcc tcgctggcgc cggctgggca  16020
acattccgag gggaccgtcc cctcggtaat ggcgaatggg acgcggccgg tcgatcgacg  16080
atccggctgc taacaaagcc cgaaaggaag ctgagttggc tgctgccacc gctgagcaat  16140
aactagcata accccttggg gcctctaaac gggtcttgag gggttttttg ctgaaaggag  16200
gaactatatc cggatcgaga tcaattctgt gagcgtatgg caaacgaagg aaaaatagtt  16260
atagtagccg cactcgatgg gacatttcaa cgtaaaccgt ttaataatat tttgaatctt  16320
attccattat ctgaaatggt ggtaaaacta actgctgtgt gtatgaaatg ctttaaggag  16380
gcttcctttt ctaaacgatt gggtgaggaa accgagatag aaataatagg aggtaatgat  16440
atgtatcaat cggtgtgtag aaagtgttac atcgactcat aatattatat tttttatcta  16500
aaaaactaaa aataaacatt gattaaattt taatataata cttaaaaatg gatgttgtgt  16560
cgttagataa accgtttatg tattttgagg aaattgataa tgagttagat tacgaaccag  16620
aaagtgcaaa tgaggtcgca aaaaaactgc cgtatcaagg acagttaaaa ctattactag  16680
```

gagaattatt ttttcttagt aagttacagc gacacggtat attagatggt gccaccgtag 16740
tgtatatagg atctgctccc ggtacacata tacgttattt gagagatcat ttctataatt 16800
taggagtgat cccgaaagga agctgagttg gctgctgcca ccgctgagca ataactagca 16860
taaccccttg gggcctctaa acgggtcttg aggggttttt tgctgaaagg aggaacgcgc 16920
ctgatgcggt attttctcct tacgcatctg tgcggtattt cacaccgcat atatggtgca 16980
ctctcagtac aatctgctct gatgccgcat agttaagcca gccccgacac ccgccaacac 17040
ccgctgacgc gccctgacgg gcttgtctgc tcccggcatc cgcttacaga caagctgtga 17100
ccgtctccgg gagctgcatg tgtcagaggt tttcaccgtc atcaccgaaa cgcgcgagac 17160
gaaagggcct cgtgatacgc ctatttttat aggttaatgt catgataata atggtttctt 17220
agacgtcagg tggcactttt cggggaaatg tgcgcggaac ccctatttgt ttatttttct 17280
aaatacattc aaatatgtat ccgctcatga gacaataacc ctgataaatg cttcaataat 17340
attgaaaaag gaagagtatg agtattcaac atttccgtgt cgcccttatt cccttttttg 17400
cggcattttg ccttcctgtt tttgctcacc cagaaacgct ggtgaaagta aaagatgctg 17460
aagatcagtt gggtgcacga gtgggttaca tcgaactgga tctcaacagc ggtaagatcc 17520
ttgagagttt tcgccccgaa gaacgttttc caatgatgag cacttttaaa gttctgctat 17580
gtggcgcggt attatcccgt attgacgccg ggcaagagca actcggtcgc cgcatacact 17640
attctcagaa tgacttggtt gagtactcac cagtcacaga aaagcatctt acggatggca 17700
tgacagtaag agaattatgc agtgctgcca taaccatgag tgataacact gcggccaact 17760
tacttctgac aacgatcgga ggaccgaagg agctaaccgc ttttttgcac aacatggggg 17820
atcatgtaac tcgccttgat cgttgggaac cggagctgaa tgaagccata ccaaacgacg 17880
agcgtgacac cacgatgcct gtagcaatgg caacaacgtt gcgcaaacta ttaactggcg 17940
aactacttac tctagcttcc cggcaacaat taatagactg gatggaggcg gataaagttg 18000
caggaccact tctgcgctcg gcccttccgg ctggctggtt tattgctgat aaatctggag 18060
ccggtgagcg tgggtctcgc ggtatcattg cagcactggg gccagatggt aagccctccc 18120
gtatcgtagt tatctacacg acggggagtc aggcaactat ggatgaacga aatagacaga 18180
tcgctgagat aggtgcctca ctgattaagc attggtaact gtcagaccaa gtttactcat 18240
atatacttta gattgattta aaacttcatt tttaatttaa aaggatctag gtgaagatcc 18300
tttttgataa tctcatgacc aaaatccctt aacgtgagtt ttcgttccac tgagcgtcag 18360
accccgtaga aaagatcaaa ggatcttctt gagatccttt ttttctgcgc gtaatctgct 18420
gcttgcaaac aaaaaaacca ccgctaccag cggtggtttg tttgccggat caagagctac 18480
caactctttt tccgaaggta actggcttca gcagagcgca gataccaaat actgtccttc 18540
tagtgtagcc gtagttaggc caccacttca agaactctgt agcaccgcct acatacctcg 18600
ctctgctaat cctgttacca gtggctgctg ccagtggcga taagtcgtgt cttaccgggt 18660
tggactcaag acgatagtta ccggataagg cgcagcggtc gggctgaacg gggggttcgt 18720
gcacacagcc cagcttggag cgaacgacct acaccgaact gagataccta cagcgtgagc 18780
attgagaaag cgccacgctt cccgaaggga gaaaggcgga caggtatccg gtaagcggca 18840
gggtcggaac aggagagcgc acgagggagc ttccaggggg aaacgcctgg tatctttata 18900
gtcctgtcgg gtttcgccac ctctgacttg agcgtcgatt tttgtgatgc tcgtcagggg 18960
ggcggagcct atggaaaaac gccagcaacg cggccttttt acggttcctg gccttttgct 19020
ggccttttgc tcacatgttc tttcctgcgt tatcccctga ttctgtggat aaccgtatta 19080

```
ccgcctttga gtgagctgat accgctcgcc gcagccgaac gaccgagcgc agcgagtcag  19140

tgagcgagga agcggaagag cgcccaatac gcaaaccgcc tctccccgcg cgttggccga  19200

ttcattaatg cagctggcac gacaggtttc ccgactggaa agcgggcagt gagcgcaacg  19260

caattaatgt gagttagctc actcattagg caccccaggc tttacacttt atgcttccgg  19320

ctcgtatgtt gtgtggaatt gtgagcggat aacaatttca cacaggaaac agctatgacc  19380

atgattacgc caagcttacg cgtcctggca ttatgcccag tacatgacct tatgggactt  19440

tcctacttgg cagtacatct acgtattagt catcgctatt accatggtga tgcggttttg  19500

gcagtacatc aatgggcgtg gatagcggtt tgactcacgg ggatttccaa gtctccaccc  19560

cattgacgtc aatgggagtt tgttttggca ccaaaatcaa cgggactttc caaaatgtcg  19620

taacaactcc gccccattga cgcaaatggg cggtaggcgt gtacggtggg aggtctatat  19680

aagcagagct cgtttagtga accgtgg                                     19707
```

<210> SEQ ID NO 4
<211> LENGTH: 20841
<212> TYPE: DNA
<213> ORGANISM: Artificial
<220> FEATURE:
<223> OTHER INFORMATION: plasmid DNA

<400> SEQUENCE: 4

```
accaaacaaa gttgggtaag gatagttcaa tcaatgatca tcttctagtg cacttaggat     60

tcaagatcct attatcaggg acaagagcag gattagggat atctcgaggc gcgtgccacc    120

atggtgacag gggaatggc aagcaagtgg gatcagaagg gtatggacat tgcctatgag     180

gaggcggcct taggttacaa agagggtggt gttcctattg gcggatgtct tatcaataac    240

aaagacggaa gtgttctcgg tcgtggtcac aacatgagat ttcaaaaggg atccgccaca    300

ctacatggtg agatctccac tttggaaaac tgtgggagat tagagggcaa agtgtacaaa    360

gataccactt tgtatacgac gctgtctcca tgcgacatgt gtacaggtgc catcatcatg    420

tatggtattc cacgctgtgt tgtcggtgag aacgttaatt tcaaaagtaa gggcgagaaa    480

tatttacaaa ctagaggtca cgaggttgtt gttgttgacg atgagaggtg taaaaagatc    540

atgaaacaat ttatcgatga aagacctcag gattggtttg aagatattgg tgaggcttcg    600

gaaccattta agaacgtcta cttgctacct caaacaaacc aattgctggg tttgtacacc    660

atcatcagaa ataagaatac aactagacct gatttcattt tctactccga tagaatcatc    720

agattgttgg ttgaagaagg tttgaaccat ctacctgtgc aaaagcaaat tgtggaaact    780

gacaccaacg aaaacttcga aggtgtctca ttcatgggta aaatctgtgg tgtttccatt    840

gtcagagctg gtgaatcgat ggagcaagga ttaagagact gttgtaggtc tgtgcgtatc    900

ggtaaaattt taattcaaag ggacgaggag actgctttac caaagttatt ctacgaaaaa    960

ttaccagagg atatatctga aaggtatgtc ttcctattag acccaatgct ggccaccggt   1020

ggtagtgcta tcatggctac agaagtcttg attaagagag gtgttaagcc agagagaatt   1080

tacttcttaa acctaatctg tagtaaggaa gggattgaaa aataccatgc cgccttccca   1140

gaggtcagaa ttgttactgg tgccctcgac agaggtctag atgaaaacaa gtatctagtt   1200

ccagggttgg gtgactttgg tgacagatac tactgtgttt aaacgcgcca tccatcattg   1260

ttataaaaaa cttaggattc aagatcctat tatcagggac aagagcagga ttagggatat   1320

ccgagatggc cacactttta aggagcttag cattgttcaa aagaaacaag gacaaaccac   1380
```

```
ccattacatc aggatccggt ggagccatca gaggaatcaa acacattatt atagtaccaa   1440
tccctggaga ttcctcaatt accactcgat ccagacttct ggaccggttg gtgaggttaa   1500
ttggaaaccc ggatgtgagc gggcccaaac taacaggggc actaataggt atattatcct   1560
tatttgtgga gtctccaggt caattgattc agaggatcac cgatgaccct gacgttagca   1620
taaggctgtt agaggttgtc cagagtgacc agtcacaatc tggccttacc ttcgcatcaa   1680
gaggtaccaa catggaggat gaggcggacc aatacttttc acatgatgat ccaattagta   1740
gtgatcaatc caggttcgga tggttcggga acaaggaaat ctcagatatt gaagtgcaag   1800
accctgaggg attcaacatg attctgggta ccatcctagc ccaaatttgg gtcttgctcg   1860
caaaggcggt tacggcccca gacacggcag ctgattcgga gctaagaagg tggataaagt   1920
acacccaaca aagaagggta gttggtgaat ttagattgga gagaaaatgg ttggatgtgg   1980
tgaggaacag gattgccgag gacctctcct tacgccgatt catggtcgct ctaatcctgg   2040
atatcaagag aacacccgga aacaaaccca ggattgctga aatgatatgt gacattgata   2100
catatatcgt agaggcagga ttagccagtt ttatcctgac tattaagttt gggatagaaa   2160
ctatgtatcc tgctcttgga ctgcatgaat ttgctggtga gttatccaca cttgagtcct   2220
tgatgaacct ttaccagcaa atgggggaaa ctgcacccta catggtaatc ctggagaact   2280
caattcagaa caagttcagt gcaggatcat accctctgct ctggagctat gccatgggag   2340
taggagtgga acttgaaaac tccatgggag gtttgaactt tggccgatct tactttgatc   2400
cagcatattt tagattaggg caagagatgg taaggaggtc agctggaaag gtcagttcca   2460
cattggcatc tgaactcggt atcactgccg aggatgcaag gcttgtttca gagattgcaa   2520
tgcatactac tgaggacaag atcagtagag cggttggacc cagacaagcc caagtatcat   2580
ttctacacgg tgatcaaagt gagaatgagc taccgagatt ggggggcaag gaagatagga   2640
gggtcaaaca gagtcgagga gaagccaggg agagctacag agaaaccggg cccagcagag   2700
caagtgatgc gagagctgcc catcttccaa ccggcacacc cctagacatt gacactgcaa   2760
cggagtccag ccaagatccg caggacagtc gaaggtcagc tgacgccctg cttaggctgc   2820
aagccatggc aggaatctcg gaagaacaag gctcagacac ggacacccct atagtgtaca   2880
atgacagaaa tcttctagac taggtgcgag aggccgaggg ccagaacaac atccgcctac   2940
catccatcat tgttataaaa aacttaggaa ccaggtccac acagccgcca gcccatcaac   3000
catccactcc cacgattgga gccaatggca gaagagcagg cacgccatgt caaaaacgga   3060
ctggaatgca tccgggctct caaggccgag cccatcggct cactggccat cgaggaagct   3120
atggcagcat ggtcagaaat atcagacaac ccaggacagg agcgagccac ctgcagggaa   3180
gagaaggcag gcagttcggg tctcagcaaa ccatgcctct cagcaattgg atcaactgaa   3240
ggcggtgcac ctcgcatccg cggtcaggga cctggagaga gcgatgacga cgctgaaact   3300
ttgggaatcc ccccaagaaa tctccaggca tcaagcactg ggttacagtg ttattacgtt   3360
tatgatcaca gcggtgaagc ggttaaggga atccaagatg ctgactctat catggttcaa   3420
tcaggccttg atggtgatag caccctctca ggaggagaca atgaatctga aaacagcgat   3480
gtggatattg gcgaacctga taccgaggga tatgctatca ctgaccgggg atctgctccc   3540
atctctatgg ggttcagggc ttctgatgtt gaaactgcag aaggagggga gatccacgag   3600
ctcctgagac tccaatccag aggcaacaac tttccgaagc ttgggaaaac tctcaatgtt   3660
cctccgcccc cggaccccgg tagggccagc acttccggga cacccattaa aaagggcaca   3720
gacgcgagat tagcctcatt tggaacggag atcgcgtctt tattgacagg tggtgcaacc   3780
```

```
caatgtgctc gaaagtcacc ctcggaacca tcagggccag gtgcacctgc ggggaatgtc   3840
cccgagtgtg tgagcaatgc cgcactgata caggagtgga cacccgaatc tggtaccaca   3900
atctccccga gatcccagaa taatgaagaa gggggagact attatgatga tgagctgttc   3960
tctgatgtcc aagatattaa aacagccttg gccaaaatac acgaggataa tcagaagata   4020
atctccaagc tagaatcact gctgttattg aagggagaag ttgagtcaat taagaagcag   4080
atcaacaggc aaaatatcag catatccacc ctggaaggac acctctcaag catcatgatc   4140
gccattcctg gacttgggaa ggatcccaac gaccccactg cagatgtcga aatcaatccc   4200
gacttgaaac ccatcatagg cagagattca ggccgagcac tggccgaagt tctcaagaaa   4260
cccgttgcca gccgacaact ccaaggaatg acaaatggac ggaccagttc cagaggacag   4320
ctgctgaagg aatttcagct aaagccgatc gggaaaaaga tgagctcagc cgtcgggttt   4380
gttcctgaca ccggccctgc atcacgcagt gtaatccgct ccattataaa atccagccgg   4440
ctagaggagg atcggaagcg ttacctgatg actctccttg atgatatcaa aggagccaat   4500
gatcttgcca agttccacca gatgctgatg aagataataa tgaagtagct acagctcaac   4560
ttacctgcca accccatgcc agtcgaccca actagtacaa cctaaatcca ttataaaaaa   4620
cttaggagca aagtgattgc ctcccaaggt ccacaatgac agagacctac gacttcgaca   4680
agtcggcatg ggacatcaaa gggtcgatcg ctccgataca acccaccacc tacagtgatg   4740
gcaggctggt gccccaggtc agagtcatag atcctggtct aggcgacagg aaggatgaat   4800
gctttatgta catgtttctg ctgggggttg ttgaggacag cgattcccta gggcctccaa   4860
tcgggcgagc atttgggttc ctgcccttag gtgttggcag atccacagca aagcccgaaa   4920
aactcctcaa agaggccact gagcttgaca tagttgttag acgtacagca gggctcaatg   4980
aaaaactggt gttctacaac aacaccccac taactctcct cacaccttgg agaaaggtcc   5040
taacaacagg gagtgtcttc aacgcaaacc aagtgtgcaa tgcggttaat ctgataccgc   5100
tcgatacccc gcagaggttc cgtgttgttt atatgagcat cacccgtctt tcggataacg   5160
ggtattacac cgttcctaga agaatgctgg aattcagatc ggtcaatgca gtggccttca   5220
acctgctggt gacccttagg attgacaagg cgataggccc tgggaagatc atcgacaata   5280
cagagcaact tcctgaggca acatttatgg tccacatcgg gaacttcagg agaaagaaga   5340
gtgaagtcta ctctgccgat tattgcaaaa tgaaaatcga aaagatgggc ctggtttttg   5400
cacttggtgg gatagggggc accagtcttc acattagaag cacaggcaaa atgagcaaga   5460
ctctccatgc acaactcggg ttcaagaaga ccttatgtta cccgctgatg gatatcaatg   5520
aagaccttaa tcgattactc tggaggagca gatgcaagat agtaagaatc caggcagttt   5580
tgcagccatc agttcctcaa gaattccgca tttacgacga cgtgatcata aatgatgacc   5640
aaggactatt caaagttctg tagaccgtag tgcccagcaa tgcccgaaaa cgaccccccct   5700
cacaatgaca gccagaaggc ccggacaaaa aagcccccctc cgaaagactc cacggaccaa   5760
gcgagaggcc agccagcagc cgacggcaag cgcgaacacc aggcggcccc agcacagaac   5820
agccctgaca caaggccacc accagccacc ccaatctgca tcctcctcgt gggacccccg   5880
aggaccaacc cccaaggctg cccccgatcc aaaccaccaa ccgcatcccc accaccccccg   5940
ggaaagaaac ccccagcaat tggaaggccc ctcccccctct tcctcaacac aagaactcca   6000
caaccgaacc gcacaagcga ccgaggtgac ccaaccgcag gcatccgact ccctagacag   6060
atcctctctc cccggcaaac taaacaaaac ttagggccaa ggaacataca cacccaacag   6120
```

-continued

```
aacccagacc ccggcccacg gcgccgcgcc cccaaccccc gacaaccaga gggagccccc   6180
aaccaatccc gccggctccc ccggtgccca caggcaggga caccaacccc cgaacagacc   6240
cagcacccaa ccatcgacaa tccaagacgg gggggccccc ccaaaaaaag gcccccaggg   6300
gccgacagcc agcaccgcga ggaagcccac ccaccccaca cacgaccacg gcaaccaaac   6360
cagaacccag accaccctgg gccaccagct cccagactcg gccatcaccc cgcagaaagg   6420
aaaggccaca acccgcgcac cccagccccg atccggcggg gagccaccca acccgaacca   6480
gcacccaaga gcgatccccg aaggaccccc gaaccgcaaa ggacatcagt atcccacagc   6540
ctctccaagt cccccggtct cctcctcttc tcgaagggac caaaagatca atccaccaca   6600
cccgacgaca ctcaactccc cacccctaaa ggagacaccg ggaatcccag aatcaagact   6660
catccaatgt ccatcatggg tctcaaggtg aacgtctctg ccatattcat ggcagtactg   6720
ttaactctcc aaacacccac cggtcaaatc cattggggca atctctctaa gataggggtg   6780
gtaggaatag gaagtgcaag ctacaaagtt atgactcgtt ccagccatca atcattagtc   6840
ataaaattaa tgcccaatat aactctcctc aataactgca cgagggtaga gattgcagaa   6900
tacaggagac tactgagaac agttttggaa ccaattagag atgcacttaa tgcaatgacc   6960
cagaatataa gaccggttca gagtgtagct tcaagtagga gacacaagag atttgcggga   7020
gtagtcctgg caggtgcggc cctaggcgtt gccacagctg ctcagataac agccggcatt   7080
gcacttcacc agtccatgct gaactctcaa gccatcgaca atctgagagc gagcctggaa   7140
actactaatc aggcaattga gacaatcaga caagcagggc aggagatgat attggctgtt   7200
cagggtgtcc aagactacat caataatgag ctgataccgt ctatgaacca actatcttgt   7260
gatttaatcg gccagaagct cgggctcaaa ttgctcagat actatacaga aatcctgtca   7320
ttatttggcc ccagtttacg ggaccccata tctgcggaga tatctatcca ggctttgagc   7380
tatgcgcttg gaggagacat caataaggtg ttagaaaagc tcggatacag tggaggtgat   7440
ttactgggca tcttagagag cggaggaata aaggcccgga taactcacgt cgacacagag   7500
tcctacttca ttgtcctcag tatagcctat ccgacgctgt ccgagattaa gggggtgatt   7560
gtccaccggc tagagggggt ctcgtacaac ataggctctc aagagtggta taccactgtg   7620
cccaagtatg ttgcaaccca agggtacctt atctcgaatt ttgatgagtc atcgtgtact   7680
ttcatgccag aggggactgt gtgcagccaa aatgccttgt acccgatgag tcctctgctc   7740
caagaatgcc tccgggggta caccaagtcc tgtgctcgta cactcgtatc cgggtctttt   7800
gggaaccggt tcattttatc acaagggaac ctaatagcca attgtgcatc aatcctttgc   7860
aagtgttaca caacaggaac gatcattaat caagaccctg acaagatcct aacatacatt   7920
gctgccgatc actgcccggt agtcgaggtg aacggcgtga ccatccaagt cgggagcagg   7980
aggtatccag acgctgtgta cttgcacaga attgacctcg gtcctcccat atcattggag   8040
aggttggacg tagggacaaa tctggggaat gcaattgcta agttggagga tgccaaggaa   8100
ttgttggagt catcggacca gatattgagg agtatgaaag gtttatcgag cactagcata   8160
gtctacatcc tgattgcagt gtgtcttgga gggttgatag ggatccccgc tttaatatgt   8220
tgctgcaggg ggcgttgtaa caaaaaggga gaacaagttg gtatgtcaag accaggccta   8280
aagcctgatc ttacgggaac atcaaaatcc tatgtaaggt cgctctgatc ctctacaact   8340
cttgaaacac aaatgtccca caagtctcct cttcgtcatc aagcaaccac cgcacccagc   8400
atcaagccca cctgaaatta tctccggctt ccctctggcc gaacaatatc ggtagttaat   8460
caaaacttag ggtgcaagat catccacaat gtcaccacaa cgagaccgga taaatgcctt   8520
```

```
ctacaaagat aacccccatc ccaagggaag taggatagtc attaacagag aacatcttat   8580
gattgataga ccttatgttt tgctggctgt tctgtttgtc atgtttctga gcttgatcgg   8640
gttgctagcc attgcaggca ttagacttca tcgggcagcc atctacaccg cagagatcca   8700
taaaagcctc agcaccaatc tagatgtaac taactcaatc gagcatcagg tcaaggacgt   8760
gctgacacca ctcttcaaaa tcatcggtga tgaagtgggc ctgaggacac ctcagagatt   8820
cactgaccta gtgaaattaa tctctgacaa gattaaattc cttaatccgg atagggagta   8880
cgacttcaga gatctcactt ggtgtatcaa cccgccagag agaatcaaat tggattatga   8940
tcaatactgt gcagatgtgg ctgctgaaga gctcatgaat gcattggtga actcaactct   9000
actggagacc agaacaacca atcagttcct agctgtctca aagggaaact gctcagggcc   9060
cactacaatc agaggtcaat tctcaaacat gtcgctgtcc ctgttagact tgtatttagg   9120
tcgaggttac aatgtgtcat ctatagtcac tatgacatcc cagggaatgt atgggggaac   9180
ttacctagtg gaaaagccta atctgagcag caaaaggtca gagttgtcac aactgagcat   9240
gtaccgagtg tttgaagtag gtgttatcag aaatccgggt ttgggggctc cggtgttcca   9300
tatgacaaac tatcttgagc aaccagtcag taatgatctc agcaactgta tggtggcttt   9360
gggggagctc aaactcgcag ccctttgtca cggggaagat tctatcacaa ttccctatca   9420
gggatcaggg aaaggtgtca gcttccagct cgtcaagcta ggtgtctgga aatccccaac   9480
cgacatgcaa tcctgggtcc ccttatcaac ggatgatcca gtgatagaca ggctttacct   9540
ctcatctcac agaggtgtta tcgctgacaa tcaagcaaaa tgggctgtcc cgacaacacg   9600
aacagatgac aagttgcgaa tggagacatg cttccaacag gcgtgtaagg gtaaaatcca   9660
agcactctgc gagaatcccg agtgggcacc attgaaggat aacaggattc cttcatacgg   9720
ggtcttgtct gttgatctga gtctgacagt tgagcttaaa atcaaaattg cttcgggatt   9780
cgggccattg atcacacacg gttcagggat ggacctatac aaatccaacc acaacaatgt   9840
gtattggctg actatcccgc caatgaagaa cctagcctta ggtgtaatca acacattgga   9900
gtggataccg agattcaagg ttagtcccta cctcttcact gtcccaatta aggaagcagg   9960
cgaagactgc catgccccaa catacctacc tgcggaggtg gatggtgatg tcaaactcag  10020
ttccaatctg gtgattctac ctggtcaaga tctccaatat gttttggcaa cctacgatac  10080
ttccagggtt gaacatgctg tggtttatta cgtttacagc ccaagccgct cattttctta  10140
cttttatcct tttaggttgc ctataaaggg ggtccccatc gaattacaag tggaatgctt  10200
cacatgggac caaaaactct ggtgccgtca cttctgtgtg cttgcggact cagaatctgg  10260
tggacatatc actcactctg ggatggtggg catgggagtc agctgcacag tcacccggga  10320
agatggaacc aatcgcagat agggctgcta gtgaaccaat cacatgatgt cacccagaca  10380
tcaggcatac ccactagtgt gaaatagaca tcagaattaa gaaaaacgta gggtccaagt  10440
ggttccccgt tatggactcg ctatctgtca accagatctt ataccctgaa gttcacctag  10500
atagcccgat agttaccaat aagatagtag ccatcctgga gtatgctcga gtccctcacg  10560
cttacagcct ggaggaccct acactgtgtc agaacatcaa gcaccgccta aaaaacggat  10620
tttccaacca aatgattata aacaatgtgg aagttgggaa tgtcatcaag tccaagctta  10680
ggagttatcc ggcccactct catattccat atccaaattg taatcaggat ttatttaaca  10740
tagaagacaa agagtcaacg aggaagatcc gtgaactcct caaaaagggg aattcgctgt  10800
actccaaagt cagtgataag gttttccaat gcttaaggga cactaactca cggcttggcc  10860
```

-continued

```
taggctccga attgagggag gacatcaagg agaaagttat taacttggga gtttacatgc  10920
acagctccca gtggtttgag ccctttctgt tttggtttac agtcaagact gagatgaggt  10980
cagtgattaa atcacaaacc catacttgcc ataggaggag acacacacct gtattcttca  11040
ctggtagttc agttgagttg ctaatctctc gtgaccttgt tgctataatc agtaaagagt  11100
ctcaacatgt atattacctg acatttgaac tggttttgat gtattgtgat gtcatagagg  11160
ggaggttaat gacagagacc gctatgacta ttgatgctag gtatacagag cttctaggaa  11220
gagtcagata catgtggaaa ctgatagatg gtttcttccc tgcactcggg aatccaactt  11280
atcaaattgt agccatgctg gagcctcttt cacttgctta cctgcagctg agggatataa  11340
cagtagaact cagaggtgct ttccttaacc actgctttac tgaaatacat gatgttcttg  11400
accaaaacgg gttttctgat gaaggtactt atcatgagtt aactgaagct ctagattaca  11460
ttttcataac tgatgacata catctgacag gggagatttt ctcatttttc agaagtttcg  11520
gccaccccag acttgaagca gtaacggctg ctgaaaatgt taggaaatac atgaatcagc  11580
ctaaagtcat tgtgtatgag actctgatga aaggtcatgc catattttgt ggaatcataa  11640
tcaacggcta tcgtgacagg cacggaggca gttggccacc gctgaccctc cccctgcatg  11700
ctgcagacac aatccggaat gctcaagctt caggtgaagg gttaacacat gagcagtgcg  11760
ttgataactg gaaatctttt gctggagtga aatttggctg ctttatgcct cttagcctgg  11820
atagtgatct gacaatgtac ctaaaggaca aggcacttgc tgctctccaa agggaatggg  11880
attcagttta cccgaaagag ttcctgcgtt acgaccctcc caagggaacc gggtcacgga  11940
ggcttgtaga tgttttcctt aatgattcga gctttgaccc atatgatgtg ataatgtatg  12000
ttgtaagtgg agcttacctc catgaccctg agttcaacct gtcttacagc ctgaaagaaa  12060
aggagatcaa ggaaacaggt agactttttg ctaaaatgac ttacaaaatg agggcatgcc  12120
aagtgattgc tgaaaatcta atctcaaacg ggattggcaa atattttaag gacaatggga  12180
tggccaagga tgagcacgat ttgactaagg cactccacac tctagctgtc tcaggagtcc  12240
ccaaagatct caaagaaagt cacagggggg ggccagtctt aaaaacctac tcccgaagcc  12300
cagtccacac aagtaccagg aacgtgagag cagcaaaagg gtttataggg ttccctcaag  12360
taattcggca ggaccaagac actgatcatc cggagaatat ggaagcttac gagacagtca  12420
gtgcatttat cacgactgat ctcaagaagt actgccttaa ttggagatat gagaccatca  12480
gcttgtttgc acagaggcta aatgagattt acggattgcc ctcatttttc cagtggctgc  12540
ataagaggct tgagacctct gtcctgtatg taagtgaccc tcattgcccc cccgaccttg  12600
acgcccatat cccgttatat aaagtcccca atgatcaaat cttcattaag taccctatgg  12660
gaggtataga agggtattgt cagaagctgt ggaccatcag caccattccc tatctatacc  12720
tggctgctta tgagagcgga gtaaggattg cttcgttagt gcaaggggac aatcagacca  12780
tagccgtaac aaaaagggta cccagcacat ggccctacaa ccttaagaaa cgggaagctg  12840
ctagagtaac tagagattac tttgtaattc ttaggcaaag gctacatgat attggccatc  12900
acctcaaggc aaatgagaca attgtttcat cacatttttt tgtctattca aaaggaatat  12960
attatgatgg gctacttgtg tcccaatcac tcaagagcat cgcaagatgt gtattctggt  13020
cagagactat agttgatgaa acaagggcag catgcagtaa tattgctaca acaatggcta  13080
aaagcatcga gagaggttat gaccgttacc ttgcatattc cctgaacgtc ctaaaagtga  13140
tacagcaaat tctgatctct cttggcttca caatcaattc aaccatgacc cgggatgtag  13200
tcatacccct cctcacaaac aacgacctct taataaggat ggcactgttg cccgctccta  13260
```

```
ttggggggat gaattatctg aatatgagca ggctgtttgt cagaaacatc ggtgatccag  13320
taacatcatc aattgctgat ctcaagagaa tgattctcgc ctcactaatg cctgaagaga  13380
ccctccatca agtaatgaca caacaaccgg gggactcttc attcctagac tgggctagcg  13440
acccttactc agcaaatctt gtatgtgtcc agagcatcac tagactcctc aagaacataa  13500
ctgcaaggtt tgtcctgatc catagtccaa acccaatgtt aaaaggatta ttccatgatg  13560
acagtaaaga agaggacgag ggactggcgg cattcctcat ggacaggcat attatagtac  13620
ctagggcagc tcatgaaatc ctggatcata gtgtcacagg ggcaagagag tctattgcag  13680
gcatgctgga taccacaaaa ggcttgattc gagccagcat gaggaagggg gggttaacct  13740
ctcgagtgat aaccagattg tccaattatg actatgaaca attcagagca gggatggtgc  13800
tattgacagg aagaaagaga aatgtcctca ttgacaaaga gtcatgttca gtgcagctgg  13860
cgagagctct aagaagccat atgtgggcga ggctagctcg aggacggcct atttacggcc  13920
ttgaggtccc tgatgtacta gaatctatgc gaggccacct tattcggcgt catgagacat  13980
gtgtcatctg cgagtgtgga tcagtcaact acggatggtt ttttgtcccc tcgggttgcc  14040
aactggatga tattgacaag gaaacatcat ccttgagagt cccatatatt ggttctacca  14100
ctgatgagag aacagacatg aagcttgcct tcgtaagagc cccaagtcga tccttgcgat  14160
ctgctgttag aatagcaaca gtgtactcat gggcttacgg tgatgatgat agctcttgga  14220
acgaagcctg gttgttggct aggcaaaggg ccaatgtgag cctggaggag ctaagggtga  14280
tcactcccat ctcaacttcg actaatttag cgcataggtt gagggatcgt agcactcaag  14340
tgaaatactc aggtacatcc cttgtccgag tggcgaggta taccacaatc tccaacgaca  14400
atctctcatt tgtcatatca gataagaagg ttgatactaa ctttatatac caacaaggaa  14460
tgcttctagg gttgggtgtt ttagaaacat tgtttcgact cgagaaagat accggatcat  14520
ctaacacggt attacatctt cacgtcgaaa cagattgttg cgtgatcccg atgatagatc  14580
atcccaggat acccagctcc cgcaagctag agctgagggc agagctatgt accaacccat  14640
tgatatatga taatgcacct ttaattgaca gagatgcaac aaggctatac acccagagcc  14700
ataggaggca ccttgtggaa tttgttacat ggtccacacc ccaactatat cacattttag  14760
ctaagtccac agcactatct atgattgacc tggtaacaaa atttgagaag gaccatatga  14820
atgaaatttc agctctcata ggggatgacg atatcaatag tttcataact gagtttctgc  14880
tcatagagcc aagattattc actatctact tgggccagtg tgcggccatc aattgggcat  14940
ttgatgtaca ttatcataga ccatcaggga aatatcagat gggtgagctg ttgtcatcgt  15000
tcctttctag aatgagcaaa ggagtgttta aggtgcttgt caatgctcta agccacccaa  15060
agatctacaa gaaattctgg cattgtggta ttatagagcc tatccatggt ccttcacttg  15120
atgctcaaaa cttgcacaca actgtgtgca acatggttta cacatgctat atgacctacc  15180
tcgacctgtt gttgaatgaa gagttagaag agttcacatt tctcttgtgt gaaagcgacg  15240
aggatgtagt accggacaga ttcgacaaca tccaggcaaa acacttatgt gttctggcag  15300
atttgtactg tcaaccaggg acctgcccac caattcgagg tctaagaccg gtagagaaat  15360
gtgcagttct aaccgaccat atcaaggcag aggctatgtt atctccagca ggatcttcgt  15420
ggaacataaa tccaattatt gtagaccatt actcatgctc tctgacttat ctccggcgag  15480
gatcgatcaa acagataaga ttgagagttg atccaggatt cattttcgac gccctcgctg  15540
aggtaaatgt cagtcagcca aagatcggca gcaacaacat ctcaaatatg agcatcaagg  15600
```

```
ctttcagacc cccacacgat gatgttgcaa aattgctcaa agatatcaac acaagcaagc  15660
acaatcttcc catttcaggg ggcaatctcg ccaattatga aatccatgct ttccgcagaa  15720
tcgggttgaa ctcatctgct tgctacaaag ctgttgagat atcaacatta attaggagat  15780
gccttgagcc aggggaggac ggcttgttct tgggtgaggg atcgggttct atgttgatca  15840
cttataaaga gatacttaaa ctaaacaagt gcttctataa tagtggggtt tccgccaatt  15900
ctagatctgg tcaaagggaa ttagcaccct atccctccga agttggcctt gtcgaacaca  15960
gaatgggagt aggtaatatt gtcaaagtgc tctttaacgg gaggcccgaa gtcacgtggg  16020
taggcagtgt agattgcttc aatttcatag ttagtaatat ccctacctct agtgtggggt  16080
ttatccattc agatatagag accttgcctg acaaagatac tatagagaag ctagaggaat  16140
tggcagccat cttatcgatg gctctgctcc tgggcaaaat aggatcaata ctggtgatta  16200
agcttatgcc tttcagcggg gattttgttc agggatttat aagttatgta gggtctcatt  16260
atagagaagt gaaccttgta taccctagat acagcaactt catctctact gaatcttatt  16320
tggttatgac agatctcaag gctaaccggc taatgaatcc tgaaaagatt aagcagcaga  16380
taattgaatc atctgtgagg acttcacctg gacttatagg tcacatccta tccattaagc  16440
aactaagctg catacaagca attgtgggag acgcagttag tagaggtgat atcaatccta  16500
ctctgaaaaa acttacacct atagagcagg tgctgatcaa ttgcgggttg gcaattaacg  16560
gacctaagct gtgcaaagaa ttgatccacc atgatgttgc ctcagggcaa gatggattgc  16620
ttaattctat actcatcctc tacagggagt tggcaagatt caaagacaac caaagaagtc  16680
aacaagggat gttccacgct taccccgtat tggtaagtag caggcaacga gaacttatat  16740
ctaggatcac ccgcaaattc tgggggcaca ttcttcttta ctccgggaac aaaaagttga  16800
taaataagtt tatccagaat ctcaagtccg gctatctgat actagactta caccagaata  16860
tcttcgttaa gaatctatcc aagtcagaga aacagattat tatgacgggg ggtttgaaac  16920
gtgagtgggt ttttaaggta acagtcaagg agaccaaaga atggtataag ttagtcggat  16980
acagtgccct gattaaggac taattggttg aactccggaa ccctaatcct gccctaggtg  17040
gttaggcatt atttgcaata tattaaagaa aactttgaaa atacgaagtt tctattccca  17100
gctttgtctg gtggccggca tggtcccagc ctcctcgctg gcgccggctg ggcaacattc  17160
cgaggggacc gtcccctcgg taatggcgaa tgggacgcgg ccggtcgatc gacgatccgg  17220
ctgctaacaa agcccgaaag gaagctgagt tggctgctgc caccgctgag caataactag  17280
cataacccct tggggcctct aaacgggtct tgaggggttt tttgctgaaa ggaggaacta  17340
tatccggatc gagatcaatt ctgtgagcgt atggcaaacg aaggaaaaat agttatagta  17400
gccgcactcg atgggacatt tcaacgtaaa ccgtttaata atattttgaa tcttattcca  17460
ttatctgaaa tggtggtaaa actaactgct gtgtgtatga aatgctttaa ggaggcttcc  17520
ttttctaaac gattgggtga ggaaaccgag atagaaataa taggaggtaa tgatatgtat  17580
caatcggtgt gtagaaagtg ttacatcgac tcataatatt atattttta tctaaaaaac  17640
taaaaataaa cattgattaa attttaatat aatacttaaa aatggatgtt gtgtcgttag  17700
ataaaccgtt tatgtatttt gaggaaattg ataatgagtt agattacgaa ccagaaagtg  17760
caaatgaggt cgcaaaaaaa ctgccgtatc aaggacagtt aaaactatta ctaggagaat  17820
tatttttct tagtaagtta cagcgacacg gtatattaga tggtgccacc gtagtgtata  17880
taggatctgc tcccggtaca catatacgtt atttgagaga tcatttctat aatttaggag  17940
tgatcccgaa aggaagctga gttggctgct gccaccgctg agcaataact agcataaccc  18000
```

-continued

```
cttggggcct ctaaacgggt cttgaggggt tttttgctga aaggaggaac gcgcctgatg  18060
cggtattttc tccttacgca tctgtgcggt atttcacacc gcatatatgg tgcactctca  18120
gtacaatctg ctctgatgcc gcatagttaa gccagccccg acacccgcca acacccgctg  18180
acgcgccctg acgggcttgt ctgctcccgg catccgctta cagacaagct gtgaccgtct  18240
ccgggagctg catgtgtcag aggttttcac cgtcatcacc gaaacgcgcg agacgaaagg  18300
gcctcgtgat acgcctattt ttataggtta atgtcatgat aataatggtt tcttagacgt  18360
caggtggcac ttttcgggga aatgtgcgcg gaacccctat ttgtttattt ttctaaatac  18420
attcaaatat gtatccgctc atgagacaat aaccctgata aatgcttcaa taatattgaa  18480
aaaggaagag tatgagtatt caacatttcc gtgtcgccct tattcccttt tttgcggcat  18540
tttgccttcc tgtttttgct cacccagaaa cgctggtgaa agtaaaagat gctgaagatc  18600
agttgggtgc acgagtgggt tacatcgaac tggatctcaa cagcggtaag atccttgaga  18660
gttttcgccc cgaagaacgt tttccaatga tgagcacttt taaagttctg ctatgtggcg  18720
cggtattatc ccgtattgac gccgggcaag agcaactcgg tcgccgcata cactattctc  18780
agaatgactt ggttgagtac tcaccagtca cagaaaagca tcttacggat ggcatgacag  18840
taagagaatt atgcagtgct gccataacca tgagtgataa cactgcggcc aacttacttc  18900
tgacaacgat cggaggaccg aaggagctaa ccgctttttt gcacaacatg ggggatcatg  18960
taactcgcct tgatcgttgg gaaccggagc tgaatgaagc cataccaaac gacgagcgtg  19020
acaccacgat gcctgtagca atggcaacaa cgttgcgcaa actattaact ggcgaactac  19080
ttactctagc ttcccggcaa caattaatag actggatgga ggcggataaa gttgcaggac  19140
cacttctgcg ctcggccctt ccggctggct ggtttattgc tgataaatct ggagccggtg  19200
agcgtgggtc tcgcggtatc attgcagcac tggggccaga tggtaagccc tcccgtatcg  19260
tagttatcta cacgacgggg agtcaggcaa ctatggatga acgaaataga cagatcgctg  19320
agataggtgc ctcactgatt aagcattggt aactgtcaga ccaagtttac tcatatatac  19380
tttagattga tttaaaactt catttttaat ttaaaaggat ctaggtgaag atcctttttg  19440
ataatctcat gaccaaaatc ccttaacgtg agttttcgtt ccactgagcg tcagaccccg  19500
tagaaaagat caaaggatct tcttgagatc ctttttttct gcgcgtaatc tgctgcttgc  19560
aaacaaaaaa accaccgcta ccagcggtgg tttgtttgcc ggatcaagag ctaccaactc  19620
tttttccgaa ggtaactggc ttcagcagag cgcagatacc aaatactgtc cttctagtgt  19680
agccgtagtt aggccaccac ttcaagaact ctgtagcacc gcctacatac ctcgctctgc  19740
taatcctgtt accagtggct gctgccagtg gcgataagtc gtgtcttacc gggttggact  19800
caagacgata gttaccggat aaggcgcagc ggtcgggctg aacggggggt tcgtgcacac  19860
agcccagctt ggagcgaacg acctacaccg aactgagata cctacagcgt gagcattgag  19920
aaagcgccac gcttcccgaa gggagaaagg cggacaggta tccggtaagc ggcagggtcg  19980
gaacaggaga gcgcacgagg gagcttccag ggggaaacgc ctggtatctt tatagtcctg  20040
tcgggtttcg ccacctctga cttgagcgtc gatttttgtg atgctcgtca ggggggcgga  20100
gcctatggaa aaacgccagc aacgcggcct ttttacggtt cctggccttt tgctggcctt  20160
ttgctcacat gttctttcct gcgttatccc ctgattctgt ggataaccgt attaccgcct  20220
ttgagtgagc tgataccgct cgccgcagcc gaacgaccga gcgcagcgag tcagtgagcg  20280
aggaagcgga agagcgccca atacgcaaac cgcctctccc cgcgcgttgg ccgattcatt  20340
```

```
aatgcagctg gcacgacagg tttcccgact ggaaagcggg cagtgagcgc aacgcaatta  20400

atgtgagtta gctcactcat taggcacccc aggctttaca ctttatgctt ccggctcgta  20460

tgttgtgtgg aattgtgagc ggataacaat ttcacacagg aaacagctat gaccatgatt  20520

acgccaagct tacgcgtcct ggcattatgc ccagtacatg accttatggg actttcctac  20580

ttggcagtac atctacgtat tagtcatcgc tattaccatg gtgatgcggt tttggcagta  20640

catcaatggg cgtggatagc ggtttgactc acggggattt ccaagtctcc accccattga  20700

cgtcaatggg agtttgtttt ggcaccaaaa tcaacgggac tttccaaaat gtcgtaacaa  20760

ctccgcccca ttgacgcaaa tgggcggtag gcgtgtacgg tgggaggtct atataagcag  20820

agctcgttta gtgaaccgtg g                                            20841
```

```
<210> SEQ ID NO 5
<211> LENGTH: 7765
<212> TYPE: DNA
<213> ORGANISM: Artificial
<220> FEATURE:
<223> OTHER INFORMATION: plasmid DNA

<400> SEQUENCE: 5

agcttgcatg cctgcaggtc aattccctgg cattatgccc agtacatgac cttatgggac     60

tttcctactt ggcagtacat ctacgtatta gtcatcgcta ttaccatggt gatgcggttt    120

tggcagtaca tcaatgcgcg tggataccgg tttgactcac ggggatttcc aagtctccac    180

cccattcacg tcaatgggag tttgttttgg caccaaaatc aacgggactt tccaaaatgt    240

cgtaacaact ccgccccatt gacgcaaatg ggcggtaggc gtgtacggtg ggaggtctat    300

ataagcagag ctcgtttagt gaaccgtcag atcgcctgga gacgccatcc acgctgtttt    360

gacctccata gaagacaccg ggaccgatcc agcctgggga tctagcctcc gcggccggga    420

acggtgcatt ggaacgcgga ttccccgtgc caagagtgac gtaagtaccg cctatagagt    480

ctataggccc acccccttgg cttcttatgc atgctatact gtttttggct tggggtctat    540

acacccccgc ttcctcatgt tataggtgat ggtatagctt agcctatagg tgtgggttat    600

tgaccattat tgaccactcc cctattggtg acgatacttt ccattactaa tccataacat    660

ggctctttgc cacaactctc tttattggct atatgccaat acactgtcct tcagagactg    720

acacggactc tgtattttta caggatgggg tctcatttat tatttacaaa ttcacatata    780

caacaccacc gtccccagtg cccgcagttt ttattaaaca taacgtggga tctccacgcg    840

aatctcgggt acgtgttccg gacatgggct cttctccggt agcggcggag ctcctacatc    900

cgagccctgc tcccatgcct ccagcgactc atggtcgctc ggcagctcct tgctcctaac    960

agtggaggcc agacttaggc acagcacgat gcccaccacc accagtgtgc cgcacaaggc   1020

cgtggcggta gggtatgtgt ctgaaaatga gctcggggag cgggcttgca ccgctgacgc   1080

atttggaaga cttaaggcag cggcagaaga agatgcaggc agctgagttg ttgtgttctg   1140

ataagagtca gaggtaactc ccgttgcggt gctgttaacg gtggagggca gtgtagtctg   1200

agcagtactc gttgctgccg cgcgcgccac cagacataat agctgacaga ctaacagact   1260

gttcctttcc atgggtcttt tctgcagtca ccgtccttga cacgatcgga tcccgggtac   1320

ctctagaaga tctgatatcg tcgacctcga ggccaccatg gccacacttt taaggagctt   1380

agcattgttc aaaagaaaca aggacaaacc acccattaca tcaggatccg gtggagccat   1440

cagaggaatc aaacacatta ttatagtacc aatccctgga gattcctcaa ttaccactcg   1500

atccagactt ctggaccggt tggtgaggtt aattggaaac ccggatgtga gcgggcccaa   1560
```

```
actaacaggg gcactaatag gtatattatc cttatttgtg gagtctccag gtcaattgat   1620
tcagaggatc accgatgacc ctgacgttag cataaggctg ttagaggttg tccagagtga   1680
ccagtcacaa tctggcctta ccttcgcatc aagaggtacc aacatggagg atgaggcgga   1740
ccaatacttt tcacatgatg atccaattag tagtgatcaa tccaggttcg gatggttcgg   1800
gaacaaggaa atctcagata ttgaagtgca agaccctgag ggattcaaca tgattctggg   1860
taccatccta gcccaaattt gggtcttgct cgcaaaggcg gttacggccc cagacacggc   1920
agctgattcg gagctaagaa ggtggataaa gtacacccaa caaagaaggg tagttggtga   1980
atttagattg gagagaaaat ggttggatgt ggtgaggaac aggattgccg aggacctctc   2040
cttacgccga ttcatggtcg ctctaatcct ggatatcaag agaacacccg gaaacaaacc   2100
caggattgct gaaatgatat gtgacattga tacatatatc gtagaggcag gattagccag   2160
ttttatcctg actattaagt ttgggataga aactatgtat cctgctcttg gactgcatga   2220
atttgctggt gagttatcca cacttgagtc cttgatgaac ctttaccagc aaatgggga   2280
aactgcaccc tacatggtaa tcctggagaa ctcaattcag aacaagttca gtgcaggatc   2340
ataccctctg ctctggagct atgccatggg agtaggagtg gaacttgaaa actccatggg   2400
aggtttgaac tttggccgat cttactttga tccagcatat tttagattag ggcaagagat   2460
ggtaaggagg tcagctggaa aggtcagttc cacattggca tctgaactcg gtatcactgc   2520
cgaggatgca aggcttgttt cagagattgc aatgcatact actgaggaca agatcagtag   2580
agcggttgga cccagacaag cccaagtatc atttctacac ggtgatcaaa gtgagaatga   2640
gctaccgaga ttgggggggca aggaagatag gagggtcaaa cagagtcgag gagaagccag   2700
ggagagctac agagaaaccg ggcccagcag agcaagtgat gcgagagctg cccatcttcc   2760
aaccggcaca cccctagaca ttgacactgc aacggagtcc agccaagatc cgcaggacag   2820
tcgaaggtca gctgacgccc tgcttaggct gcaagccatg gcaggaatct cggaagaaca   2880
aggctcagac acggacaccc ctatagtgta caatgacaga aatcttctag actaggtgcg   2940
agaggccgag ggccagaaca acatccgcct accatccatc attctcgagg aattctagat   3000
cccacgtcac tattgtatac tctatattat actctatgtt atactctgta atcctactca   3060
ataaacgtgt cacgcctgtg aaaccgtact aagtctcccg tgtcttctta tcaccatcag   3120
gtgacatcct cgcccaggct gtcaatcatg ccggtatcga ttccagtagc accggcccca   3180
cgctgacaac ccactcttgc agcgttagca gcgcccctct taacaagccg acccccacca   3240
gcgtcgcggt tactaacact cctctccccg acctgcagcc caagctctag agggccctat   3300
tctatagtgt cacctaaatg ctagagctcg ctgatcagcc tcgactgtgc cttctagttg   3360
ccagccatct gttgtttgcc cctcccccgt gccttccttg accctggaag gtgccactcc   3420
cactgtcctt tcctaataaa atgaggaaat tgcatcgcat tgtctgagta ggtgtcattc   3480
tattctgggg ggtggggtgg ggcaggacag caagggggag gattgggaag acaatagcag   3540
gcatgctggg gatgcggtgg gctctatggc ttctgaggcg gaaagaacca gctggggctc   3600
tagggggtat ccccacgcgc cctgtagcgg cgcattaagc gcggcgggtg tggtggttac   3660
gcgcagcgtg accgctacac ttgccagcgc cctagcgccc gctcctttcg ctttcttccc   3720
ttcctttctc gccacgttcg ccggctttcc ccgtcaagct ctaaatcggg gcatcccttt   3780
agggttccga tttagtgctt tacggcacct cgaccccaaa aaacttgatt agggtgatgg   3840
ttcacgtagt gggccatcgc cctgatagac ggtttttcgc cctttgacgt tggagtccac   3900
```

```
gttctttaat agtggactct tgttccaaac tggaacaaca ctcaacccta tctcggtcta   3960

ttcttttgat ttataaggga ttttggggat ttcggcctat tggttaaaaa atgagctgat   4020

ttaacaaaaa tttaacgcga attaattctg tggaatgtgt gtcagttagg gtgtggaaag   4080

tccccaggct ccccaggcag gcagaagtat gcaaagcatg catctcaatt agtcagcaac   4140

caggtgtgga aagtccccag gctccccagc aggcagaagt atgcaaagca tgcatctcaa   4200

ttagtcagca accatagtcc cgcccctaac tccgcccatc ccgcccctaa ctccgcccag   4260

ttccgcccat tctccgcccc atggctgact aatttttttt atttatgcag aggccgaggc   4320

cgcctctgcc tctgagctat tccagaagta gtgaggaggc ttttttggag gcctaggctt   4380

ttgcaaaaag ctcccgggag cttgtatatc cattttcgga tctgatcaag agacaggatg   4440

aggatcgttt cgcatgattg aacaagatgg attgcacgca ggttctccgg ccgcttgggt   4500

ggagaggcta ttcggctatg actgggcaca acagacaatc ggctgctctg atgccgccgt   4560

gttccggctg tcagcgcagg ggcgcccggt tctttttgtc aagaccgacc tgtccggtgc   4620

cctgaatgaa ctgcaggacg aggcagcgcg gctatcgtgg ctggccacga cgggcgttcc   4680

ttgcgcagct gtgctcgacg ttgtcactga agcgggaagg gactggctgc tattgggcga   4740

agtgccgggg caggatctcc tgtcatctca ccttgctcct gccgagaaag tatccatcat   4800

ggctgatgca atgcggcggc tgcatacgct tgatccggct acctgcccat tcgaccacca   4860

agcgaaacat cgcatcgagc gagcacgtac tcggatggaa gccggtcttg tcgatcagga   4920

tgatctggac gaagagcatc aggggctcgc gccagccgaa ctgttcgcca ggctcaaggc   4980

gcgcatgccc gacggcgagg atctcgtcgt gacccatggc gatgcctgct tgccgaatat   5040

catggtggaa aatggccgct tttctggatt catcgactgt ggccggctgg gtgtggcgga   5100

ccgctatcag gacatagcgt tggctacccg tgatattgct gaagagcttg gcggcgaatg   5160

ggctgaccgc ttcctcgtgc tttacggtat cgccgctccc gattcgcagc gcatcgcctt   5220

ctatcgcctt cttgacgagt tcttctgagc gggactctgg ggttcgaaat gaccgaccaa   5280

gcgacgccca acctgccatc acgagatttc gattccaccg ccgccttcta tgaaaggttg   5340

ggcttcggaa tcgttttccg ggacgccggc tggatgatcc tccagcgcgg ggatctcatg   5400

ctggagttct tcgcccaccc caacttgttt attgcagctt ataatggtta caaataaagc   5460

aatagcatca caaatttcac aaataaagca tttttttcac tgcattctag ttgtggtttg   5520

tccaaactca tcaatgtatc ttatcatgtc tgtataccgt cgacctctag ctagagcttg   5580

gcgtaatcat ggtcatagct gtttcctgtg tgaaattgtt atccgctcac aattccacac   5640

aacatacgag ccggaagcat aaagtgtaaa gcctggggtg cctaatgagt gagctaactc   5700

acattaattg cgttgcgctc actgcccgct ttccagtcgg gaaacctgtc gtgccagctg   5760

cattaatgaa tcggccaacg cgcggggaga ggcggtttgc gtattgggcg ctcttccgct   5820

tcctcgctca ctgactcgct gcgctcggtc gttcggctgc ggcgagcggt atcagctcac   5880

tcaaaggcgg taatacggtt atccacagaa tcaggggata acgcaggaaa gaacatgtga   5940

gcaaaaggcc agcaaaaggc caggaaccgt aaaaaggccg cgttgctggc gtttttccat   6000

aggctccgcc cccctgacga gcatcacaaa aatcgacgct caagtcagag gtggcgaaac   6060

ccgacaggac tataaagata ccaggcgttt ccccctggaa gctccctcgt gcgctctcct   6120

gttccgaccc tgccgcttac cggatacctg tccgcctttc tcccttcggg aagcgtggcg   6180

ctttctcaat gctcacgctg taggtatctc agttcggtgt aggtcgttcg ctccaagctg   6240

ggctgtgtgc acgaaccccc cgttcagccc gaccgctgcg ccttatccgg taactatcgt   6300
```

```
cttgagtcca acccggtaag acacgactta tcgccactgg cagcagccac tggtaacagg   6360

attagcagag cgaggtatgt aggcggtgct acagagttct tgaagtggtg gcctaactac   6420

ggctacacta gaaggacagt atttggtatc tgcgctctgc tgaagccagt taccttcgga   6480

aaaagagttg gtagctcttg atccggcaaa caaaccaccg ctggtagcgg tggttttttt   6540

gtttgcaagc agcagattac gcgcagaaaa aaaggatctc aagaagatcc tttgatcttt   6600

tctacggggt ctgacgctca gtggaacgaa aactcacgtt aagggatttt ggtcatgaga   6660

ttatcaaaaa ggatcttcac ctagatcctt ttaaattaaa aatgaagttt taaatcaatc   6720

taaagtatat atgagtaaac ttggtctgac agttaccaat gcttaatcag tgaggcacct   6780

atctcagcga tctgtctatt tcgttcatcc atagttgcct gactccccgt cgtgtagata   6840

actacgatac gggagggctt accatctggc cccagtgctg caatgatacc gcgagaccca   6900

cgctcaccgg ctccagattt atcagcaata aaccagccag ccggaagggc cgagcgcaga   6960

agtggtcctg caactttatc cgcctccatc cagtctatta attgttgccg ggaagctaga   7020

gtaagtagtt cgccagttaa tagtttgcgc aacgttgttg ccattgctac aggcatcgtg   7080

gtgtcacgct cgtcgtttgg tatggcttca ttcagctccg gttcccaacg atcaaggcga   7140

gttacatgat cccccatgtt gtgcaaaaaa gcggttagct ccttcggtcc tccgatcgtt   7200

gtcagaagta agttggccgc agtgttatca ctcatggtta tggcagcact gcataattct   7260

cttactgtca tgccatccgt aagatgcttt tctgtgactg gtgagtactc aaccaagtca   7320

ttctgagaat agtgtatgcg gcgaccgagt tgctcttgcc cggcgtcaat acgggataat   7380

accgcgccac atagcagaac tttaaaagtg ctcatcattg gaaaacgttc ttcggggcga   7440

aaactctcaa ggatcttacc gctgttgaga tccagttcga tgtaacccac tcgtgcaccc   7500

aactgatctt cagcatcttt tactttcacc agcgtttctg ggtgagcaaa aacaggaagg   7560

caaaatgccg caaaaaaggg aataagggcg acacggaaat gttgaatact catactcttc   7620

ctttttcaat attattgaag catttatcag ggttattgtc tcatgagcgg atacatattt   7680

gaatgtattt agaaaaataa acaaataggg gttccgcgca catttccccg aaaagtgcca   7740

cctgacgtcg acggatcggg agatc                                         7765
```

<210> SEQ ID NO 6
<211> LENGTH: 7723
<212> TYPE: DNA
<213> ORGANISM: Artificial
<220> FEATURE:
<223> OTHER INFORMATION: plasmid DNA

<400> SEQUENCE: 6

```
agcttgcatg cctgcaggtc aattccctgg cattatgccc agtacatgac cttatgggac     60

tttcctactt ggcagtacat ctacgtatta gtcatcgcta ttaccatggt gatgcggttt    120

tggcagtaca tcaatgcgcg tggataccgg tttgactcac ggggatttcc aagtctccac    180

cccattcacg tcaatgggag tttgttttgg caccaaaatc aacgggactt tccaaaatgt    240

cgtaacaact ccgccccatt gacgcaaatg ggcggtaggc gtgtacggtg ggaggtctat    300

ataagcagag ctcgtttagt gaaccgtcag atcgcctgga gacgccatcc acgctgtttt    360

gacctccata gaagacaccg ggaccgatcc agcctgggga tctagcctcc gcggccggga    420

acggtgcatt ggaacgcgga ttccccgtgc caagagtgac gtaagtaccg cctatagagt    480

ctataggccc acccccttgg cttcttatgc atgctatact gtttttggct tggggtctat    540
```

-continued

```
acacccccgc ttcctcatgt tataggtgat ggtatagctt agcctatagg tgtgggttat    600
tgaccattat tgaccactcc cctattggtg acgatacttt ccattactaa tccataacat    660
ggctctttgc cacaactctc tttattggct atatgccaat acactgtcct tcagagactg    720
acacggactc tgtattttta caggatgggg tctcatttat tatttacaaa ttcacatata    780
caacaccacc gtccccagtg cccgcagttt ttattaaaca taacgtggga tctccacgcg    840
aatctcgggt acgtgttccg gacatgggct cttctccggt agcggcggag ctcctacatc    900
cgagccctgc tcccatgcct ccagcgactc atggtcgctc ggcagctcct tgctcctaac    960
agtggaggcc agacttaggc acagcacgat gcccaccacc accagtgtgc cgcacaaggc   1020
cgtggcggta gggtatgtgt ctgaaaatga gctcggggag cgggcttgca ccgctgacgc   1080
atttggaaga cttaaggcag cggcagaaga agatgcaggc agctgagttg ttgtgttctg   1140
ataagagtca gaggtaactc ccgttgcggt gctgttaacg gtggagggca gtgtagtctg   1200
agcagtactc gttgctgccg cgcgcgccac cagacataat agctgacaga ctaacagact   1260
gttcctttcc atgggtcttt tctgcagtca ccgtccttga cacgatcgga tcccgggtac   1320
ctctagaaga tctgatatcg tcgacctcga ggccaccatg gcagaagagc aggcacgcca   1380
tgtcaaaaac ggactggaat gcatccgggc tctcaaggcc gagcccatcg gctcactggc   1440
catcgaggaa gctatggcag catggtcaga aatatcagac aacccaggac aggagcgagc   1500
cacctgcagg gaagagaagg caggcagttc gggtctcagc aaaccatgcc tctcagcaat   1560
tggatcaact gaaggcggtg cacctcgcat ccgcggtcag ggacctggag agagcgatga   1620
cgacgctgaa actttgggaa tcccccaag aaatctccag gcatcaagca ctgggttaca    1680
gtgttattac gtttatgatc acagcggtga agcggttaag ggaatccaag atgctgactc   1740
tatcatggtt caatcaggcc ttgatggtga tagcaccctc tcaggaggag acaatgaatc   1800
tgaaaacagc gatgtggata ttggcgaacc tgataccgag ggatatgcta tcactgaccg   1860
gggatctgct cccatctcta tggggttcag ggcttctgat gttgaaactg cagaaggagg   1920
ggagatccac gagctcctga gactccaatc cagaggcaac aactttccga agcttgggaa   1980
aactctcaat gttcctccgc ccccggaccc cggtagggcc agcacttccg ggacacccat   2040
taaaaagggc acagacgcga gattagcctc atttggaacg gagatcgcgt ctttattgac   2100
aggtggtgca acccaatgtg ctcgaaagtc accctcggaa ccatcagggc caggtgcacc   2160
tgcggggaat gtccccgagt gtgtgagcaa tgccgcactg atacaggagt ggacacccga   2220
atctggtacc acaatctccc cgagatccca gaataatgaa gaagggggag actattatga   2280
tgatgagctg ttctctgatg tccaagatat taaaacagcc ttggccaaaa tacacgagga   2340
taatcagaag ataatctcca agctagaatc actgctgtta ttgaagggag aagttgagtc   2400
aattaagaag cagatcaaca ggcaaaatat cagcatatcc accctggaag gacacctctc   2460
aagcatcatg atcgccattc ctggacttgg gaaggatccc aacgacccca ctgcagatgt   2520
cgaaatcaat cccgacttga aacccatcat aggcagagat tcaggccgag cactggccga   2580
agttctcaag aaacccgttg ccagccgaca actccaagga atgacaaatg gacggaccag   2640
ttccagagga cagctgctga aggaatttca gctaaagccg atcgggaaaa agatgagctc   2700
agccgtcggg tttgttcctg acaccggccc tgcatcacgc agtgtaatcc gctccattat   2760
aaaatccagc cggctagagg aggatcggaa gcgttacctg atgactctcc ttgatgatat   2820
caaaggagcc aatgatcttg ccaagttcca ccagatgctg atgaagataa taatgaagta   2880
gctacagctc aacttacctg ccaaccccat gccagtcgac ccaactagta caacctaaat   2940
```

```
cctcgaggaa ttctagatcc cacgtcacta ttgtatactc tatattatac tctatgttat   3000
actctgtaat cctactcaat aaacgtgtca cgcctgtgaa accgtactaa gtctcccgtg   3060
tcttcttatc accatcaggt gacatcctcg cccaggctgt caatcatgcc ggtatcgatt   3120
ccagtagcac cggccccacg ctgacaaccc actcttgcag cgttagcagc gcccctctta   3180
acaagccgac ccccaccagc gtcgcggtta ctaacactcc tctccccgac ctgcagccca   3240
agctctagag ggccctattc tatagtgtca cctaaatgct agagctcgct gatcagcctc   3300
gactgtgcct tctagttgcc agccatctgt tgtttgcccc tcccccgtgc cttccttgac   3360
cctggaaggt gccactccca ctgtcctttc ctaataaaat gaggaaattg catcgcattg   3420
tctgagtagg tgtcattcta ttctgggggg tggggtgggg caggacagca agggggagga   3480
ttgggaagac aatagcaggc atgctgggga tgcggtgggc tctatggctt ctgaggcgga   3540
aagaaccagc tggggctcta gggggtatcc ccacgcgccc tgtagcggcg cattaagcgc   3600
ggcgggtgtg gtggttacgc gcagcgtgac cgctacactt gccagcgccc tagcgcccgc   3660
tcctttcgct ttcttccctt cctttctcgc cacgttcgcc ggctttcccc gtcaagctct   3720
aaatcggggc atccctttag ggttccgatt tagtgcttta cggcacctcg accccaaaaa   3780
acttgattag ggtgatggtt cacgtagtgg gccatcgccc tgatagacgg tttttcgccc   3840
tttgacgttg gagtccacgt tctttaatag tggactcttg ttccaaactg gaacaacact   3900
caaccctatc tcggtctatt cttttgattt ataagggatt ttggggattt cggcctattg   3960
gttaaaaaat gagctgattt aacaaaaatt taacgcgaat taattctgtg gaatgtgtgt   4020
cagttagggt gtggaaagtc cccaggctcc ccaggcaggc agaagtatgc aaagcatgca   4080
tctcaattag tcagcaacca ggtgtggaaa gtccccaggc tccccagcag gcagaagtat   4140
gcaaagcatg catctcaatt agtcagcaac catagtcccg cccctaactc cgcccatccc   4200
gcccctaact ccgcccagtt ccgcccattc tccgccccat ggctgactaa ttttttttat   4260
ttatgcagag gccgaggccg cctctgcctc tgagctattc cagaagtagt gaggaggctt   4320
ttttggaggc ctaggctttt gcaaaaagct cccgggagct tgtatatcca ttttcggatc   4380
tgatcaagag acaggatgag gatcgtttcg catgattgaa caagatggat tgcacgcagg   4440
ttctccggcc gcttgggtgg agaggctatt cggctatgac tgggcacaac agacaatcgg   4500
ctgctctgat gccgccgtgt tccggctgtc agcgcagggg cgcccggttc tttttgtcaa   4560
gaccgacctg tccggtgccc tgaatgaact gcaggacgag gcagcgcggc tatcgtggct   4620
ggccacgacg ggcgttcctt gcgcagctgt gctcgacgtt gtcactgaag cgggaaggga   4680
ctggctgcta ttgggcgaag tgccggggca ggatctcctg tcatctcacc ttgctcctgc   4740
cgagaaagta tccatcatgg ctgatgcaat gcggcggctg catacgcttg atccggctac   4800
ctgcccattc gaccaccaag cgaaacatcg catcgagcga gcacgtactc ggatggaagc   4860
cggtcttgtc gatcaggatg atctggacga agagcatcag gggctcgcgc cagccgaact   4920
gttcgccagg ctcaaggcgc gcatgcccga cggcgaggat ctcgtcgtga cccatggcga   4980
tgcctgcttg ccgaatatca tggtggaaaa tggccgcttt tctggattca tcgactgtgg   5040
ccggctgggt gtggcggacc gctatcagga catagcgttg gctacccgtg atattgctga   5100
agagcttggc ggcgaatggg ctgaccgctt cctcgtgctt tacggtatcg ccgctcccga   5160
ttcgcagcgc atcgccttct atcgccttct tgacgagttc ttctgagcgg gactctgggg   5220
ttcgaaatga ccgaccaagc gacgcccaac ctgccatcac gagatttcga ttccaccgcc   5280
```

-continued

```
gccttctatg aaaggttggg cttcggaatc gttttccggg acgccggctg gatgatcctc   5340
cagcgcgggg atctcatgct ggagttcttc gcccacccca acttgtttat tgcagcttat   5400
aatggttaca aataaagcaa tagcatcaca aatttcacaa ataaagcatt tttttcactg   5460
cattctagtt gtggtttgtc caaactcatc aatgtatctt atcatgtctg tataccgtcg   5520
acctctagct agagcttggc gtaatcatgg tcatagctgt ttcctgtgtg aaattgttat   5580
ccgctcacaa ttccacacaa catacgagcc ggaagcataa agtgtaaagc ctggggtgcc   5640
taatgagtga gctaactcac attaattgcg ttgcgctcac tgcccgcttt ccagtcggga   5700
aacctgtcgt gccagctgca ttaatgaatc ggccaacgcg cggggagagg cggtttgcgt   5760
attgggcgct cttccgcttc ctcgctcact gactcgctgc gctcggtcgt tcggctgcgg   5820
cgagcggtat cagctcactc aaaggcggta atacggttat ccacagaatc aggggataac   5880
gcaggaaaga acatgtgagc aaaaggccag caaaaggcca ggaaccgtaa aaaggccgcg   5940
ttgctggcgt ttttccatag gctccgcccc cctgacgagc atcacaaaaa tcgacgctca   6000
agtcagaggt ggcgaaaccc gacaggacta taaagatacc aggcgtttcc ccctggaagc   6060
tccctcgtgc gctctcctgt tccgaccctg ccgcttaccg gatacctgtc cgcctttctc   6120
ccttcgggaa gcgtggcgct ttctcaatgc tcacgctgta ggtatctcag ttcggtgtag   6180
gtcgttcgct ccaagctggg ctgtgtgcac gaaccccccg ttcagcccga ccgctgcgcc   6240
ttatccggta actatcgtct tgagtccaac ccggtaagac acgacttatc gccactggca   6300
gcagccactg gtaacaggat tagcagagcg aggtatgtag gcggtgctac agagttcttg   6360
aagtggtggc ctaactacgg ctacactaga aggacagtat ttggtatctg cgctctgctg   6420
aagccagtta ccttcggaaa aagagttggt agctcttgat ccggcaaaca aaccaccgct   6480
ggtagcggtg gtttttttgt ttgcaagcag cagattacgc gcagaaaaaa aggatctcaa   6540
gaagatcctt tgatcttttc tacggggtct gacgctcagt ggaacgaaaa ctcacgttaa   6600
gggattttgg tcatgagatt atcaaaaagg atcttcacct agatcctttt aaattaaaaa   6660
tgaagtttta aatcaatcta aagtatatat gagtaaactt ggtctgacag ttaccaatgc   6720
ttaatcagtg aggcacctat ctcagcgatc tgtctatttc gttcatccat agttgcctga   6780
ctccccgtcg tgtagataac tacgatacgg gagggcttac catctggccc cagtgctgca   6840
atgataccgc gagacccacg ctcaccggct ccagatttat cagcaataaa ccagccagcc   6900
ggaagggccg agcgcagaag tggtcctgca actttatccg cctccatcca gtctattaat   6960
tgttgccggg aagctagagt aagtagttcg ccagttaata gtttgcgcaa cgttgttgcc   7020
attgctacag gcatcgtggt gtcacgctcg tcgtttggta tggcttcatt cagctccggt   7080
tcccaacgat caaggcgagt tacatgatcc cccatgttgt gcaaaaaagc ggttagctcc   7140
ttcggtcctc cgatcgttgt cagaagtaag ttggccgcag tgttatcact catggttatg   7200
gcagcactgc ataattctct tactgtcatg ccatccgtaa gatgcttttc tgtgactggt   7260
gagtactcaa ccaagtcatt ctgagaatag tgtatgcggc gaccgagttg ctcttgcccg   7320
gcgtcaatac gggataatac cgcgccacat agcagaactt taaaagtgct catcattgga   7380
aaacgttctt cggggcgaaa actctcaagg atcttaccgc tgttgagatc cagttcgatg   7440
taacccactc gtgcacccaa ctgatcttca gcatctttta ctttcaccag cgtttctggg   7500
tgagcaaaaa caggaaggca aaatgccgca aaaaagggaa taagggcgac acggaaatgt   7560
tgaatactca tactcttcct ttttcaatat tattgaagca tttatcaggg ttattgtctc   7620
atgagcggat acatatttga atgtatttag aaaaataaac aaataggggt tccgcgcaca   7680
```

```
tttccccgaa aagtgccacc tgacgtcgac ggatcgggag atc                7723


<210> SEQ ID NO 7
<211> LENGTH: 12739
<212> TYPE: DNA
<213> ORGANISM: Artificial
<220> FEATURE:
<223> OTHER INFORMATION: plasmid DNA

<400> SEQUENCE: 7

agcttgcatg cctgcaggtc aattccctgg cattatgccc agtacatgac cttatgggac     60

tttcctactt ggcagtacat ctacgtatta gtcatcgcta ttaccatggt gatgcggttt    120

tggcagtaca tcaatgcgcg tggataccgg tttgactcac ggggatttcc aagtctccac    180

cccattcacg tcaatgggag tttgttttgg caccaaaatc aacgggactt tccaaaatgt    240

cgtaacaact ccgccccatt gacgcaaatg ggcggtaggc gtgtacggtg ggaggtctat    300

ataagcagag ctcgtttagt gaaccgtcag atcgcctgga gacgccatcc acgctgtttt    360

gacctccata gaagacaccg ggaccgatcc agcctgggga tctagcctcc gcggccggga    420

acggtgcatt ggaacgcgga ttccccgtgc caagagtgac gtaagtaccg cctatagagt    480

ctataggccc acccccttgg cttcttatgc atgctatact gtttttggct tggggtctat    540

acacccccgc ttcctcatgt tataggtgat ggtatagctt agcctatagg tgtgggttat    600

tgaccattat tgaccactcc cctattggtg acgatacttt ccattactaa tccataacat    660

ggctctttgc cacaactctc tttattggct atatgccaat acactgtcct tcagagactg    720

acacggactc tgtattttta caggatgggg tctcatttat tatttacaaa ttcacatata    780

caacaccacc gtccccagtg cccgcagttt ttattaaaca taacgtggga tctccacgcg    840

aatctcgggt acgtgttccg gacatgggct cttctccggt agcggcggag ctcctacatc    900

cgagccctgc tcccatgcct ccagcgactc atggtcgctc ggcagctcct tgctcctaac    960

agtggaggcc agacttaggc acagcacgat gcccaccacc accagtgtgc cgcacaaggc   1020

cgtggcggta gggtatgtgt ctgaaaatga gctcggggag cgggcttgca ccgctgacgc   1080

atttggaaga cttaaggcag cggcagaaga agatgcaggc agctgagttg ttgtgttctg   1140

ataagagtca gaggtaactc ccgttgcggt gctgttaacg gtggagggca gtgtagtctg   1200

agcagtactc gttgctgccg cgcgcgccac cagacataat agctgacaga ctaacagact   1260

gttcctttcc atgggtcttt tctgcagtca ccgtccttga cacgatcgga tcccgggtac   1320

ctctagaaga tctgatatcg tcgacctcga cgccaccatg gactcgctat ctgtcaacca   1380

gatcttatac cctgaagttc acctagatag cccgatagtt accaataaga tagtagccat   1440

cctggagtat gctcgagtcc ctcacgctta cagcctggag gaccctacac tgtgtcagaa   1500

catcaagcac cgcctaaaaa acggattttc caaccaaatg attataaaca atgtggaagt   1560

tgggaatgtc atcaagtcca agcttaggag ttatccggcc cactctcata ttccatatcc   1620

aaattgtaat caggatttat ttaacataga agacaaagag tcaacgagga agatccgtga   1680

actcctcaaa aaggggaatt cgctgtactc caaagtcagt gataaggttt tccaatgctt   1740

aagggacact aactcacggc ttggcctagg ctccgaattg agggaggaca tcaaggagaa   1800

agttattaac ttgggagttt acatgcacag ctcccagtgg tttgagccct ttctgttttg   1860

gtttacagtc aagactgaga tgaggtcagt gattaaatca caaacccata cttgccatag   1920

gaggagacac acacctgtat tcttcactgg tagttcagtt gagttgctaa tctctcgtga   1980
```

```
ccttgttgct ataatcagta aagagtctca acatgtatat tacctgacat ttgaactggt   2040
tttgatgtat tgtgatgtca tagaggggag gttaatgaca gagaccgcta tgactattga   2100
tgctaggtat acagagcttc taggaagagt cagatacatg tggaaactga tagatggttt   2160
cttccctgca ctcgggaatc caacttatca aattgtagcc atgctggagc ctctttcact   2220
tgcttacctg cagctgaggg atataacagt agaactcaga ggtgctttcc ttaaccactg   2280
ctttactgaa atacatgatg ttcttgacca aaacgggttt tctgatgaag gtacttatca   2340
tgagttaact gaagctctag attacatttt cataactgat gacatacatc tgacagggga   2400
gattttctca tttttcagaa gtttcggcca ccccagactt gaagcagtaa cggctgctga   2460
aaatgttagg aaatacatga atcagcctaa agtcattgtg tatgagactc tgatgaaagg   2520
tcatgccata ttttgtggaa tcataatcaa cggctatcgt gacaggcacg gaggcagttg   2580
gccaccgctg accctccccc tgcatgctgc agacacaatc cggaatgctc aagcttcagg   2640
tgaagggtta acacatgagc agtgcgttga taactggaaa tcttttgctg gagtgaaatt   2700
tggctgcttt atgcctctta gcctggatag tgatctgaca atgtacctaa aggacaaggc   2760
acttgctgct ctccaaaggg aatgggattc agtttacccg aaagagttcc tgcgttacga   2820
ccctcccaag ggaaccgggt cacggaggct tgtagatgtt ttccttaatg attcgagctt   2880
tgacccatat gatgtgataa tgtatgttgt aagtggagct tacctccatg accctgagtt   2940
caacctgtct tacagcctga aagaaaagga gatcaaggaa acaggtagac tttttgctaa   3000
aatgacttac aaaatgaggg catgccaagt gattgctgaa aatctaatct caaacgggat   3060
tggcaaatat tttaaggaca atgggatggc caaggatgag cacgatttga ctaaggcact   3120
ccacactcta gctgtctcag gagtccccaa agatctcaaa gaaagtcaca ggggggggcc   3180
agtcttaaaa acctactccc gaagcccagt ccacacaagt accaggaacg tgagagcagc   3240
aaaagggttt atagggttcc ctcaagtaat tcggcaggac caagacactg atcatccgga   3300
gaatatggaa gcttacgaga cagtcagtgc atttatcacg actgatctca agaagtactg   3360
ccttaattgg agatatgaga ccatcagctt gtttgcacag aggctaaatg agatttacgg   3420
attgccctca tttttccagt ggctgcataa gaggcttgag acctctgtcc tgtatgtaag   3480
tgaccctcat tgcccccccg accttgacgc ccatatcccg ttatataaag tccccaatga   3540
tcaaatcttc attaagtacc ctatgggagg tatagaaggg tattgtcaga agctgtggac   3600
catcagcacc attccctatc tatacctggc tgcttatgag agcggagtaa ggattgcttc   3660
gttagtgcaa ggggacaatc agaccatagc cgtaacaaaa agggtaccca gcacatggcc   3720
ctacaacctt aagaaacggg aagctgctag agtaactaga gattactttg taattcttag   3780
gcaaaggcta catgatattg gccatcacct caaggcaaat gagacaattg tttcatcaca   3840
tttttttgtc tattcaaaag gaatatatta tgatgggcta cttgtgtccc aatcactcaa   3900
gagcatcgca agatgtgtat tctggtcaga gactatagtt gatgaaacaa gggcagcatg   3960
cagtaatatt gctacaacaa tggctaaaag catcgagaga ggttatgacc gttaccttgc   4020
atattccctg aacgtcctaa aagtgataca gcaaattctg atctctcttg gcttcacaat   4080
caattcaacc atgacccggg atgtagtcat acccctcctc acaaacaacg acctcttaat   4140
aaggatggca ctgttgcccg ctcctattgg ggggatgaat tatctgaata tgagcaggct   4200
gtttgtcaga aacatcggtg atccagtaac atcatcaatt gctgatctca agagaatgat   4260
tctcgcctca ctaatgcctg aagagaccct ccatcaagta atgacacaac aaccggggga   4320
ctcttcattc ctagactggg ctagcgaccc ttactcagca aatcttgtat gtgtccagag   4380
```

```
catcactaga ctcctcaaga acataactgc aaggtttgtc ctgatccata gtccaaaccc   4440
aatgttaaaa ggattattcc atgatgacag taaagaagag gacgagggac tggcggcatt   4500
cctcatggac aggcatatta tagtacctag ggcagctcat gaaatcctgg atcatagtgt   4560
cacaggggca agagagtcta ttgcaggcat gctggatacc acaaaaggct tgattcgagc   4620
cagcatgagg aaggggggt taacctctcg agtgataacc agattgtcca attatgacta    4680
tgaacaattc agagcaggga tggtgctatt gacaggaaga aagagaaatg tcctcattga   4740
caaagagtca tgttcagtgc agctggcgag agctctaaga agccatatgt gggcgaggct   4800
agctcgagga cggcctattt acggccttga ggtccctgat gtactagaat ctatgcgagg   4860
ccaccttatt cggcgtcatg agacatgtgt catctgcgag tgtggatcag tcaactacgg   4920
atggtttttt gtcccctcgg gttgccaact ggatgatatt gacaaggaaa catcatcctt   4980
gagagtccca tatattggtt ctaccactga tgagagaaca gacatgaagc ttgccttcgt   5040
aagagcccca agtcgatcct tgcgatctgc tgttagaata gcaacagtgt actcatgggc   5100
ttacggtgat gatgatagct cttggaacga agcctggttg ttggctaggc aaagggccaa   5160
tgtgagcctg gaggagctaa gggtgatcac tcccatctca acttcgacta atttagcgca   5220
taggttgagg gatcgtagca ctcaagtgaa atactcaggt acatcccttg tccgagtggc   5280
gaggtatacc acaatctcca acgacaatct ctcatttgtc atatcagata agaaggttga   5340
tactaacttt atataccaac aaggaatgct tctagggttg ggtgttttag aaacattgtt   5400
tcgactcgag aaagataccg gatcatctaa cacggtatta catcttcacg tcgaaacaga   5460
ttgttgcgtg atcccgatga tagatcatcc caggataccc agctcccgca agctagagct   5520
gagggcagag ctatgtacca acccattgat atatgataat gcacctttaa ttgacagaga   5580
tgcaacaagg ctatacaccc agagccatag gaggcacctt gtggaatttg ttacatggtc   5640
cacaccccaa ctatatcaca ttttagctaa gtccacagca ctatctatga ttgacctggt   5700
aacaaaattt gagaaggacc atatgaatga aatttcagct ctcatagggg atgacgatat   5760
caatagtttc ataactgagt ttctgctcat agagccaaga ttattcacta tctacttggg   5820
ccagtgtgcg gccatcaatt gggcatttga tgtacattat catagaccat cagggaaata   5880
tcagatgggt gagctgttgt catcgttcct ttctagaatg agcaaaggag tgtttaaggt   5940
gcttgtcaat gctctaagcc acccaaagat ctacaagaaa ttctggcatt gtggtattat   6000
agagcctatc catggtcctt cacttgatgc tcaaaacttg cacacaactg tgtgcaacat   6060
ggtttacaca tgctatatga cctacctcga cctgttgttg aatgaagagt tagaagagtt   6120
cacatttctc ttgtgtgaaa gcgacgagga tgtagtaccg gacagattcg acaacatcca   6180
ggcaaaacac ttatgtgttc tggcagattt gtactgtcaa ccagggacct gcccaccaat   6240
tcgaggtcta agaccggtag agaaatgtgc agttctaacc gaccatatca aggcagaggc   6300
tatgttatct ccagcaggat cttcgtggaa cataaatcca attattgtag accattactc   6360
atgctctctg acttatctcc ggcgaggatc gatcaaacag ataagattga gagttgatcc   6420
aggattcatt ttcgacgccc tcgctgaggt aaatgtcagt cagccaaaga tcggcagcaa   6480
caacatctca aatatgagca tcaaggcttt cagaccccca cacgatgatg ttgcaaaatt   6540
gctcaaagat atcaacacaa gcaagcacaa tcttcccatt tcagggggca atctcgccaa   6600
ttatgaaatc catgctttcc gcagaatcgg gttgaactca tctgcttgct acaaagctgt   6660
tgagatatca acattaatta ggagatgcct tgagccaggg gaggacggct tgttcttggg   6720
```

-continued

```
tgagggatcg ggttctatgt tgatcactta taaagagata cttaaactaa acaagtgctt   6780

ctataatagt ggggtttccg ccaattctag atctggtcaa agggaattag caccctatcc   6840

ctccgaagtt ggccttgtcg aacacagaat gggagtaggt aatattgtca aagtgctctt   6900

taacgggagg cccgaagtca cgtgggtagg cagtgtagat tgcttcaatt tcatagttag   6960

taatatccct acctctagtg tggggtttat ccattcagat atagagacct tgcctgacaa   7020

agatactata gagaagctag aggaattggc agccatctta tcgatggctc tgctcctggg   7080

caaaatagga tcaatactgg tgattaagct tatgcctttc agcggggatt ttgttcaggg   7140

atttataagt tatgtagggt ctcattatag agaagtgaac cttgtatacc ctagatacag   7200

caacttcatc tctactgaat cttatttggt tatgacagat ctcaaggcta accggctaat   7260

gaatcctgaa aagattaagc agcagataat tgaatcatct gtgaggactt cacctggact   7320

tataggtcac atcctatcca ttaagcaact aagctgcata caagcaattg tgggagacgc   7380

agttagtaga ggtgatatca atcctactct gaaaaaactt acacctatag agcaggtgct   7440

gatcaattgc gggttggcaa ttaacggacc taagctgtgc aaagaattga tccaccatga   7500

tgttgcctca gggcaagatg gattgcttaa ttctatactc atcctctaca gggagttggc   7560

aagattcaaa gacaaccaaa gaagtcaaca agggatgttc cacgcttacc ccgtattggt   7620

aagtagcagg caacgagaac ttatatctag gatcacccgc aaattctggg ggcacattct   7680

tctttactcc gggaacaaaa agttgataaa taagtttatc cagaatctca agtccggcta   7740

tctgatacta gacttacacc agaatatctt cgttaagaat ctatccaagt cagagaaaca   7800

gattattatg acggggggtt tgaaacgtga gtgggttttt aaggtaacag tcaaggagac   7860

caaagaatgg tataagttag tcggatacag tgccctgatt aaggactaat tggttgaact   7920

ccggaaccct aatcctgccc taggtggtta ggcattattt gcagaattct agatcccacg   7980

tcactattgt atactctata ttatactcta tgttatactc tgtaatccta ctcaataaac   8040

gtgtcacgcc tgtgaaaccg tactaagtct cccgtgtctt cttatcacca tcaggtgaca   8100

tcctcgccca ggctgtcaat catgccggta tcgattccag tagcaccggc cccacgctga   8160

caacccactc ttgcagcgtt agcagcgccc ctcttaacaa gccgaccccc accagcgtcg   8220

cggttactaa cactcctctc cccgacctgc agcccaagct ctagagggcc ctattctata   8280

gtgtcaccta aatgctagag ctcgctgatc agcctcgact gtgccttcta gttgccagcc   8340

atctgttgtt tgcccctccc ccgtgccttc cttgaccctg gaaggtgcca ctcccactgt   8400

cctttcctaa taaaatgagg aaattgcatc gcattgtctg agtaggtgtc attctattct   8460

ggggggtggg gtggggcagg acagcaaggg ggaggattgg gaagacaata gcaggcatgc   8520

tggggatgcg gtgggctcta tggcttctga ggcggaaaga accagctggg gctctagggg   8580

gtatccccac gcgccctgta gcggcgcatt aagcgcggcg ggtgtggtgg ttacgcgcag   8640

cgtgaccgct acacttgcca gcgccctagc gcccgctcct ttcgctttct tcccttcctt   8700

tctcgccacg ttcgccggct ttccccgtca agctctaaat cggggcatcc ctttagggtt   8760

ccgatttagt gctttacggc acctcgaccc caaaaaactt gattagggtg atggttcacg   8820

tagtgggcca tcgccctgat agacggtttt tcgccctttg acgttggagt ccacgttctt   8880

taatagtgga ctcttgttcc aaactggaac aacactcaac cctatctcgg tctattcttt   8940

tgatttataa gggattttgg ggatttcggc ctattggtta aaaaatgagc tgatttaaca   9000

aaaatttaac gcgaattaat tctgtggaat gtgtgtcagt tagggtgtgg aaagtcccca   9060

ggctccccag gcaggcagaa gtatgcaaag catgcatctc aattagtcag caaccaggtg   9120
```

```
tggaaagtcc ccaggctccc cagcaggcag aagtatgcaa agcatgcatc tcaattagtc   9180
agcaaccata gtcccgcccc taactccgcc catcccgccc ctaactccgc ccagttccgc   9240
ccattctccg ccccatggct gactaatttt ttttatttat gcagaggccg aggccgcctc   9300
tgcctctgag ctattccaga agtagtgagg aggctttttt ggaggcctag gcttttgcaa   9360
aaagctcccg ggagcttgta tatccatttt cggatctgat caagagacag gatgaggatc   9420
gtttcgcatg attgaacaag atggattgca cgcaggttct ccggccgctt gggtggagag   9480
gctattcggc tatgactggg cacaacagac aatcggctgc tctgatgccg ccgtgttccg   9540
gctgtcagcg caggggcgcc cggttctttt tgtcaagacc gacctgtccg gtgccctgaa   9600
tgaactgcag gacgaggcag cgcggctatc gtggctggcc acgacgggcg ttccttgcgc   9660
agctgtgctc gacgttgtca ctgaagcggg aagggactgg ctgctattgg gcgaagtgcc   9720
ggggcaggat ctcctgtcat ctcaccttgc tcctgccgag aaagtatcca tcatggctga   9780
tgcaatgcgg cggctgcata cgcttgatcc ggctacctgc ccattcgacc accaagcgaa   9840
acatcgcatc gagcgagcac gtactcggat ggaagccggt cttgtcgatc aggatgatct   9900
ggacgaagag catcaggggc tcgcgccagc cgaactgttc gccaggctca aggcgcgcat   9960
gcccgacggc gaggatctcg tcgtgaccca tggcgatgcc tgcttgccga atatcatggt  10020
ggaaaatggc cgcttttctg gattcatcga ctgtggccgg ctgggtgtgg cggaccgcta  10080
tcaggacata gcgttggcta cccgtgatat tgctgaagag cttggcggcg aatgggctga  10140
ccgcttcctc gtgctttacg gtatcgccgc tcccgattcg cagcgcatcg ccttctatcg  10200
ccttcttgac gagttcttct gagcgggact ctggggttcg aaatgaccga ccaagcgacg  10260
cccaacctgc catcacgaga tttcgattcc accgccgcct tctatgaaag gttgggcttc  10320
ggaatcgttt tccgggacgc cggctggatg atcctccagc gcggggatct catgctggag  10380
ttcttcgccc accccaactt gtttattgca gcttataatg gttacaaata aagcaatagc  10440
atcacaaatt tcacaaataa agcatttttt tcactgcatt ctagttgtgg tttgtccaaa  10500
ctcatcaatg tatcttatca tgtctgtata ccgtcgacct ctagctagag cttggcgtaa  10560
tcatggtcat agctgtttcc tgtgtgaaat tgttatccgc tcacaattcc acacaacata  10620
cgagccggaa gcataaagtg taaagcctgg ggtgcctaat gagtgagcta actcacatta  10680
attgcgttgc gctcactgcc cgctttccag tcgggaaacc tgtcgtgcca gctgcattaa  10740
tgaatcggcc aacgcgcggg gagaggcggt ttgcgtattg ggcgctcttc cgcttcctcg  10800
ctcactgact cgctgcgctc ggtcgttcgg ctgcggcgag cggtatcagc tcactcaaag  10860
gcggtaatac ggttatccac agaatcaggg gataacgcag gaaagaacat gtgagcaaaa  10920
ggccagcaaa aggccaggaa ccgtaaaaag gccgcgttgc tggcgttttt ccataggctc  10980
cgcccccctg acgagcatca caaaaatcga cgctcaagtc agaggtggcg aaacccgaca  11040
ggactataaa gataccaggc gtttccccct ggaagctccc tcgtgcgctc tcctgttccg  11100
accctgccgc ttaccggata cctgtccgcc tttctccctt cgggaagcgt ggcgctttct  11160
caatgctcac gctgtaggta tctcagttcg gtgtaggtcg ttcgctccaa gctgggctgt  11220
gtgcacgaac cccccgttca gcccgaccgc tgcgccttat ccggtaacta tcgtcttgag  11280
tccaacccgg taagacacga cttatcgcca ctggcagcag ccactggtaa caggattagc  11340
agagcgaggt atgtaggcgg tgctacagag ttcttgaagt ggtggcctaa ctacggctac  11400
actagaagga cagtatttgg tatctgcgct ctgctgaagc cagttacctt cggaaaaaga  11460
```

```
gttggtagct cttgatccgg caaacaaacc accgctggta gcggtggttt ttttgtttgc  11520
aagcagcaga ttacgcgcag aaaaaaagga tctcaagaag atcctttgat cttttctacg  11580
gggtctgacg ctcagtggaa cgaaaactca cgttaaggga ttttggtcat gagattatca  11640
aaaaggatct tcacctagat ccttttaaat taaaaatgaa gttttaaatc aatctaaagt  11700
atatatgagt aaacttggtc tgacagttac caatgcttaa tcagtgaggc acctatctca  11760
gcgatctgtc tatttcgttc atccatagtt gcctgactcc ccgtcgtgta gataactacg  11820
atacgggagg gcttaccatc tggccccagt gctgcaatga taccgcgaga cccacgctca  11880
ccggctccag atttatcagc aataaaccag ccagccggaa gggccgagcg cagaagtggt  11940
cctgcaactt tatccgcctc catccagtct attaattgtt gccgggaagc tagagtaagt  12000
agttcgccag ttaatagttt gcgcaacgtt gttgccattg ctacaggcat cgtggtgtca  12060
cgctcgtcgt ttggtatggc ttcattcagc tccggttccc aacgatcaag gcgagttaca  12120
tgatccccca tgttgtgcaa aaaagcggtt agctccttcg gtcctccgat cgttgtcaga  12180
agtaagttgg ccgcagtgtt atcactcatg gttatggcag cactgcataa ttctcttact  12240
gtcatgccat ccgtaagatg cttttctgtg actggtgagt actcaaccaa gtcattctga  12300
gaatagtgta tgcggcgacc gagttgctct tgcccggcgt caatacggga taataccgcg  12360
ccacatagca gaactttaaa agtgctcatc attggaaaac gttcttcggg gcgaaaactc  12420
tcaaggatct taccgctgtt gagatccagt tcgatgtaac ccactcgtgc acccaactga  12480
tcttcagcat cttttacttt caccagcgtt tctgggtgag caaaaacagg aaggcaaaat  12540
gccgcaaaaa agggaataag ggcgacacgg aaatgttgaa tactcatact cttccttttt  12600
caatattatt gaagcattta tcagggttat tgtctcatga gcggatacat atttgaatgt  12660
atttagaaaa ataaacaaat aggggttccg cgcacatttc cccgaaaagt gccacctgac  12720
gtcgacggat cgggagatc                                               12739
```

<210> SEQ ID NO 8
<211> LENGTH: 20546
<212> TYPE: DNA
<213> ORGANISM: Artificial
<220> FEATURE:
<223> OTHER INFORMATION: plasmid DNA

<400> SEQUENCE: 8

```
accaaacaaa gttgggtaag gatagttcaa tcaatgatca tcttctagtg cacttaggat     60
tcaagatcct attatcaggg acaagagcag gattagggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtgaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcgg gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
```

```
aggacctctc cttacgccga ttcatggtcg ctctaatcct ggatatcaag agaacacccg     840
gaaacaaacc caggattgct gaaatgatat gtgacattga tacatatatc gtagaggcag     900
gattagccag ttttatcctg actattaagt ttgggataga aactatgtat cctgctcttg     960
gactgcatga atttgctggt gagttatcca cacttgagtc cttgatgaac ctttaccagc    1020
aaatgggggga aactgcaccc tacatggtaa tcctggagaa ctcaattcag aacaagttca   1080
gtgcaggatc ataccctctg ctctggagct atgccatggg agtaggagtg gaacttgaaa    1140
actccatggg aggtttgaac tttggccgat cttactttga tccagcatat tttagattag    1200
ggcaagagat ggtaaggagg tcagctggaa aggtcagttc cacattggca tctgaactcg    1260
gtatcactgc cgaggatgca aggcttgttt cagagattgc aatgcatact actgaggaca    1320
agatcagtag agcggttgga cccagacaag cccaagtatc atttctacac ggtgatcaaa    1380
gtgagaatga gctaccgaga ttgggggggca aggaagatag gagggtcaaa cagagtcgag   1440
gagaagccag ggagagctac agagaaaccg ggcccagcag agcaagtgat gcgagagctg    1500
cccatcttcc aaccggcaca cccctagaca ttgacactgc aacggagtcc agccaagatc    1560
cgcaggacag tcgaaggtca gctgacgccc tgcttaggct gcaagccatg gcaggaatct    1620
cggaagaaca aggctcagac acggacaccc ctatagtgta caatgacaga aatcttctag    1680
actaggtgcg agaggccgag ggccagaaca acatccgcct accatccatc attgttataa    1740
aaaacttagg aaccaggtcc acacagccgc cagcccatca accatccact cccacgattg    1800
gagccaatgg cagaagagca ggcacgccat gtcaaaaacg gactggaatg catccgggct    1860
ctcaaggccg agcccatcgg ctcactggcc atcgaggaag ctatggcagc atggtcagaa    1920
atatcagaca acccaggaca ggagcgagcc acctgcaggg aagagaaggc aggcagttcg    1980
ggtctcagca aaccatgcct ctcagcaatt ggatcaactg aaggcggtgc acctcgcatc    2040
cgcggtcagg gacctggaga gagcgatgac gacgctgaaa ctttgggaat ccccccaaga    2100
aatctccagg catcaagcac tgggttacag tgttattacg tttatgatca cagcggtgaa    2160
gcggttaagg gaatccaaga tgctgactct atcatggttc aatcaggcct tgatggtgat    2220
agcaccctct caggaggaga caatgaatct gaaaacagcg atgtggatat tggcgaacct    2280
gataccgagg gatatgctat cactgaccgg ggatctgctc ccatctctat ggggttcagg    2340
gcttctgatg ttgaaactgc agaaggaggg gagatccacg agctcctgag actccaatcc    2400
agaggcaaca actttccgaa gcttgggaaa actctcaatg ttcctccgcc cccggacccc    2460
ggtagggcca gcacttccgg gacacccatt aaaaagggca cagacgcgag attagcctca    2520
tttggaacgg agatcgcgtc tttattgaca ggtggtgcaa cccaatgtgc tcgaaagtca    2580
ccctcggaac catcagggcc aggtgcacct gcggggaatg tccccgagtg tgtgagcaat    2640
gccgcactga tacaggagtg gacacccgaa tctggtacca caatctcccc gagatcccag    2700
aataatgaag aagggggaga ctattatgat gatgagctgt tctctgatgt ccaagatatt    2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctggaagg acacctctca agcatcatga tcgccattcc tggacttggg    2940
aaggatccca acgaccccac tgcagatgtc gaaatcaatc ccgacttgaa acccatcata    3000
ggcagagatt caggccgagc actggccgaa gttctcaaga aacccgttgc cagccgacaa    3060
ctccaaggaa tgacaaatgg acggaccagt tccagaggac agctgctgaa ggaatttcag    3120
```

-continued

```
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagtcc tccatcattg ttataaaaaa cttaggaacc aggtccatac   3420
accgtacgct cgaggcgcgt gccaccatgg tgacaggggg aatggcaagc aagtgggatc   3480
agaagggtat ggacattgcc tatgaggagg cggccttagg ttacaaagag ggtggtgttc   3540
ctattggcgg atgtcttatc aataacaaag acggaagtgt tctcggtcgt ggtcacaaca   3600
tgagatttca aaagggatcc gccacactac atggtgagat ctccactttg gaaaactgtg   3660
ggagattaga gggcaaagtg tacaaagata ccactttgta tacgacgctg tctccatgcg   3720
acatgtgtac aggtgccatc atcatgtatg gtattccacg ctgtgttgtc ggtgagaacg   3780
ttaatttcaa aagtaagggc gagaaatatt tacaaactag aggtcacgag gttgttgttg   3840
ttgacgatga gaggtgtaaa aagatcatga aacaatttat cgatgaaaga cctcaggatt   3900
ggtttgaaga tattggtgag gcttcggaac catttaagaa cgtctacttg ctacctcaaa   3960
caaaccaatt gctgggtttg tacaccatca tcagaaataa gaatacaact agacctgatt   4020
tcattttcta ctccgataga atcatcagat tgttggttga agaaggtttg aaccatctac   4080
ctgtgcaaaa gcaaattgtg gaaactgaca ccaacgaaaa cttcgaaggt gtctcattca   4140
tgggtaaaat ctgtggtgtt tccattgtca gagctggtga atcgatggag caaggattaa   4200
gagactgttg taggtctgtg cgtatcggta aaattttaat tcaaagggac gaggagactg   4260
ctttaccaaa gttattctac gaaaaattac cagaggatat atctgaaagg tatgtcttcc   4320
tattagaccc aatgctggcc accggtggta gtgctatcat ggctacagaa gtcttgatta   4380
agagaggtgt taagccagag agaatttact tcttaaacct aatctgtagt aaggaaggga   4440
ttgaaaaata ccatgccgcc ttcccagagg tcagaattgt tactggtgcc ctcgacagag   4500
gtctagatga aaacaagtat ctagttccag ggttgggtga ctttggtgac agatactact   4560
gtgtttaaac gcgcgacgtc tagtacaacc taaatccatt ataaaaaact taggagcaaa   4620
gtgattgcct cccaaggtcc acaatgacag agacctacga cttcgacaag tcggcatggg   4680
acatcaaagg gtcgatcgct ccgatacaac ccaccaccta cagtgatggc aggctggtgc   4740
cccaggtcag agtcatagat cctggtctag gcgacaggaa ggatgaatgc tttatgtaca   4800
tgtttctgct gggggttgtt gaggacagcg attccctagg gcctccaatc gggcgagcat   4860
ttgggttcct gcccttaggt gttggcagat ccacagcaaa gcccgaaaaa ctcctcaaag   4920
aggccactga gcttgacata gttgttagac gtacagcagg gctcaatgaa aaactggtgt   4980
tctacaacaa caccccacta actctcctca caccttggag aaaggtccta acaacaggga   5040
gtgtcttcaa cgcaaaccaa gtgtgcaatg cggttaatct gataccgctc gataccccgc   5100
agaggttccg tgttgtttat atgagcatca cccgtctttc ggataacggg tattacaccg   5160
ttcctagaag aatgctggaa ttcagatcgg tcaatgcagt ggccttcaac ctgctggtga   5220
cccttaggat tgacaaggcg ataggccctg ggaagatcat cgacaataca gagcaacttc   5280
ctgaggcaac atttatggtc cacatcggga acttcaggag aaagaagagt gaagtctact   5340
ctgccgatta ttgcaaaatg aaaatcgaaa agatgggcct ggtttttgca cttggtggga   5400
tagggggcac cagtcttcac attagaagca caggcaaaat gagcaagact ctccatgcac   5460
aactcgggtt caagaagacc ttatgttacc cgctgatgga tatcaatgaa gaccttaatc   5520
```

```
gattactctg gaggagcaga tgcaagatag taagaatcca ggcagttttg cagccatcag   5580
ttcctcaaga attccgcatt tacgacgacg tgatcataaa tgatgaccaa ggactattca   5640
aagttctgta gaccgtagtg cccagcaatg cccgaaaacg acccccctca caatgacagc   5700
cagaaggccc ggacaaaaaa gccccctccg aaagactcca cggaccaagc gagaggccag   5760
ccagcagccg acggcaagcg cgaacaccag gcggccccag cacagaacag ccctgacaca   5820
aggccaccac cagccacccc aatctgcatc ctcctcgtgg gacccccgag gaccaacccc   5880
caaggctgcc cccgatccaa accaccaacc gcatccccac cacccccggg aaagaaaccc   5940
ccagcaattg gaaggcccct cccctcttc ctcaacacaa gaactccaca accgaaccgc   6000
acaagcgacc gaggtgaccc aaccgcaggc atccgactcc ctagacagat cctctctccc   6060
cggcaaacta aacaaaactt agggccaagg aacatacaca cccaacagaa cccagacccc   6120
ggcccacggc gccgcgcccc caaccccga caaccagagg gagcccccaa ccaatcccgc   6180
cggctccccc ggtgcccaca ggcagggaca ccaaccccg aacagaccca gcacccaacc   6240
atcgacaatc caagacgggg gggccccccc aaaaaaaggc ccccaggggc cgacagccag   6300
caccgcgagg aagcccaccc accccacaca cgaccacggc aaccaaacca gaacccagac   6360
caccctgggc caccagctcc cagactcggc catcaccccg cagaaaggaa aggccacaac   6420
ccgcgcaccc cagccccgat ccggcgggga gccacccaac ccgaaccagc acccaagagc   6480
gatccccgaa ggacccccga accgcaaagg acatcagtat cccacagcct ctccaagtcc   6540
cccggtctcc tcctcttctc gaagggacca aaagatcaat ccaccacacc cgacgacact   6600
caactcccca cccctaaagg agacaccggg aatcccagaa tcaagactca tccaatgtcc   6660
atcatgggtc tcaaggtgaa cgtctctgcc atattcatgg cagtactgtt aactctccaa   6720
acacccaccg gtcaaatcca ttggggcaat ctctctaaga taggggtggt aggaatagga   6780
agtgcaagct acaaagttat gactcgttcc agccatcaat cattagtcat aaaattaatg   6840
cccaatataa ctctcctcaa taactgcacg agggtagaga ttgcagaata caggagacta   6900
ctgagaacag ttttggaacc aattagagat gcacttaatg caatgaccca gaatataaga   6960
ccggttcaga gtgtagcttc aagtaggaga cacaagagat ttgcgggagt agtcctggca   7020
ggtgcggccc taggcgttgc cacagctgct cagataacag ccggcattgc acttcaccag   7080
tccatgctga actctcaagc catcgacaat ctgagagcga gcctggaaac tactaatcag   7140
gcaattgaga caatcagaca agcagggcag gagatgatat tggctgttca gggtgtccaa   7200
gactacatca ataatgagct gataccgtct atgaaccaac tatcttgtga tttaatcggc   7260
cagaagctcg ggctcaaatt gctcagatac tatacagaaa tcctgtcatt atttggcccc   7320
agtttacggg accccatatc tgcggagata tctatccagg ctttgagcta tgcgcttgga   7380
ggagacatca ataaggtgtt agaaaagctc ggatacagtg gaggtgattt actgggcatc   7440
ttagagagcg gaggaataaa ggcccggata actcacgtcg acacagagtc ctacttcatt   7500
gtcctcagta tagcctatcc gacgctgtcc gagattaagg gggtgattgt ccaccggcta   7560
gagggggtct cgtacaacat aggctctcaa gagtggtata ccactgtgcc caagtatgtt   7620
gcaacccaag ggtaccttat ctcgaatttt gatgagtcat cgtgtacttt catgccagag   7680
gggactgtgt gcagccaaaa tgccttgtac ccgatgagtc ctctgctcca agaatgcctc   7740
cgggggtaca ccaagtcctg tgctcgtaca ctcgtatccg ggtcttttgg gaaccggttc   7800
attttatcac aagggaacct aatagccaat tgtgcatcaa tcctttgcaa gtgttacaca   7860
```

```
acaggaacga tcattaatca agaccctgac aagatcctaa catacattgc tgccgatcac   7920
tgcccggtag tcgaggtgaa cggcgtgacc atccaagtcg ggagcaggag gtatccagac   7980
gctgtgtact tgcacagaat tgacctcggt cctcccatat cattggagag gttggacgta   8040
gggacaaatc tggggaatgc aattgctaag ttggaggatg ccaaggaatt gttggagtca   8100
tcggaccaga tattgaggag tatgaaaggt ttatcgagca ctagcatagt ctacatcctg   8160
attgcagtgt gtcttggagg gttgataggg atccccgctt taatatgttg ctgcaggggg   8220
cgttgtaaca aaaagggaga acaagttggt atgtcaagac caggcctaaa gcctgatctt   8280
acgggaacat caaaatccta tgtaaggtcg ctctgatcct ctacaactct tgaaacacaa   8340
atgtcccaca agtctcctct tcgtcatcaa gcaaccaccg cacccagcat caagcccacc   8400
tgaaattatc tccggcttcc ctctggccga acaatatcgg tagttaatca aaacttaggg   8460
tgcaagatca tccacaatgt caccacaacg agaccggata aatgccttct acaaagataa   8520
cccccatccc aagggaagta ggatagtcat taacagagaa catcttatga ttgatagacc   8580
ttatgttttg ctggctgttc tgtttgtcat gtttctgagc ttgatcgggt tgctagccat   8640
tgcaggcatt agacttcatc gggcagccat ctacaccgca gagatccata aaagcctcag   8700
caccaatcta gatgtaacta actcaatcga gcatcaggtc aaggacgtgc tgacaccact   8760
cttcaaaatc atcggtgatg aagtgggcct gaggacacct cagagattca ctgacctagt   8820
gaaattaatc tctgacaaga ttaaattcct taatccggat agggagtacg acttcagaga   8880
tctcacttgg tgtatcaacc cgccagagag aatcaaattg gattatgatc aatactgtgc   8940
agatgtggct gctgaagagc tcatgaatgc attggtgaac tcaactctac tggagaccag   9000
aacaaccaat cagttcctag ctgtctcaaa gggaaactgc tcagggccca ctacaatcag   9060
aggtcaattc tcaaacatgt cgctgtccct gttagacttg tatttaggtc gaggttacaa   9120
tgtgtcatct atagtcacta tgacatccca gggaatgtat gggggaactt acctagtgga   9180
aaagcctaat ctgagcagca aaaggtcaga gttgtcacaa ctgagcatgt accgagtgtt   9240
tgaagtaggt gttatcagaa atccgggttt gggggctccg gtgttccata tgacaaacta   9300
tcttgagcaa ccagtcagta atgatctcag caactgtatg gtggctttgg gggagctcaa   9360
actcgcagcc ctttgtcacg gggaagattc tatcacaatt ccctatcagg gatcagggaa   9420
aggtgtcagc ttccagctcg tcaagctagg tgtctggaaa tccccaaccg acatgcaatc   9480
ctgggtcccc ttatcaacgg atgatccagt gatagacagg ctttacctct catctcacag   9540
aggtgttatc gctgacaatc aagcaaaatg ggctgtcccg acaacacgaa cagatgacaa   9600
gttgcgaatg gagacatgct tccaacaggc gtgtaagggt aaaatccaag cactctgcga   9660
gaatcccgag tgggcaccat tgaaggataa caggattcct tcatacgggg tcttgtctgt   9720
tgatctgagt ctgacagttg agcttaaaat caaaattgct tcgggattcg ggccattgat   9780
cacacacggt tcagggatgg acctatacaa atccaaccac aacaatgtgt attggctgac   9840
tatcccgcca atgaagaacc tagccttagg tgtaatcaac acattggagt ggataccgag   9900
attcaaggtt agtccctacc tcttcactgt cccaattaag gaagcaggcg aagactgcca   9960
tgccccaaca tacctacctg cggaggtgga tggtgatgtc aaactcagtt ccaatctggt  10020
gattctacct ggtcaagatc tccaatatgt tttggcaacc tacgatactt ccagggttga  10080
acatgctgtg gtttattacg tttacagccc aagccgctca ttttcttact tttatccttt  10140
taggttgcct ataaaggggg tccccatcga attacaagtg gaatgcttca catgggacca  10200
aaaactctgg tgccgtcact tctgtgtgct tgcggactca gaatctggtg gacatatcac  10260
```

```
tcactctggg atggtgggca tgggagtcag ctgcacagtc acccgggaag atggaaccaa  10320
tcgcagatag ggctgctagt gaaccaatca catgatgtca cccagacatc aggcataccc  10380
actagtgtga aatagacatc agaattaaga aaaacgtagg gtccaagtgg ttccccgtta  10440
tggactcgct atctgtcaac cagatcttat accctgaagt tcacctagat agcccgatag  10500
ttaccaataa gatagtagcc atcctggagt atgctcgagt ccctcacgct tacagcctgg  10560
aggaccctac actgtgtcag aacatcaagc accgcctaaa aaacggattt tccaaccaaa  10620
tgattataaa caatgtggaa gttgggaatg tcatcaagtc caagcttagg agttatccgg  10680
cccactctca tattccatat ccaaattgta atcaggattt atttaacata gaagacaaag  10740
agtcaacgag gaagatccgt gaactcctca aaaaggggaa ttcgctgtac tccaaagtca  10800
gtgataaggt tttccaatgc ttaagggaca ctaactcacg gcttggccta ggctccgaat  10860
tgagggagga catcaaggag aaagttatta acttgggagt ttacatgcac agctcccagt  10920
ggtttgagcc ctttctgttt tggtttacag tcaagactga gatgaggtca gtgattaaat  10980
cacaaaccca tacttgccat aggaggagac acacacctgt attcttcact ggtagttcag  11040
ttgagttgct aatctctcgt gaccttgttg ctataatcag taaagagtct caacatgtat  11100
attacctgac atttgaactg gttttgatgt attgtgatgt catagagggg aggttaatga  11160
cagagaccgc tatgactatt gatgctaggt atacagagct tctaggaaga gtcagataca  11220
tgtggaaact gatagatggt ttcttccctg cactcgggaa tccaacttat caaattgtag  11280
ccatgctgga gcctctttca cttgcttacc tgcagctgag ggatataaca gtagaactca  11340
gaggtgcttt ccttaaccac tgctttactg aaatacatga tgttcttgac caaaacgggt  11400
tttctgatga aggtacttat catgagttaa ctgaagctct agattacatt ttcataactg  11460
atgacataca tctgacaggg gagattttct cattttcag aagtttcggc caccccagac  11520
ttgaagcagt aacggctgct gaaaatgtta ggaaatacat gaatcagcct aaagtcattg  11580
tgtatgagac tctgatgaaa ggtcatgcca tattttgtgg aatcataatc aacggctatc  11640
gtgacaggca cggaggcagt tggccaccgc tgaccctccc cctgcatgct gcagacacaa  11700
tccggaatgc tcaagcttca ggtgaagggt taacacatga gcagtgcgtt gataactgga  11760
aatcttttgc tggagtgaaa tttggctgct ttatgcctct tagcctggat agtgatctga  11820
caatgtacct aaaggacaag gcacttgctg ctctccaaag ggaatgggat tcagtttacc  11880
cgaaagagtt cctgcgttac gaccctccca agggaaccgg gtcacggagg cttgtagatg  11940
ttttccttaa tgattcgagc tttgacccat atgatgtgat aatgtatgtt gtaagtggag  12000
cttacctcca tgaccctgag ttcaacctgt cttacagcct gaaagaaaag gagatcaagg  12060
aaacaggtag actttttgct aaaatgactt acaaaatgag ggcatgccaa gtgattgctg  12120
aaaatctaat ctcaaacggg attggcaaat attttaagga caatgggatg gccaaggatg  12180
agcacgattt gactaaggca ctccacactc tagctgtctc aggagtcccc aaagatctca  12240
aagaaagtca caggggggggg ccagtcttaa aaacctactc ccgaagccca gtccacacaa  12300
gtaccaggaa cgtgagagca gcaaaagggt ttatagggtt ccctcaagta attcggcagg  12360
accaagacac tgatcatccg gagaatatgg aagcttacga gacagtcagt gcatttatca  12420
cgactgatct caagaagtac tgccttaatt ggagatatga gaccatcagc ttgtttgcac  12480
agaggctaaa tgagatttac ggattgccct catttttcca gtggctgcat aagaggcttg  12540
agacctctgt cctgtatgta agtgaccctc attgcccccc cgaccttgac gcccatatcc  12600
```

```
cgttatataa agtccccaat gatcaaatct tcattaagta ccctatggga ggtatagaag  12660
ggtattgtca gaagctgtgg accatcagca ccattcccta tctatacctg gctgcttatg  12720
agagcggagt aaggattgct tcgttagtgc aaggggacaa tcagaccata gccgtaacaa  12780
aaagggtacc cagcacatgg ccctacaacc ttaagaaacg ggaagctgct agagtaacta  12840
gagattactt tgtaattctt aggcaaaggc tacatgatat tggccatcac ctcaaggcaa  12900
atgagacaat tgtttcatca catttttttg tctattcaaa aggaatatat tatgatgggc  12960
tacttgtgtc ccaatcactc aagagcatcg caagatgtgt attctggtca gagactatag  13020
ttgatgaaac aagggcagca tgcagtaata ttgctacaac aatggctaaa agcatcgaga  13080
gaggttatga ccgttacctt gcatattccc tgaacgtcct aaaagtgata cagcaaattc  13140
tgatctctct tggcttcaca atcaattcaa ccatgacccg ggatgtagtc atacccctcc  13200
tcacaaacaa cgacctctta ataaggatgg cactgttgcc cgctcctatt ggggggatga  13260
attatctgaa tatgagcagg ctgtttgtca gaaacatcgg tgatccagta acatcatcaa  13320
ttgctgatct caagagaatg attctcgcct cactaatgcc tgaagagacc ctccatcaag  13380
taatgacaca acaaccgggg gactcttcat tcctagactg ggctagcgac ccttactcag  13440
caaatcttgt atgtgtccag agcatcacta gactcctcaa gaacataact gcaaggtttg  13500
tcctgatcca tagtccaaac ccaatgttaa aaggattatt ccatgatgac agtaaagaag  13560
aggacgaggg actggcggca ttcctcatgg acaggcatat tatagtacct agggcagctc  13620
atgaaatcct ggatcatagt gtcacagggg caagagagtc tattgcaggc atgctggata  13680
ccacaaaagg cttgattcga gccagcatga ggaagggggg gttaacctct cgagtgataa  13740
ccagattgtc caattatgac tatgaacaat tcagagcagg gatggtgcta ttgacaggaa  13800
gaaagagaaa tgtcctcatt gacaaagagt catgttcagt gcagctggcg agagctctaa  13860
gaagccatat gtgggcgagg ctagctcgag gacggcctat ttacggcctt gaggtccctg  13920
atgtactaga atctatgcga ggccacctta ttcggcgtca tgagacatgt gtcatctgcg  13980
agtgtggatc agtcaactac ggatggtttt ttgtcccctc gggttgccaa ctggatgata  14040
ttgacaagga aacatcatcc ttgagagtcc catatattgg ttctaccact gatgagagaa  14100
cagacatgaa gcttgccttc gtaagagccc caagtcgatc cttgcgatct gctgttagaa  14160
tagcaacagt gtactcatgg gcttacggtg atgatgatag ctcttggaac gaagcctggt  14220
tgttggctag gcaaagggcc aatgtgagcc tggaggagct aagggtgatc actcccatct  14280
caacttcgac taatttagcg cataggttga gggatcgtag cactcaagtg aaatactcag  14340
gtacatccct tgtccgagtg gcgaggtata ccacaatctc caacgacaat ctctcatttg  14400
tcatatcaga taagaaggtt gatactaact ttatatacca acaaggaatg cttctagggt  14460
tgggtgtttt agaaacattg tttcgactcg agaaagatac cggatcatct aacacggtat  14520
tacatcttca cgtcgaaaca gattgttgcg tgatcccgat gatagatcat cccaggatac  14580
ccagctcccg caagctagag ctgagggcag agctatgtac caacccattg atatatgata  14640
atgcaccttt aattgacaga gatgcaacaa ggctatacac ccagagccat aggaggcacc  14700
ttgtggaatt tgttacatgg tccacacccc aactatatca cattttagct aagtccacag  14760
cactatctat gattgacctg gtaacaaaat ttgagaagga ccatatgaat gaaatttcag  14820
ctctcatagg ggatgacgat atcaatagtt tcataactga gtttctgctc atagagccaa  14880
gattattcac tatctacttg ggccagtgtg cggccatcaa ttgggcattt gatgtacatt  14940
atcatagacc atcagggaaa tatcagatgg gtgagctgtt gtcatcgttc ctttctagaa  15000
```

```
tgagcaaagg agtgtttaag gtgcttgtca atgctctaag ccacccaaag atctacaaga  15060
aattctggca ttgtggtatt atagagccta tccatggtcc ttcacttgat gctcaaaact  15120
tgcacacaac tgtgtgcaac atggtttaca catgctatat gacctacctc gacctgttgt  15180
tgaatgaaga gttagaagag ttcacatttc tcttgtgtga aagcgacgag gatgtagtac  15240
cggacagatt cgacaacatc caggcaaaac acttatgtgt tctggcagat ttgtactgtc  15300
aaccagggac ctgcccacca attcgaggtc taagaccggt agagaaatgt gcagttctaa  15360
ccgaccatat caaggcagag gctatgttat ctccagcagg atcttcgtgg aacataaatc  15420
caattattgt agaccattac tcatgctctc tgacttatct ccggcgagga tcgatcaaac  15480
agataagatt gagagttgat ccaggattca ttttcgacgc cctcgctgag gtaaatgtca  15540
gtcagccaaa gatcggcagc aacaacatct caaatatgag catcaaggct ttcagacccc  15600
cacacgatga tgttgcaaaa ttgctcaaag atatcaacac aagcaagcac aatcttccca  15660
tttcaggggg caatctcgcc aattatgaaa tccatgcttt ccgcagaatc gggttgaact  15720
catctgcttg ctacaaagct gttgagatat caacattaat taggagatgc cttgagccag  15780
gggaggacgg cttgttcttg ggtgagggat cgggttctat gttgatcact tataaagaga  15840
tacttaaact aaacaagtgc ttctataata gtggggtttc cgccaattct agatctggtc  15900
aaagggaatt agcaccctat ccctccgaag ttggccttgt cgaacacaga atgggagtag  15960
gtaatattgt caaagtgctc tttaacggga ggcccgaagt cacgtgggta ggcagtgtag  16020
attgcttcaa tttcatagtt agtaatatcc ctacctctag tgtggggttt atccattcag  16080
atatagagac cttgcctgac aaagatacta tagagaagct agaggaattg gcagccatct  16140
tatcgatggc tctgctcctg ggcaaaatag gatcaatact ggtgattaag cttatgcctt  16200
tcagcgggga ttttgttcag ggatttataa gttatgtagg gtctcattat agagaagtga  16260
accttgtata ccctagatac agcaacttca tctctactga atcttatttg gttatgacag  16320
atctcaaggc taaccggcta atgaatcctg aaaagattaa gcagcagata attgaatcat  16380
ctgtgaggac ttcacctgga cttataggtc acatcctatc cattaagcaa ctaagctgca  16440
tacaagcaat tgtgggagac gcagttagta gaggtgatat caatcctact ctgaaaaaac  16500
ttacacctat agagcaggtg ctgatcaatt gcgggttggc aattaacgga cctaagctgt  16560
gcaaagaatt gatccaccat gatgttgcct cagggcaaga tggattgctt aattctatac  16620
tcatcctcta cagggagttg gcaagattca aagacaacca aagaagtcaa caagggatgt  16680
tccacgctta ccccgtattg gtaagtagca ggcaacgaga acttatatct aggatcaccc  16740
gcaaattctg gggcacatt cttctttact ccgggaacaa aaagttgata aataagttta  16800
tccagaatct caagtccggc tatctgatac tagacttaca ccagaatatc ttcgttaaga  16860
atctatccaa gtcagagaaa cagattatta tgacgggggg tttgaaacgt gagtgggttt  16920
ttaaggtaac agtcaaggag accaaagaat ggtataagtt agtcggatac agtgccctga  16980
ttaaggacta attggttgaa ctccggaacc ctaatcctgc cctaggtggt taggcattat  17040
ttgcaatata ttaaagaaaa ctttgaaaat acgaagtttc tattcccagc tttgtctggt  17100
ggccggcatg gtcccagcct cctcgctggc gccggctggg caacattccg aggggaccgt  17160
cccctcggta atggcgaatg ggacgcggcc ggtcgatcga cgatccggct gctaacaaag  17220
cccgaaagga agctgagttg gctgctgcca ccgctgagca ataactagca taaccccttg  17280
gggcctctaa acgggtcttg aggggttttt tgctgaaagg aggaactata tccggatcga  17340
```

```
gatcaattct gtgagcgtat ggcaaacgaa ggaaaaatag ttatagtagc cgcactcgat  17400
gggacatttc aacgtaaacc gtttaataat attttgaatc ttattccatt atctgaaatg  17460
gtggtaaaac taactgctgt gtgtatgaaa tgctttaagg aggcttcctt ttctaaacga  17520
ttgggtgagg aaaccgagat agaaataata ggaggtaatg atatgtatca atcggtgtgt  17580
agaaagtgtt acatcgactc ataatattat atttttatc taaaaaacta aaaataaaca  17640
ttgattaaat tttaatataa tacttaaaaa tggatgttgt gtcgttagat aaaccgttta  17700
tgtattttga ggaaattgat aatgagttag attacgaacc agaaagtgca aatgaggtcg  17760
caaaaaaact gccgtatcaa ggacagttaa aactattact aggagaatta tttttcttta  17820
gtaagttaca gcgacacggt atattagatg gtgccaccgt agtgtatata ggatctgctc  17880
ccggtacaca tatacgttat ttgagagatc atttctataa tttaggagtg atcccgaaag  17940
gaagctgagt tggctgctgc caccgctgag caataactag cataacccct tggggcctct  18000
aaacgggtct tgaggggttt tttgctgaaa ggaggaacgc gcctgatgcg gtattttctc  18060
cttacgcatc tgtgcggtat ttcacaccgc atatatggtg cactctcagt acaatctgct  18120
ctgatgccgc atagttaagc cagccccgac acccgccaac acccgctgac gcgccctgac  18180
gggcttgtct gctcccggca tccgcttaca gacaagctgt gaccgtctcc gggagctgca  18240
tgtgtcagag gttttcaccg tcatcaccga aacgcgcgag acgaaagggc ctcgtgatac  18300
gcctattttt ataggttaat gtcatgataa taatggtttc ttagacgtca ggtggcactt  18360
ttcggggaaa tgtgcgcgga acccctattt gtttattttt ctaaatacat tcaaatatgt  18420
atccgctcat gagacaataa ccctgataaa tgcttcaata atattgaaaa aggaagagta  18480
tgagtattca acatttccgt gtcgccctta ttcccttttt tgcggcattt tgccttcctg  18540
tttttgctca cccagaaacg ctggtgaaag taaaagatgc tgaagatcag ttgggtgcac  18600
gagtgggtta catcgaactg gatctcaaca gcggtaagat ccttgagagt tttcgccccg  18660
aagaacgttt tccaatgatg agcactttta aagttctgct atgtggcgcg gtattatccc  18720
gtattgacgc cgggcaagag caactcggtc gccgcataca ctattctcag aatgacttgg  18780
ttgagtactc accagtcaca gaaaagcatc ttacggatgg catgacagta agagaattat  18840
gcagtgctgc cataaccatg agtgataaca ctgcggccaa cttacttctg acaacgatcg  18900
gaggaccgaa ggagctaacc gcttttttgc acaacatggg ggatcatgta actcgccttg  18960
atcgttggga accggagctg aatgaagcca taccaaacga cgagcgtgac accacgatgc  19020
ctgtagcaat ggcaacaacg ttgcgcaaac tattaactgg cgaactactt actctagctt  19080
cccggcaaca attaatagac tggatggagg cggataaagt tgcaggacca cttctgcgct  19140
cggcccttcc ggctggctgg tttattgctg ataaatctgg agccggtgag cgtgggtctc  19200
gcggtatcat tgcagcactg gggccagatg gtaagccctc ccgtatcgta gttatctaca  19260
cgacggggag tcaggcaact atggatgaac gaaatagaca gatcgctgag ataggtgcct  19320
cactgattaa gcattggtaa ctgtcagacc aagtttactc atatatactt tagattgatt  19380
taaaacttca tttttaattt aaaaggatct aggtgaagat cctttttgat aatctcatga  19440
ccaaaatccc ttaacgtgag ttttcgttcc actgagcgtc agaccccgta gaaaagatca  19500
aaggatcttc ttgagatcct ttttttctgc gcgtaatctg ctgcttgcaa acaaaaaaac  19560
caccgctacc agcggtggtt tgtttgccgg atcaagagct accaactctt tttccgaagg  19620
taactggctt cagcagagcg cagataccaa atactgtcct tctagtgtag ccgtagttag  19680
gccaccactt caagaactct gtagcaccgc ctacatacct cgctctgcta atcctgttac  19740
```

```
cagtggctgc tgccagtggc gataagtcgt gtcttaccgg gttggactca agacgatagt  19800

taccggataa ggcgcagcgg tcgggctgaa cggggggttc gtgcacacag cccagcttgg  19860

agcgaacgac ctacaccgaa ctgagatacc tacagcgtga gcattgagaa agcgccacgc  19920

ttcccgaagg gagaaaggcg gacaggtatc cggtaagcgg cagggtcgga acaggagagc  19980

gcacgaggga gcttccaggg ggaaacgcct ggtatcttta tagtcctgtc gggtttcgcc  20040

acctctgact tgagcgtcga tttttgtgat gctcgtcagg ggggcggagc ctatggaaaa  20100

acgccagcaa cgcggccttt ttacggttcc tggccttttg ctggcctttt gctcacatgt  20160

tctttcctgc gttatcccct gattctgtgg ataaccgtat taccgccttt gagtgagctg  20220

ataccgctcg ccgcagccga acgaccgagc gcagcgagtc agtgagcgag gaagcggaag  20280

agcgcccaat acgcaaaccg cctctccccg cgcgttggcc gattcattaa tgcagctggc  20340

acgacaggtt tcccgactgg aaagcgggca gtgagcgcaa cgcaattaat gtgagttagc  20400

tcactcatta ggcaccccag gctttacact ttatgcttcc ggctcgtatg ttgtgtggaa  20460

ttgtgagcgg ataacaattt cacacaggaa acagctatga ccatgattac gccaagctta  20520

cgcgtgtaat acgactcact ataggg                                      20546
```

<210> SEQ ID NO 9
<211> LENGTH: 21759
<212> TYPE: DNA
<213> ORGANISM: Artificial
<220> FEATURE:
<223> OTHER INFORMATION: plasmid DNA

<400> SEQUENCE: 9

```
accaaacaaa gttgggtaag gatagttcaa tcaatgatca tcttctagtg cacttaggat     60

tcaagatcct attatcaggg acaagagcag gattagggat atctcgaggc gcgtgccacc    120

atgacctctc gccgctccgt gaagtcgggt ccgcgggagg ttccgcgcga tgagtacgag    180

gatctgtact acaccccgtc ttcaggtatg gcgagtcccg atagtccgcc tgacacctcc    240

cgccgtggcg ccctacagac acgctcgcgc cagaggggcg aggtccgttt cgtccagtac    300

gacgagtcgg attatgccct ctacgggggc tcgtcatccg aagacgacga acacccggag    360

gtcccccgga cgcggcgtcc cgtttccggg gcggttttgt ccggcccggg gcctgcgcgg    420

gcgcctccgc cacccgctgg gtccggaggg gccggacgca cacccaccac cgcccccccgg    480

gccccccgaa cccagcgggt ggcgactaag gcccccgcgg ccccggcggc ggagaccacc    540

cgcggcagga aatcggccca gccagaatcc gccgcactcc cagacgcccc cgcctcgacg    600

gcgccaaccc gatccaagac acccgcgcag gggctggcca gaaagctgca ctttagcacc    660

gcccccccaa accccgacgc gccatggacc ccccgggtgg ccggctttaa caagcgcgtc    720

ttctgcgccg cggtcgggcg cctggcggcc atgcatgccc ggatggcggc ggtccagctc    780

tgggacatgt cgcgtccgcg cacagacgaa gacctcaacg aactccttgg catcaccacc    840

atccgcgtga cggtctgcga gggcaaaaac ctgcttcagc gcgccaacga gttggtgaat    900

ccagacgtgg tgcaggacgt tgacgcggcc acggcgactc gagggcgttc tgcggcgtcg    960

cgccccaccg agcgacctcg agccccagcc cgctccgctt ctcgccccag acggcccgtc   1020

gaggatatcg ccaccatggt gacaggggga atggcaagca agtgggatca gaagggtatg   1080

gacattgcct atgaggaggc ggccttaggt tacaaagagg gtggtgttcc tattggcgga   1140

tgtcttatca ataacaaaga cggaagtgtt ctcggtcgtg gtcacaacat gagatttcaa   1200
```

```
aagggatccg ccacactaca tggtgagatc tccactttgg aaaactgtgg gagattagag   1260
ggcaaagtgt acaaagatac cactttgtat acgacgctgt ctccatgcga catgtgtaca   1320
ggtgccatca tcatgtatgg tattccacgc tgtgttgtcg gtgagaacgt taatttcaaa   1380
agtaagggcg agaaatattt acaaactaga ggtcacgagg ttgttgttgt tgacgatgag   1440
aggtgtaaaa agatcatgaa acaatttatc gatgaaagac ctcaggattg gtttgaagat   1500
attggtgagg cttcggaacc atttaagaac gtctacttgc tacctcaaac aaaccaattg   1560
ctgggtttgt acaccatcat cagaaataag aatacaacta gacctgattt cattttctac   1620
tccgatagaa tcatcagatt gttggttgaa gaaggtttga accatctacc tgtgcaaaag   1680
caaattgtgg aaactgacac caacgaaaac ttcgaaggtg tctcattcat gggtaaaatc   1740
tgtggtgttt ccattgtcag agctggtgaa tcgatggagc aaggattaag agactgttgt   1800
aggtctgtgc gtatcggtaa aattttaatt caaagggacg aggagactgc tttaccaaag   1860
ttattctacg aaaaattacc agaggatata tctgaaaggt atgtcttcct attagaccca   1920
atgctggcca ccggtggtag tgctatcatg gctacagaag tcttgattaa gagaggtgtt   1980
aagccagaga gaatttactt cttaaaccta atctgtagta aggaagggat tgaaaaatac   2040
catgccgcct tcccagaggt cagaattgtt actggtgccc tcgacagagg tctagatgaa   2100
aacaagtatc tagttccagg gttgggtgac tttggtgaca gatactactg tgtttaataa   2160
acgcgccatc catcattgtt ataaaaaact taggattcaa gatcctatta tcagggacaa   2220
gagcaggatt agggatatcc gagatggcca cacttttaag gagcttagca ttgttcaaaa   2280
gaaacaagga caaaccaccc attacatcag gatccggtgg agccatcaga ggaatcaaac   2340
acattattat agtaccaatc cctggagatt cctcaattac cactcgatcc agacttctgg   2400
accggttggt gaggttaatt ggaaacccgg atgtgagcgg gcccaaacta acaggggcac   2460
taataggtat attatcctta tttgtggagt ctccaggtca attgattcag aggatcaccg   2520
atgaccctga cgttagcata aggctgttag aggttgtcca gagtgaccag tcacaatctg   2580
gccttacctt cgcatcaaga ggtaccaaca tggaggatga ggcggaccaa tacttttcac   2640
atgatgatcc aattagtagt gatcaatcca ggttcggatg gttcgggaac aaggaaatct   2700
cagatattga agtgcaagac cctgagggat tcaacatgat tctgggtacc atcctagccc   2760
aaatttgggt cttgctcgca aaggcggtta cggccccaga cacggcagct gattcggagc   2820
taagaaggtg gataaagtac acccaacaaa gaagggtagt tggtgaattt agattggaga   2880
gaaaatggtt ggatgtggtg aggaacagga ttgccgagga cctctcctta cgccgattca   2940
tggtcgctct aatcctggat atcaagagaa cacccggaaa caaacccagg attgctgaaa   3000
tgatatgtga cattgataca tatatcgtag aggcaggatt agccagtttt atcctgacta   3060
ttaagtttgg gatagaaact atgtatcctg ctcttggact gcatgaattt gctggtgagt   3120
tatccacact tgagtccttg atgaaccttt accagcaaat gggggaaact gcaccctaca   3180
tggtaatcct ggagaactca attcagaaca agttcagtgc aggatcatac cctctgctct   3240
ggagctatgc catgggagta ggagtggaac ttgaaaactc catgggaggt ttgaactttg   3300
gccgatctta ctttgatcca gcatatttta gattagggca agagatggta aggaggtcag   3360
ctggaaaggt cagttccaca ttggcatctg aactcggtat cactgccgag gatgcaaggc   3420
ttgtttcaga gattgcaatg catactactg aggacaagat cagtagagcg gttggaccca   3480
gacaagccca agtatcattt ctacacggtg atcaaagtga gaatgagcta ccgagattgg   3540
ggggcaagga agataggagg gtcaaacaga gtcgaggaga agccagggag agctacagag   3600
```

```
aaaccgggcc cagcagagca agtgatgcga gagctgccca tcttccaacc ggcacacccc   3660
tagacattga cactgcaacg gagtccagcc aagatccgca ggacagtcga aggtcagctg   3720
acgccctgct taggctgcaa gccatggcag gaatctcgga agaacaaggc tcagacacgg   3780
acacccctat agtgtacaat gacagaaatc ttctagacta ggtgcgagag gccgagggcc   3840
agaacaacat ccgcctacca tccatcattg ttataaaaaa cttaggaacc aggtccacac   3900
agccgccagc ccatcaacca tccactccca cgattggagc caatggcaga agagcaggca   3960
cgccatgtca aaaacggact ggaatgcatc cgggctctca aggccgagcc catcggctca   4020
ctggccatcg aggaagctat ggcagcatgg tcagaaatat cagacaaccc aggacaggag   4080
cgagccacct gcagggaaga gaaggcaggc agttcgggtc tcagcaaacc atgcctctca   4140
gcaattggat caactgaagg cggtgcacct cgcatccgcg gtcagggacc tggagagagc   4200
gatgacgacg ctgaaacttt gggaatcccc ccaagaaatc tccaggcatc aagcactggg   4260
ttacagtgtt attacgttta tgatcacagc ggtgaagcgg ttaagggaat ccaagatgct   4320
gactctatca tggttcaatc aggccttgat ggtgatagca ccctctcagg aggagacaat   4380
gaatctgaaa acagcgatgt ggatattggc gaacctgata ccgagggata tgctatcact   4440
gaccggggat ctgctcccat ctctatgggg ttcagggctt ctgatgttga aactgcagaa   4500
ggaggggaga tccacgagct cctgagactc caatccagag gcaacaactt tccgaagctt   4560
gggaaaactc tcaatgttcc tccgccccccg gaccccggta gggccagcac ttccgggaca   4620
cccattaaaa agggcacaga cgcgagatta gcctcatttg gaacggagat cgcgtcttta   4680
ttgacaggtg gtgcaaccca atgtgctcga aagtcaccct cggaaccatc agggccaggt   4740
gcacctgcgg ggaatgtccc cgagtgtgtg agcaatgccg cactgataca ggagtggaca   4800
cccgaatctg gtaccacaat ctccccgaga tcccagaata atgaagaagg gggagactat   4860
tatgatgatg agctgttctc tgatgtccaa gatattaaaa cagccttggc caaaatacac   4920
gaggataatc agaagataat ctccaagcta gaatcactgc tgttattgaa gggagaagtt   4980
gagtcaatta agaagcagat caacaggcaa aatatcagca tatccaccct ggaaggacac   5040
ctctcaagca tcatgatcgc cattcctgga cttgggaagg atcccaacga ccccactgca   5100
gatgtcgaaa tcaatcccga cttgaaaccc atcataggca gagattcagg ccgagcactg   5160
gccgaagttc tcaagaaacc cgttgccagc cgacaactcc aaggaatgac aaatggacgg   5220
accagttcca gaggacagct gctgaaggaa tttcagctaa agccgatcgg gaaaaagatg   5280
agctcagccg tcgggtttgt tcctgacacc ggccctgcat cacgcagtgt aatccgctcc   5340
attataaaat ccagccggct agaggaggat cggaagcgtt acctgatgac tctccttgat   5400
gatatcaaag gagccaatga tcttgccaag ttccaccaga tgctgatgaa gataataatg   5460
aagtagctac agctcaactt acctgccaac cccatgccag tcgacccaac tagtacaacc   5520
taaatccatt ataaaaaact taggagcaaa gtgattgcct cccaaggtcc acaatgacag   5580
agacctacga cttcgacaag tcggcatggg acatcaaagg gtcgatcgct ccgatacaac   5640
ccaccaccta cagtgatggc aggctggtgc cccaggtcag agtcatagat cctggtctag   5700
gcgacaggaa ggatgaatgc tttatgtaca tgtttctgct gggggttgtt gaggacagcg   5760
attccctagg gcctccaatc gggcgagcat ttgggttcct gcccttaggt gttggcagat   5820
ccacagcaaa gcccgaaaaa ctcctcaaag aggccactga gcttgacata gttgttagac   5880
gtacagcagg gctcaatgaa aaactggtgt tctacaacaa caccccacta actctcctca   5940
```

```
caccttggag aaaggtccta acaacaggga gtgtcttcaa cgcaaaccaa gtgtgcaatg   6000
cggttaatct gataccgctc gataccccgc agaggttccg tgttgtttat atgagcatca   6060
cccgtctttc ggataacggg tattacaccg ttcctagaag aatgctggaa ttcagatcgg   6120
tcaatgcagt ggccttcaac ctgctggtga cccttaggat tgacaaggcg ataggccctg   6180
ggaagatcat cgacaataca gagcaacttc ctgaggcaac atttatggtc cacatcggga   6240
acttcaggag aaagaagagt gaagtctact ctgccgatta ttgcaaaatg aaaatcgaaa   6300
agatgggcct ggtttttgca cttggtggga tagggggcac cagtcttcac attagaagca   6360
caggcaaaat gagcaagact ctccatgcac aactcgggtt caagaagacc ttatgttacc   6420
cgctgatgga tatcaatgaa gaccttaatc gattactctg gaggagcaga tgcaagatag   6480
taagaatcca ggcagttttg cagccatcag ttcctcaaga attccgcatt tacgacgacg   6540
tgatcataaa tgatgaccaa ggactattca aagttctgta gaccgtagtg cccagcaatg   6600
cccgaaaacg accccctca caatgacagc cagaaggccc ggacaaaaaa gcccccctccg   6660
aaagactcca cggaccaagc gagaggccag ccagcagccg acggcaagcg cgaacaccag   6720
gcggccccag cacagaacag ccctgacaca aggccaccac cagccacccc aatctgcatc   6780
ctcctcgtgg gacccccgag gaccaacccc caaggctgcc cccgatccaa accaccaacc   6840
gcatccccac cacccccggg aaagaaaccc ccagcaattg gaaggcccct cccccctcttc   6900
ctcaacacaa gaactccaca accgaaccgc acaagcgacc gaggtgaccc aaccgcaggc   6960
atccgactcc ctagacagat cctctctccc cggcaaacta aacaaaactt agggccaagg   7020
aacatacaca cccaacagaa cccagacccc ggcccacggc gccgcgcccc caacccccga   7080
caaccagagg gagcccccaa ccaatcccgc cggctccccc ggtgcccaca ggcagggaca   7140
ccaacccccg aacagaccca gcacccaacc atcgacaatc caagacgggg gggccccccc   7200
aaaaaaaggc ccccaggggc cgacagccag caccgcgagg aagcccaccc accccacaca   7260
cgaccacggc aaccaaacca gaacccagac caccctgggc caccagctcc cagactcggc   7320
catcaccccg cagaaaggaa aggccacaac ccgcgcaccc cagccccgat ccggcgggga   7380
gccacccaac ccgaaccagc acccaagagc gatccccgaa ggacccccga accgcaaagg   7440
acatcagtat cccacagcct ctccaagtcc cccggtctcc tcctcttctc gaagggacca   7500
aaagatcaat ccaccacacc cgacgacact caactcccca cccctaaagg agacaccggg   7560
aatcccagaa tcaagactca tccaatgtcc atcatgggtc tcaaggtgaa cgtctctgcc   7620
atattcatgg cagtactgtt aactctccaa acacccaccg gtcaaatcca ttggggcaat   7680
ctctctaaga taggggtggt aggaatagga agtgcaagct acaaagttat gactcgttcc   7740
agccatcaat cattagtcat aaaattaatg cccaatataa ctctcctcaa taactgcacg   7800
agggtagaga ttgcagaata caggagacta ctgagaacag ttttggaacc aattagagat   7860
gcacttaatg caatgaccca gaatataaga ccggttcaga gtgtagcttc aagtaggaga   7920
cacaagagat ttgcgggagt agtcctggca ggtgcggccc taggcgttgc cacagctgct   7980
cagataacag ccggcattgc acttcaccag tccatgctga actctcaagc catcgacaat   8040
ctgagagcga gcctggaaac tactaatcag gcaattgaga caatcagaca agcagggcag   8100
gagatgatat tggctgttca gggtgtccaa gactacatca ataatgagct gataccgtct   8160
atgaaccaac tatcttgtga tttaatcggc cagaagctcg ggctcaaatt gctcagatac   8220
tatacagaaa tcctgtcatt atttggcccc agtttacggg accccatatc tgcggagata   8280
tctatccagg ctttgagcta tgcgcttgga ggagacatca ataaggtgtt agaaaagctc   8340
```

```
ggatacagtg gaggtgattt actgggcatc ttagagagcg gaggaataaa ggcccggata   8400

actcacgtcg acacagagtc ctacttcatt gtcctcagta tagcctatcc gacgctgtcc   8460

gagattaagg gggtgattgt ccaccggcta gagggggtct cgtacaacat aggctctcaa   8520

gagtggtata ccactgtgcc caagtatgtt gcaacccaag ggtaccttat ctcgaatttt   8580

gatgagtcat cgtgtacttt catgccagag gggactgtgt gcagccaaaa tgccttgtac   8640

ccgatgagtc ctctgctcca agaatgcctc cgggggtaca ccaagtcctg tgctcgtaca   8700

ctcgtatccg ggtcttttgg gaaccggttc attttatcac aagggaacct aatagccaat   8760

tgtgcatcaa tcctttgcaa gtgttacaca acaggaacga tcattaatca agaccctgac   8820

aagatcctaa catacattgc tgccgatcac tgcccggtag tcgaggtgaa cggcgtgacc   8880

atccaagtcg ggagcaggag gtatccagac gctgtgtact tgcacagaat tgacctcggt   8940

cctcccatat cattggagag gttggacgta gggacaaatc tggggaatgc aattgctaag   9000

ttggaggatg ccaaggaatt gttggagtca tcggaccaga tattgaggag tatgaaaggt   9060

ttatcgagca ctagcatagt ctacatcctg attgcagtgt gtcttggagg gttgataggg   9120

atccccgctt taatatgttg ctgcaggggg cgttgtaaca aaaagggaga acaagttggt   9180

atgtcaagac caggcctaaa gcctgatctt acgggaacat caaaatccta tgtaaggtcg   9240

ctctgatcct ctacaactct tgaaacacaa atgtcccaca agtctcctct tcgtcatcaa   9300

gcaaccaccg cacccagcat caagcccacc tgaaattatc tccggcttcc ctctggccga   9360

acaatatcgg tagttaatca aaacttaggg tgcaagatca tccacaatgt caccacaacg   9420

agaccggata aatgccttct acaaagataa cccccatccc aagggaagta ggatagtcat   9480

taacagagaa catcttatga ttgatagacc ttatgttttg ctggctgttc tgtttgtcat   9540

gtttctgagc ttgatcgggt tgctagccat tgcaggcatt agacttcatc gggcagccat   9600

ctacaccgca gagatccata aaagcctcag caccaatcta gatgtaacta actcaatcga   9660

gcatcaggtc aaggacgtgc tgacaccact cttcaaaatc atcggtgatg aagtgggcct   9720

gaggacacct cagagattca ctgacctagt gaaattaatc tctgacaaga ttaaattcct   9780

taatccggat agggagtacg acttcagaga tctcacttgg tgtatcaacc cgccagagag   9840

aatcaaattg gattatgatc aatactgtgc agatgtggct gctgaagagc tcatgaatgc   9900

attggtgaac tcaactctac tggagaccag aacaaccaat cagttcctag ctgtctcaaa   9960

gggaaactgc tcagggccca ctacaatcag aggtcaattc tcaaacatgt cgctgtccct  10020

gttagacttg tatttaggtc gaggttacaa tgtgtcatct atagtcacta tgacatccca  10080

gggaatgtat gggggaactt acctagtgga aaagcctaat ctgagcagca aaaggtcaga  10140

gttgtcacaa ctgagcatgt accgagtgtt tgaagtaggt gttatcagaa atccgggttt  10200

gggggctccg gtgttccata tgacaaacta tcttgagcaa ccagtcagta atgatctcag  10260

caactgtatg gtggctttgg gggagctcaa actcgcagcc ctttgtcacg gggaagattc  10320

tatcacaatt ccctatcagg gatcagggaa aggtgtcagc ttccagctcg tcaagctagg  10380

tgtctggaaa tccccaaccg acatgcaatc ctgggtcccc ttatcaacgg atgatccagt  10440

gatagacagg ctttacctct catctcacag aggtgttatc gctgacaatc aagcaaaatg  10500

ggctgtcccg acaacacgaa cagatgacaa gttgcgaatg gagacatgct tccaacaggc  10560

gtgtaagggt aaaatccaag cactctgcga gaatcccgag tgggcaccat tgaaggataa  10620

caggattcct tcatacgggg tcttgtctgt tgatctgagt ctgacagttg agcttaaaat  10680
```

```
caaaattgct tcgggattcg ggccattgat cacacacggt tcagggatgg acctatacaa  10740
atccaaccac aacaatgtgt attggctgac tatcccgcca atgaagaacc tagccttagg  10800
tgtaatcaac acattggagt ggataccgag attcaaggtt agtccctacc tcttcactgt  10860
cccaattaag gaagcaggcg aagactgcca tgccccaaca tacctacctg cggaggtgga  10920
tggtgatgtc aaactcagtt ccaatctggt gattctacct ggtcaagatc tccaatatgt  10980
tttggcaacc tacgatactt ccagggttga acatgctgtg gtttattacg tttacagccc  11040
aagccgctca ttttcttact tttatccttt taggttgcct ataaaggggg tccccatcga  11100
attacaagtg gaatgcttca catgggacca aaaactctgg tgccgtcact tctgtgtgct  11160
tgcggactca gaatctggtg gacatatcac tcactctggg atggtgggca tgggagtcag  11220
ctgcacagtc acccgggaag atggaaccaa tcgcagatag ggctgctagt gaaccaatca  11280
catgatgtca cccagacatc aggcataccc actagtgtga aatagacatc agaattaaga  11340
aaaacgtagg gtccaagtgg ttccccgtta tggactcgct atctgtcaac cagatcttat  11400
accctgaagt tcacctagat agcccgatag ttaccaataa gatagtagcc atcctggagt  11460
atgctcgagt ccctcacgct tacagcctgg aggaccctac actgtgtcag aacatcaagc  11520
accgcctaaa aaacggattt tccaaccaaa tgattataaa caatgtggaa gttgggaatg  11580
tcatcaagtc caagcttagg agttatccgg cccactctca tattccatat ccaaattgta  11640
atcaggattt atttaacata gaagacaaag agtcaacgag gaagatccgt gaactcctca  11700
aaaaggggaa ttcgctgtac tccaaagtca gtgataaggt tttccaatgc ttaagggaca  11760
ctaactcacg gcttggccta ggctccgaat tgagggagga catcaaggag aaagttatta  11820
acttgggagt ttacatgcac agctcccagt ggtttgagcc ctttctgttt tggtttacag  11880
tcaagactga gatgaggtca gtgattaaat cacaaaccca tacttgccat aggaggagac  11940
acacacctgt attcttcact ggtagttcag ttgagttgct aatctctcgt gaccttgttg  12000
ctataatcag taaagagtct caacatgtat attacctgac atttgaactg gttttgatgt  12060
attgtgatgt catagagggg aggttaatga cagagaccgc tatgactatt gatgctaggt  12120
atacagagct tctaggaaga gtcagataca tgtggaaact gatagatggt ttcttccctg  12180
cactcgggaa tccaacttat caaattgtag ccatgctgga gcctctttca cttgcttacc  12240
tgcagctgag ggatataaca gtagaactca gaggtgcttt ccttaaccac tgctttactg  12300
aaatacatga tgttcttgac caaaacgggt tttctgatga aggtacttat catgagttaa  12360
ctgaagctct agattacatt ttcataactg atgacataca tctgacaggg gagatttttct  12420
catttttcag aagtttcggc caccccagac ttgaagcagt aacggctgct gaaaatgtta  12480
ggaaatacat gaatcagcct aaagtcattg tgtatgagac tctgatgaaa ggtcatgcca  12540
tattttgtgg aatcataatc aacggctatc gtgacaggca cggaggcagt tggccaccgc  12600
tgaccctccc cctgcatgct gcagacacaa tccggaatgc tcaagcttca ggtgaagggt  12660
taacacatga gcagtgcgtt gataactgga aatcttttgc tggagtgaaa tttggctgct  12720
ttatgcctct tagcctggat agtgatctga caatgtacct aaaggacaag gcacttgctg  12780
ctctccaaag ggaatgggat tcagtttacc cgaaagagtt cctgcgttac gaccctccca  12840
agggaaccgg gtcacggagg cttgtagatg ttttccttaa tgattcgagc tttgacccat  12900
atgatgtgat aatgtatgtt gtaagtggag cttacctcca tgaccctgag ttcaacctgt  12960
cttacagcct gaaagaaaag gagatcaagg aaacaggtag actttttgct aaaatgactt  13020
acaaaatgag ggcatgccaa gtgattgctg aaaatctaat ctcaaacggg attggcaaat  13080
```

```
attttaagga caatgggatg gccaaggatg agcacgattt gactaaggca ctccacactc  13140
tagctgtctc aggagtcccc aaagatctca aagaaagtca caggggggggg ccagtcttaa  13200
aaacctactc ccgaagccca gtccacacaa gtaccaggaa cgtgagagca gcaaaagggt  13260
ttatagggtt ccctcaagta attcggcagg accaagacac tgatcatccg gagaatatgg  13320
aagcttacga gacagtcagt gcatttatca cgactgatct caagaagtac tgccttaatt  13380
ggagatatga gaccatcagc ttgtttgcac agaggctaaa tgagatttac ggattgccct  13440
catttttcca gtggctgcat aagaggcttg agacctctgt cctgtatgta agtgaccctc  13500
attgcccccc cgaccttgac gcccatatcc cgttatataa agtccccaat gatcaaatct  13560
tcattaagta ccctatggga ggtatagaag ggtattgtca gaagctgtgg accatcagca  13620
ccattcccta tctatacctg gctgcttatg agagcggagt aaggattgct tcgttagtgc  13680
aaggggacaa tcagaccata gccgtaacaa aaagggtacc cagcacatgg ccctacaacc  13740
ttaagaaacg ggaagctgct agagtaacta gagattactt tgtaattctt aggcaaaggc  13800
tacatgatat tggccatcac ctcaaggcaa atgagacaat tgtttcatca catttttttg  13860
tctattcaaa aggaatatat tatgatgggc tacttgtgtc ccaatcactc aagagcatcg  13920
caagatgtgt attctggtca gagactatag ttgatgaaac aagggcagca tgcagtaata  13980
ttgctacaac aatggctaaa agcatcgaga gaggttatga ccgttacctt gcatattccc  14040
tgaacgtcct aaaagtgata cagcaaattc tgatctctct tggcttcaca atcaattcaa  14100
ccatgacccg ggatgtagtc atacccctcc tcacaaacaa cgacctctta ataaggatgg  14160
cactgttgcc cgctcctatt ggggggatga attatctgaa tatgagcagg ctgtttgtca  14220
gaaacatcgg tgatccagta acatcatcaa ttgctgatct caagagaatg attctcgcct  14280
cactaatgcc tgaagagacc ctccatcaag taatgacaca acaaccgggg gactcttcat  14340
tcctagactg ggctagcgac ccttactcag caaatcttgt atgtgtccag agcatcacta  14400
gactcctcaa gaacataact gcaaggtttg tcctgatcca tagtccaaac ccaatgttaa  14460
aaggattatt ccatgatgac agtaaagaag aggacgaggg actggcggca ttcctcatgg  14520
acaggcatat tatagtacct agggcagctc atgaaatcct ggatcatagt gtcacagggg  14580
caagagagtc tattgcaggc atgctggata ccacaaaagg cttgattcga gccagcatga  14640
ggaagggggg gttaacctct cgagtgataa ccagattgtc caattatgac tatgaacaat  14700
tcagagcagg gatggtgcta ttgacaggaa gaaagagaaa tgtcctcatt gacaaagagt  14760
catgttcagt gcagctggcg agagctctaa gaagccatat gtgggcgagg ctagctcgag  14820
gacggcctat ttacggcctt gaggtccctg atgtactaga atctatgcga ggccacctta  14880
ttcggcgtca tgagacatgt gtcatctgcg agtgtggatc agtcaactac ggatggtttt  14940
ttgtcccctc gggttgccaa ctggatgata ttgacaagga aacatcatcc ttgagagtcc  15000
catatattgg ttctaccact gatgagagaa cagacatgaa gcttgccttc gtaagagccc  15060
caagtcgatc cttgcgatct gctgttagaa tagcaacagt gtactcatgg gcttacggtg  15120
atgatgatag ctcttggaac gaagcctggt tgttggctag gcaaagggcc aatgtgagcc  15180
tggaggagct aagggtgatc actcccatct caacttcgac taatttagcg cataggttga  15240
gggatcgtag cactcaagtg aaatactcag gtacatccct tgtccgagtg gcgaggtata  15300
ccacaatctc caacgacaat ctctcatttg tcatatcaga taagaaggtt gatactaact  15360
ttatatacca acaaggaatg cttctagggt tgggtgtttt agaaacattg tttcgactcg  15420
```

```
agaaagatac cggatcatct aacacggtat tacatcttca cgtcgaaaca gattgttgcg  15480
tgatcccgat gatagatcat cccaggatac ccagctcccg caagctagag ctgagggcag  15540
agctatgtac caacccattg atatatgata atgcaccttt aattgacaga gatgcaacaa  15600
ggctatacac ccagagccat aggaggcacc ttgtggaatt tgttacatgg tccacacccc  15660
aactatatca cattttagct aagtccacag cactatctat gattgacctg gtaacaaaat  15720
ttgagaagga ccatatgaat gaaatttcag ctctcatagg ggatgacgat atcaatagtt  15780
tcataactga gtttctgctc atagagccaa gattattcac tatctacttg ggccagtgtg  15840
cggccatcaa ttgggcattt gatgtacatt atcatagacc atcagggaaa tatcagatgg  15900
gtgagctgtt gtcatcgttc ctttctagaa tgagcaaagg agtgtttaag gtgcttgtca  15960
atgctctaag ccacccaaag atctacaaga aattctggca ttgtggtatt atagagccta  16020
tccatggtcc ttcacttgat gctcaaaact tgcacacaac tgtgtgcaac atggtttaca  16080
catgctatat gacctacctc gacctgttgt tgaatgaaga gttagaagag ttcacatttc  16140
tcttgtgtga aagcgacgag gatgtagtac cggacagatt cgacaacatc caggcaaaac  16200
acttatgtgt tctggcagat ttgtactgtc aaccagggac ctgcccacca attcgaggtc  16260
taagaccggt agagaaatgt gcagttctaa ccgaccatat caaggcagag gctatgttat  16320
ctccagcagg atcttcgtgg aacataaatc caattattgt agaccattac tcatgctctc  16380
tgacttatct ccggcgagga tcgatcaaac agataagatt gagagttgat ccaggattca  16440
ttttcgacgc cctcgctgag gtaaatgtca gtcagccaaa gatcggcagc aacaacatct  16500
caaatatgag catcaaggct ttcagacccc cacacgatga tgttgcaaaa ttgctcaaag  16560
atatcaacac aagcaagcac aatcttccca tttcaggggg caatctcgcc aattatgaaa  16620
tccatgcttt ccgcagaatc gggttgaact catctgcttg ctacaaagct gttgagatat  16680
caacattaat taggagatgc cttgagccag gggaggacgg cttgttcttg ggtgagggat  16740
cgggttctat gttgatcact tataaagaga tacttaaact aaacaagtgc ttctataata  16800
gtggggtttc cgccaattct agatctggtc aaagggaatt agcaccctat ccctccgaag  16860
ttggccttgt cgaacacaga atgggagtag gtaatattgt caaagtgctc tttaacggga  16920
ggcccgaagt cacgtgggta ggcagtgtag attgcttcaa tttcatagtt agtaatatcc  16980
ctacctctag tgtggggttt atccattcag atatagagac cttgcctgac aaagatacta  17040
tagagaagct agaggaattg gcagccatct tatcgatggc tctgctcctg ggcaaaatag  17100
gatcaatact ggtgattaag cttatgcctt tcagcgggga ttttgttcag ggatttataa  17160
gttatgtagg gtctcattat agagaagtga accttgtata ccctagatac agcaacttca  17220
tctctactga atcttatttg gttatgacag atctcaaggc taaccggcta atgaatcctg  17280
aaaagattaa gcagcagata attgaatcat ctgtgaggac ttcacctgga cttataggtc  17340
acatcctatc cattaagcaa ctaagctgca tacaagcaat tgtgggagac gcagttagta  17400
gaggtgatat caatcctact ctgaaaaaac ttacacctat agagcaggtg ctgatcaatt  17460
gcgggttggc aattaacgga cctaagctgt gcaaagaatt gatccaccat gatgttgcct  17520
cagggcaaga tggattgctt aattctatac tcatcctcta cagggagttg gcaagattca  17580
aagacaacca aagaagtcaa caagggatgt tccacgctta ccccgtattg gtaagtagca  17640
ggcaacgaga acttatatct aggatcaccc gcaaattctg gggcacatt cttctttact  17700
ccgggaacaa aaagttgata aataagttta tccagaatct caagtccggc tatctgatac  17760
tagacttaca ccagaatatc ttcgttaaga atctatccaa gtcagagaaa cagattatta  17820
```

```
tgacgggggg tttgaaacgt gagtgggttt ttaaggtaac agtcaaggag accaaagaat  17880
ggtataagtt agtcggatac agtgccctga ttaaggacta attggttgaa ctccggaacc  17940
ctaatcctgc cctaggtggt taggcattat ttgcaatata ttaaagaaaa ctttgaaaat  18000
acgaagtttc tattcccagc tttgtctggt ggccggcatg gtcccagcct cctcgctggc  18060
gccggctggg caacattccg aggggaccgt cccctcggta atggcgaatg ggacgcggcc  18120
ggtcgatcga cgatccggct gctaacaaag cccgaaagga agctgagttg gctgctgcca  18180
ccgctgagca ataactagca taaccccttg gggcctctaa acgggtcttg aggggttttt  18240
tgctgaaagg aggaactata tccggatcga gatcaattct gtgagcgtat ggcaaacgaa  18300
ggaaaaatag ttatagtagc cgcactcgat gggacatttc aacgtaaacc gtttaataat  18360
attttgaatc ttattccatt atctgaaatg gtggtaaaac taactgctgt gtgtatgaaa  18420
tgctttaagg aggcttcctt ttctaaacga ttgggtgagg aaaccgagat agaaataata  18480
ggaggtaatg atatgtatca atcggtgtgt agaaagtgtt acatcgactc ataatattat  18540
atttttatc taaaaaacta aaaataaaca ttgattaaat tttaatataa tacttaaaaa  18600
tggatgttgt gtcgttagat aaaccgttta tgtattttga ggaaattgat aatgagttag  18660
attacgaacc agaaagtgca aatgaggtcg caaaaaaact gccgtatcaa ggacagttaa  18720
aactattact aggagaatta ttttttctta gtaagttaca gcgacacggt atattagatg  18780
gtgccaccgt agtgtatata ggatctgctc ccggtacaca tatacgttat ttgagagatc  18840
atttctataa tttaggagtg atcccgaaag gaagctgagt tggctgctgc caccgctgag  18900
caataactag cataacccct tggggcctct aaacgggtct tgaggggttt tttgctgaaa  18960
ggaggaacgc gcctgatgcg gtattttctc cttacgcatc tgtgcggtat ttcacaccgc  19020
atatatggtg cactctcagt acaatctgct ctgatgccgc atagttaagc cagccccgac  19080
acccgccaac acccgctgac gcgccctgac gggcttgtct gctcccggca tccgcttaca  19140
gacaagctgt gaccgtctcc gggagctgca tgtgtcagag gttttcaccg tcatcaccga  19200
aacgcgcgag acgaaagggc ctcgtgatac gcctattttt ataggttaat gtcatgataa  19260
taatggtttc ttagacgtca ggtggcactt ttcggggaaa tgtgcgcgga acccctattt  19320
gtttattttt ctaaatacat tcaaatatgt atccgctcat gagacaataa ccctgataaa  19380
tgcttcaata atattgaaaa aggaagagta tgagtattca acatttccgt gtcgccctta  19440
ttcccttttt tgcggcattt tgccttcctg tttttgctca cccagaaacg ctggtgaaag  19500
taaaagatgc tgaagatcag ttgggtgcac gagtgggtta catcgaactg gatctcaaca  19560
gcggtaagat ccttgagagt tttcgccccg aagaacgttt tccaatgatg agcactttta  19620
aagttctgct atgtggcgcg gtattatccc gtattgacgc cgggcaagag caactcggtc  19680
gccgcataca ctattctcag aatgacttgg ttgagtactc accagtcaca gaaaagcatc  19740
ttacggatgg catgacagta agagaattat gcagtgctgc cataaccatg agtgataaca  19800
ctgcggccaa cttacttctg acaacgatcg gaggaccgaa ggagctaacc gcttttttgc  19860
acaacatggg ggatcatgta actcgccttg atcgttggga accggagctg aatgaagcca  19920
taccaaacga cgagcgtgac accacgatgc ctgtagcaat ggcaacaacg ttgcgcaaac  19980
tattaactgg cgaactactt actctagctt cccggcaaca attaatagac tggatggagg  20040
cggataaagt tgcaggacca cttctgcgct cggcccttcc ggctggctgg tttattgctg  20100
ataaatctgg agccggtgag cgtgggtctc gcggtatcat tgcagcactg gggccagatg  20160
```

-continued

```
gtaagccctc ccgtatcgta gttatctaca cgacggggag tcaggcaact atggatgaac  20220

gaaatagaca gatcgctgag ataggtgcct cactgattaa gcattggtaa ctgtcagacc  20280

aagtttactc atatatactt tagattgatt taaaacttca tttttaattt aaaaggatct  20340

aggtgaagat cctttttgat aatctcatga ccaaaatccc ttaacgtgag ttttcgttcc  20400

actgagcgtc agaccccgta gaaaagatca aaggatcttc ttgagatcct ttttttctgc  20460

gcgtaatctg ctgcttgcaa acaaaaaaac caccgctacc agcggtggtt tgtttgccgg  20520

atcaagagct accaactctt tttccgaagg taactggctt cagcagagcg cagataccaa  20580

atactgtcct tctagtgtag ccgtagttag gccaccactt caagaactct gtagcaccgc  20640

ctacatacct cgctctgcta atcctgttac cagtggctgc tgccagtggc gataagtcgt  20700

gtcttaccgg gttggactca agacgatagt taccggataa ggcgcagcgg tcgggctgaa  20760

cggggggttc gtgcacacag cccagcttgg agcgaacgac ctacaccgaa ctgagatacc  20820

tacagcgtga gcattgagaa agcgccacgc ttcccgaagg gagaaaggcg gacaggtatc  20880

cggtaagcgg cagggtcgga acaggagagc gcacgaggga gcttccaggg ggaaacgcct  20940

ggtatcttta tagtcctgtc gggtttcgcc acctctgact tgagcgtcga tttttgtgat  21000

gctcgtcagg ggggcggagc ctatggaaaa acgccagcaa cgcggccttt ttacggttcc  21060

tggccttttg ctggcctttt gctcacatgt tctttcctgc gttatcccct gattctgtgg  21120

ataaccgtat taccgccttt gagtgagctg ataccgctcg ccgcagccga acgaccgagc  21180

gcagcgagtc agtgagcgag gaagcggaag agcgcccaat acgcaaaccg cctctccccg  21240

cgcgttggcc gattcattaa tgcagctggc acgacaggtt tcccgactgg aaagcgggca  21300

gtgagcgcaa cgcaattaat gtgagttagc tcactcatta ggcaccccag gctttacact  21360

ttatgcttcc ggctcgtatg ttgtgtggaa ttgtgagcgg ataacaattt cacacaggaa  21420

acagctatga ccatgattac gccaagctta cgcgtcctgg cattatgccc agtacatgac  21480

cttatgggac tttcctactt ggcagtacat ctacgtatta gtcatcgcta ttaccatggt  21540

gatgcggttt tggcagtaca tcaatgggcg tggatagcgg tttgactcac ggggatttcc  21600

aagtctccac cccattgacg tcaatgggag tttgttttgg caccaaaatc aacgggactt  21660

tccaaaatgt cgtaacaact ccgccccatt gacgcaaatg ggcggtaggc gtgtacggtg  21720

ggaggtctat ataagcagag ctcgtttagt gaaccgtgg                         21759
```